United States Patent
Schönbrunn et al.

(10) Patent No.: US 12,391,676 B2
(45) Date of Patent: Aug. 19, 2025

(54) BRD4-JAK2 INHIBITORS

(71) Applicant: H. LEE MOFFITT CANCER CENTER AND RESEARCH INSTITUTE, INC., Tampa, FL (US)

(72) Inventors: Ernst Schönbrunn, Tampa, FL (US); Nicholas J. Lawrence, Tampa, FL (US); Harshani R. Lawrence, Tampa, FL (US); Gary Reuther, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 1008 days.

(21) Appl. No.: 17/274,265

(22) PCT Filed: Sep. 9, 2019

(86) PCT No.: PCT/US2019/050148
§ 371 (c)(1),
(2) Date: Mar. 8, 2021

(87) PCT Pub. No.: WO2020/051572
PCT Pub. Date: Mar. 12, 2020

(65) Prior Publication Data
US 2022/0119370 A1    Apr. 21, 2022

Related U.S. Application Data

(60) Provisional application No. 62/728,436, filed on Sep. 7, 2018.

(51) Int. Cl.
| C07D 403/12 | (2006.01) |
| C07D 401/12 | (2006.01) |
| C07D 401/14 | (2006.01) |
| C07D 403/14 | (2006.01) |
| C07D 405/14 | (2006.01) |
| C07D 413/14 | (2006.01) |
| C07D 471/04 | (2006.01) |

(52) U.S. Cl.
CPC ......... *C07D 403/12* (2013.01); *C07D 401/12* (2013.01); *C07D 401/14* (2013.01); *C07D 403/14* (2013.01); *C07D 405/14* (2013.01); *C07D 413/14* (2013.01); *C07D 471/04* (2013.01)

(58) Field of Classification Search
CPC .. C07D 403/12; C07D 401/12; C07D 401/14; C07D 403/14; C07D 405/14; C07D 413/14
See application file for complete search history.

(56) References Cited

U.S. PATENT DOCUMENTS

| 10,106,507 B2* | 10/2018 | Shönbrunn | A61K 31/519 |
| 10,526,291 B2* | 1/2020 | Schönbrunn | C07D 239/95 |
| 2012/0149687 A1 | 6/2012 | Lee et al. | |
| 2017/0210730 A1 | 7/2017 | Bhide et al. | |
| 2021/0355088 A1* | 11/2021 | Schönbrunn | A61K 45/06 |
| 2023/0303499 A1* | 9/2023 | Lawrence | A61K 45/06 514/275 |

FOREIGN PATENT DOCUMENTS

| WO | WO-2015117053 A1 * | 8/2015 | A61K 31/18 |
| WO | WO-2016022460 A1 * | 2/2016 | A61K 31/505 |
| WO | WO-2016201370 A1 * | 12/2016 | A61K 31/4162 |
| WO | WO-2017066428 A1 * | 4/2017 | A61K 45/06 |
| WO | WO-2018098561 A1 * | 6/2018 | A61K 31/498 |

OTHER PUBLICATIONS

Paulson et al. "Design, Synthesis, and Characterization of a Fluorescence Polarization Pan-BET Bromodomain Probe", 2018, ACS Medicinal Chemistry Letters, 9, pp. 1149-1305 (Year: 2018).*
Rothman et al. "The use of common genetic polymorphisms to enhance the epidemiologic study of environmental carcinogens", 2000, Biochemica et Biophysica Acta, 1471, C1-C10 (Year: 2000).*
Ember et al. "Potent Dual BET Bromodomain-Kinase Inhibitors as Value-Added Multitargeted Chemical Probes and Cancer Therapeutics", 2017, Molecular Cancer Therapeutics, 16, pp. 1054-1067 (Year: 2017).*
International Search Report and Written Opinion in PCT/US2019/050148. Mailed Jan. 9, 2020. 10 pages.

* cited by examiner

*Primary Examiner* — Jeffrey H Murray
*Assistant Examiner* — Madeline E Braun
(74) *Attorney, Agent, or Firm* — Meunier Carlin & Curfman LLC

(57) ABSTRACT

Disclosed herein are compounds that are inhibitors of BDR4 and their use in the treatment of cancer. Methods of screening for selective inhibitors of BDR4 are also disclosed. In certain aspects, disclosed are compounds of Formula I through IV.

10 Claims, 3 Drawing Sheets

BRD4-JAK2 INHIBITORS

CROSS REFERENCE TO RELATED APPLICATIONS

This application is a United States National Phase Patent Application of International Patent Application Number PCT/US2019/050148, filed on Sep. 9, 2019, which claims the benefit of priority to U.S. Provisional Application No. 62/728,436, filed Sep. 7, 2018, which is incorporated by reference herein in its entirety.

FIELD

The subject matter disclosed herein relates generally to cancer therapy and to anti-cancer compounds. More specifically, the subject matter disclosed herein relates to inhibitors of BDR4 and their use in the treatment of cancer. Methods of screening for selective inhibitors of BDR4 are also disclosed.

BACKGROUND

Bromodomain (BRD)-containing proteins are essential for the recognition of acetylated lysine (KAc) residues of histones during transcriptional activation (Sanchez et al., The role of human bromodomains in chromatin biology and gene transcription. *Current opinion in drug discovery & development* 2009, 12, 659-65). BRDs have emerged as promising drug targets for a number of disease pathways that are characterized by changes in the epigenetic cell signature (Id.; Filippakopoulos et al., Selective inhibition of BET bromodomains. *Nature* 2010, 468, 1067-731). To date, only a few structurally diverse BRD inhibitors have been reported, all of which specifically target the KAc recognition sites of the bromodomain and extra terminal (BET) family of proteins (BRD2, BRD3, BRD4, and BRDT), each containing two tandem BRDs (Hewings et al., Progress in the development and application of small molecule inhibitors of bromodomain-acetyl-lysine interactions. *J Med Chem* 2012, 55, 9393-413; Muller et al., Bromodomains as therapeutic targets. *Expert Rev Mol Med* 2011, 13, e29; Prinjha et al., Place your BETs: the therapeutic potential of bromodomains. *Trends Pharmacol Sci* 2012, 33, 146-53). BET-inhibitors exert a broad spectrum of desirable biological effects such as anticancer and anti-inflammatory properties (Delmore et al., BET bromodomain inhibition as a therapeutic strategy to target c-Myc. *Cell* 2011, 146, 904-17; Matzuk et al., Small-Molecule Inhibition of BRDT for Male Contraception. *Cell* 2012, 150, 673-684; Mertz et al., Targeting MYC dependence in cancer by inhibiting BET bromodomains. *Proc Nat Acad Sci USA* 2011, 108, 16669-74; Ott et al., BET bromodomain inhibition targets both c-Myc and IL7R in high-risk acute lymphoblastic leukemia. *Blood* 2012, 120, 2843-52; Puissant et al., Targeting MYCN in neuroblastoma by BET bromodomain inhibition. *Cancer Discov* 2013, 3, 308-23). Of these, I-BET-762 (GSK525762) has recently entered clinical trials for the treatment of NUT midline carcinoma (Mirguet et al., Discovery of epigenetic regulator I-BET762: lead optimization to afford a clinical candidate inhibitor of the BET bromodomains. *J Med Chem* 2013, 56, 7501-15). Intense efforts are currently underway to discover new chemical scaffolds for hit-to-lead development campaigns of BET inhibitors as novel therapeutics (Filippakopoulos et al., Benzodiazepines and benzotriazepines as protein interaction inhibitors targeting bromodomains of the BET family. *Bioorg Med Chem* 2012, 20, 1878-86; Fish et al., Identification of a chemical probe for bromo and extra C-terminal bromodomain inhibition through optimization of a fragment-derived hit. *J Med Chem* 2012, 55, 9831-7; Mirguet et al., Naphthyridines as Novel BET Family Bromodomain Inhibitors. *Chem Med Chem* 2014, 9, 580-9; Seal et al., Identification of a novel series of BET family bromodomain inhibitors: binding mode and profile of I-BET151 (GSK1210151A). *Bioorg & Med Chem Lett* 2012, 22, 2968-72). Recently, BETs were discovered that interact with diverse kinase inhibitors (Martin et al., Cyclin-dependent kinase inhibitor dinaciclib interacts with the acetyl-lysine recognition site of bromodomains. *Chem Biol* 2013, 8, 2360; Ember et al., The acetyl-lysine binding site of bromodomain-containing protein 4 (BRD4) interacts with diverse kinase inhibitors. *Chem Biol* 2014; Ciceri et al., Dual kinase-bromodomain inhibitors for rationally designed polypharmacology. *Nat Chem Biol* 2014). Among these, the PLK1 inhibitor BI2536 and the JAK2/FLT3 inhibitors TG101348 and TG101209 inhibited the binding of KAc peptide to BRD4 with $IC_{50}$ values of 0.03 and 0.13 µM, respectively, and showed strong downregulation of c-Myc in MM.1S cells. These activities were similar to that of the prototypic BET inhibitor JQ1, the most potent BRD4 inhibitor described to date. Furthermore, TG101348, but not JAK2 inhibitors that lack BET and FLT3 activity, potently inhibited proliferation of MV4-11 AML cells ($IC_{50}$=79 nM)(Id.). AML is often driven by BETs and mutant FLT38 (Smith et al., Validation of ITD mutations in FLT3 as a therapeutic target in human acute myeloid leukaemia. *Nature* 2012, 485, 260-3) and the findings by Knapp and colleagues provided compelling evidence of an oncology indication that could be exploited through dual targeting of kinases and bromodomains. What are thus needed are new BRD inhibitors, for example, those with dual targeting activity, and uses of such inhibitors to treat various cancers. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anti-cancer compounds. More specifically, the subject matter disclosed herein relates to inhibitors of BDRs, e.g., BDR4, and their use in the treatment of cancer. Methods of screening for new BDR inhibitors are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
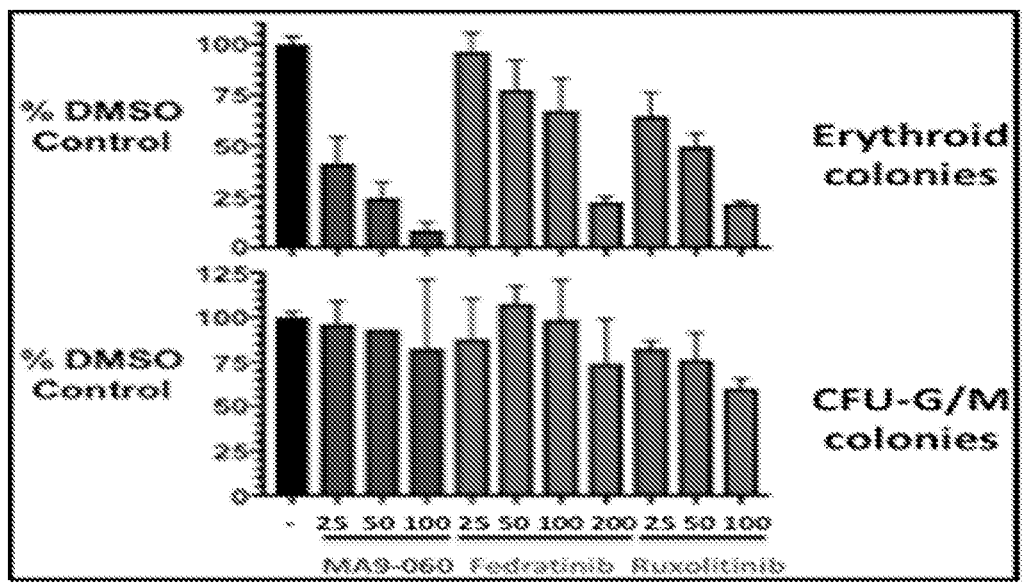
FIG. 1 shows the dual JAK2-BET Inhibitor MA9-060 is more effective than Fedratinib or Ruxolitinib at inhibiting the neoplastic growth of primary MPN patient cells. Epo-independent (neoplastic) erythroid and CFU-G/M colony formation of PBMCs from a JAK2-V617F+ myelofibrosis patient were assessed in the presence of the indicated concentrations of MA9-060, fedratinib, and ruxolitinib. Colony formation was determined after 2 weeks and is indicated relative to no drug (DMSO). CFU-G/M colony growth was not affected by MA9-060 suggesting the compound is not non-specifically toxic to primary human hematopoietic progenitor cells. Similar results were obtained with 4 of 4 patient samples.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A''$ is used herein as merely a generic substitutent in the definitions below.

The term "alkoxy" as used herein is an alkyl group bound through a single, terminal ether linkage; that is, an "alkoxy" group can be defined as $—OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O—.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN The term "azido" as used herein is represented by the formula —$N_3$.

The term "sulfonyl" is used herein to refer to the sulfo-oxo group represented by the formula —$S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use.

Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective. Reference will now be made in detail to specific aspects of the disclosed materials, compounds, compositions, articles, and methods, examples of which are illustrated in the accompanying Examples.

Compounds

TG101348 and TG101209 contain a bisanilinopyrimidine scaffold which is critical for the interaction with the hinge-region of the ATP site of JAK2 and FLT3 (Siu et al., 2-Amino-[1,2,4]triazolo[1,5-a]pyridines as JAK2 inhibitors. *Bioorg & Med Chem Lett* 2013, 23, 5014-21). In BRD4, this scaffold directly interacts with Asn140 and Pro82, residues critical for the interaction with KAc residues in all BETs. This binding mode in the KAc site indicates that other bisanilinopyrimidine-containing compounds can interact with BRD4 in the same manner. Bisanilinopyrimidines were developed as potent inhibitors of Aurora A (Lawrence et al., Development of o-chlorophenyl substituted pyrimidines as exceptionally potent aurora kinase inhibitors. *J Med Chem* 2012, 55, 7392-416). Initial cocrystallization screening of BRD4 against five such Aurora inhibitors revealed that one compound, YL5-081-1, indeed interacted with the KAc site of BRD4 as expected from the structures with TG101348/TG101209. The new structural information provided by this work led to the hypothesis of this proposal that bisanilinopyrimidine-containing compounds can be tailored to potently inhibit BRD4 with simultaneous activity against JAK2, FLT3 or Aurora kinases.

Thus, disclosed are compounds that are BDR4 inhibitors. These disclosed compounds can be used in various compositions as anti-cancer therapeutics.

In certain embodiments, the disclosed compounds have the chemical structure shown in Formula I.

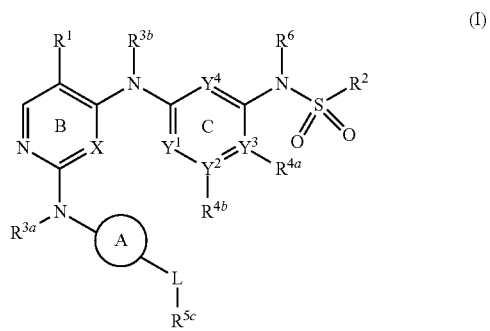

(I)

wherein
ring A is substituted or unsubstituted aryl or substituted or unsubstituted heteroaryl,
X is selected from CH or N;
$Y^1$, $Y^2$, $Y^3$, and $Y^4$, independently for each occurrence, is selected from C, CH or N, wherein when $Y^2$ or $Y^3$ are independently N, $R^{4a}$ or $R^{4b}$ is absent;
$R^1$ is halogen, $C_1$-$C_6$ alkyl, $C_1$-$C_6$ haloalkyl, cyano, nitro, halogen, amino, substituted or unsubstituted amide, or substituted or unsubstituted $C_2$-$C_5$ heteroaryl;
$R^2$ is OH, $C_1$-$C_{10}$ alkyl, $C_1$-$C_6$ alkoxy, $C_3$-$C_{10}$ cycloalkyl, $C_5$-$C_8$ cycloheteroalkyl, wherein said $C_1$-$C_6$ alkyl, $C_1$-$C_6$ alkoxy, $C_3$-$C_{10}$ cycloalkyl, and $C_5$-$C_8$ cycloheteroalkyl groups are optionally substituted one or more times with a group selected from halogen, hydroxy, $C_1$-$C_8$ alkyl, carboxyl, amino, nitro, cyano, isocyano, and combinations thereof;
$R^{3a}$ and $R^{3b}$ are independently selected from hydrogen and substituted or unsubstituted $C_1$-$C_6$ alkyl;
$R^{4a}$ and $R^{4b}$ are independently selected from hydrogen, $C_1$-$C_6$ alkyl, $C_1$-$C_6$ haloalkyl, $C_1$-$C_6$ alkoxy, $C_3$-$C_{10}$ cycloalkyl, $C_5$-$C_8$ cycloheteroalkyl, halogen, hydroxy, amino, nitro, cyano, isocyano, wherein said $C_1$-$C_6$ alkyl, $C_1$-$C_6$ alkoxy, $C_3$-$C_{10}$ cycloalkyl, and $C_5$-$C_8$ cycloheteroalkyl groups are optionally substituted one or more times with a group selected from halogen, hydroxy, $C_1$-$C_8$ alkyl, carboxyl, amino, nitro, cyano, isocyano, and combinations thereof;

$R^{5c}$ is selected from substituted or unsubstituted $C_3$-$C_{10}$ cycloalkyl, substituted or unsubstituted $C_5$-$C_8$ cycloheteroalkyl, substituted or unsubstituted $C_3$-$C_{10}$ cycloalkenyl, substituted or unsubstituted $C_5$-$C_8$ cycloheteroalkenyl, substituted or unsubstituted aryl, substituted or unsubstituted heteroaryl, hydroxyl, alkoxyl;

$R^6$ is selected from hydrogen and substituted or unsubstituted $C_1$-$C_6$ alkyl; or $R^{4a}$ and $R^6$ combine with the intervening atoms to which they are attached to form a substituted or unsubstituted heterocyclic ring fused to ring C; and L is a linker selected from a bond or a substituted or unsubstituted $C_1$-$C_6$ alkyl, substituted or unsubstituted $C_1$-$C_6$ heteroalkyl, substituted or unsubstituted $C_1$-$C_6$ ether, substituted or unsubstituted $C_1$-$C_6$ amide, substituted or unsubstituted $C_1$-$C_6$ amine, substituted or unsubstituted $C_1$-$C_6$ carbonyl, substituted or unsubstituted $C_1$-$C_6$ ester;

or a salt thereof.

In certain embodiments of Formula I, the disclosed compounds have the chemical structure shown in Formula I-A.

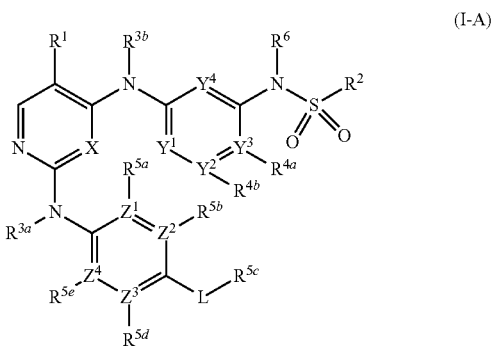

(I-A)

wherein

X is selected from CH or N;

$Y^1$, $Y^2$, $Y^3$, and $Y^4$, independently for each occurrence, is selected from C, CH or N, wherein when $Y^2$ or $Y^3$ are independently N, $R^{4a}$ or $R^{4b}$ is absent;

$Z^1$, $Z^2$, $Z^3$, and $Z^4$, independently for each occurrence, is selected from C, CH or N;

$R^1$ is halogen, $C_1$-$C_6$ alkyl, $C_1$-$C_6$ haloalkyl, cyano, nitro, halogen, amino, substituted or unsubstituted amide, or substituted or unsubstituted $C_2$-$C_5$ heteroaryl;

$R^2$ is $C_1$-$C_{10}$ alkyl OR $C_1$-$C_6$ alkoxy, wherein said $C_1$-$C_6$ alkyl, $C_1$-$C_6$ alkoxy groups are optionally substituted one or more times with a group selected from halogen, hydroxy, $C_1$-$C_5$ alkyl, carboxyl, amino, nitro, cyano, isocyano, and combinations thereof;

$R^{3a}$ and $R^{3b}$ are independently selected from hydrogen and substituted or unsubstituted $C_1$-$C_3$ alkyl;

$R^{4a}$ and $R^{4b}$ are independently selected from hydrogen, $C_1$-$C_6$ alkyl, $C_1$-$C_6$ haloalkyl, $C_1$-$C_6$ alkoxy, $C_3$-$C_{10}$ cycloalkyl, $C_5$-$C_8$ cycloheteroalkyl, halogen, hydroxy, amino, nitro, cyano, isocyano, wherein said $C_1$-$C_6$ alkyl, $C_1$-$C_6$ alkoxy, $C_3$-$C_{10}$ cycloalkyl, and $C_5$-$C_8$ cycloheteroalkyl groups are optionally substituted one or more times with a group selected from halogen, hydroxy, $C_1$-$C_8$ alkyl, carboxyl, amino, nitro, cyano, isocyano, and combinations thereof;

$R^{5a}$, $R^{5d}$, and $R^{5e}$ are independently selected from hydrogen, $C_1$-$C_6$ alkyl, $C_1$-$C_6$ alkoxy, $C_3$-$C_{10}$ cycloalkyl, $C_5$-$C_8$ cycloheteroalkyl, halogen, hydroxy, amino, nitro, cyano, isocyano, wherein said $C_1$-$C_6$ alkyl, $C_1$-$C_6$ alkoxy, $C_3$-$C_{10}$ cycloalkyl, and $C_5$-$C_8$ cycloheteroalkyl groups are optionally substituted one or more times with a group selected from halogen, hydroxy, $C_1$-$C^8$ alkyl, carboxyl, amino, $C_1$-$C^8$ alkylamine, or $C_1$-$C_5$ alkoxyl substituted with a heterocyle, nitro, cyano, isocyano, and combinations thereof, wherein for each occurrence when $Z^1$, $Z^2$, $Z^3$, or $Z^4$ is N, then $R^{5a}$, $R^{5b}$, $R^{5d}$, or $R^{5e}$ is absent;

$R^{5b}$ is selected from hydrogen, halogen, hydroxy, amino, nitro, cyano, $C_1$-$C_6$ alkyl, or $C_1$-$C_6$ alkoxy, $R^{5c}$ is selected from substituted or unsubstituted $C_3$-$C_{10}$ cycloalkyl, substituted or unsubstituted $C_5$-$C_8$ cycloheteroalkyl, substituted or unsubstituted $C_3$-$C_{10}$ cycloalkenyl, substituted or unsubstituted $C_5$-$C_8$ cycloheteroalkenyl, substituted or unsubstituted aryl, substituted or unsubstituted heteroaryl, hydroxyl, alkoxyl;

$R^6$ is selected from hydrogen and substituted or unsubstituted $C_1$-$C_6$ alkyl; or $R^{4a}$ and $R^6$ combine with the intervening atoms to which they are attached to form a substituted or unsubstituted heterocyclic ring fused to ring C; and L is a linker selected from a bond or a substituted or unsubstituted $C_1$-$C_6$ alkyl, substituted or unsubstituted $C_1$-$C_6$ heteroalkyl, substituted or unsubstituted $C_1$-$C_6$ ether, substituted or unsubstituted $C_1$-$C_6$ amide, substituted or unsubstituted $C_1$-$C_6$ amine, substituted or unsubstituted $C_1$-$C_6$ carbonyl, substituted or unsubstituted $C_1$-$C_6$ ester;

or a salt thereof.

In further embodiments of Formula I, the disclosed compounds have the chemical structure shown in Formula I-B:

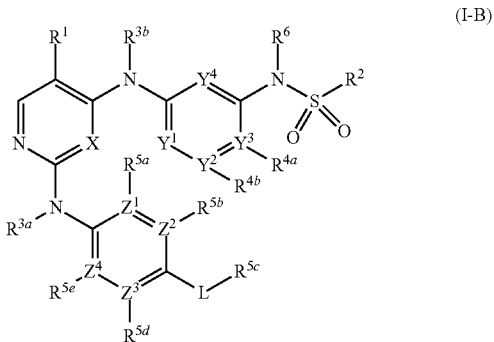

(I-B)

wherein $Y^1$, $Y^2$, $Y^3$, and $Y^4$, independently for each occurrence, is selected from C, CH or N, wherein when $Y^2$ or $Y^3$ are independently N, $R^{4a}$ or $R^{4b}$ is absent;

$Z^1$, $Z^2$, $Z^3$, and $Z^4$, independently for each occurrence, is selected from C, CH or N;

$R^1$ is halogen, $C_1$-$C_6$ alkyl, $C_1$-$C_6$ haloalkyl, cyano, nitro, halogen, amino, substituted or unsubstituted amide, or substituted or unsubstituted $C_2$-$C_5$ heteroaryl;

$R^2$ is $C_1$-$C_{10}$ alkyl OR $C_1$-$C_6$ alkoxy, wherein said $C_1$-$C_6$ alkyl, $C_1$-$C_6$ alkoxy groups are optionally substituted one or more times with a group selected from halogen, hydroxy, $C_1$-$C_8$ alkyl, carboxyl, amino, nitro, cyano, isocyano, and combinations thereof;

$R^{3a}$ and $R^{3b}$ are independently selected from hydrogen and substituted or unsubstituted $C_1$-$C_3$ alkyl;

$R^{4a}$ and $R^{4b}$ are independently selected from hydrogen, $C_1$-$C_6$ alkyl, $C_1$-$C_6$ haloalkyl, $C_1$-$C_6$ alkoxy, $C_3$-$C_{10}$ cycloalkyl, $C_5$-$C_8$ cycloheteroalkyl, halogen, hydroxy, amino, nitro, cyano, isocyano, wherein said $C_1$-$C_6$ alkyl, $C_1$-$C_6$ alkoxy, $C_3$-$C_{10}$ cycloalkyl, and $C_5$-$C_8$ cycloheteroalkyl groups are optionally substituted one or more times with a group selected from halogen, hydroxy, $C_1$-$C_8$ alkyl, carboxyl, amino, nitro, cyano, isocyano, and combinations thereof;

$R^{5a}$, $R^{5d}$, and $R^{5e}$ are independently selected from hydrogen, $C_1$-$C_6$ alkyl, $C_1$-$C_6$ alkoxy, $C_3$-$C_{10}$ cycloalkyl, $C_5$-$C_8$ cycloheteroalkyl, halogen, hydroxy, amino, nitro, cyano, isocyano, wherein said $C_1$-$C_6$ alkyl, $C_1$-$C_6$ alkoxy, $C_3$-$C_{10}$ cycloalkyl, and $C_5$-$C_8$ cycloheteroalkyl groups are optionally substituted one or more times with a group selected from halogen, hydroxy, $C_1$-$C_8$ alkyl, carboxyl, amino, $C_1$-$C_8$ alkylamine, or $C_1$-$C_5$ alkoxyl substituted with a heterocycle, nitro, cyano, isocyano, and combinations thereof, wherein for each occurrence when $Z^1$, $Z^2$, $Z^3$, or $Z^4$ is N, then $R^{5a}$, $R^{5b}$, $R^{5d}$, or $R^{5e}$ is absent;

$R^{5b}$ is selected from hydrogen, halogen, hydroxy, amino, nitro, cyano, $C_1$-$C_6$ alkyl, or $C_1$-$C_6$ alkoxy, $R^{5c}$ is selected from substituted or unsubstituted $C_3$-$C_{10}$ cycloalkyl, substituted or unsubstituted $C_5$-$C_8$ cycloheteroalkyl, substituted or unsubstituted $C_3$-$C_{10}$ cycloalkenyl, substituted or unsubstituted $C_5$-$C_8$ cycloheteroalkenyl, substituted or unsubstituted aryl, substituted or unsubstituted heteroaryl, hydroxyl, alkoxyl;

$R^6$ is selected from hydrogen and substituted or unsubstituted $C_1$-$C_6$ alkyl; or $R^{4a}$ and $R^6$ combine with the intervening atoms to which they are attached to form a substituted or unsubstituted heterocyclic ring fused to ring C; and L is a linker selected from a bond or a substituted or unsubstituted $C_1$-$C_6$ alkyl, substituted or unsubstituted $C_1$-$C_6$ heteroalkyl, substituted or unsubstituted $C_1$-$C_6$ ether, substituted or unsubstituted $C_1$-$C_6$ amide, substituted or unsubstituted $C_1$-$C_6$ amine, substituted or unsubstituted $C_1$-$C_6$ carbonyl, substituted or unsubstituted $C_1$-$C_6$ ester;

or a salt thereof.

In further embodiments of Formula I, the disclosed compounds have the chemical structure shown in Formula I-C:

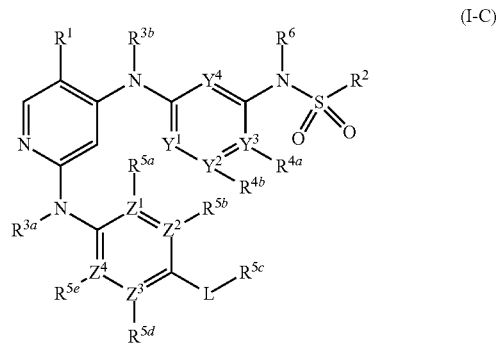

(I-C)

wherein
- $Y^1$, $Y^2$, $Y^3$, and $Y^4$, independently for each occurrence, is selected from C, CH or N, wherein when $Y^2$ or $Y^3$ are independently N, $R^{4a}$ or $R^{4b}$ is absent;
- $Z^1$, $Z^2$, $Z^3$, and $Z^4$, independently for each occurrence, is selected from C, CH or N
- $R^1$ is halogen, $C_1$-$C_6$ alkyl, $C_1$-$C_6$ haloalkyl, cyano, nitro, halogen, amino, substituted or unsubstituted amide, or substituted or unsubstituted $C_2$-$C_5$ heteroaryl;
- $R^2$ is $C_1$-$C_{10}$ alkyl OR $C_1$-$C_6$ alkoxy, wherein said $C_1$-$C_6$ alkyl, $C_1$-$C_6$ alkoxy groups are optionally substituted one or more times with a group selected from halogen, hydroxy, $C_1$-$C_8$ alkyl, carboxyl, amino, nitro, cyano, isocyano, and combinations thereof;
- $R^{3a}$ and $R^{3b}$ are independently selected from hydrogen and substituted or unsubstituted $C_1$-$C_3$ alkyl;
- $R^{4a}$ and $R^{4b}$ are independently selected from hydrogen, $C_1$-$C_6$ alkyl, $C_1$-$C_6$ haloalkyl, $C_1$-$C_6$ alkoxy, $C_3$-$C_{10}$ cycloalkyl, $C_5$-$C_8$ cycloheteroalkyl, halogen, hydroxy, amino, nitro, cyano, isocyano, wherein said $C_1$-$C_6$ alkyl, $C_1$-$C_6$ alkoxy, $C_3$-$C_{10}$ cycloalkyl, and $C_5$-$C_8$ cycloheteroalkyl groups are optionally substituted one or more times with a group selected from halogen, hydroxy, $C_1$-$C_8$ alkyl, carboxyl, amino, nitro, cyano, isocyano, and combinations thereof;
- $R^{5a}$, $R^{5d}$, and $R^{5e}$ are independently selected from hydrogen, $C_1$-$C_6$ alkyl, $C_1$-$C_6$ alkoxy, $C_3$-$C_{10}$ cycloalkyl, $C_5$-$C_8$ cycloheteroalkyl, halogen, hydroxy, amino, nitro, cyano, isocyano, wherein said $C_1$-$C_6$ alkyl, $C_1$-$C_6$ alkoxy, $C_3$-$C_{10}$ cycloalkyl, and $C_5$-$C_8$ cycloheteroalkyl groups are optionally substituted one or more times with a group selected from halogen, hydroxy, $C_1$-$C^8$ alkyl, carboxyl, amino, $C_1$-$C^8$ alkylamine, or $C_1$-$C_5$ alkoxyl substituted with a heterocyle, nitro, cyano, isocyano, and combinations thereof,
  wherein for each occurrence when $Z^1$, $Z^2$, $Z^3$, or $Z^4$ is N, then $R^{5a}$, $R^{5b}$, $R^{5d}$, or $R^{5e}$ is absent;
- $R^{5b}$ is selected from hydrogen, halogen, hydroxy, amino, nitro, cyano, $C_1$-$C_6$ alkyl, or $C_1$-$C_6$ alkoxy,
- $R^{5c}$ is selected from substituted or unsubstituted $C_3$-$C_{10}$ cycloalkyl, substituted or unsubstituted $C_5$-$C_8$ cycloheteroalkyl, substituted or unsubstituted $C_3$-$C_{10}$ cycloalkenyl, substituted or unsubstituted $C_5$-$C_8$ cycloheteroalkenyl, substituted or unsubstituted aryl, substituted or unsubstituted heteroaryl, hydroxyl, alkoxyl;
- $R^6$ is selected from hydrogen and substituted or unsubstituted $C_1$-$C_6$ alkyl; or $R^{4a}$ and $R^6$ combine with the intervening atoms to which they are attached to form a substituted or unsubstituted heterocyclic ring fused to ring C; and
- L is a linker selected from a bond or a substituted or unsubstituted $C_1$-$C_6$ alkyl, substituted or unsubstituted $C_1$-$C_6$ heteroalkyl, substituted or unsubstituted $C_1$-$C_6$ ether, substituted or unsubstituted $C_1$-$C_6$ amide, substituted or unsubstituted $C_1$-$C_6$ amine, substituted or unsubstituted $C_1$-$C_6$ carbonyl, substituted or unsubstituted $C_1$-$C_6$ ester;
- or salt thereof.

In certain embodiments of Formula I, I-A, I-B, and I-C, $R^1$ can be $C_1$-$C_6$ alkyl. For example, $R^1$ can be methyl, ethyl, or propyl. In specific examples, $R^1$ is methyl. In other specific examples, $R^1$ is ethyl. In other examples $R^1$ is $CF_3$. In further embodiments of Formula I, I-A, I-B, and I-C, $R^1$ can be substituted or unsubstituted amide, or substituted or unsubstituted $C_2$-$C_5$ heteroaryl. For example, $R^1$ can be unsubstituted amide. In some examples, $R^1$ is substituted or unsubstituted $C_2$-$C_5$ heteroaryl.

In certain embodiments of Formula I, I-A, I-B, and I-C, $R^2$ is $C_1$-$C_{10}$ alkyl, e.g., methyl, ethyl, n-propyl, isopropyl, n-butyl, isobutyl, tert-butyl, pentyl, or hexyl. In some examples, $R^2$ can be a $C_2$-$C_6$ alkyl. Preferably, $R^2$ is a $C_4$ alkyl such as tert-butyl.

In certain embodiments of Formula I, I-A, I-B, and I-C, $R^{3a}$ and $R^{3b}$ are both hydrogen. In certain instances, $R^{3a}$ is hydrogen and $R^{3b}$ is not hydrogen. In certain instances, $R^{3a}$ is not hydrogen and $R^{3b}$ is hydrogen.

In certain embodiments of Formula I, I-A, I-B, and I-C, $R^{4a}$ can be selected from hydrogen, halogen, or $R^{4a}$ and $R^6$ combine with atoms to which they are attached to form a cycloalkenyl ring or a cycloheteroalkenyl ring. For example, $R^{4a}$ can be halogen, e.g., fluoro, chloro, or bromo. In some examples, $R^{4a}$ can be hydrogen. In other examples, $R^{4a}$ and $R^6$ can combine with atoms to which they are attached to form a $C_5$-$C_6$ cycloalkenyl ring. In some examples, $R^{4a}$ is absent. In certain embodiments of Formula I, I-A, I-B, and I-C, $R^{4b}$ can be selected from hydrogen, halogen. For example, $R^{4b}$ can be halogen, e.g., fluoro, chloro, or bromo. In some examples, $R^{4b}$ can be hydrogen. In some examples, $R^{4b}$ is absent. In certain embodiments of Formula I, I-A, I-B, and I-C, $R^{4a}$ and $R^{4b}$ are independently selected from hydrogen, halogen, or $R^{4a}$ and $R^6$ combine with intervening atoms to which they are attached to form a substituted or unsubstituted heterocyclic ring.

In certain embodiments of Formula I, I-A, I-B, and I-C, $R^{5a}$ and $R^{5e}$ are both hydrogen. In other examples, $R^{5a}$ and $R^{5d}$ and $R^{5e}$ are all hydrogen. In other examples, $R^{5b}$ is halogen, e.g., fluoro or chloro. In other examples, $R^{5a}$ is halogen, e.g., fluoro or chloro. In other examples, $R^{5d}$ is halogen, e.g., fluoro or chloro. In other examples, $R^{5d}$ is halogen, e.g., fluoro or chloro. In other examples, $R^{5b}$ and $R^{5d}$ are hydrogen or halogen. In certain preferred embodiments, $R^{5a}$, $R^{5e}$, $R^{3a}$ and $R^{3b}$ are each hydrogen. In certain preferred embodiments, $R^{5b}$ and $R^{5d}$ are both hydrogen. In other examples, at least one of $R^{5b}$ and $R^{5d}$ are halogen. For example, $R^{5b}$ and $R^{5d}$ can both be halogen, preferably fluoro. In some embodiments, at least one of $R^{5b}$ and $R^{5d}$ are methyl. In further examples of Formula I, I-A, I-B, and I-C, at least one of $R^4$, $R^5$, $R^{5b}$, $R^{5c}$, $R^{5d}$, and $R^{5e}$ are halogen. In further examples of Formula I, I-A, I-B, and I-C, $R^{5b}$ can be a halogen such as fluoro, chloro, or bromo, preferably fluoro.

In some instance the compound of Formula I, I-A, or I-B or I-C is characterized, wherein $R^{5c}$ can be substituted or unsubstituted $C_5$-$C_8$ cycloheteroalkyl, substituted or unsubstituted heteroaryl, substituted or unsubstituted $C_1$-$C_6$ heteroalkyl, or substituted or unsubstituted $C_1$-$C_6$ amide. For example, $R^{5c}$ can be substituted or unsubstituted $C_5$-$C_8$ cycloheteroalkyl or a substituted or unsubstituted $C_3$-$C_8$ cycloalkyl. In specific examples the $C_5$-$C_8$ cycloheteroalkyl or $C_3$-$C_8$ cycloalkyl can be substituted with $C_1$-$C_8$ alkyl, $C_1$-$C_8$ alkylamine, $C_1$-$C_8$ alkoxy, or substituted heterocycle. Exemplary $C_5$-$C_8$ cycloheteroalkyl and $C_3$-$C_5$ cycloalkyl include

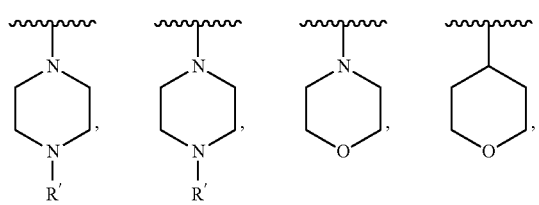

-continued

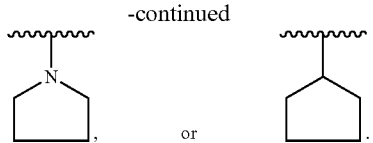

wherein R' can be hydrogen, substituted or unsubstituted $C_1$-$C_8$ alkyl, substituted or unsubstituted $C_1$-$C_8$ alkylamine, substituted or unsubstituted $C_1$-$C_8$ alkoxyl, substituted or unsubstituted alkylheterocyle, or substituted or unsubstituted heterocyle.

As described herein, L is a linker. In certain embodiments of Formula I, I-A, I-B, and I-C, L can be a bond. In other embodiments of Formula I, I-A, I-B, and I-C, L can be selected from substituted or unsubstituted $C_1$-$C_6$ heteroalkyl, or substituted or unsubstituted $C_1$-$C_6$ amide. For example, L can be an unsubstituted $C_1$-$C_6$ heteroalkyl comprising a heteroatom selected from O, N, or S, or an unsubstituted $C_1$-$C_6$ amide.

In certain embodiments of Formula I, I-A, I-B, and I-C, $R^6$ is hydrogen.

In certain embodiments of Formula I, I-A, I-B, and I-C, X is CH. In other embodiments of Formula I, I-A, and I-B, X is N.

In certain embodiments of Formula I, I-A, I-B, and I-C, $Y^1$ is CH. In other embodiments of Formula I, I-A, I-B, and I-C, $Y^1$ is N. In certain embodiments of Formula I, I-A, I-B, and I-C, $Y^2$ is CH. In other embodiments of Formula I, I-A, I-B, and I-C, $Y^2$ is N. In certain embodiments of Formula I, I-A, I-B, and I-C, $Y^3$ is CH. In other embodiments of Formula I, I-A, I-B, and I-C, $Y^3$ is N. In certain embodiments of Formula I, I-A, I-B, and I-C, $Y^4$ is CH. In other embodiments of Formula I, I-A, I-B, and I-C, $Y^4$ is N.

In certain embodiments of Formula I, I-A, I-B, and I-C, $Y^3$ and $Y^4$ are both C. In certain embodiments of Formula I, I-A, I-B, and I-C, at least one of $Y^3$ and $Y^4$ are N. In certain embodiments of Formula I, I-A, I-B, and I-C, at least one of $Y^1$, $Y^2$, $Y^3$, and $Y^4$ are N. In certain embodiments of Formula I, I-A, I-B, and I-C, $Y^1$, $Y^2$, $Y^3$, and $Y^4$ are all C or CH.

In certain embodiments of Formula I, I-A, I-B, and I-C, $Z^1$ is CH. In other embodiments of Formula I, I-A, I-B, and I-C, $Z^1$ is N. In certain embodiments of Formula I, I-A, I-B, and I-C, $Z^2$ is CH. In other embodiments of Formula I, I-A, I-B, and I-C, $Z^2$ is N. In certain embodiments of Formula I, I-A, I-B, and I-C, $Z^3$ is CH. In other embodiments of Formula I, I-A, I-B, and I-C, $Z^3$ is N. In certain embodiments of Formula I, I-A, I-B, and I-C, $Z^4$ is CH. In other embodiments of Formula I, I-A, I-B, and I-C, $Z^4$ is N.

In certain embodiments of Formula I, I-A, I-B, and I-C, $Z^1$ and $Z^4$ are both C. In certain embodiments of Formula I, I-A, I-B, and I-C, at least one of $Z^1$ and $Z^4$ are N. In certain embodiments of Formula I, I-A, I-B, and I-C, at least one of $Z^1$, $Z^2$, $Z^3$, and $Z^4$ are N. In certain embodiments of Formula I, I-A, I-B, and I-C, $Z^1$, $Z^2$, $Z^3$, and $Z^4$ are all C or CH.

Specific examples of compounds disclosed herein are in Table 1.

TABLE 1

| Structure and Molecular Wt | Co-crystal | DSF ΔTm (° C.) | Estimated BRD4-1 IC50 (μM) | Comments |
|---|---|---|---|---|
| M.W. = 548.08 | Yes | 13 ± 0.05 | 0.001 | JAK2 IC50 = 2.73 nM (n = 2) |
| M.W. = 719.20 | Yes | 11 ± 0.02 | 0.0046 | |

TABLE 1-continued

| Structure and Molecular Wt | Co-crystal | DSF ΔTm (° C.) | Estimated BRD4-1 IC50 (μM) | Comments |
|---|---|---|---|---|
| M.W. = 570.73 | Yes | 9.4 ± 0.09 | 0.0157 | |
| MW = 561.11 | | 14.2 | | GI50: 0.087 μM (UKE1 cells) GI50: 0.18 μM (UKE1 cells), 0.028 μM (BAF3-JAK2-VF cells), 0.054 (SET2 cells) Mouse microsome 100%, Human 42.6% MM1.S cells IC50: 0.043 μM |
| MW = 562.11 | | 11.1 | | MM1.S cells IC50: 0.16 μM |

TABLE 1-continued
| Structure and Molecular Wt | Co-crystal | DSF ΔTm (° C.) | Estimated BRD4-1 IC50 (μM) | Comments |
|---|---|---|---|---|
| MW = 543,13 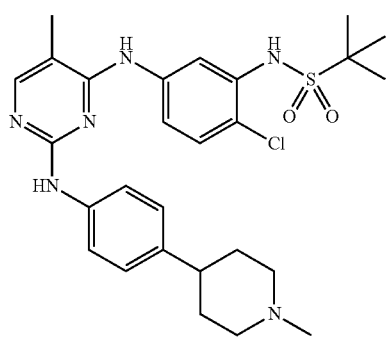 | | 12.3 | | GI50: 0.28 μM (UKE1 cells) Mouse microsome 81% GI50: 0.34 μM (UKE1 cells), 0.099 μM (BaF3-JAK2-VF cells),m 0.240 (SET2 cells) MM1.S cells IC50: 0.11 μM |
| MW = 508.69 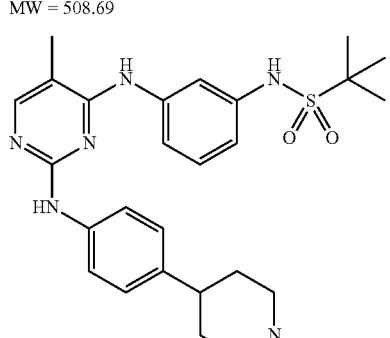 | | 10.6 | | GI50: 0.22 μM (UKE1 cells) MM1.S cells IC50: 0.091 μM |
| SY3-038 MW = 526.68 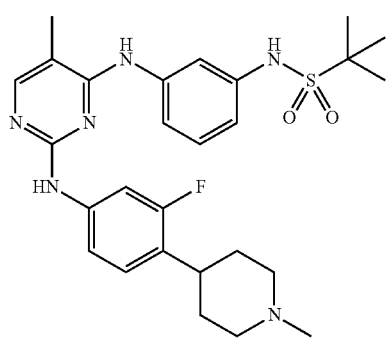 | | 12.3 | | GI50: 0.11 μM (UKE1 cells) |

TABLE 1-continued

| Structure and Molecular Wt | Co-crystal | DSF ΔTm (° C.) | Estimated BRD4-1 IC50 (μM) | Comments |
|---|---|---|---|---|
| MW = 527.66 (structure) | | 11.1 | | MM1.S cells IC50: 0.22 μM |
| (structure) | | 9.6 ± 0.9 | | |
| (structure) | | 8.9 ± 0.2 | | |
| (structure) | | 12.0 ± 0.01 | | |

TABLE 1-continued

| Structure and Molecular Wt | Co-crystal | DSF ΔTm (° C.) | Estimated BRD4-1 IC50 (μM) | Comments |
|---|---|---|---|---|
| [Structure: pyrimidine with CF3, NH-aryl-Cl-NHSO2tBu, and NH-aryl-F-(N-methylpiperidine)] | | 10.4 ± 0.1 | | |
| [Structure: 5-methylpyrimidine with NH-aryl-Cl-NHSO2tBu, and NH-aryl-F-O-(ethylpyrrolidine)] | | 15.1 ± 0.1 | | |
| [Structure: 5-methylpyrimidine with NH-aryl-Cl-NHSO2tBu, and NH-aryl-O-(ethylpyrrolidine)] | | 12.9 ± 0.1 | | |

TABLE 1-continued
| Structure and Molecular Wt | Co-crystal | DSF ΔTm (° C.) | Estimated BRD4-1 IC50 (μM) | Comments |
|---|---|---|---|---|
| | | | 12.6 ± 0.1 | |
| | | | | |
Other examples of compounds disclosed herein include
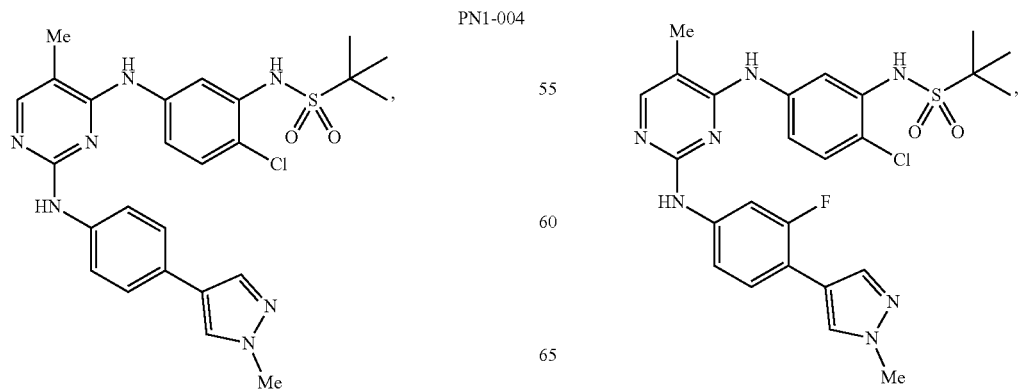

PN1-006
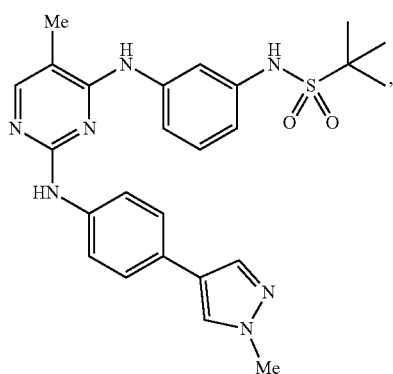
PN1-007
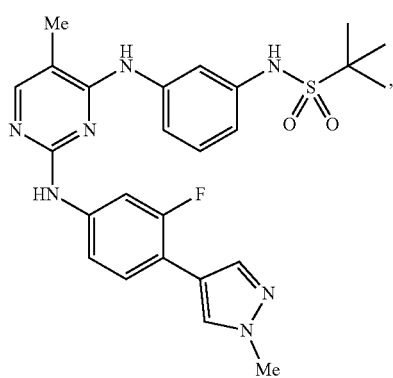
PN1-037
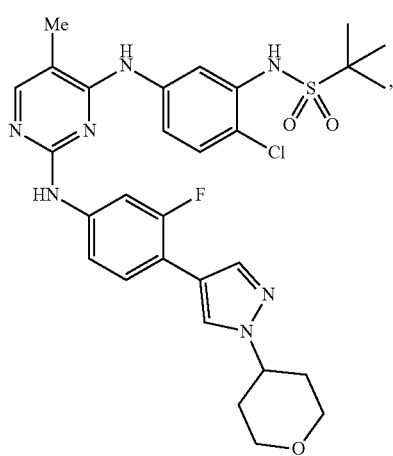
PN1-038
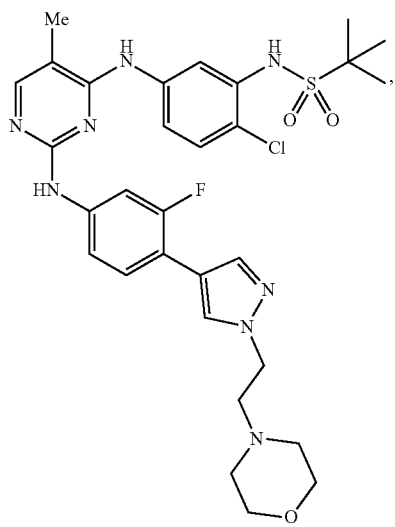
PN1-039
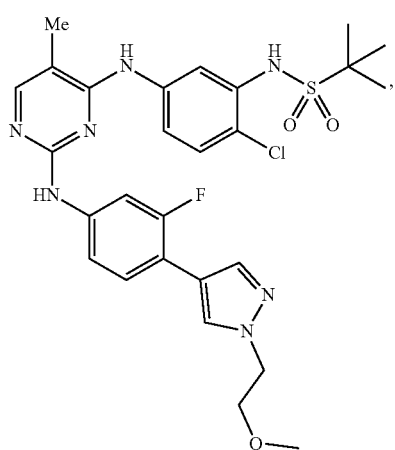
PN1-040
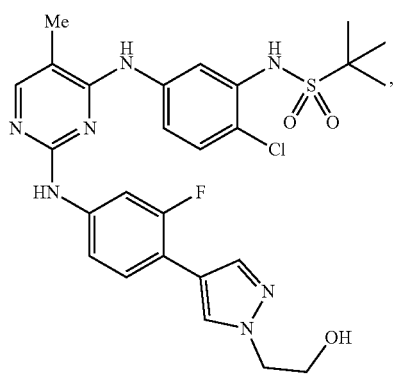

-continued
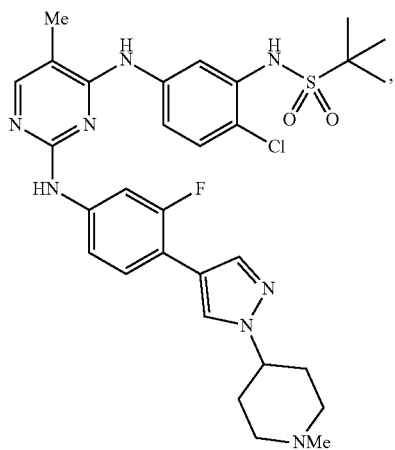
PN1-048
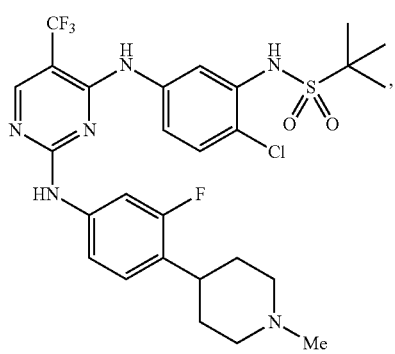
PN1-050
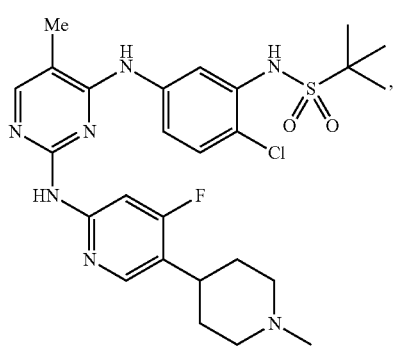
PN1-064
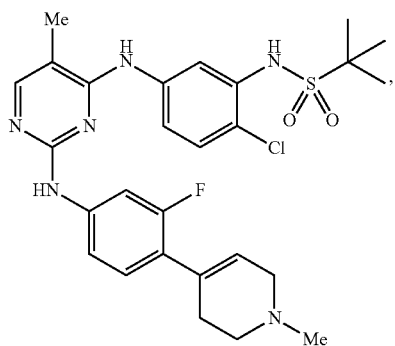
PN1-101
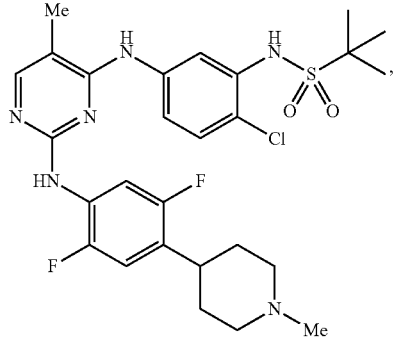
PN1-102
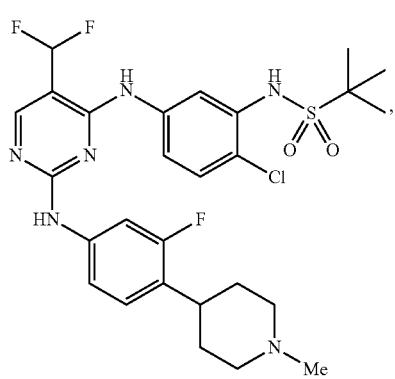
PN1-117
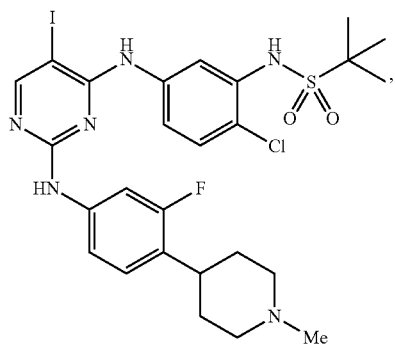
PN1-118
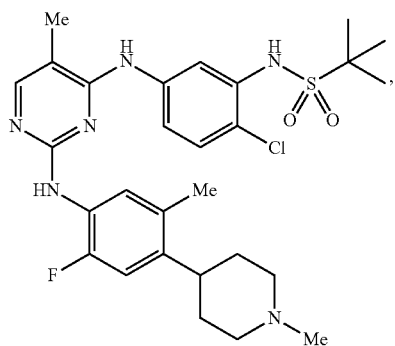
PN1-119

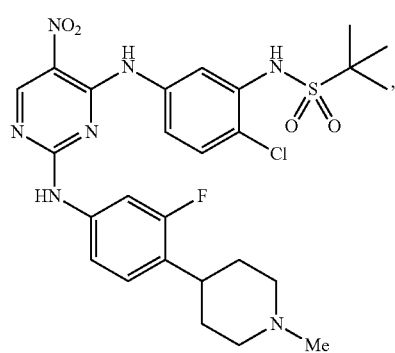
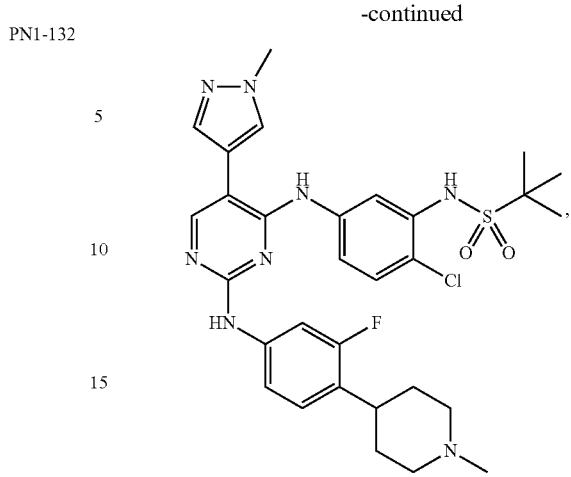

PN2-042
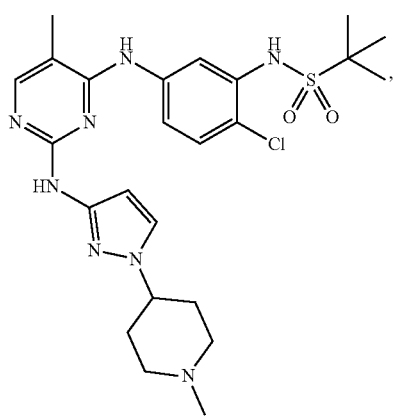
PN2-064
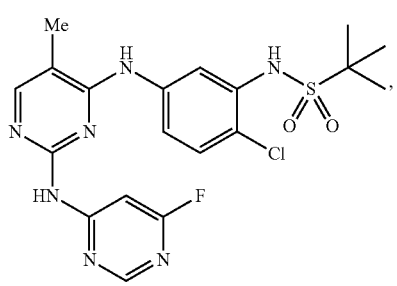
PN2-080
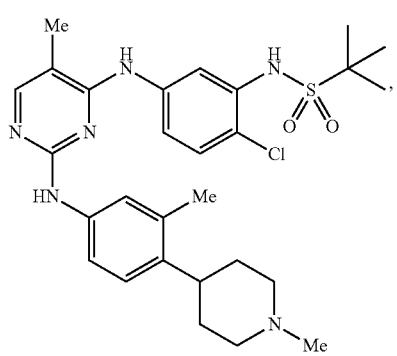
PN2-081
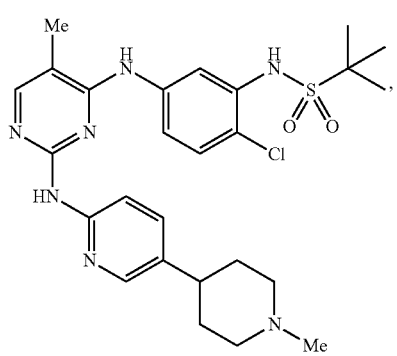
PN2-082
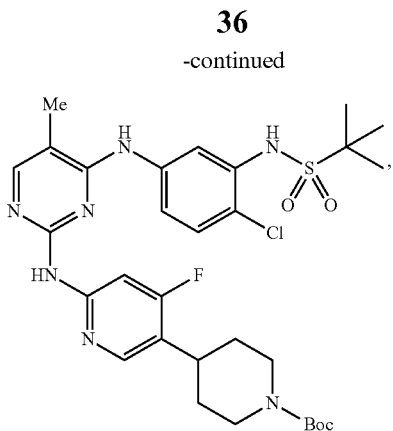
PN2-084
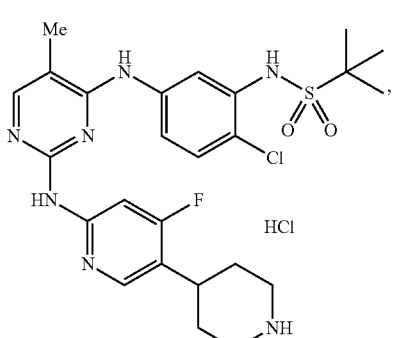
PN2-085
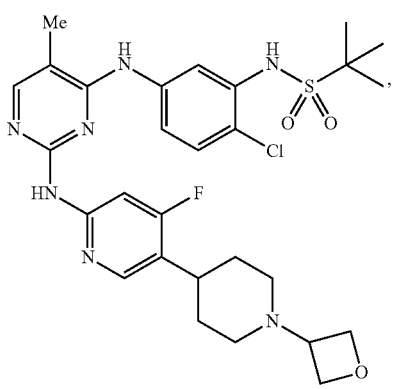
PN2-089
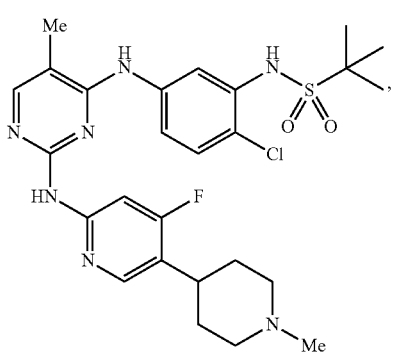

-continued

PN2-091

PN2-102

PN2-103

PN2-116

PN2-117

PN2-118

PN2-122

PN2-123

-continued
PN2-124
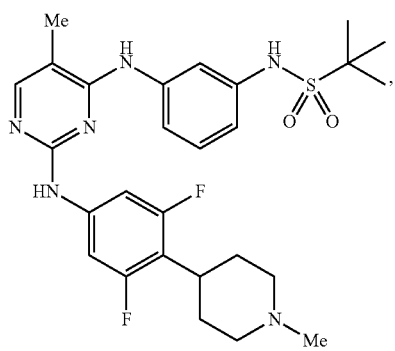
PN2-128
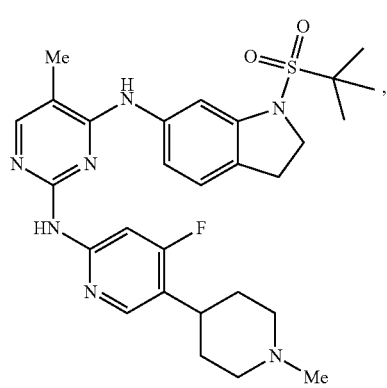
PN2-129
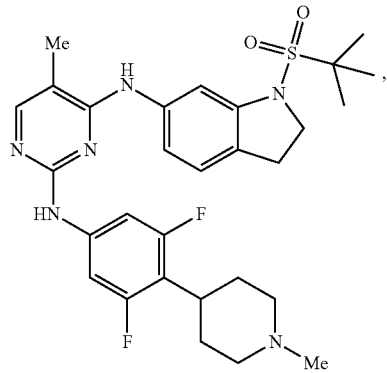
PN2-173
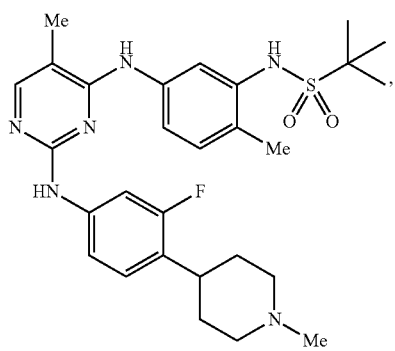
-continued
PN2-174
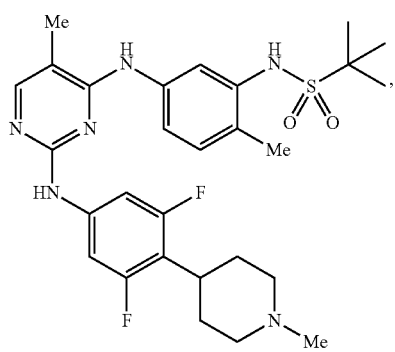
PN2-175
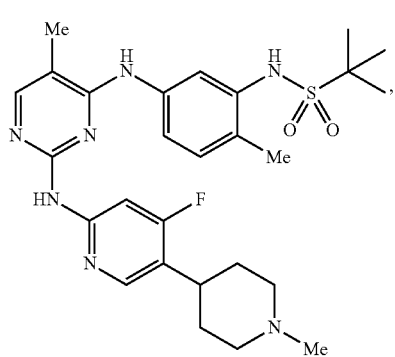
PN3-052
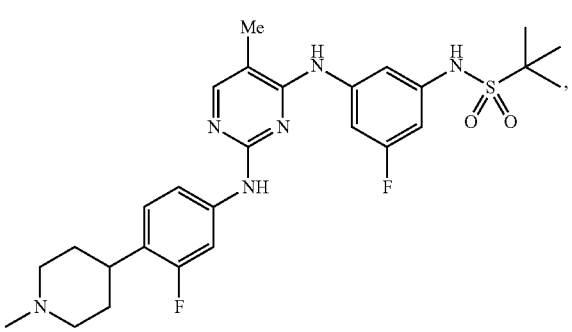
PN3-053
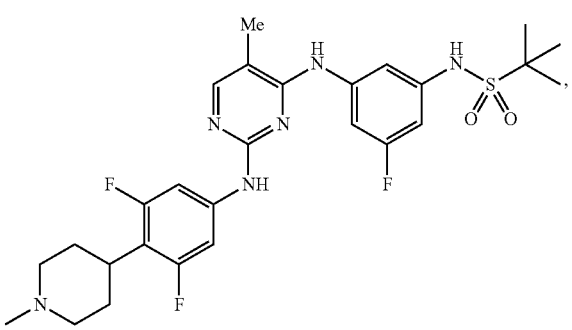

-continued
PN3-054
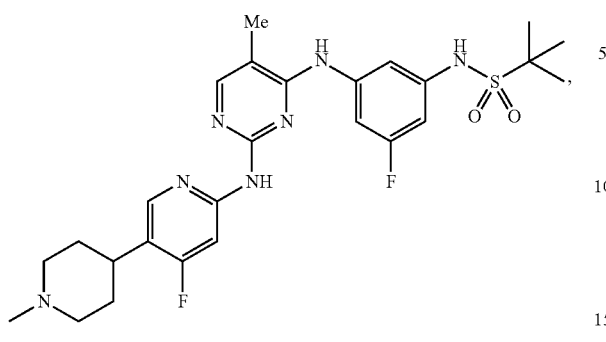
PN3-099
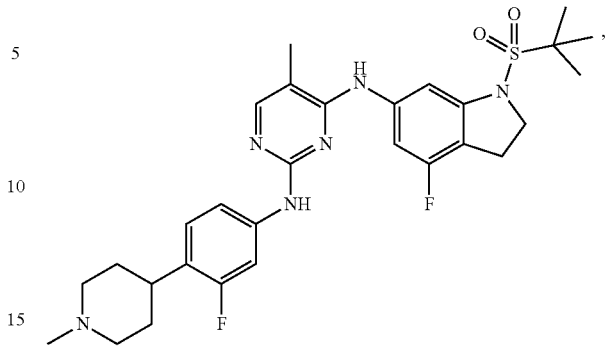
PN3-074
PN3-100
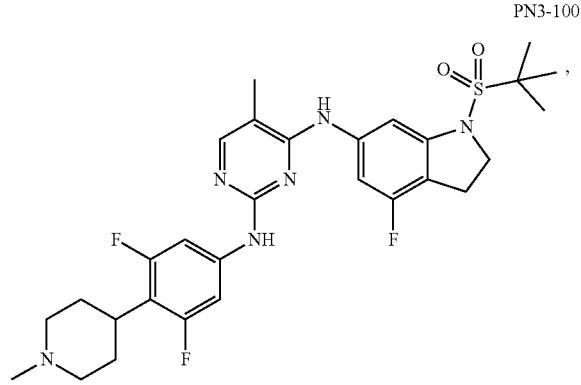
PN3-075
PN3-108
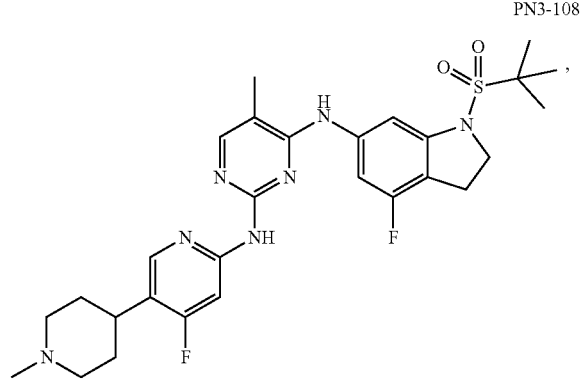
PN3-076
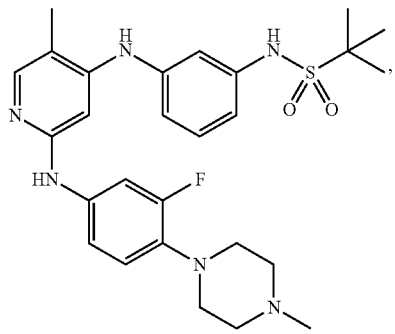

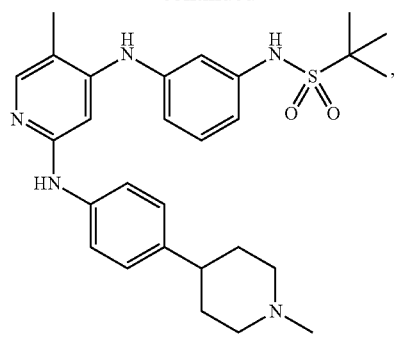
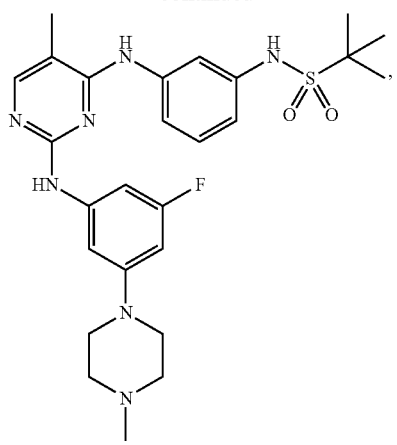
MA9-024
MA9-036

- MA9-037.bisformate
- MA9-042
- MA9-050
- MA9-060
- MA9-062
- MA9-064
- MA9-086
- MA9-168

MA9-169
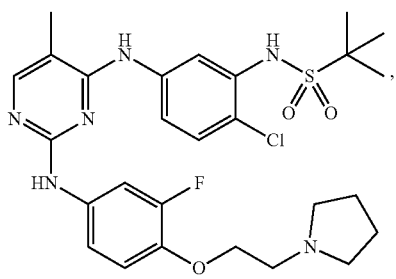
MA9-176
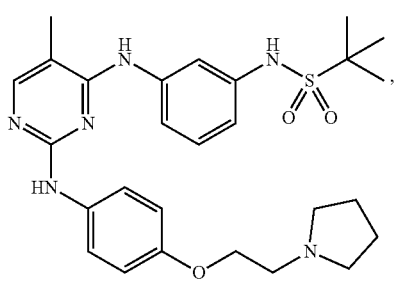
MA9-177
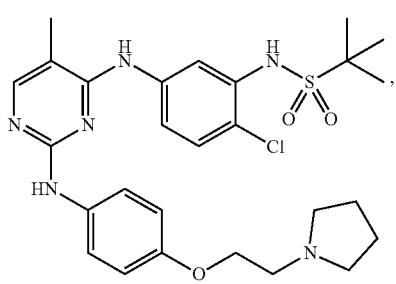
MA9-178
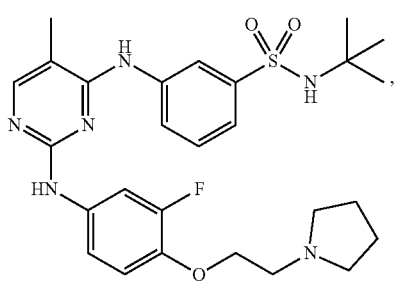
MA9-179
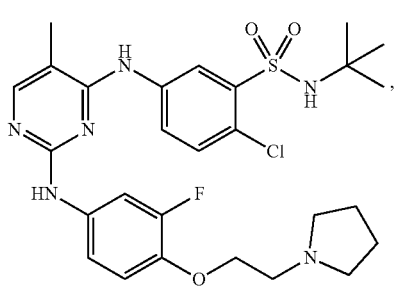
MA10-148
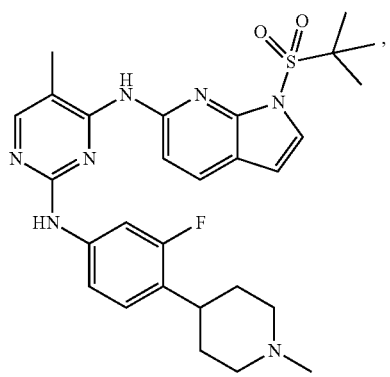
MA10-149
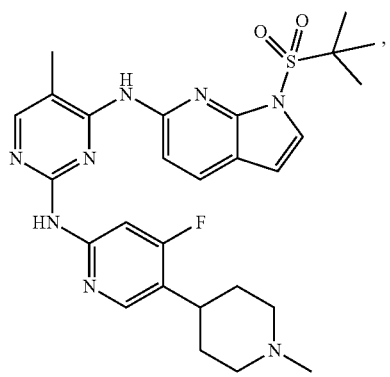
MA10-174
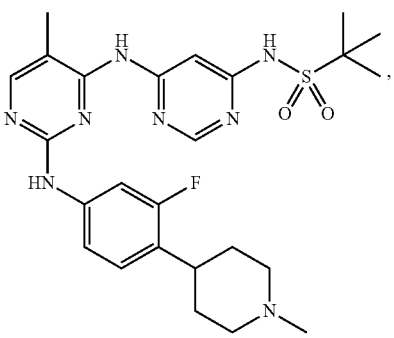
MA10-175
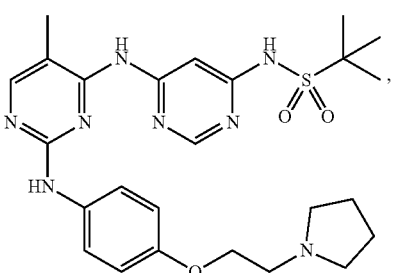
MA10-176
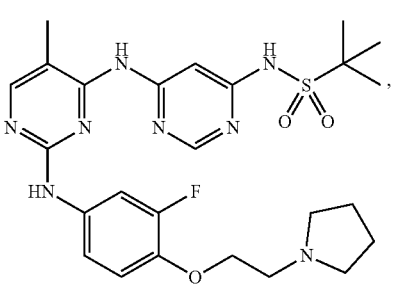

MA10-178
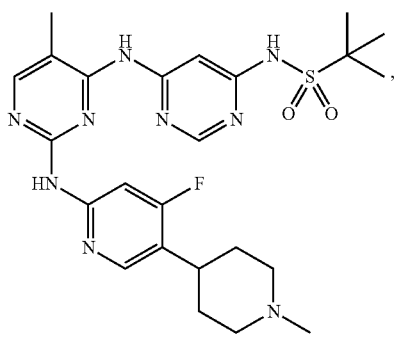
MA10-179
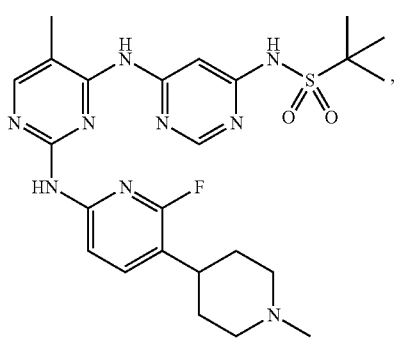
MA11-003
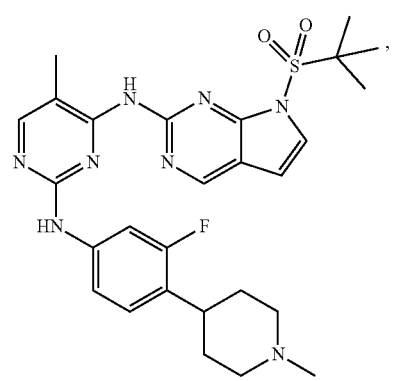
MA11-006
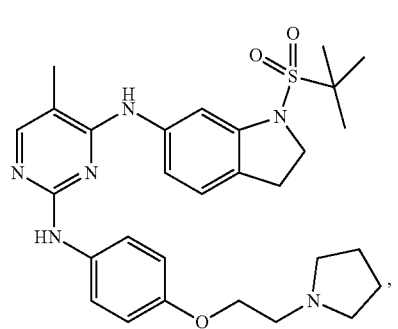
MA11-007
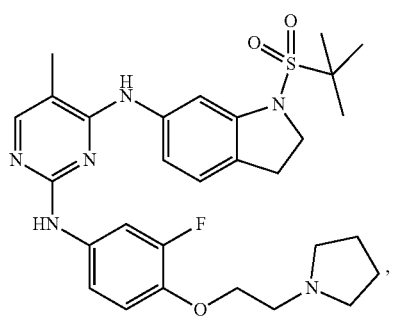
MA11-009
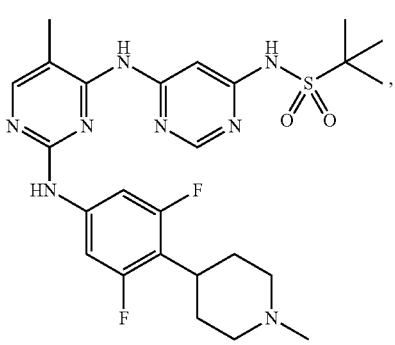
MA11-012
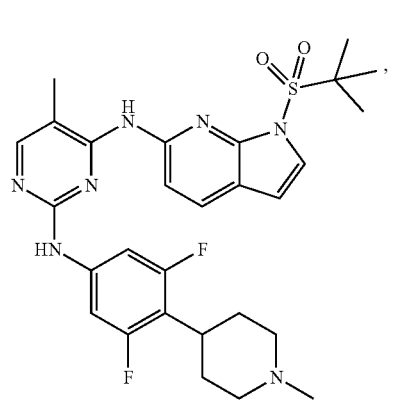
MA11-016
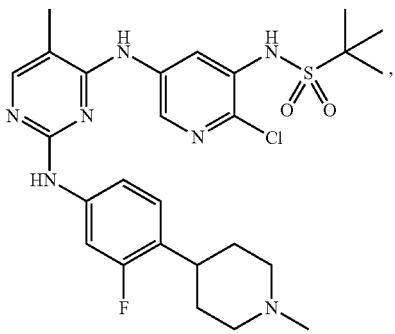

-continued

MA11-017
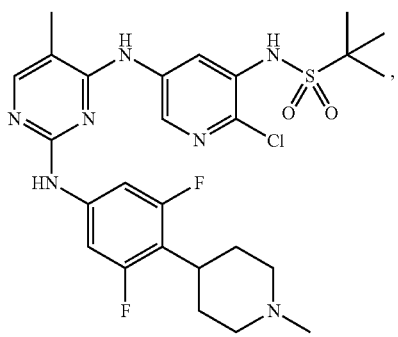

MA11-022
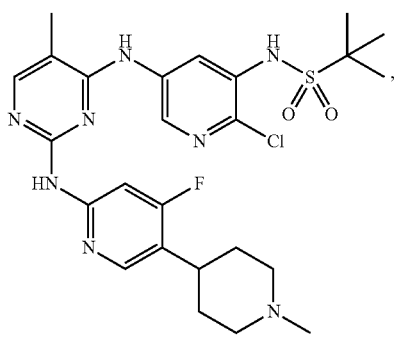

MA11-032
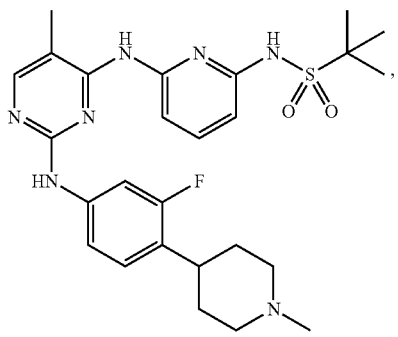

MA11-035
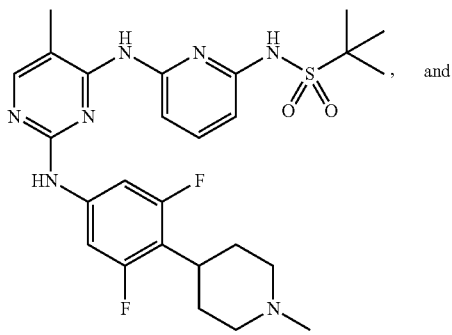, and

-continued

MA11-038
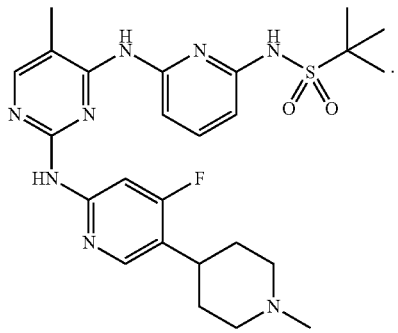

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy,* 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Method of Screening

Also disclosed herein are methods of identifying a putative anti-cancer compound comprising contacting BDR4 with a target compound and determining whether the compound binds the BDR4, wherein the compound that binds BDR4 is identified as a putative anti-cancer compound.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Cellular activity of promising compounds is assessed using MM.1S and MV4-11 AML cells using c-Myc levels as biomarker (6-12 hr treatment) and antiproliferative activity (48-72 hr treatment) as described (Ciceri et al., Dual kinase-bromodomain inhibitors for rationally designed polypharmacology. *Nat Chem Biol* 2014). The most potent BRD4 inhibitors are profiled against representative panels of kinases and BRDs to assess potency and specificity using commercial services.

Compounds could be prepared following a scheme as shown below. Further the disclosed compounds can be prepared as described in WO2017/066428, which is incorporated by reference herein in its entity for methods of synthesis.

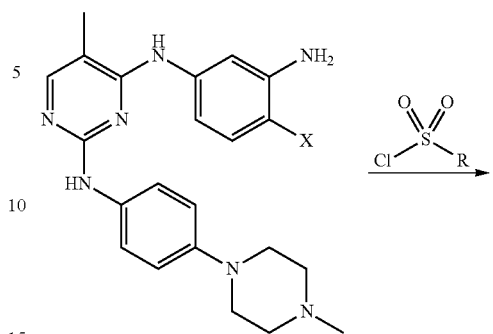

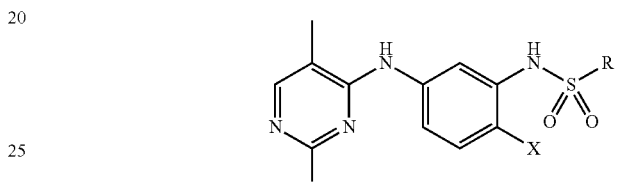

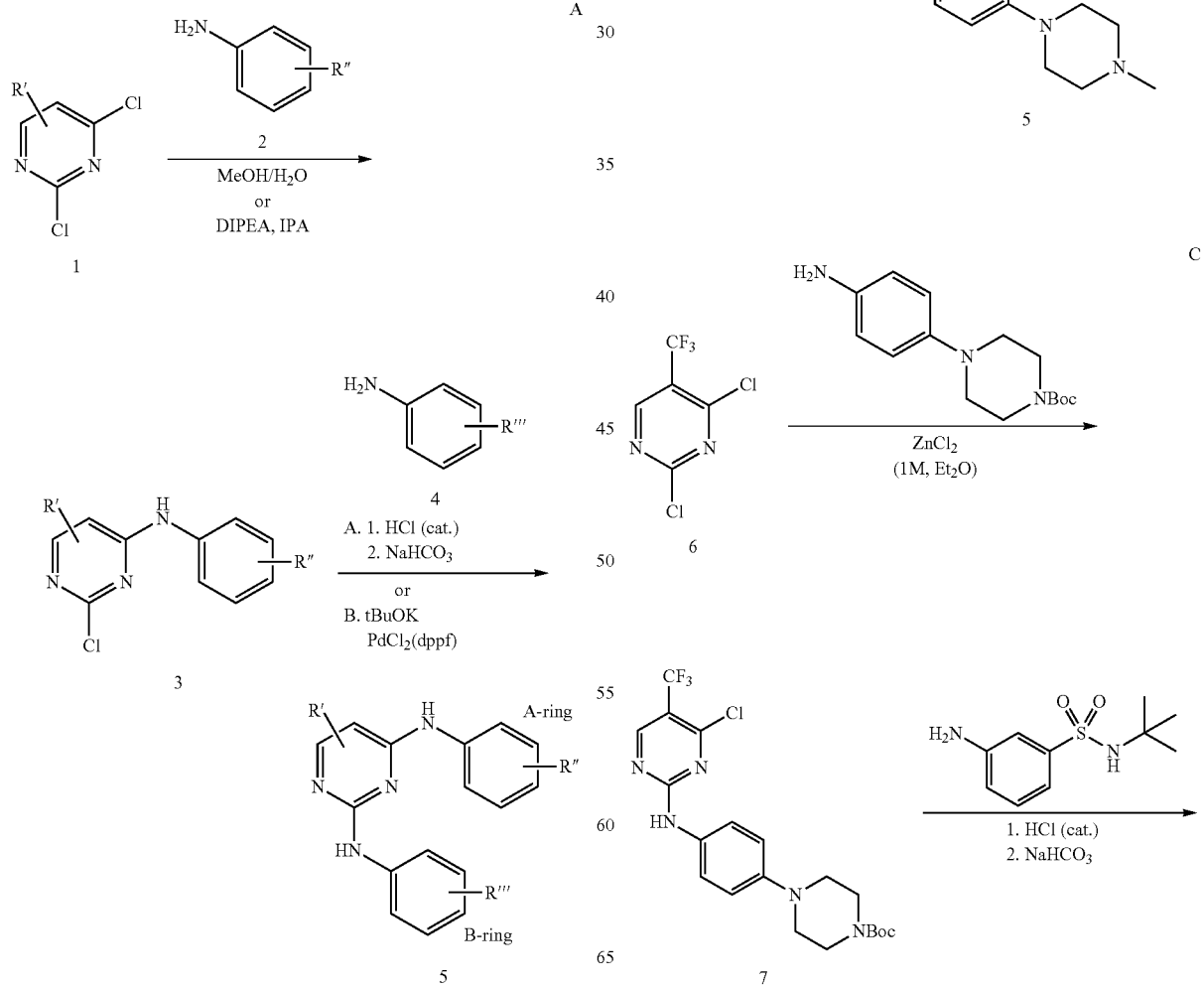

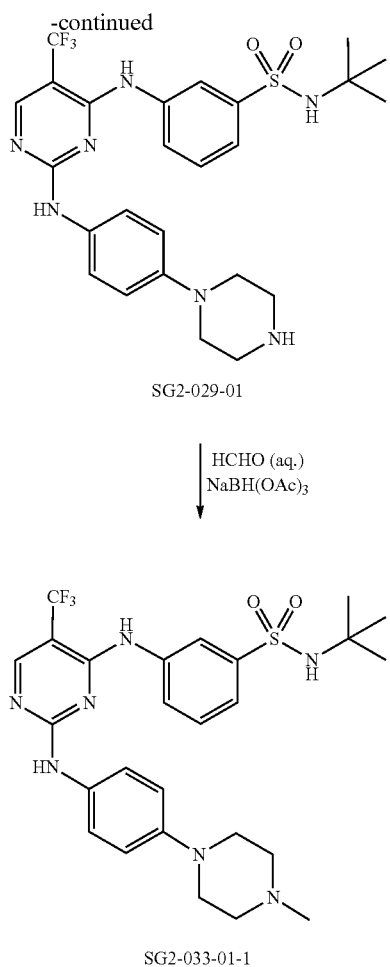

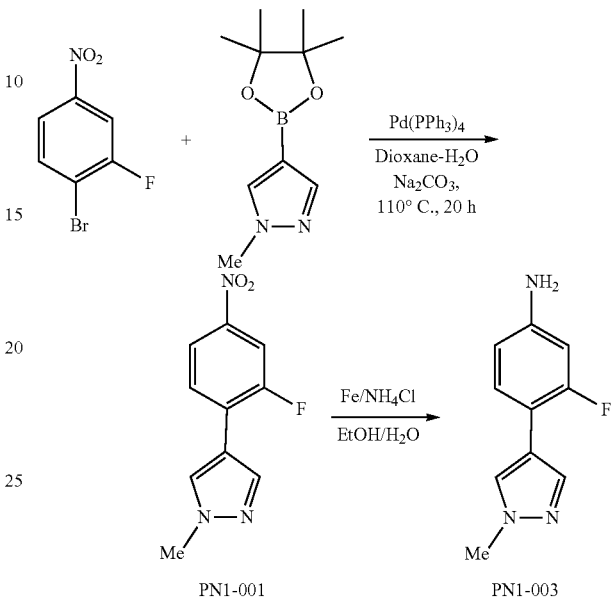

PN1-001                    PN1-003

Method x: A mixture of 4-anilino-pyrimidine intermediate 3 (50 mg, 1.0 equiv.), the corresponding aniline B-ring aniline (1.0 equiv.), 2 drops of 4 M HCl, and EtOH (1 mL) was heated in a microwave reactor at 160° C. for 15 minutes. The reaction mixture was diluted with EtOAc (20 mL) and washed with saturated NaHCO$_3$ (20 mL). The aqueous layer was then re-extracted with EtOAc (20 mL). The combined organic layers were dried over Na$_2$SO$_4$ and concentrated under reduced pressure. Unless otherwise mentioned, all products were purified via Column chromatography using DCM/MeOH (0-10%).

Experimental Procedures and Characterization Data for Precursors

General Procedure A: Suzuki Cross-Coupling Between Aryl Bromides and Boronic Esters Method 1: Dioxane (40 mL), H$_2$O (10 mL) and Na$_2$CO$_3$ (3.2 equiv.) were combined in a 250 mL round-bottomed flask equipped with a stir bar under argon atmosphere and then degassed using argon for about 15 min. Both 1-bromo-2-fluoro-4-nitrobenzene (1.0 equiv.) and boronic esters (1.4 equiv.) were then added to the round-bottomed flask under argon and degassed for another 15 min. Finally Pd(PPh$_3$)$_4$ catalyst (0.033 equiv.) was added and after degassing for 5 min, the reaction placed in pre-heated oil bath to 110° C. for 12 h with vigorous stirring. The reaction was cooled to room temperature, the mixture diluted with EtOAc (2×25 mL) and washed with water (100 mL) and brine (50 mL). The combined organic layers were dried (Na$_2$SO$_4$) and concentrated under vacuum in a rotary evaporator. The pure nitrobenzene intermediates were obtained by trituration using EtOAc and Hexanes.

Method 2: A mixture of aryl bromide (1.0 equiv.), boronic ester (1.1 equiv.), Cs$_2$CO$_3$ (3.0 equiv.), were dissolved in dioxane H$_2$O (4/1 v/v) (degassed for 10 minutes). Finally, Pd(dppf)$_2$Cl$_2$ (5 mol %) was added under argon and the mixture was heated at reflux for 2 h. After confirming the reaction completion (TLC, HPLC-MS), the mixture was partitioned between EtOAc (2×25 mL) and water (5 mL). The organic layer was washed with brine (~50 mL), dried (Na$_2$SO$_4$) and evaporated under reduced pressure. The residue was purified by chromatography to provide the nitrobenzene intermediates.

PN1-001

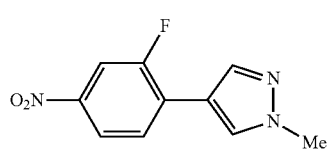

4-(2-Fluoro-4-nitrophenyl)-1-methyl-1H-pyrazole (PN1-001). This was prepared using procedure A (method 1) from 1-bromo-2-fluoro-4-nitrobenzene (2.0 g, 9.1 mmol, 1.0 equiv.), 1-methyl-4-(4,4,5,5-tetramethyl-1,3,2-dioxaborolan-2-yl)-1H-pyrazole (2.7 g, 12.8 mmol, 1.4 equiv.), Na$_2$CO$_3$ (3.0 g, 29.0 mmol, 3.2 equiv.) and Pd(PPh$_3$)$_4$ (350 mg, 0.3 mmol, 0.033 equiv.) in dioxane (40 mL) and H$_2$O (10 mL). The title nitroarene PN1-001 was isolated, after purification by trituration using EtOAc and hexanes, as a white solid (1.38 g, 69%). $^1$H NMR (500 MHz, CDCl$_3$) 8.05 (ddd, J=8.6, 2.3, 0.7 Hz, 1H), 8.00 (dd, J=10.8, 2.3 Hz, 1H), 7.93 (d, J=1.0 Hz, 1H), 7.93-7.88 (m, 1H), 7.70 (dd, J=8.7, 7.5 Hz, 1H), 3.99 (s, 3H).

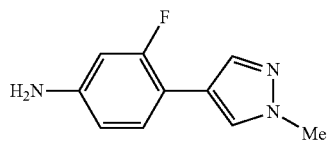

PN1-003

3-Fluoro-4-(1-methyl-1H-pyrazol-4-yl)aniline (PN1-003). This was prepared by reduction of PN1-001 (1.2 g, 5.42 mmol) with Pd/C (10%, 124 mg) in the presence of H$_2$ in MeOH (20 mL). The mixture was stirred at room temperature for 12 h. The mixture was filtered over celite and concentrated to provide the title aniline derivative PN1-003 (0.94 g, 91%) as a brown solid $^1$H NMR (500 MHz, DMSO-d$_6$) δ: 7.96-7.79 (m, 1H), 7.71 (dd, J=1.5, 0.8 Hz, 1H), 7.33 (dd, J=9.1, 8.1 Hz, 1H), 6.50-6.21 (m, 2H), 5.39 (s, 2H), 3.88 (s, 3H). $^{13}$C NMR (125 MHz, DMSO-d$_6$) δ: 159.96 (d, J=242.1 Hz), 149.32 (d, J=11.7 Hz), 136.55 (d, J=3.8 Hz), 128.49 (d, J=6.7 Hz), 128.10 (d, J=6.4 Hz), 116.80 (d, J=1.8 Hz), 110.89 (d, J=2.1 Hz), 107.57 (d, J=14.7 Hz), 100.96 (d, J=25.0 Hz). $^{19}$F NMR (479 MHz, DMSO-d$_6$) δ: −115.67 (dd, J=13.4, 9.2 Hz). HPLC-MS (ESI+): m/z 192.1 [100%, (M+H)$^+$].

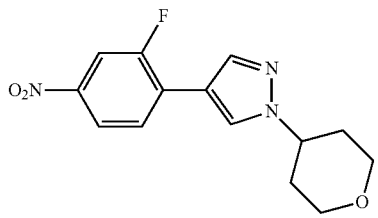

PN1-027

4-(2-Fluoro-4-nitrophenyl)-1-(tetrahydro-2H-pyran-4-yl)-1H-pyrazole (PN1-027). This was prepared using procedure A (method 1) from 1-bromo-2-fluoro-4-nitrobenzene (1.54 g, 7.0 mmol, 1.0 equiv.), 1-(tetrahydro-2H-pyran-4-yl)-4-(4,4,5,5-tetramethyl-1,3,2-dioxaborolan-2-yl)-1H-pyrazole (2.73 g, 9.8 mmol, 1.4 equiv.), Na$_2$CO$_3$ (2.4 g, 22.5 mmol, 3.2 equiv.) and Pd(PPh$_3$)$_4$ (266 mg, 0.231 mmol, 0.033 equiv.) in dioxane (30 mL) and H$_2$O (9 mL). The title nitroarene PN1-027 was isolated, after purification by trituration using EtOAc and hexanes, as a brown solid (1.79 g, 89%). $^1$H NMR (500 MHz, CDCl$_3$) δ: 8.09-8.03 (m, 1H), 8.00 (dd, J=10.8, 2.3 Hz, 1H), 7.96 (d, J=2.3 Hz, 2H), 7.71 (dd, J=8.6, 7.4 Hz, 1H), 4.53-4.35 (m, 1H), 4.17-4.05 (m, 2H), 3.65-3.50 (m, 2H), 2.41-1.96 (m, 4H). $^{19}$F NMR (479 MHz, DMSO-d$_6$) δ: −119.26 (s).

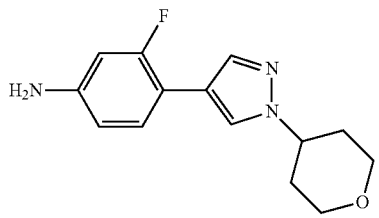

PN1-029

3-Fluoro-4-(1-(tetrahydro-2H-pyran-4-yl)-1H-pyrazol-4-yl)aniline (PN1-029). This was prepared by reduction of PN1-027 (290 mg, 1.0 mmol) with Fe (170 mg, 3.0 mmol, 3.0 equiv.) and NH$_4$Cl (270 mg, 5.0 mmol, 5.0 equiv.) in EtOH (3 mL)/H$_2$O (2 mL) at 80° C. for 12 h. The reaction mixture was then filtered through the celite and washed twice with EtOAc (2×25 mL). The solution was washed with water and organic layer was dried (Na$_2$SO$_4$) and evaporated to dryness to afford the title compound PN1-029 after work-up as a brown powder (0.22 g, 85%). $^1$H NMR (500 MHz, CDCl$_3$) δ: 7.77 (t, J=1.0 Hz, 1H), 7.71 (dd, J=2.3, 0.7 Hz, 1H), 7.30 (t, J=8.4 Hz, 1H), 6.55-6.40 (m, 2H), 4.45-4.30 (m, 1H), 4.23-4.03 (m, 2H), 3.75 (s, 2H), 3.65-3.49 (m, 2H), 2.17-2.08 (m, 4H). $^{13}$C NMR (125 MHz, CDCl$_3$) δ:160.04 (d, J=245.4 Hz), 146.33 (d, J=11.2 Hz), 136.73 (d, J=2.8 Hz), 128.24 (d, J=6.3 Hz), 124.49 (d, J=7.8 Hz), 116.48 (d, J=1.9 Hz), 111.20 (d, J=2.6 Hz), 110.49 (d, J=14.7 Hz), 102.58 (d, J=25.6 Hz), 66.90, 58.24, 33.37. $^{19}$F NMR (479 MHz, CDCl$_3$) δ: −114.68.

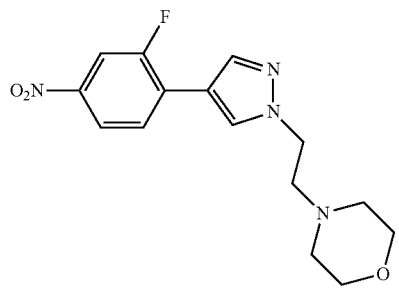

PN1-028

4-(2-(4-(2-Fluoro-4-nitrophenyl)-1H-pyrazol-1-yl)ethyl)morpholine (PN1-028). This was prepared using procedure A (method 1) from 1-bromo-2-fluoro-4-nitrobenzene (1.54 g, 7.0 mmol, 1.0 equiv.), 4-(2-(4-(4,4,5,5-tetramethyl-1,3,2-dioxaborolan-2-yl)-1H-pyrazol-1-yl)ethyl)morpholine (3.0 g, 9.8 mmol, 1.4 equiv.), Na$_2$CO$_3$ (2.4 g, 22.5 mmol, 3.2 equiv.) and Pd(PPh$_3$)$_4$ (266 mg, 0.231 mmol, 0.033 equiv.) in dioxane (30 mL) and H$_2$O (9 mL). The title nitroarene PN1-028 was isolated after chromatography using (EtOAc/hexanes) as a light brown powder (1.86 g, 83%). $^1$H NMR (500 MHz, CDCl$_3$) δ: 8.06-8.01 (m, 2H), 7.98 (dd, J=10.8, 2.3 Hz, 1H), 7.93 (d, J=0.9 Hz, 1H), 4.29 (t, J=6.4 Hz, 2H), 3.94-3.43 (m, 4H), 2.84 (t, J=6.5 Hz, 2H), 2.58-2.34 (m, 4H).

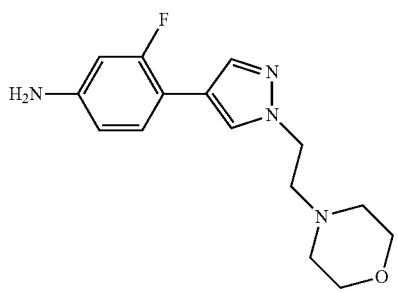

PN1-032

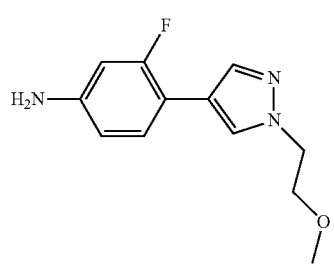

PN1-034

3-Fluoro-4-(1-(2-morpholinoethyl)-1H-pyrazol-4-yl)aniline (PN1-032). This was prepared by reduction of PN1-028 (320 mg, 1.0 mmol) with Fe (170 mg, 3.0 mmol, 3.0 equiv.) and NH$_4$Cl (270 mg, 5.0 mmol, 5.0 equiv.) in EtOH (3 mL)/H$_2$O (2 mL) at 80° C. for 12 h. The reaction mixture was then filtered through the celite and washed twice with EtOAc (2×25 mL). Then the solution was washed with water and organic layer was dried (Na$_2$SO$_4$) and evaporated to dryness to afford the title compound PN1-032 after work-up as a brown powder (0.23 g, 79%). $^1$H NMR (500 MHz, CDCl$_3$) δ: 7.76-7.70 (m, 2H), 7.29 (t, J=8.4 Hz, 1H), 6.60-6.42 (m, 2H), 4.25 (t, J=6.7 Hz, 2H), 3.75 (s, 2H), 3.87-3.49 (m, 4H), 2.83 (t, J=6.7 Hz, 2H), 2.59-2.39 (m, 4H). $^{13}$C NMR (125 MHz, CDCl$_3$) δ: 160.04 (d, J$^1$=245.3 Hz), 146.32 (d, J=11.1 Hz), 137.01 (d, J=2.7 Hz), 128.22 (d, J=6.3 Hz), 127.60 (d, J=7.8 Hz), 116.63 (d, J=2.1 Hz), 111.18 (d, J=2.6 Hz), 110.49 (d, J=14.7 Hz), 102.58 (d, J=25.8 Hz), 66.92, 58.23, 53.68, 49.74. $^{19}$F NMR (479 MHz, CDCl$_3$) δ: −114.61. HRMS (ESI+): m/z calcd for C$_{15}$H$_{20}$FN$_4$O (M+H)$^+$ 291.1621, found 291.1616.

3-Fluoro-4-(1-(2-methoxyethyl)-1H-pyrazol-4-yl)aniline (PN1-034). This was prepared by reduction of PN1-031 (265 mg, 1.0 mmol) with Fe (170 mg, 3.0 mmol, 3.0 equiv.) and NH$_4$Cl (270 mg, 5.0 mmol, 5.0 equiv.) in EtOH (3 mL)/H$_2$O (3 mL) at 80° C. for 12 h. The reaction mixture was then filtered through the celite and washed twice with EtOAc (2×25 mL). The solution was washed with water and organic layer was dried (Na$_2$SO$_4$) and evaporated to dryness to afford the title compound PN1-034 after work-up as a brown powder (0.22 g, 93%). $^1$H NMR (500 MHz, CDCl$_3$) δ: 7.87-7.70 (m, 2H), 7.49-7.27 (m, 1H), 6.63-6.34 (m, 2H), 4.30 (t, J=5.3 Hz, 2H), 3.85-3.70 (m, 2H), 3.76-3.67 (m, 2H), 3.34 (s, 3H). $^{13}$C NMR (125 MHz, CDCl$_3$) δ: 160.05 (d, J=245.6 Hz), 146.25 (d, J=11.0 Hz), 137.24 (d, J=3.2 Hz), 128.26 (d, J=6.4 Hz), 127.93 (d, J=7.4 Hz), 116.68 (d, J=1.9 Hz), 111.17 (d, J=2.6 Hz), 110.59 (d, J=14.6 Hz), 102.59 (d, J=25.9 Hz), 71.25, 59.03, 52.22. $^{19}$F NMR (479 MHz, CDCl$_3$) δ: −114.51. HRMS (ESI+): m/z calcd for C$_{12}$H$_{14}$FN$_3$O (M+H)$^+$ 236.1199, found 236.1194.

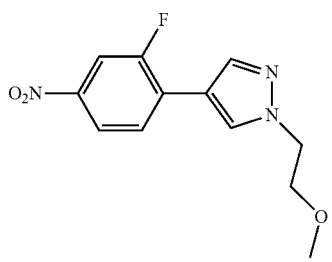

PN1-031

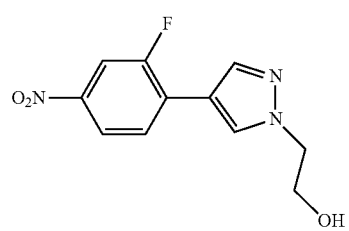

PN1-033

4-(2-Fluoro-4-nitrophenyl)-1-(2-methoxyethyl)-1H-pyrazole (PN1-031). This was prepared using procedure A (method 1) from 1-bromo-2-fluoro-4-nitrobenzene (616 mg, 2.8 mmol, 1.0 equiv.), 1-(2-methoxyethyl)-4-(4,4,5,5-tetramethyl-[1,3,2]dioxaborolan-2-yl)-1H-pyrazole (1.0 g, 4.0 mmol, 1.4 equiv.), Na$_2$CO$_3$ (954 mg, 22.5 mmol, 3.2 equiv.) and Pd(PPh$_3$)$_4$ (110 mg, 0.093 mmol, 0.033 equiv.) in dioxane (15 mL) and H$_2$O (5 mL). The title nitroarene PN1-031 was isolated after purification by trituration using EtOAc and hexanes as yellow powder (0.47 g, 72%). $^1$H NMR (500 MHz, CDCl$_3$) δ: 8.06 (ddd, J=8.7, 2.3, 0.7 Hz, 1H), 8.05-7.99 (m, 2H), 7.99 (t, J=1.0 Hz, 1H), 7.73 (dd, J=8.6, 7.4 Hz, 1H), 4.42-4.32 (m, 2H), 3.82 (dd, J=5.5, 4.7 Hz, 2H), 3.38 (s, 3H).

2-(4-(2-Fluoro-4-nitrophenyl)-1H-pyrazol-1-yl)ethan-1-ol (PN1-033). This was prepared using procedure A (method 1) from 1-bromo-2-fluoro-4-nitrobenzene (1.54 g, 7.0 mmol, 1.0 equiv.), 2-[4-(4,4,5,5-tetramethyl-1,3,2-dioxaborolan-2-yl)-1H-pyrazol-1-yl]ethanol (2.33 g, 9.8 mmol, 1.4 equiv.), Na$_2$CO$_3$ (2.4 g, 22.5 mmol, 3.2 equiv.) and Pd(PPh$_3$)$_4$ (110 mg, 0.231 mmol, 0.033 equiv.) in dioxane (30 mL) and H$_2$O (9 mL). The title nitroarene PN1-033 was isolated after purification by trituration using EtOAc and hexanes as light brown powder (1.39 g, 79%). $^1$H NMR (500 MHz, CDCl$_3$) δ: 8.05 (ddd, J=8.5, 2.3, 0.7 Hz, 1H), 8.04-7.95 (m, 3H), 7.70 (dd, J=8.6, 7.4 Hz, 1H), 4.38-4.23 (m, 2H), 4.17-3.99 (m, 2H), 2.79 (t, J=5.8 Hz, 1H).

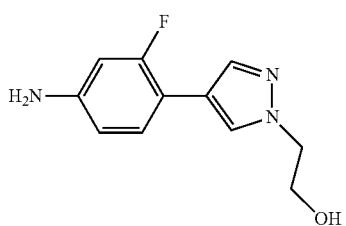

PN1-035

2-(4-(4-Amino-2-fluorophenyl)-1H-pyrazol-1-yl)ethan-1-ol (PN1-035). This was prepared by reduction of PN1-033 (380 mg, 1.5 mmol) with Fe (252 mg, 4.5 mmol, 3.0 equiv.) and NH$_4$Cl (405 mg, 5.0 mmol, 5.0 equiv.) in EtOH (4 mL)/H$_2$O (3 mL) at 80° C. for 12 h. The reaction mixture was then filtered through the celite and washed twice with EtOAc (2×25 mL). The solution was washed with water and organic layer was dried (Na$_2$SO$_4$) and evaporated to dryness to afforded the title compound PN1-035 after work-up as a brown powder (0.2 g, 61%). $^1$H NMR (500 MHz, DMSO-d$_6$) δ: 7.87 (d, J=2.2 Hz, 1H), 7.68 (d, J=1.4 Hz, 1H), 7.29 (t, J=8.7 Hz, 1H), 6.48-6.26 (m, 2H), 5.35 (s, 2H), 4.89 (t, J=5.3 Hz, 1H), 4.14 (t, J=5.6 Hz, 2H), 3.73 (q, J=5.6 Hz, 2H). $^{13}$C NMR (125 MHz, DMSO-d$_6$) δ: 159.95 (d, J=242.0 Hz), 149.27 (d, J=11.6 Hz), 136.57 (d, J=3.8 Hz), 128.17 (dd, J=72.0, 6.6 Hz), 116.43, 110.89 (d, J=2.1 Hz), 107.62 (d, J=14.6 Hz), 100.95 (d, J=25.0 Hz), 60.58, 54.49. $^{19}$F NMR (479 MHz, DMSO-d$_6$) δ: −115.68. HRMS (ESI+): m/z calcd for C$_{11}$H$_{12}$FN$_3$O (M+H)$^+$ 222.1043, found 222.1038.

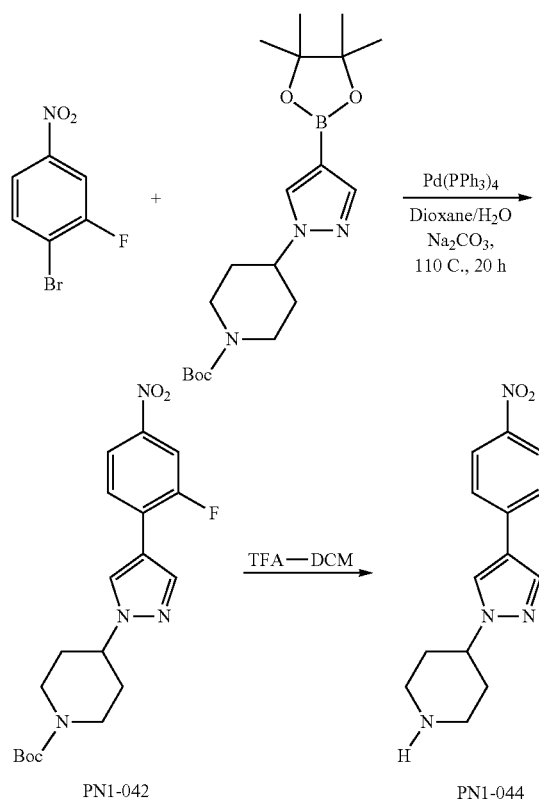

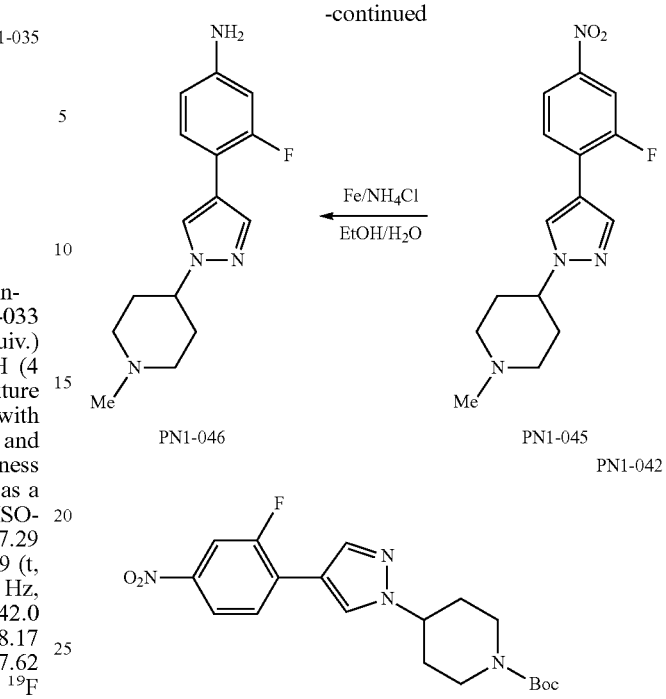

tert-Butyl 4-(4-(2-fluoro-4-nitrophenyl)-1H-pyrazol-1-yl)piperidine-1-carboxylate (PN1-042). According to the general procedure A (method 1), the reaction of 1-bromo-2-fluoro-4-nitrobenzene (2.0 g, 9.1 mmol, 1.0 equiv.), 2-[4-(4,4,5,5-tetramethyl-1,3,2-dioxaborolan-2-yl)-1H-pyrazol-1-yl]ethanol (4.8 g, 12.75 mmol, 1.4 equiv.), Na$_2$CO$_3$ (3.0 g, 29.1 mmol, 3.2 equiv.) and Pd(PPh$_3$)$_4$ (350 mg, 0.3 mmol, 0.033 equiv.) in dioxane (40 mL) and H$_2$O (10 mL) afforded the nitrobenzene intermediate PN1-042 (2.9 g, 81%) after purification by trituration using EtOAc and hexanes. $^1$H NMR (500 MHz, DMSO-d$_6$) δ: 8.49 (dd, J=2.1, 0.8 Hz, 1H), 8.18 (dd, J=11.1, 2.3 Hz, 1H), 8.13-8.07 (m, 2H), 8.04 (dd, J=8.7, 7.6 Hz, 1H), 4.47 (ddt, J=11.5, 8.0, 4.0 Hz, 1H), 4.18-3.89 (m, 2H), 2.93 (s, 2H), 2.32-2.00 (m, 2H), 1.92-1.71 (m, 2H), 1.43 (s, 9H).

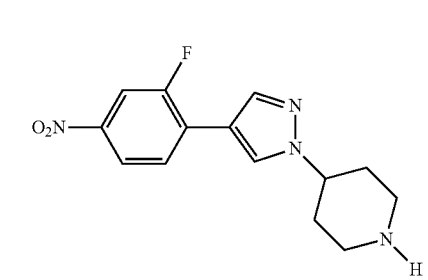

4-(4-(2-Fluoro-4-nitrophenyl)-1H-pyrazol-1-yl)piperidine (PN1-044). To PN1-042 (975 g, 2.5 mmol) in DCM (5 mL) was added TFA (5 mL, 58 mmol) under an argon atmosphere and the reaction mixture was stirred at room temperature. After consumption of the starting material (2 h), the solvents were removed in vacuo and the residue was dissolved with DCM (10 mL). The mixture was cooled to 0° C. and neutralized with sat aq NaHCO$_3$. The resulting heterogeneous mixture was allowed to warm to room temperature and stir for 1 h. The mixture was separated and the aqueous phase washed thoroughly with DCM (10×2 mL).

The combined organic layers were dried ($Na_2SO_4$) and evaporated to provide pure PN1-044 (0.66 g, 89%). $^1$H NMR (500 MHz, DMSO-$d_6$) δ: 8.43 (d, J=1.9 Hz, 1H), 8.17 (dd, J=11.2, 2.3 Hz, 1H), 8.13-8.06 (m, 2H), 8.04 (dd, J=8.6, 7.6 Hz, 1H), 4.30 (tt, J=11.6, 4.1 Hz, 1H), 3.05 (dt, J=13.8, 3.6 Hz, 2H), 2.60 (td, J=12.4, 2.5 Hz, 2H), 2.19 (bs, 1H), 1.98 (ddd, J=11.7, 4.6, 2.1 Hz, 2H), 1.83 (qd, J=12.1, 4.1 Hz, 2H).

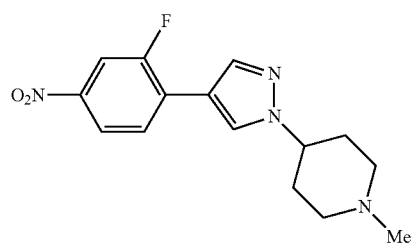

PN1-045

4-(4-(2-Fluoro-4-nitrophenyl)-1H-pyrazol-1-yl)-1-methylpiperidine (PN1-045). Oven dried 250 mL round bottom flask was charged with PN1-044 (720 mg, 2.5 mmo, 1.0 equiv.) in MeOH (125 mL) under argon. Formaldehyde (1.9 mL of 37% aq. solution, 25 mmol, 10 equiv.) was then added slowly and the mixture stirred at room temperature. After 2 h at room temperature, NaBH(OMe)$_3$ (1.0 mg, 5.0 mmol, 2.0 equiv.) was added at 0° C. and stirred at room temperature. After consumption of starting material (6 h) the reaction mixture was quenched with water (5 mL) and extracted with EtOAc (2×10 mL). The combined organic layers were dried over ($Na_2SO_4$) and evaporated. The residue was purified by trituration using EtOAc/hexanes to provide pure of PN1-045 (0.3 g, 40%). $^1$H NMR (500 MHz, DMSO-$d_6$) δ: 8.49 (m, 1H), 8.26-8.14 (m, 2H), 8.12 (dd, J=8.8, 2.4 Hz, 1H), 8.07 (dd, J=8.6, 7.4 Hz, 1H), 4.56 (m, 1H), 3.48 (m, 2H), 3.11 (m, 2H), 2.76 (s, 3H), 2.37-2.19 (m, 4H).

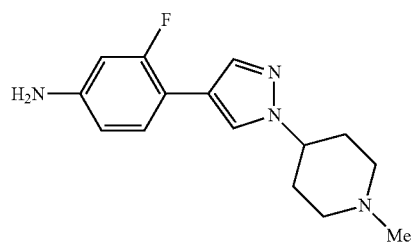

PN1-046

3-Fluoro-4-(1-(1-methylpiperidin-4-yl)-1H-pyrazol-4-yl) aniline (PN1-046). According to the general procedure B, the reaction of PN1-045 (304 mg, 1.0 mmol, 1.0 equiv.) with Fe (170 mg, 3.0 mmol, 3.0 equiv.) and NH$_4$Cl (270 mg, 5.0 mmol, 5.0 equiv.) in EtOH/H$_2$O afforded the title compound PN1-046 after work-up. (0.24 g, 88%). $^1$H NMR (500 MHz, DMSO-$d_6$) δ: 7.92 (d, J=1.7 Hz, 1H), 7.68 (d, J=1.5 Hz, 1H), 7.29 (t, J=8.7 Hz, 1H), 6.62-6.28 (m, 2H), 5.34 (s, 3H), 4.10 (p, J=7.5 Hz, 1H), 3.02-2.72 (m, 2H), 2.19 (s, 3H), 2.07-1.81 (m, 6H). $^{13}$C NMR (125 MHz, DMSO-$d_6$) δ: 159.98 (d, J=242.1 Hz), 149.29 (d, J=11.5 Hz), 136.33 (d, J=4.5 Hz), 128.57 (d, J=6.6 Hz), 125.25 (d, J=5.6 Hz), 116.41 (d, J=1.8 Hz), 110.88 (d, J=2.1 Hz), 107.66 (d, J=14.5 Hz), 100.95 (d, J=25.0 Hz), 58.54, 54.64, 46.24, 32.52. $^{19}$F NMR (479 MHz, DMSO-$d_6$) δ: −115.65 (dd, J=13.5, 9.3 Hz). HPLC-MS (ESI+): m/z 275.2 [100%, (M+H)$^+$]. HRMS (ESI+): m/z calcd for $C_{15}H_{19}FN_4$ (M+H)$^+$ 274.1598, found 274.1574.

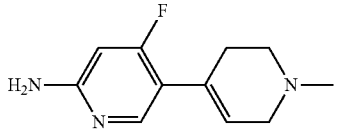

PN1-054

4-Fluoro-1'-methyl-1',2',3',6'-tetrahydro-[3,4'-bipyridin]-6-amine (PN1-094). This was prepared using procedure A (method 2) from 4-fluoro-5-bromo-2-aminopyridine (4.0 g, 21.0 mmol, 1.0 equiv.), 1-methyl-4-(4,4,5,5-tetramethyl-1,3,2-dioxaborolan-2-yl)-1,2,3,6-tetrahydropyridine (6.7 g, 30.0 mmol, 1.4 equiv.), Cs$_2$CO$_3$ (17.0 g, 7.0 mmol, 2.5 equiv.) and Pd(dppf)$_2$Cl$_2$ (506 mg, 0.693 mmol, 0.033 equiv.) in dioxane (100 mL) and H$_2$O (30 mL). The title nitroarene PN1-054 was isolated after chromatography using (DCM/MeOH) as a brown powder (2.6 g, 60%). $^1$H NMR (500 MHz, DMSO-$d_6$) δ: 7.87 (d, J=11.7 Hz, 1H), 6.20 (s, 2H), 6.17 (d, J=13.9 Hz, 1H), 5.82 (dq, J=3.4, 1.7 Hz, 1H), 2.96 (q, J=2.9 Hz, 2H), 2.63-2.44 (m, 3H), 2.44-2.32 (m, 2H), 2.25 (s, 3H). HPLC-MS (ESI+): m/z 208.2 [100%, (M+H)$^+$].

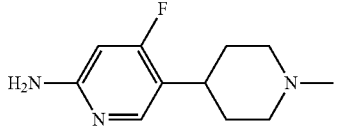

PN1-055

4-Fluoro-5-(1-methylpiperidin-4-yl)pyridin-2-amine (PN1-055). A 250-mL, two-necked, round bottom flask with a magnetic stirring bar was charged with 10% palladium on carbon (260 mg) and the reaction flask flushed with nitrogen for 5 min. MeOH (10 mL) was added carefully and resulting mixture was degassed for 10 min. A solution of PN1-054 (2.6 g, 12.5 mmol) in MeOH (5 ml) was added to above solution under argon flow and then degassed for another 10 min. Then 3 cycles of vacuum/argon was performed before placing a H$_2$ balloon to the reaction mixture. After complete conversion of starting material (12 h), the reaction mixture was filtered through the celite and evaporated under vacuum to afford the title compound PN1-055 as a white powder (2.3 g, 87%). $^1$H NMR (500 MHz, DMSO-$d_6$) δ: 7.80 (d, J=11.2 Hz, 1H), 6.26-5.98 (m, 3H), 2.83 (dt, J=11.1, 2.8 Hz, 2H), 2.48-2.36 (m, 1H), 2.17 (s, 3H), 1.90 (dd, J=11.4, 3.2 Hz, 2H), 1.66 (qd, J=10.8, 9.5, 4.2 Hz, 4H). $^{13}$C NMR (125 MHz, DMSO-$d_6$) δ: 167.83 (d, J=253.8 Hz), 161.02 (d, J=11.7 Hz), 148.45 (d, J=6.9 Hz), 117.41 (d, J=12.8 Hz), 93.74 (d, J=20.9 Hz), 56.29, 46.65, 33.68, 32.17. $^{19}$F NMR (479 MHz, DMSO-$d_6$) δ: −111.79 (t, J=12.2 Hz). HPLC-MS (ESI+): m/z 210.3 [100%, (M+H)$^+$]. HRMS (ESI+): m/z calcd for $C_{11}H_{16}FN_3$ (M+H)$^+$ 210.1407, found 210.1399.

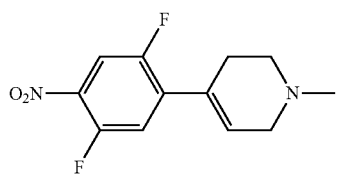

PN1-091

4-(2,5-Difluoro-4-nitrophenyl)-1-methyl-1,2,3,6-tetrahydropyridine (PN1-091). This was prepared using procedure A (method 1) from 1-bromo-2,5-difluoro-4-nitrobenzene (1.06 g, 4.45 mmol, 1.0 equiv.), 1-methyl-4-(4,4,5,5-tetramethyl-1,3,2-dioxaborolan-2-yl)-1,2,3,6-tetrahydropyridine (1.1 g, 4.95 mmol, 1.2 equiv.), $Na_2CO_3$ (1.5 g, 13.2 mmol, 3.0 equiv.) and $Pd(PPh_3)_4$ (175 mg, 0.149 mmol, 0.033 equiv.) in dioxane (20 mL) and $H_2O$ (5 mL). The title nitroarene PN1-091 was isolated after chromatography using (EtOAc/hexanes) as a light brown powder (0.46 g, 40%). $^1H$ NMR (500 MHz, $CDCl_3$) δ: 7.72 (dd, J=10.1, 6.2 Hz, 1H), 7.13 (dd, J=11.5, 6.1 Hz, 1H), 6.17 (tt, J=3.4, 1.6 Hz, 1H), 3.10 (q, J=3.0 Hz, 2H), 2.61 (t, J=5.6 Hz, 2H), 2.49 (ddt, J=4.1, 2.7, 1.4 Hz, 2H), 2.34 (s, 3H).

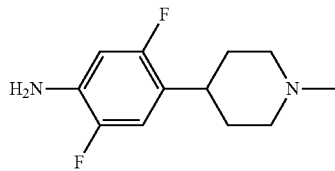

PN1-098

2,5-Difluoro-4-(1-methylpiperidin-4-yl)aniline (PN1-098). A 250-mL, two-necked, round bottom flask with a magnetic stirring bar was charged with 10% palladium on carbon (35 mg) and the reaction flask flushed with nitrogen for 5 min. MeOH (5 mL) was added carefully and resulting mixture was degassed for 10 min. A solution of PN1-091 (0.33 g, 1.5 mmol) in MeOH (3 mL) was added to above solution under argon flow and then degassed for another 10 min. Then 3 cycles of vacuum/argon was performed before placing a $H_2$ balloon to the reaction mixture. After complete conversion of starting material, the reaction mixture was filtered through the celite and evaporated under vacuum to afford title compound PN1-098 as a white powder (0.26 g, 78%). $^1H$ NMR (500 MHz, DMSO-$d_6$) δ: 6.76 (dd, J=11.8, 6.6 Hz, 1H), 6.37 (dd, J=11.0, 7.6 Hz, 1H), 3.62 (s, 2H), 3.07-2.77 (m, 2H), 2.71-2.47 (m, 1H), 2.25 (s, 3H), 2.04-1.85 (m, 3H), 1.84-1.45 (m, 4H). $^{13}C$ NMR (125 MHz, DMSO-$d_6$) δ:156.66 (d, J=235.6 Hz), 147.36 (d, J=232.9 Hz), 135.99 (dd, J=15.4, 12.1 Hz), 119.35 (dd, J=17.8, 5.7 Hz), 113.78 (dd, J=20.9, 7.5 Hz), 102.81 (dd, J=28.7, 5.0 Hz), 56.24, 46.61, 34.24, 32.30. $^{19}F$ NMR (479 MHz, DMSO-$d_6$) δ: −125.22 (td, J=11.6, 10.7, 6.3 Hz), −139.98 (dd, J=13.6, 7.7 Hz). HPLC-MS (ESI+): m/z 227.2 [100%, (M+H)$^+$]. HRMS (ESI+): m/z calcd for $C_{12}H_{16}F_2N_2$ (M+H)$^+$ 227.1360, found 217.1353.

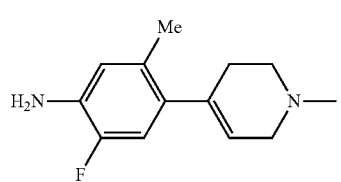

PN1-099

2-Fluoro-5-methyl-4-(1-methyl-1,2,3,6-tetrahydropyridin-4-yl)aniline (PN2-099). This was prepared using procedure A (method 2) from 1-bromo-2-methyl-4-nitro-5-fluorobenzene (834 mg, 4.1 mmol, 1.0 equiv.), 1-methyl-4-(4,4,5,5-tetramethyl-1,3,2-dioxaborolan-2-yl)-1,2,3,6-tetrahydropyridine, (1.0 g, 4.5 mmol, 1.1 equiv.), $Cs_2CO_3$ (3.9 g, 12.0 mmol, 3.0 equiv.) and $Pd(dppf)_2Cl_2$ (140 mg, 0.225 mmol, 0.05 equiv.) in dioxane (20 mL) and $H_2O$ (5 mL). The title nitroarene PN1-099 was isolated after chromatography using (DCM/MeOH) as a brown powder (0.47 g, 52%). $^1H$ NMR (500 MHz, DMSO-$d_6$) δ: 6.67 (d, J=12.3 Hz, 1H), 6.60-6.52 (m, 1H), 5.44 (p, J=1.7 Hz, 1H), 4.94 (s, 2H), 2.93 (d, J=3.1 Hz, 2H), 2.54-2.47 (m, 3H), 2.26 (s, 3H), 2.24-2.20 (m, 1H), 2.09 (s, 3H). HPLC-MS (ESI+): m/z 221.2 [100%, (M+H)$^+$].

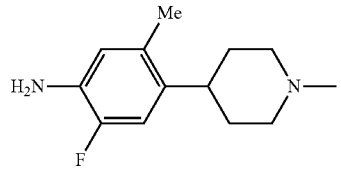

PN1-109

2-Fluoro-5-methyl-4-(1-methylpiperidin-4-yl)aniline (PN1-109): A 250-mL, two-necked, round bottom flask with a magnetic stirrer bar was charged with 10% palladium on carbon (25 mg) and the reaction flask flushed with nitrogen for 5 min. MeOH (5 mL) was added carefully and resulting mixture was degassed for 10 min. A solution of PN1-099 (0.22 g, 1.0 mmol) in MeOH (3 mL) was added to above solution under argon flow and then degassed for another 10 min. Then 3 cycles of vacuum/argon was performed before placing a $H_2$ balloon to the reaction mixture. After complete conversion of starting material, the reaction mixture was filtered through the celite and evaporated under vacuum to afford title compound PN1-109 as a white powder (0.19 g, 87%). $^1H$ NMR (500 MHz, DMSO-$d_6$) δ: 6.77 (d, J=12.7 Hz, 1H), 6.49 (d, J=9.2 Hz, 1H), 3.44 (s, 3H), 2.96-2.77 (m, 3H), 2.55-2.39 (m, 1H), 2.25 (s, 4H), 2.13 (d, J=0.9 Hz, 3H), 2.04-1.85 (m, 2H), 1.74-1.51 (m, 4H). $^{13}C$ NMR (125 MHz, DMSO-$d_6$) δ: 149.82 (d, J=233.8 Hz), 133.79 (d, J=13.0 Hz), 132.62 (d, J=5.1 Hz), 130.82 (d, J=2.8 Hz), 118.48 (d, J=4.5 Hz), 112.19 (d, J=18.5 Hz), 56.54, 46.67, 37.07, 32.90, 18.70. $^{19}F$ NMR (479 MHz, DMSO-$d_6$) δ: −138.25 (dd, J=13.1, 9.5 Hz). HRMS (ESI+): m/z calcd for $C_{13}H_{19}FN_2$ (M+H)$^+$ 223.1611, found 223.1603.

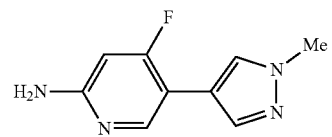

PN2-020

4-Fluoro-5-(1-methyl-1H-pyrazol-4-yl)pyridin-2-amine (PN2-020). This was prepared using procedure A (method 2) from 4-fluoro-5-bromo-2-aminopyridine (570 mg, 3.0 mmol, 1.0 equiv.), 1-methyl-4-(4,4,5,5-tetramethyl-1,3,2-dioxaborolan-2-yl)-1H-pyrazole (882 mg, 4.2 mmol, 1.4 equiv.), $Cs_2CO_3$ (2.4 g, 7.5 mmol, 2.5 equiv.) and $Pd(dppf)_2Cl_2$ (73 mg, 0.099 mmol, 0.033 equiv.) in dioxane (20 mL) and $H_2O$ (5 mL). The nitroarene PN2-020 was isolated after chromatography using (EtOAc/hexane) as a brown powder (0.4 g, 69%). $^1$H NMR (500 MHz, DMSO-$d_6$) δ: 8.23 (d, J=11.5 Hz, 1H), 7.94 (t, J=1.3 Hz, 1H), 7.73 (t, J=1.0 Hz, 1H), 6.27 (d, J=13.3 Hz, 1H), 6.18 (s, 2H), 3.86 (s, 3H). $^{13}$C NMR (125 MHz, DMSO-$d_6$) δ:165.86 (d, J=255.2 Hz), 160.81 (d, J=11.4 Hz), 148.26 (d, J=5.8 Hz), 136.51 (d, J=3.0 Hz), 128.36 (d, J=4.9 Hz), 113.70, 106.72 (d, J=12.3 Hz), 93.90 (d, J=20.4 Hz), 38.99. $^{19}$F NMR (479 MHz, DMSO-$d_6$) δ: −108.52 (t, J=12.4 Hz). HPLC-MS (ESI+): m/z 193.2 [100%, (M+H)$^+$]. HRMS (ESI+): m/z calcd for $C_9H_9FN_4$ (M+H)$^+$ 193.0889, found 193.0882.

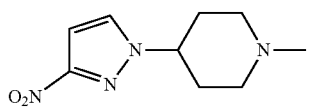

PN2-029

1-Methyl-4-(3-nitro-1H-pyrazol-1-yl)piperidine (PN2-029): An oven-dried flask equipped with a stir bar was charged with 4-hydroxy-N-methylpiperidine (400 mg, 3.54 mmol, 1.0 equiv.), 3-nitro-1H-pyrazole (404 mg, 3.54 mmol, 1.0 equiv.) and $PPh_3$ (1.6, 4.24 mmol, 1.2 equiv.) in THF (12 mL). Diisopropyl azodicarboxylate (940 mg, 4.64 mmol, 1.3 equiv.) was added very slowly over 2 minutes and the resulting reaction mixture was stirred for 6 hours at room temperature. The crude mixture was evaporated to dryness and purified using 10% MeOH in DCM to obtain the nitropyrazole PN2-029 as a yellow powder (0.42 g, 57%). $^1$H NMR (500 MHz, CDCl$_3$) δ: 8.28-8.11 (m, 1H), 8.07 (d, J=0.8 Hz, 1H), 4.19-4.04 (m, 1H), 2.98 (d, J=11.9 Hz, 1H), 2.33 (s, 3H), 2.26-2.08 (m, 4H), 2.11-1.91 (m, 2H).

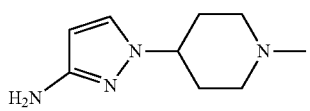

PN2-040

1-(1-Methylpiperidin-4-yl)-1H-pyrazol-3-amine (PN2-040). A 250-mL, two-necked, round bottom flask with a magnetic stirrer bar was charged with 10% palladium on carbon (113 mg) and the reaction flask flushed with nitrogen for 5 min. MeOH (10 mL) was added carefully and resulting mixture was degassed for 10 min. A solution of PN1-029 (1.13 g, 5.4 mmol) in MeOH (5 mL) was added to above solution under argon flow and then degassed for another 10 min. Then 3 cycles of vacuum/Argon was performed before placing the H$_2$ balloon to the reaction mixture. After complete conversion of starting material, the reaction mixture was filtered through the celite and evaporated under vacuum to afford title compound PN2-040 as a white powder (0.84 g, 87%). $^1$H NMR (500 MHz, DMSO-$d_6$) δ: 7.05 (d, J=0.9 Hz, 1H), 6.90 (d, J=0.9 Hz, 1H), 3.88 (dt, J=10.7, 5.6 Hz, 1H), 2.81 (dt, J=12.2, 3.4 Hz, 2H), 2.18 (s, 3H), 1.99 (td, J=11.5, 3.2 Hz, 2H), 1.92-1.80 (m, 4H). $^{13}$C NMR (125 MHz, DMSO-$d_6$) δ:130.91, 129.23, 114.83, 58.22, 54.69, 46.24, 32.51. HRMS (ESI+): m/z calcd for $C_9H_{16}N_4$(M+H)$^+$ 180.1375, found 180.1375.

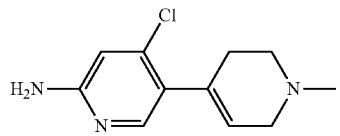

PN2-50

4-Chloro-1'-methyl-1',2',3',6'-tetrahydro-[3,4'-bipyridin]-6-amine (PN2-050): According to the general procedure A (method 2), the reaction of 5-bromo-4-chloro-pyridin-2-ylamine (581 mg, 2.8 mmol, 1.0 equiv.), 1-methyl-4-(4,4,5,5-tetramethyl-1,3,2-dioxaborolan-2-yl)-1,2,3,6-tetrahydro-pyridine (875 mg, 4.0 mmol, 1.4 equiv.), $Cs_2CO_3$ (2.3 g, 7.0 mmol, 2.5 equiv.) and $Pd(dppf)_2Cl_2$ (68 mg, 0.0093 mmol, 0.033 equiv.) in dioxane (13 mL) and $H_2O$ (3 mL) afforded the aminopyridine intermediate PN2-050 as brown oil after purification by chromatography (0.48 g, 77%). $^1$H NMR (500 MHz, CDCl$_3$) δ: 7.85 (s, 1H), 6.50 (s, 1H), 5.66 (dt, J=3.4, 1.7 Hz, 1H), 4.48 (s, 2H), 3.09 (d, J=3.0 Hz, 2H), 2.64 (t, J=5.6 Hz, 2H), 2.47 (ddd, J=5.5, 2.8, 1.7 Hz, 2H), 2.40 (s, 3H).

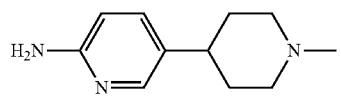

PN2-066

5-(1-Methylpiperidin-4-yl)pyridin-2-amine (PN2-066): A 250-mL, two-necked, round bottom flask with a magnetic stirring bar was charged with 10% palladium on carbon (50 mg) and the reaction flask flushed with nitrogen for 5 min. MeOH (5 mL) was added carefully and resulting mixture was degassed for 10 min. A solution of PN2-050 (0.45 g, 2.0 mmol) in MeOH (3 mL) was added to above solution under argon flow and then degassed for another 10 min. Then 3 cycles of vacuum/argon was performed before placing a H$_2$ balloon to the reaction mixture. After complete conversion of starting material, the reaction mixture was filtered through the celite and evaporated under vacuum to afford the title compound PN2-066 as a brown powder (0.3 g, 67%). $^1$H NMR (500 MHz, DMSO-$d_6$) δ: 7.80 (d, J=11.2 Hz, 1H), 6.26-5.98 (m, 3H), 2.83 (dt, J=11.1, 2.8 Hz, 2H), 2.48-2.36 (m, 1H), 2.17 (s, 3H), 1.90 (dd, J=11.4, 3.2 Hz, 2H), 1.66 (qd, J=10.8, 9.5, 4.2 Hz, 4H). $^{13}$C NMR (125 MHz, DMSO-$d_6$) δ:154.81, 142.04, 135.34, 128.10, 113.11, 53.53, 42.87, 34.94, 29.37. HPLC-MS (ESI+): m/z 192.3 [100%, (M+H)$^+$]. HRMS (ESI+): m/z calcd for $C_{11}H_{17}N_3$(M+H)$^+$ 191.1422, found 191.1421.

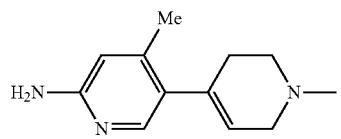

PN2-052

1',4-Dimethyl-1',2',3',6'-tetrahydro-[3,4'-bipyridin]-6-amine (PN2-052): According to the general procedure A (method 2), the reaction of 2-amino-5-bromo-4-methylpyridine (555 mg, 3.0 mmol, 1.0 equiv.), 1-methyl-4-(4,4,5,5-tetramethyl-1,3,2-dioxaborolan-2-yl)-1,2,3,6-tetrahydropyridine (60 mg, 4.2 mmol, 1.4 equiv.), Cs$_2$CO$_3$ (2.4 g, 7.5 mmol, 2.5 equiv.) and Pd(dppf)$_2$Cl$_2$ (73 mg, 0.0099 mmol, 0.033 equiv.) in dioxane (13 mL) and H$_2$O (3 mL) afforded the aminopyridine intermediate PN2-052 as a light brown powder after purification by chromatography (0.38 g, 63%). $^1$H NMR (500 MHz, DMSO-d$_6$) δ: 8.60 (s, 1H), 7.26 (s, 1H), 6.70 (s, 2H), 6.53-6.38 (m, 1H), 3.97 (q, J=2.9 Hz, 2H), 3.68-3.47 (m, 3H), 3.29 (s, 3H), 3.28-3.24 (m, 2H), 3.11 (s, 3H). HPLC-MS (ESI+): m/z 204.2 [40%, (M+H)$^+$].

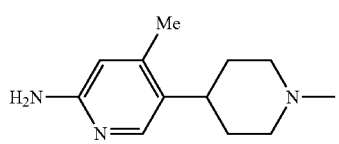

PN2-068

4-Methyl-5-(1-methylpiperidin-4-yl)pyridin-2-amine (PN2-068). A 250-mL, two-necked, round bottom flask with a magnetic stirbar was charged with 10% palladium on carbon (50 mg) and the reaction flask flushed with nitrogen for 5 min. MeOH (10 mL) was added carefully and resulting mixture was degassed for 10 min. A solution of PN2-052 (0.41 g, 2.0 mmol) in MeOH (3 mL) was added to above solution under argon flow and then degassed for another 10 min. Then 3 cycles of vacuum/argon was performed before placing a H$_2$ balloon to the reaction mixture. After complete conversion of starting material, the reaction mixture was filtered through the celite and evaporated under vacuum to afford the title compound PN2-068 as a brown powder (0.34 g, 83%). $^1$H NMR (500 MHz, DMSO-d$_6$) δ: 7.69 (s, 1H), 6.22 (s, 1H), 5.52 (s, 2H), 2.90-2.80 (m, 2H), 2.42 (s, 2H), 2.18 (s, 3H), 2.13 (s, 3H), 2.00-1.88 (m, 2H), 1.62 (dd, J=8.1, 3.3 Hz, 4H). $^{13}$C NMR (125 MHz, DMSO-d$_6$) δ: 158.35, 145.61, 144.88, 128.45, 109.20, 56.62, 46.70, 35.42, 32.92, 18.94. HPLC-MS (ESI+): m/z 206.3 [60%, (M+H)$^+$]. HRMS (ESI+): m/z calcd for C$_{12}$H$_{19}$N$_3$(M+H)$^+$ 205.1580, found 205.1579.

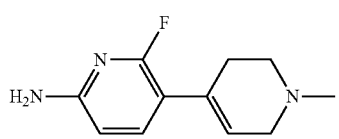

PN2-098

2-Fluoro-1'-methyl-1',2',3',6'-tetrahydro-[3,4'-bipyridin]-6-amine (PN2-098). According to the general procedure A (method 2), the reaction of 5-bromo-6-fluoropyridin-2-amine (955 mg, 5.0 mmol, 1.0 equiv.), 1-methyl-4-(4,4,5,5-tetramethyl-1,3,2-dioxaborolan-2-yl)-1,2,3,6-tetrahydropyridine (1.4 g, 6.0 mmol, 1.2 equiv.), Cs$_2$CO$_3$ (4.1 g, 12.5 mmol, 2.5 equiv.) Pd(dppf)$_2$Cl$_2$ (120 mg, 0.165 mmol, 0.033 equiv.) in dioxane (25 mL) and H$_2$O (7.5 mL), afforded the aminopyridine PN2-098 as a brown powder after purification by chromatography (0.53 g, 51%). $^1$H NMR (500 MHz, DMSO-d$_6$) δ: 7.45 (dd, J=10.8, 8.2 Hz, 1H), 6.41-6.06 (m, 3H), 5.87-5.78 (m, 1H), 3.02-2.86 (m, 2H), 2.53-2.45 (m, 3H), 2.37 (dq, J=5.6, 2.7, 2.0 Hz, 2H), 2.25 (s, 3H). HPLC-MS (ESI+): m/z 208.2 [100%, (M+H)$^+$].

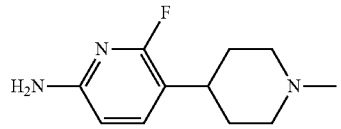

PN2-100

6-Fluoro-5-(1-methylpiperidin-4-yl)pyridin-2-amine (PN2-100). A 250-mL, two-necked, round bottom flask with a magnetic stirrer bar was charged with 10% palladium on carbon (50 mg) and the reaction flask flushed with nitrogen for 5 min. MeOH (10 mL) was added carefully and resulting mixture was degassed for 10 min. A solution of PN2-098 (0.51 g, 2.5 mmol) in MeOH (5 mL) was added to above solution under argon flow and then degassed for another 10 min. Then 3 cycles of vacuum/argon was performed before placing a H$_2$ balloon to the reaction mixture. After complete conversion of starting material, the reaction mixture was filtered through the celite and evaporated under vacuum to afford the title compound PN2-100 as a brown powder (0.47 g, 90%). $^1$H NMR (500 MHz, DMSO-d$_6$) δ: 7.44 (dd, J=10.5, 8.1 Hz, 1H), 6.32 (dd, J=8.1, 1.7 Hz, 1H), 6.11 (s, 2H), 3.01-2.75 (m, 2H), 2.50 (td, J=9.6, 5.3 Hz, 1H), 2.00-1.83 (m, 2H), 1.83-1.54 (m, 4H). $^{13}$C NMR (125 MHz, DMSO-d$_6$) δ:160.22 (d, J=231.9 Hz), 157.60 (d, J=18.1 Hz), 139.97 (d, J=6.4 Hz), 111.62 (d, J=29.5 Hz), 105.19 (d, J=4.1 Hz), 56.24, 46.65, 34.15 (d, J=2.5 Hz), 32.15. $^{19}$F NMR (479 MHz, DMSO-d$_6$) δ: -77.17 (d, J=10.4 Hz). HPLC-MS (ESI+): m/z 210.2 [100%, (M+H)$^+$]. HRMS (ESI+): m/z calcd for C$_{11}$H$_{16}$FN$_3$ (M+H)$^+$ 209.1329, found 209.1328.

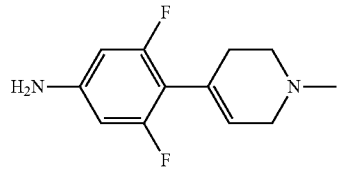

PN2-119

3,5-Difluoro-4-(1-methyl-1,2,3,6-tetrahydropyridin-4-yl) aniline (PN2-119). According to the general procedure A (method 2), the reaction of 4-bromo-3,5-difluoroaniline (2.1 g, 10.0 mmol, 1.0 equiv.), 1-methyl-4-(4,4,5,5-tetramethyl-1,3,2-dioxaborolan-2-yl)-1,2,3,6-tetrahydropyridine (1.4 g, 12 mmol, 1.2 equiv.), Cs$_2$CO$_3$ (8.1 g, 25 mmol, 2.5 equiv.) and Pd(dppf)$_2$Cl$_2$ (241 mg, 0.33 mmol, 0.033 equiv.) in dioxane (50 mL) and H$_2$O (15 mL) afforded the aniline intermediate PN2-119 as white powder after purification by chromatography (1.45 g, 63%). $^1$H NMR (500 MHz, CDCl$_3$) δ: 6.20-6.07 (m, 1H), 5.72 (tt, J=1.8, 0.9 Hz, 0H), 3.08 (q, J=2.9 Hz, 1H), 2.63 (t, J=5.7 Hz, 1H), 2.45-2.41 (m, 1H), 2.39 (s, 1H). $^{19}$F NMR (479 MHz, DMSO-d$_6$) δ: -113.36 (d, J=8.9 Hz). HPLC-MS (ESI+): m/z 225.2 [100%, (M+H)$^+$].

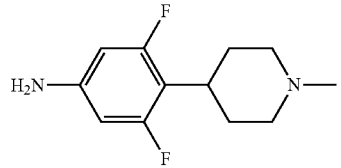

PN2-120

3,5-Difluoro-4-(1-methylpiperidin-4-yl)aniline (PN2-120). A 250-mL, two-necked, round bottom flask with a magnetic stirred bar was charged with 10% palladium on carbon (150 mg) and the reaction flask flushed with nitrogen for 5 min. MeOH (10 mL) was added carefully and resulting mixture was degassed for 10 min. A solution of PN2-119 (1.45 g, 6.5 mmol) in MeOH (5 mL) was added to above solution under argon flow and then degassed for another 10 min. Then 3 cycles of vacuum/argon was performed before placing a H$_2$ balloon to the reaction mixture. After complete conversion of starting material, the reaction mixture was filtered through the celite and evaporated under vacuum to afford the title compound PN2-120 as a brown powder (1.3 g, 89%). $^1$H NMR (500 MHz, DMSO-d$_6$) δ: 6.14 (d, J=11.5 Hz, 2H), 5.49 (s, 2H), 2.82 (dd, J=8.6, 2.1 Hz, 2H), 2.72-2.58 (m, 1H), 2.16 (s, 3H), 2.08-1.80 (m, 4H), 1.63-1.48 (m, 2H). $^{13}$C NMR (125 MHz, DMSO-d$_6$) δ:162.01 (dd, J=240.4, 13.3 Hz), 149.46 (d, J=14.8 Hz), 106.83, 97.15 (d, J=29.5 Hz), 56.58, 46.67, 31.94, 31.03. $^{19}$F NMR (479 MHz, DMSO-d$_6$) δ: −114.81 (d, J=12.2 Hz). HPLC-MS (ESI+): m/z 227.2 [100%, (M+H)$^+$]. HRMS (ESI+): m/z calcd for C$_{12}$H$_{16}$F$_2$N$_2$ (M+H)$^+$ 226.1282, found 226.1285.

Procedure B:

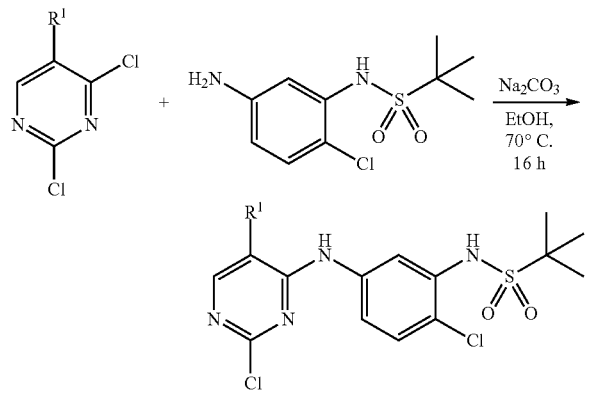

Both starting materials and Na$_2$CO$_3$ were placed in microwave vial and EtOH was added. The resulting reaction mixture was then placed in pre-heated oil bath at 70° C. After completion of stating material (HPLC-MS), the crude reaction was quenched with water and partitioned between EtOAc (~50 mL). The organic layer was washed with brine (~5 mL), dried (Na$_2$SO$_4$) and evaporated under reduced pressure. The residue was purified trituration using a Hex/EtOAc solvent mixture.

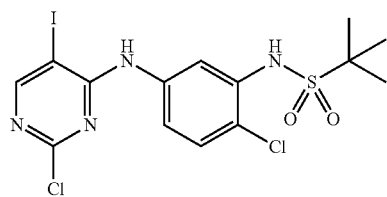

PN1-008

N-(2-Chloro-5-((2-chloro-5-iodopyrimidin-4-yl)amino)phenyl)-2-methylpropane-2-sulfonamide (PN1-008). According to the general procedure B, the reaction of 2,4-dichloro-5-iodopyrimidine (346 mg, 1.26 mmol, 1.0 equiv.), N-(5-amino-2-chlorophenyl)-2-methylpropane-2-sulfonamide (SG3-105) (302 mg, 1.15 mmol, 1.0 equiv.), Na$_2$CO$_3$ (136 mg, 1.26 mmol, 1.1 equiv.) in EtOH (6.0 mL) for 16 h at 70° C., afforded the title compound PN1-008 after trituration (Hex/EtOAc) as a brown powder (390 mg, 67%). $^1$H NMR (500 MHz, DMSO-d$_6$) δ: 9.35 (s, 1H), 9.03 (s, 1H), 8.59 (s, 1H), 7.83 (d, J=2.5 Hz, 1H), 7.47 (d, J=8.7 Hz, 1H), 7.40 (dd, J=8.7, 2.5 Hz, 1H), 1.34 (s, 9H). $^{13}$C NMR (125 MHz, DMSO-d$_6$) δ: 165.31, 160.97, 159.10, 137.68, 129.67, 123.64, 122.20, 121.93, 78.61, 60.89, 24.48. HPLC-MS (ESI+): m/z 501.0 [60%, (M+H)$^+$]. HRMS (ESI+): m/z calcd for C$_{14}$H$_{16}$Cl$_2$I$_1$N$_4$O$_2$S (M+H)$^+$ 500.9410, found 500.9405.

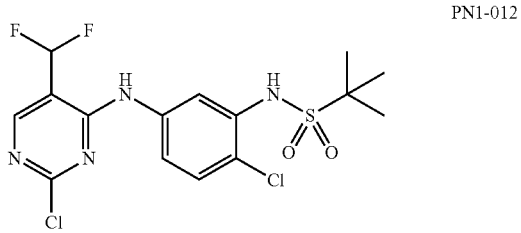 [SMILES: CC(C)(C)S(=O)(=O)Nc1cc(Nc2nc(Cl)ncc2C(F)F)ccc1Cl]

PN1-012

N-(2-Chloro-5-((2-chloro-5-(difluoromethyl)pyrimidin-4-yl)amino)phenyl)-2-methylpropane-2-sulfonamide (PN1-012). According to the general procedure B, the reaction of 2,4-dichloro-5-(difluoromethyl)pyrimidine (124.0 mg, 0.64 mmol, 1.1 equiv.), N-(5-amino-2-chlorophenyl)-2-methylpropane-2-sulfonamide (SG3-105) (150.0 mg, 0.56 mmol, 1.0 equiv.), Na$_2$CO$_3$ (67 mg, 2.2 mmol, 1.1 equiv.) in EtOH (5.0 mL) for 16 h at 70° C., afforded the title compound PN1-012 after trituration (Hex/EtOAc) as a brown powder (116 mg, 49%). $^1$H NMR (500 MHz, DMSO-d$_6$) δ: 9.61 (s, 1H), 9.40 (s, 1H), 8.47 (d, J=1.3 Hz, 1H), 7.83 (d, J=2.2 Hz, 1H), 7.63-7.42 (m, 2H), 7.43-7.14 (m, 1H), 1.34 (s, 9H). $^{13}$C NMR (125 MHz, DMSO-d$_6$) δ: 161.34, 158.48 (t, J=3.9 Hz), 156.31 (t, J$^3$=7.4 Hz), 137.31, 136.15, 129.97, 123.60, 111.64 (t, J=23.2 Hz), 110.26 (t, J$^1$=234.7 Hz), 61.12, 24.39. $^{19}$F NMR (479 MHz, DMSO-d$_6$) δ: −117.03 (d, J=53.7 Hz). HPLC-MS (ESI+): m/z 425.1 [70%, (M+H)$^+$]. HRMS (ESI+): m/z calcd for C$_{15}$H$_{17}$Cl$_2$F$_2$N$_4$O$_2$S (M+H)$^+$ 425.0412, found 425.0406.

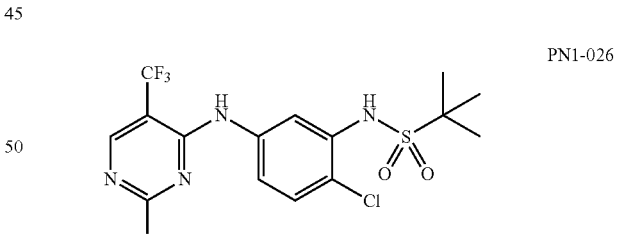

PN1-026

N-(2-Chloro-5-((2-chloro-5-(trifluoromethyl)pyrimidin-4-yl)amino)phenyl)-2-methylpropane-2-sulfonamide (PN1-026). According to the general procedure B, the reaction of 2,4-dichloro-5-trifluoromethylpyrimidine (471 mg, 2.2 mmol, 1.1 equiv.), N-(5-amino-2-chlorophenyl)-2-methylpropane-2-sulfonamide (SG3-105) (525.5 mg, 2.0 mmol, 1.0 equiv.), Na$_2$CO$_3$ (240 mg, 2.2 mmol, 1.1 equiv.) in EtOH (10.0 mL) for 16 h at 70° C., afforded the title compound PN1-026 after trituration (Hex/EtOAc) as a white powder (408 mg, 42%). $^1$H NMR (500 MHz, DMSO-d$_6$) δ: 9.62 (s, 1H), 9.42 (s, 1H), 8.76-8.52 (m, 1H), 7.73 (d, J=2.5 Hz, 1H), 7.51 (d, J=8.6 Hz, 1H), 7.33 (dd, J=8.7, 2.5 Hz, 1H), 1.34 (s, 9H). $^{13}$C NMR (125 MHz, DMSO-d$_6$) δ: 162.74, 157.87, 157.39 (q, J$^3$=5.4 Hz), 136.67, 136.11, 129.86, 124.71, 124.00, 123.93, 120.36 (q, J=272.18 Hz), 106.51 (q, J$^2$=32.6 Hz), 61.12, 24.38. $^{19}$F NMR (479 MHz, DMSO-d$_6$) δ: −61.72. HPLC-MS (ESI+): m/z 443.1 [80%, (M+H)$^+$]. HRMS (ESI+): m/z calcd for $C_{15}H_{16}Cl_2F_3N_4O_2S$ (M+H)$^+$ 443.0318, found 443.0316.

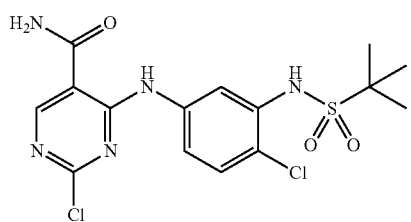

PN1-126

2-Chloro-4-((4-chloro-3-((1,1-dimethylethyl)sulfonamido)phenyl)amino)pyrimidine-5-carboxamide (PN1-126). According to the general procedure C, the reaction of 2,4-dichloro-pyrimidine-5-carboxylic acid amide (80.0 mg, 0.42 mmol, 1.0 equiv.), N-(5-amino-2-chlorophenyl)-2-methylpropane-2-sulfonamide (SG3-105) (100.0 mg, 0.38 mmol, 1.0 equiv.), Na$_2$CO$_3$ (50 mg, 0.46 mmol, 1.2 equiv.) in EtOH (2.0 mL) for 16 h at 70° C., afforded the title compound PN1-126 after trituration (Hex/EtOAc) as a white powder (55.5 mg, 35%). $^1$H NMR (500 MHz, DMSO-d$_6$) δ: 11.60 (s, 1H), 9.39 (s, 1H), 8.81 (s, 1H), 8.47 (s, 1H), 8.00 (s, 1H), 7.91 (d, J=2.4 Hz, 1H), 7.67-7.38 (m, 2H), 1.34 (s, 9H). $^{13}$C NMR (500 MHz, DMSO-d$_6$) δ: 162.74, 157.87, 157.40, 157.36, 136.67, 136.11, 129.86, 124.71, 124.68, 123.99, 123.93, 61.12, 24.39. HPLC-MS (ESI+): m/z 418.1 [90%, (M+H)$^+$].

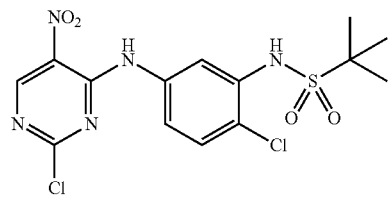

PN1-127

N-(2-Chloro-5-((2-chloro-5-nitropyrimidin-4-yl)amino)phenyl)-2-methylpropane-2-sulfonamide (PN1-127). According to the general procedure C, the reaction of 2,4-Dichloro-5-nitropyrimidine (81.0 mg, 0.256 mmol, 1.0 equiv.), N-(5-amino-2-chlorophenyl)-2-methylpropane-2-sulfonamide (SG3-105) (100.0 mg, 0.38 mmol, 1.0 equiv.), Na$_2$CO$_3$ (50 mg, 0.46 mmol, 1.2 equiv.) in EtOH (2.0 mL) for 16 h at 70° C., afforded the title compound PN1-127 after trituration (Hex/EtOAc) as a yellow powder (116 mg, 73%). $^1$H NMR (500 MHz, DMSO-d$_6$) δ: 10.50 (s, 1H), 9.44 (s, 1H), 9.16 (s, 1H), 7.85 (d, J=2.5 Hz, 1H), 7.55 (d, J=8.7 Hz, 1H), 7.39 (dd, J=8.7, 2.6 Hz, 1H), 1.35 (s, 9H). $^{13}$C NMR (500 MHz, DMSO-d$_6$) δ:162.31, 158.03, 154.27, 136.23, 136.05, 130.08, 128.59, 125.14, 123.58, 123.53, 61.16, 24.40. HPLC-MS_(ESI+): m/z 420.1 [20%, (M+H)$^+$]. HRMS (ESI+): m/z calcd for $C_{14}H_{16}Cl_2NSO_2S$ (M+H)$^+$ 420.0295, found 420.0300.

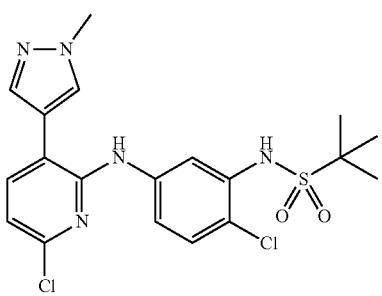

PN1-129

N-(2-Chloro-5-((2-chloro-5-(1-methyl-1H-pyrazol-4-yl)pyrimidin-4-yl)amino)phenyl)-2-methylpropane-2-sulfonamide (PN1-129). The iodopyrimdine PN1-008 (100 mg, 0.2 mmol, 1.0 equiv.), 1-methyl-4-(4,4,5,5-tetramethyl-1,3,2-dioxaborolan-2-yl)-1,2,3,6-tetrahydropyridine, 1-methyl-4-(4,4,5,5-tetramethyl-1,3,2-dioxaborolan-2-yl)-1H-pyrazole (60 mg, 0.28 mmol, 1.4 equiv.) and Na$_2$CO$_3$ (68 mg, 0.64 mmol, 3.2 equiv.) were dissolved in dioxane (1 mL) and H$_2$O (0.3 mL), (degassed for 10 minutes). Finally, Pd(PPh$_3$)$_4$ (7.6 mg, 0.0066 mmol, 0.033 equiv.) was added under argon and the reaction was heated at reflux for 16 h. After confirming the reaction completion (TLC, HPLC-MS), the mixture was partitioned between EtOAc (2×200 mL) and water (3×100 mL). The organic layer was washed with brine (~50 mL), dried (Na$_2$SO$_4$) and evaporated under reduced pressure. The residue was purified by trituration to provide pure PN1-129 as a white powder (84.5 mg, 93%). $^1$H NMR (500 MHz, DMSO-d$_6$) δ: 9.28 (s, 1H), 8.87 (s, 1H), 8.17 (s, 1H), 8.10 (s, 1H), 7.84 (s, 1H), 7.74 (s, 1H), 7.39 (s, 2H), 3.91 (s, 3H), 1.33 (s, 9H). HRMS (ESI+): m/z calcd for $C_{25}H_{28}ClN_7O_2S$ (M+H)$^+$ 454.0746, found 454.0748.

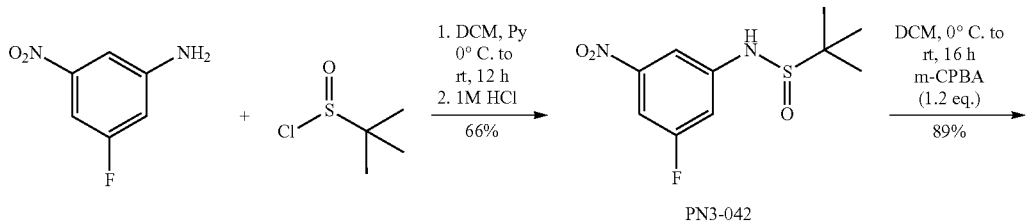

PN3-042

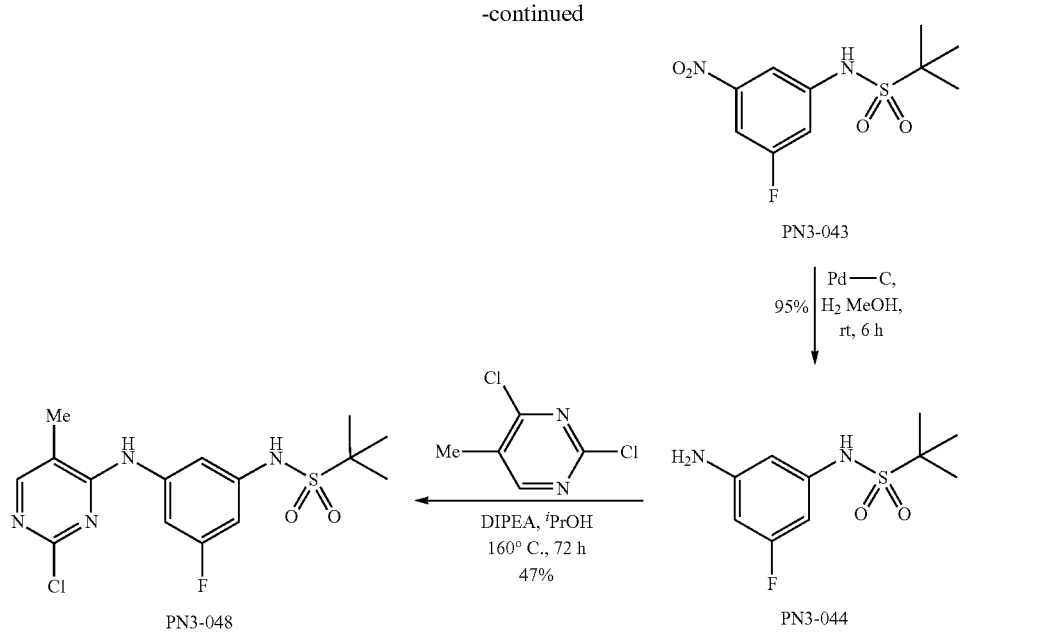

PN3-048    PN3-044

PN3-042

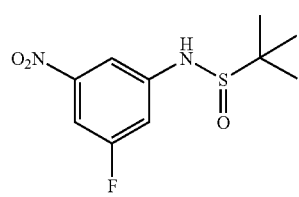

PN3-043

N-(3-Fluoro-5-nitrophenyl)-2-methylpropane-2-sulfinamide (PN3-042): To 3-fluoro-5-nitroaniline (0.842 g, 5.4 mmol, 1.0 equiv.) and pyridine (1.3 mL, 16.2 mmol, 3.0 equiv. mmol) in DCM (1 mL) was added t-butylsulfinyl chloride (0.740 mL, 5.94 mmol, 1.1 equiv.) in DCM (2 mL) at room temperature under argon. The mixture was stirred overnight at room temperature. The reaction mixture was diluted with EtOAc (10 mL) and washed with HCl (1 M aq. solution, 10 mL), water (10 mL), and brine (10 mL). The organic layer was dried (Na$_2$SO$_4$) and concentrated under reduced pressure. The resulting residue was purified via column chromatography (SiO$_2$) eluting with hexanes/EtOAc (20%) to give the title compound PN3-042 as a light yellow solid (0.924 g, 66%). $^1$H NMR (500 MHz, DMSO-d$_6$) δ: 8.84 (s, 1H), 7.79 (td, J=2.1, 0.8 Hz, 1H), 7.61 (dt, J=8.6, 2.2 Hz, 1H), 7.36 (dt, J=10.5, 2.2 Hz, 1H), 1.27 (s, 9H). $^{19}$F NMR (479 MHz, DMSO-d$_6$) δ: −112.51 (m). HPLC-MS (ESI+): m/z 283.1 [100%, (M+Na)$^+$], 521.2 [80%, (2M+H)$^+$], 543.2 [100%, (2M+Na)$^+$].

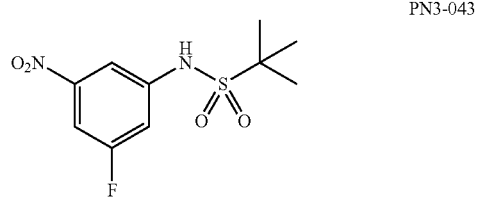 [SMILES: CC(C)(C)S(=O)(=O)Nc1cc(F)cc([N+](=O)[O-])c1]

PN3-043

N-(3-Fluoro-5-nitrophenyl)-2-methylpropane-2-sulfonamide (PN3-043). To PN2-042 (0.854 g, 3.3 mmol, 1.0 equiv.) in DCM (5 mL) was added m-CPBA (65%, 0.674 g, 3.9 mmol, 1.2 equiv.) under argon. The mixture was stirred at room temperature for 12 h at room temperature. The reaction mixture was diluted with DCM (50 mL) and washed with saturated NaHCO$_3$ (2×50 mL) and brine (50 mL). The organic layer was dried (Na$_2$SO$_4$) and concentrated under reduced pressure. The resulting solid was triturated using EtOAc/hexanes to give the title compound PN2-043 as a yellow solid (0.81 g, 89%). $^1$H NMR (500 MHz, DMSO-d$_6$) δ: 7.62 (dd, J=2.3, 1.7 Hz, 1H), 7.11 (dt, J=12.4, 2.2 Hz, 1H), 7.06 (dt, J=8.7, 2.3 Hz, 1H), 1.24 (s, 9H). $^{19}$F NMR (479 MHz, DMSO-d$_6$) δ: −112.51 (m). HPLC-MS (ESI+): m/z 299.1 [100%, (M+Na)$^+$].

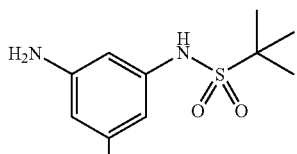

PN3-044

N-(3-Amino-5-fluorophenyl)-2-methylpropane-2-sulfonamide (PN3-044). A 250-mL, two-necked, round bottom flask with a magnetic stirrer bar was charged with 10% palladium on carbon (80 mg) and the reaction flask flushed with nitrogen for 5 min. MeOH (10 mL) was added carefully and resulting mixture was degassed for 10 min. The nitroarene PN3-043 (800 mg) in MeOH (5 mL) was added to above solution under argon flow and then degassed for another 10 min. Then 3 cycles of vacuum/argon was performed before placing a H₂ balloon to the reaction mixture. After complete conversion of starting material, the reaction mixture was filtered through the celite and evaporated under vacuum to afford title compound PN3-044 as a white powder (0.68 g, 95%). ¹H NMR (500 MHz, DMSO-d₆) δ: 6.13 (dt, J=12.7, 2.1 Hz, 1H), 6.09 (t, J=1.9 Hz, 1H), 5.66 (dt, J=11.3, 2.2 Hz, 1H), 4.89 (s, 2H), 1.20 (s, 9H). ¹⁹F NMR (479 MHz, DMSO-d₆) δ: −115.5 (m). HPLC-MS (ESI+): m/z 247.1 [100%, (M+H)⁺], 515.2 [10%, (2M+Na)⁺].

N-(3-((2-Chloro-5-methylpyrimidin-4-yl)amino)-5-fluorophenyl)-2-methylpropane-2-sulfonamide (PN3-048). A mixture of 2,4-dichloro-5-methylpyrimidine (0.430 g, 2.64 mmol, 1.0 equiv.), PN3-044 (0.650 g, 2.64 mmol, 1.0 equiv.), and DIPEA (1.1 mL, 7.9 mmol, 2.4 equiv.) in isopropanol (10 mL) was stirred and heated at 160° C. After 3 days, reaction was quenched with water and extracted with EtOAc (2×10 mL). The combined organic layers were dried (Na₂SO₄) and evaporated under vacuum. The residue was purified by chromatography to afford title compound PN3-048 as a light yellow powder (0.460 g, 47%). ¹H NMR (500 MHz, DMSO-d₆) δ: 9.92 (s, 1H), 9.00 (s, 1H), 8.11 (d, J=1.0 Hz, 1H), 7.50 (d, J=2.0 Hz, 1H), 7.30 (dd, J=11.2, 2.1 Hz, 1H), 6.83 (dd, J=10.7, 2.1 Hz, 1H), 2.18 (d, J=0.9 Hz, 3H), 1.33 (s, 9H). ¹⁹F NMR (479 MHz, DMSO-d₆) δ: −111.97 (d, J=11.1 Hz). HPLC-MS (ESI+): m/z 373.1 [100%, (M+H)⁺], 767.1 [20%, (2M+Na)⁺]. HRMS (ESI+): m/z calcd for C₁₄H₁₅ClFN₄O₂S (M+H)⁺ 372.0523, found 372.0716.

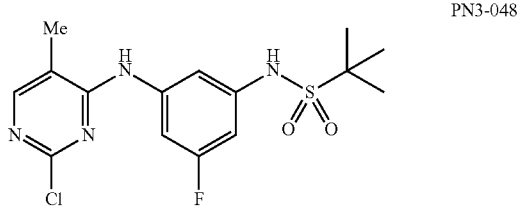 [SMILES: Cc1cnc(Cl)nc1Nc1cc(F)cc(NS(=O)(=O)C(C)(C)C)c1]

PN3-048

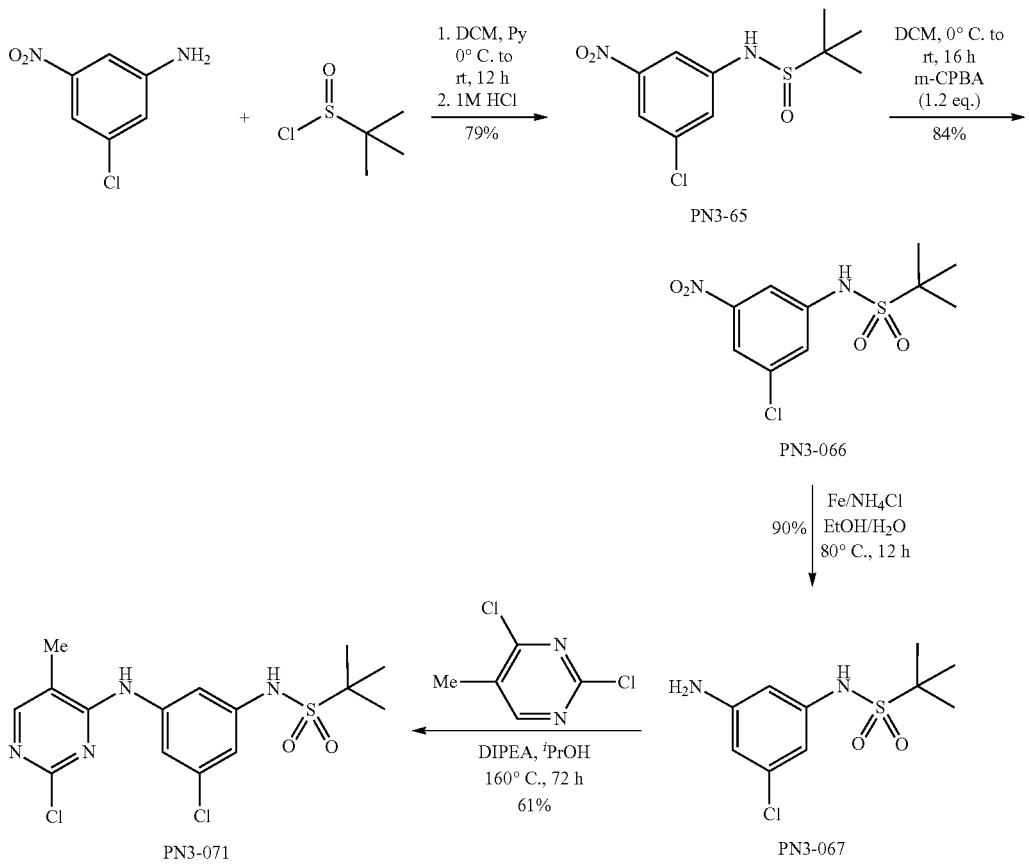

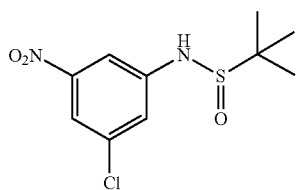

PN3-065

N-(3-Chloro-5-nitrophenyl)-2-methylpropane-2-sulfinamide (PN3-065). To 3-chloro-5-nitroaniline (1.0 g, 5.8 mmol, 1.0 equiv.) and pyridine (1.4 mL, 17.4 mmol, 3.0 equiv.) in DCM (1 mL) was added t-butylsulfinyl chloride (0.87 mL, 6.9 mmol, 1.1 equiv.) in DCM (2 mL) at room temperature under argon. The mixture was stirred overnight at room temperature. The reaction mixture was diluted with EtOAc (10 mL) and washed with HCl (1 M aq. solution, 10 mL), water (10 mL), and brine (10 mL). The organic layer was dried ($Na_2SO_4$) and concentrated under reduced pressure. The resulting residue was purified via column chromatography ($SiO_2$) eluting with hexanes/EtOAc (20%) to give the title compound PN3-065 as a light yellow solid (1.27 g, 79%). $^1$H NMR (500 MHz, DMSO-$d_6$) δ: 8.82 (s, 1H), 7.87 (t, J=2.1 Hz, 1H), 7.78 (t, J=1.9 Hz, 1H), 7.54 (t, J=2.0 Hz, 1H), 1.27 (s, 9H). HPLC-MS (ESI+): m/z 299.1 [100%, (M+Na)$^+$], 577.1 [90%, (2M+Na)$^+$].

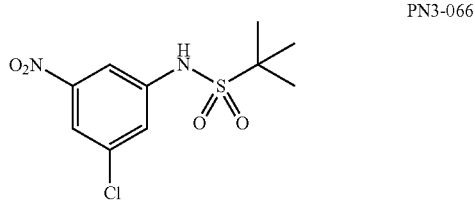 [SMILES: CC(C)(C)S(=O)(=O)Nc1cc(Cl)cc([N+](=O)[O-])c1]

PN3-066

N-(3-Chloro-5-nitrophenyl)-2-methylpropane-2-sulfonamide (PN3-066): To PN2-065 (1.2 g, 4.34 mmol, 1.0 equiv.) in DCM (15 mL) was added m-CPBA (65%, 0.9 g, 5.2 mmol, 1.2 equiv.) under argon. The mixture was stirred at room temperature for 12 h at room temperature. The reaction mixture was diluted with DCM (50 mL) and washed with saturated $NaHCO_3$ (2×50 mL) and brine (50 mL). The organic layer was dried ($Na_2SO_4$) and concentrated under reduced pressure. The resulting solid was triturated using EtOAc/hexanes to give the title compound PN2-043 as a yellow solid (1.1 g, 87%). $^1$H NMR (500 MHz, DMSO-$d_6$) δ: 8.06 (t, J=2.0 Hz, 1H), 7.87 (t, J=2.0 Hz, 1H), 7.65 (t, J=2.0 Hz, 1H), 1.32 (s, 9H). HPLC-MS (ESI+): m/z 315.1 [100%, (M+Na)$^+$].

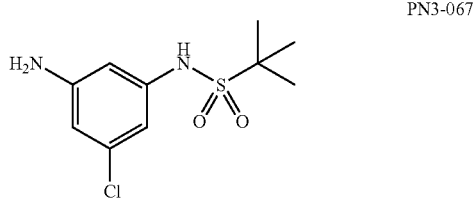

PN3-067

N-(3-Amino-5-chlorophenyl)-2-methylpropane-2-sulfonamide (PN3-067). Scheme has been corrected. A 50 mL pressure tube equipped with a stir bar was charged with PN3-066 (0.85 g, 2.9 mmol, 1.0 equiv.), Fe (0.486 g, 8.7 mmol, 3.0 equiv.), $NH_4Cl$ (0.776 g, 14.5 mmol, 5.0 equiv.) and then 18 mL of EtOH and 5 mL of $H_2O$. The resulting reaction was stirred for at 80° C. until complete consumption of starting material. The crude reaction mixture was filtered through the celite and quenched with water and extracted with EtOAc (volume) to afford the title compound PN3-128 as a white powder (0.7 g, 92%). $^1$H NMR (500 MHz, DMSO-$d_6$) δ: 9.50 (s, 1H), 6.48 (t, J=1.9 Hz, 1H), 6.44 (t, J=1.9 Hz, 1H), 6.25 (t, J=2.0 Hz, 1H), 5.48 (s, 2H), 1.27 (s, 9H). HPLC-MS (ESI+): m/z 263.1 [100%, (M+H)$^+$], 547.1 [10%, (2M+Na)$^+$].

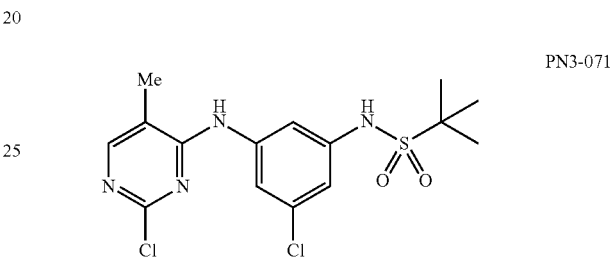

PN3-071

N-(3-Chloro-5-((2-chloro-5-methylpyrimidin-4-yl)amino)phenyl)-2-methylpropane-2-sulfonamide (PN3-071). A mixture of 2,4-dichloro-5-methylpyrimidine (0.532 g, 2.64 mmol, 1.0 equiv.), PN3-067 (0.840 g, 3.26 mmol, 1.0 equiv.), and DIPEA (1.4 mL, 7.9 mmol, 2.4 equiv.) in isopropanol (12 mL) was stirred and heated at 160° C. After 3 days, reaction was quenched with water and extracted with EtOAc (2×10 mL). The combined organic layers were dried ($Na_2SO_4$) and evaporated under vacuum. The residue was subjected to chromatography to afford title compound PN3-071 as a light yellow powder (0.77 g, 61%). $^1$H NMR (500 MHz, DMSO-$d_6$) δ: 9.93 (s, 1H), 8.99 (s, 1H), 8.33 (m, 1H), 7.67 (t, J=1.9 Hz, 1H), 7.48 (t, J=1.9 Hz, 1H), 7.03 (t, J=1.9 Hz, 1H), 2.18 (d, J=0.9 Hz, 3H), 1.33 (s, 9H). HPLC-MS (ESI+): m/z 389.1 [100%, (M+H)$^+$], 801.1 [10%, (2M+Na)$^+$]. HRMS (ESI+): m/z calcd for $C_{14}H_{15}Cl_2N_4O_2S$ (M+H)$^+$ 388.0528, found 388.0597.

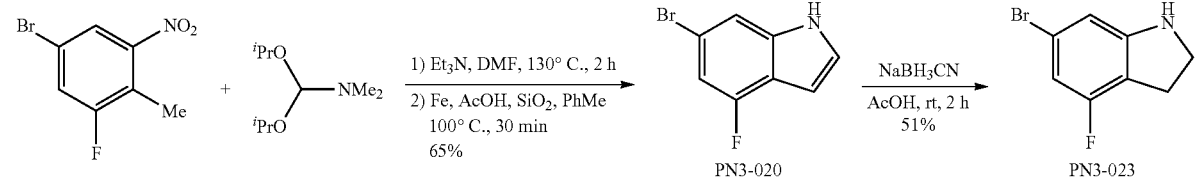

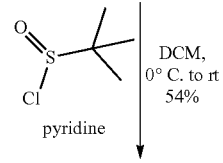

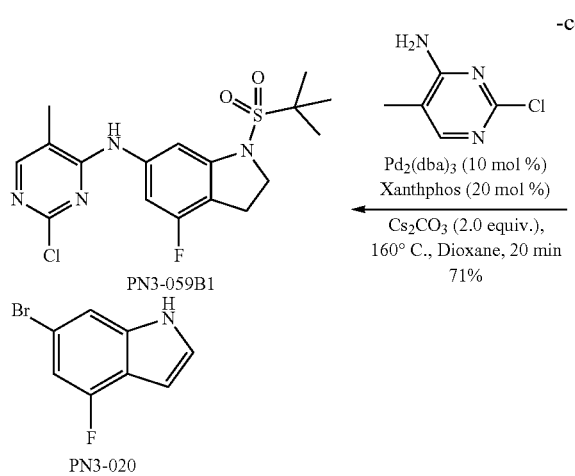

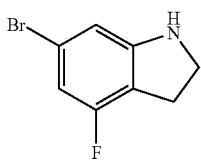

6-Bromo-4-fluoro-1H-indole (PN3-020). A dry 100-mL round bottom flask was charged with 4-bromo-2-fluoro-6-nitrotoluene (4.0 g; 17.0 mmol, 1 equiv.), N,N-dimethylformamide diisopropyl acetal (7.9 mL; 38.0 mmol; 2.2 equiv.), triethylamine (2.6 mL; 18.7 mmol; 1.1 equiv.), anhydrous DMF (15 mL) and the mixture stirred at 130° C. for 2 h. After removal of the solvent in vacuo, the residue was dissolved in a mixture of toluene (30 mL) and acetic acid (40 mL), followed by the addition of iron (19.0 g; 340.0 mmol; 20 equiv.) and silica (18 g). The dark red mixture was heated to 100° C. with vigorous stirring for 6 h. The mixture was then cooled to room temperature, diluted with EtOAc (100 mL), filtered and the solids were thoroughly washed with EtOAc (2×50 mL). The combined filtrates were washed with sat. aq. $Na_2S_2O_5$ (15 mL), sat. aq. $NaHCO_3$ (15 mL) and brine (15 mL), dried ($Na_2SO_4$) and concentrated in vacuo to give the title compound PN3-020 as brown oil (2.34 g, 65%). $^1$H NMR (500 MHz, DMSO-$d_6$) δ: 8.21 (s, 1H), 7.27 (d, J=1.2 Hz, 1H), 7.09 (t, J=2.8 Hz, 1H), 6.88 (dd, J=9.6, 1.4 Hz, 1H), 6.54 (t, J=2.5 Hz, 1H). HPLC-MS (ESI+): m/z 214.1 [100%, (M+H)$^+$].

6-Bromo-4-fluoroindoline (PN3-023). To PN3-020 (1.5 g, 7.0 mmol, 1.0 equiv.) in AcOH (3 mmol) at room temperature was added $NaBH_3CN$ (0.88 g, 14.0 mmol, 2 eq.). The reaction was stirred at the same temperature for 2-4 h. The completion of the reaction was monitored by HPLC. Upon completion, water was added and the reaction mixture was concentrated to dryness. Water (20 mL) was added to the crude residue and the reaction mixture was extracted with EtOAc (2×20 mL). The combined organic layers were washed with saturated aqueous $NaHCO_3$ (10 mL), brine (10 mL), dried ($Na_2SO_4$) filtered and concentrated. The residue was purified by column chromatography ($SiO_2$) eluting with hexanes/EtOAc (20%) to give the title compound PN3-023 as a brown oil (1.1 g, 51%). $^1$H NMR (500 MHz, DMSO-$d_6$) δ: 6.47 (dd, J=8.2, 1.5 Hz, 1H), 6.44 (d, J=1.5 Hz, 1H), 3.54 (t, J=8.5 Hz, 2H), 2.93 (td, J=8.6, 1.0 Hz, 2H). HPLC-MS (ESI+): m/z 216.1 [100%, (M+H)$^+$].

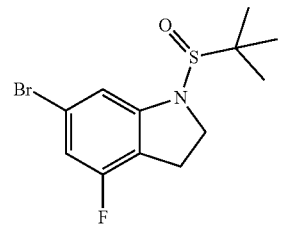

6-Bromo-1-(tert-butylsulfinyl)-4-fluoroindoline (PN3-030). PN3-023 (0.91 g, 4.16 mmol, 1.0 equiv.) and pyridine (1.1 mL, 12.6 mmol, 3.0 equiv.) in DCM (15 mL) was added t-butylsulfinyl chloride (0.620 mL, 5.0 mmol, 1.2 equiv.) in DCM (1 mL) at room temperature under argon. The mixture was stirred overnight at room temperature. The reaction mixture was diluted with EtOAc (10 mL) and washed with HCl (1 M aq. solution, 10 mL), water (10 mL), and brine (10 mL). The organic layer was dried ($Na_2SO_4$) and concentrated under reduced pressure. The resulting residue was purified via column chromatography ($SiO_2$) eluting with hexanes/EtOAc (50%) to give the title compound PN3-030 as a light brown powder (0.72 g, 54%). $^1$H NMR (500 MHz, DMSO-$d_6$) δ: 6.62 (dd, J=8.4, 1.6 Hz, 1H), 6.55 (d, J=1.6 Hz, 1H), 3.54 (t, J=8.6 Hz, 2H), 3.15 (m, 2H), 1.17 (s, 9H). $^{19}$F NMR (479 MHz, DMSO-$d_6$) δ: −116.71 (d, J=8.4 Hz). HPLC-MS (ESI+): m/z 342.1 [60%, (M+Na)$^+$], 663.1 [100%, (2M+Na)$^+$].

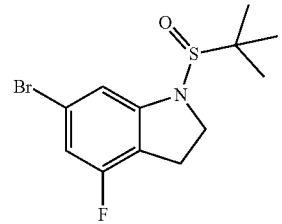

6-Bromo-1-(tert-butylsulfonyl)-4-fluoroindoline (PN3-058): To PN2-030 (0.72, 2.2 mmol, 1.0 equiv.) in DCM (15 mL) was added m-CPBA (65%, 0.46 g, 2.7 mmol, 1.2 equiv.) under Argon. The mixture was stirred at room temperature for 12 h at room temperature. The reaction mixture was diluted with DCM (50 mL) and washed with saturated NaHCO$_3$ (2×50 mL) and brine (50 mL). The organic layer was dried (Na$_2$SO$_4$) and concentrated under reduced pressure. The resulting solid was triturated using EtOAc/hexanes to give the title compound PN3-058 as a light yellow solid (0.54 g, 71%). $^1$H NMR (500 MHz, DMSO-d$_6$) δ: 7.18 (d, J=1.5 Hz, 1H), 7.14 (dd, J=8.2, 1.5 Hz, 1H), 4.12 (d, J=8.7 Hz, 2H), 3.12 (t, J=8.5 Hz, 2H), 1.39 (s, 9H). $^{19}$F NMR (479 MHz, DMSO-d$_6$) δ: −115.50 (d, J=8.1 Hz). HPLC-MS (ESI+): m/z 358.1 [100%, (M+Na)$^+$], 695.1 [10%, (2M+Na)$^+$].

PN3-059

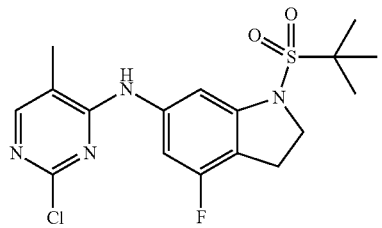

1-(tert-Butylsulfonyl)-N-(2-chloro-5-methylpyrimidin-4-yl)-4-fluoroindolin-6-amine (PN3-059). The bromoindoline PN3-058 (0.4 g, 1.2 mmol, 1.2 equiv.), 2-chloro-5-methylpyrimidin-4-amine (143.1 mg, 1.0 mmol, 1.0 equiv.), Pd$_2$(dba)$_3$ (91.5 mg, 0.1 mmol), Xanthphos (115.5 mg, 0.2 mmol), and Cs$_2$CO$_3$ (0.65 g, 2.0 mmol, 2.0 equiv.) were combined as a mixture, in a pressure tube, in degassed toluene (0.8 mL) and heated at 90° C. for 16 h under N$_2$. The reaction mixture was cooled to room temperature and partitioned between saturated aqueous NH$_4$Cl (20 mL) and EtOAc (10 mL). The layers were separated, and the aqueous layer was extracted twice more with EtOAc (10 mL). The combined organic extracts were washed with brine, dried (MgSO$_4$), and concentrated under reduced pressure to give yellow oil which was purified by flash chromatography (SiO$_2$) to provide PN3-059 as a light yellow solid (0.28 g, 71%). $^1$H NMR (500 MHz, DMSO-d$_6$) δ: 8.95 (s, 1H), 8.09 (d, J=1.0 Hz, 1H), 7.53 (d, J=1.6 Hz, 1H), 7.20 (dd, J=11.1, 1.7 Hz, 1H), 4.13 (t, J=8.4 Hz, 2H), 3.13 (t, J=8.5 Hz, 2H), 2.18 (d, J=0.9 Hz, 3H), 1.43 (s, 9H). $^{19}$F NMR (479 MHz, DMSO-d$_6$) δ: −117.83 (d, J=11.2 Hz). HPLC-MS (ESI+): m/z 399.2 [100%, (M+Na)$^+$], 819.1 [90%, (2M+Na)$^+$].
Routes to Dianilinopyrimdines: Procedure C:

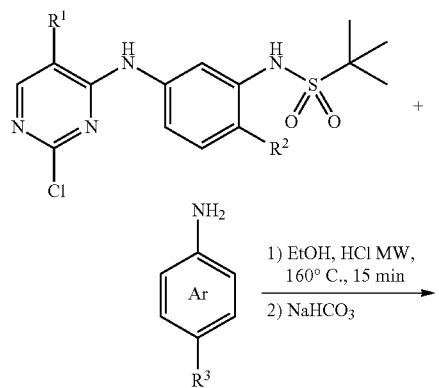

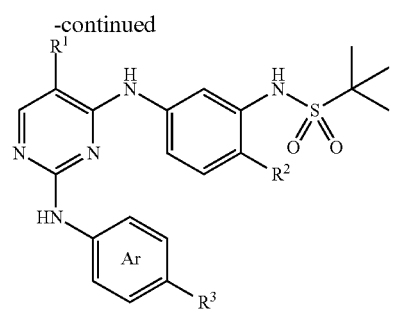

Both starting materials were placed in a microwave vial and EtOH (1.0 mL) was added. After stirring the reaction mixture for 5 min at room temperature, HCl (1 mL, 4 M) was added and the reaction was heated in a microwave reactor at 160° C. for 15 min. After confirming the complete consumption of starting material (HPLC-MS), the crude reaction mixture was partitioned between EtOAc (~50 mL) and NaHCO$_3$ (~10 mL). The organic layer was washed with brine (~5 mL), dried (Na$_2$SO$_4$) and concentrated under reduced pressure. The residue was purified using 4 g SiO$_2$, eluting with a gradient of DCM-MeOH (up to 15% MeOH) to obtain the title compound.

PN1-004

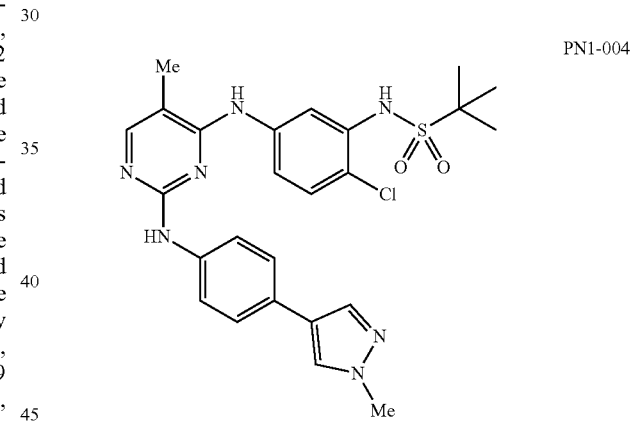

N-(2-Chloro-5-((5-methyl-2-((4-(1-methyl-1H-pyrazol-4-yl)phenyl)amino)pyrimidin-4-yl)amino)phenyl)-2-methylpropane-2-sulfonamide (PN1-004). This was prepared using procedure C from SG3-012 (100.0 mg, 0.256 mmol, 1.0 equiv.), 4-(1-methyl-1H-pyrazol-4-yl)aniline (45.0 mg, 0.256 mmol, 1.0 equiv.), EtOH (1.0 mL) and 4M HCl (1.0 mL) for 15 min at 160° C. The title compound PN1-004 was isolated after trituration (Hex/EtOAc) as a light brown powder (20 mg, 15%). HPLC: 98% [tR=12.0 min, gradient MeOH-water (with 0.1% formic acid), 5-95% over 20 min.]. $^1$H NMR (500 MHz, DMSO-d$_6$) δ 9.34 (s, 1H), 8.91 (s, 1H), 8.49 (s, 1H), 7.99 (s, 1H), 7.93 (d, J=1.0 Hz, 1H), 7.91 (d, J=2.6 Hz, 1H), 7.79-7.73 (m, 2H), 7.67-7.57 (m, 2H), 7.40 (dd, J=8.7, 2.6 Hz, 2H), 3.85 (s, 3H), 2.12 (s, 3H), 1.33 (s, 9H). HPLC-MS (ESI+): m/z 526.3 [40%, (M+H)$^+$]. HRMS (ESI+): m/z calcd for C$_{25}$H$_{28}$ClN$_7$O$_2$S (M+H)$^+$ 526.1786, found 526.1779.

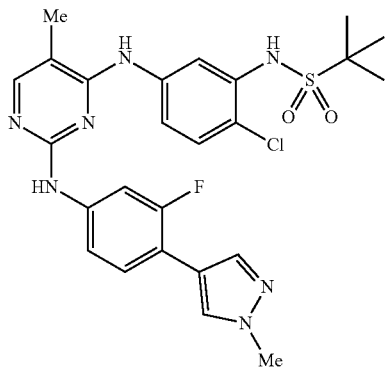

PN1-005

N-(2-Chloro-5-((2-((3-fluoro-4-(1-methyl-1H-pyrazol-4-yl)phenyl)amino)-5-methylpyrimidin-4-yl)amino)phenyl)-2-methylpropane-2-sulfonamide (PN1-005). This was prepared using procedure C from SG3-012 (100.0 mg, 0.256 mmol, 1.0 equiv.), PN1-003 (50.0 mg, 0.256 mmol, 1.0 equiv.), EtOH (1.0 mL) and 4M HCl (1.0 mL) for 15 min at 160° C. The title compound PN1-005 was isolated after trituration (Hex/EtOAc) as a light brown powder (80 mg, 57%). HPLC: 97% [$t_R$=14.95 min, gradient MeOH-water (with 0.1% formic acid), 5-95% over 20 min.]. $^1$H NMR (500 MHz, DMSO-$d_6$) δ 9.34 (s, 1H), 9.19 (s, 1H), 8.58 (s, 1H), 8.02-7.94 (m, 2H), 7.86-7.78 (m, 2H), 7.80-7.69 (m, 2H), 7.50 (t, J=8.8 Hz, 1H), 7.44-7.32 (m, 2H), 3.88 (s, 3H), 2.13 (d, J=0.9 Hz, 3H), 1.33 (s, 9H). $^{19}$F NMR (479 MHz, DMSO-$d_6$) δ: −114.70. HPLC-MS (ESI+): m/z 544.2 [100%, (M+H)$^+$], 272.7 [20% (M+2H)$^{2+}$]. HRMS (ESI+): m/z calcd for $C_{25}H_{27}ClFN_7O_2S$ (M+H)$^+$ 543.1692, found 543.1686.

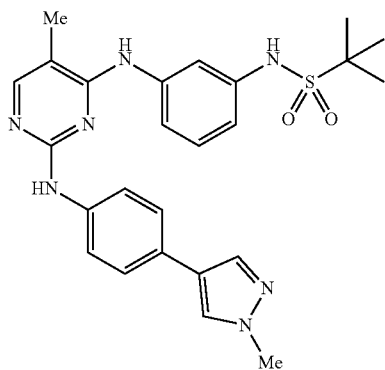

PN1-006

2-Methyl-N-(3-((5-methyl-2-((4-(1-methyl-1H-pyrazol-4-yl)phenyl)amino)pyrimidin-4-yl)amino)phenyl)propane-2-sulfonamide (PN1-006). This was prepared using procedure C from SG3-053 (91.0 mg, 0.256 mmol, 1.0 equiv.), 4-(1-methyl-1H-pyrazol-4-yl)aniline (45.0 mg, 0.256 mmol, 1.0 equiv.), EtOH (1.0 mL) and 4M HCl (1.0 mL) for 15 min at 160° C. The title compound PN1-006 was isolated after trituration (Hex/EtOAc) as a light brown powder (55 mg, 43%). HPLC: 98% [$t_R$=12.0 min, gradient MeOH-water (with 0.1% formic acid), 5-95% over 20 min.]. $^1$H NMR (500 MHz, DMSO-$d_6$) δ 9.60 (s, 1H), 8.85 (s, 1H), 8.38 (s, 1H), 7.98 (d, J=0.8 Hz, 1H), 7.90 (d, J=0.9 Hz, 1H), 7.75 (d, J=0.8 Hz, 1H), 7.65 (d, J=8.7 Hz, 1H), 7.56 (t, J=2.1 Hz, 1H), 7.52-7.47 (m, 1H), 7.35 (d, J=8.7 Hz, 1H), 7.25 (t, J=8.1 Hz, 1H), 7.03 (ddd, J=8.1, 2.2, 1.0 Hz, 1H), 3.85 (s, 3H), 2.30-1.92 (m, 3H), 1.30 (s, 9H). HPLC-MS (ESI+): m/z 492.3 [100%, (M+H)$^+$]. HRMS (ESI+): m/z calcd for $C_{25}H_{29}N_7O_2S$ (M+H)$^+$ 492.2176, found 492.2170.

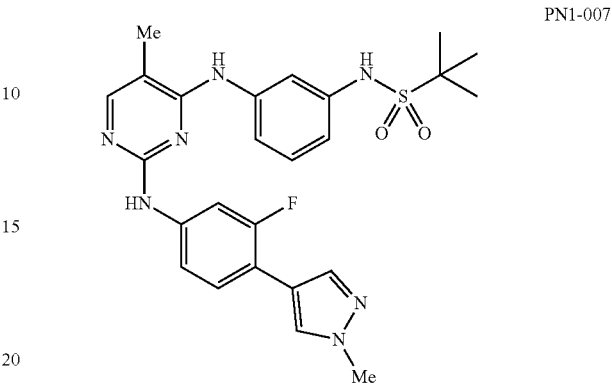

PN1-007

N-(3-((2-((3-Fluoro-4-(1-methyl-1H-pyrazol-4-yl)phenyl)amino)-5-methylpyrimidin-4-yl)amino)phenyl)-2-methylpropane-2-sulfonamide (PN1-007). This was prepared using procedure C from SG3-053 (91.0 mg, 0.256 mmol, 1.0 equiv.), PN1-003 (50.0 mg, 0.256 mmol, 1.0 equiv.), EtOH (1.0 mL) and 4M HCl (1.0 mL) for 15 min at 160° C. The title compound PN1-007 was isolated after trituration (Hex/EtOAc) as a light brown powder (57.4 mg, 44%). HPLC: 98% [$t_R$=12.0 min, gradient MeOH-water (with 0.1% formic acid), 5-95% over 20 min.]. $^1$H NMR (500 MHz, DMSO-$d_6$) δ: 9.66 (s, 1H), 9.19 (s, 1H), 8.51 (s, 1H), 8.03 (d, J=2.1 Hz, 1H), 7.99 (d, J=0.9 Hz, 1H), 7.87-7.73 (m, 2H), 7.60-7.47 (m, 3H), 7.42 (dd, J=8.5, 2.1 Hz, 1H), 7.31 (t, J=8.1 Hz, 1H), 7.10 (ddd, J=8.1, 2.2, 0.9 Hz, 1H), 3.93 (s, 3H), 2.21-2.08 (m, 3H), 1.34 (s, 9H). $^{19}$F NMR (479 MHz, DMSO-$d_6$) δ: −114.53 (dd, J=14.6, 9.4 Hz). HPLC-MS (ESI+): m/z 510.2 [100% (M+H)$^{2+}$]. HRMS (ESI+): m/z calcd for $C_{25}H_{29}FN_7O_2S$ (M+H)$^+$ 510.2082, found 509.2074.

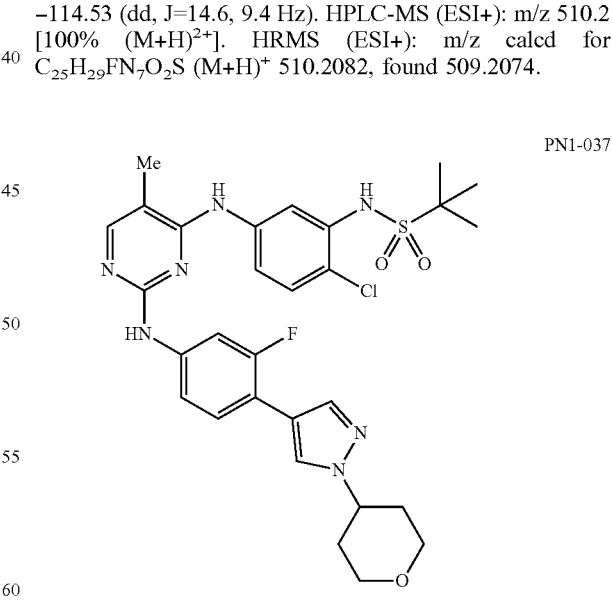

PN1-037

N-(2-chloro-5-((2-((3-fluoro-4-(1-(tetrahydro-2H-pyran-4-yl)-1H-pyrazol-4-yl)phenyl)amino)-5-methylpyrimidin-4-yl)amino)phenyl)-2-methylpropane-2-sulfonamide (PN1-037). This was prepared using procedure C from SG3-012 (100.0 mg, 0.256 mmol, 1.0 equiv.), PN1-029 (67.0 mg, 0.256 mmol, 1.0 equiv.), EtOH (1.0 mL) and 4M HCl (1.0 mL) for 15 min at 160° C. The title compound PN1-037 was isolated after chromatography as a light brown powder (58 mg, 37%). HPLC: 95% [$t_R$=16.27 min, gradient MeOH-water (with 0.1% formic acid), 5-95% over 20 min.]. $^1$H NMR (500 MHz, DMSO-$d_6$) δ: 9.34 (s, 1H), 9.19 (s, 1H), 8.58 (s, 1H), 8.11-8.04 (m, 1H), 7.97 (d, J=0.9 Hz, 1H), 7.82 (dd, J=3.8, 2.0 Hz, 2H), 7.81-7.68 (m, 2H), 7.52 (t, J=8.8 Hz, 1H), 7.44-7.34 (m, 2H), 4.48-4.37 (m, 1H), 4.04-3.89 (m, 2H), 3.53-3.41 (m, 2H), 2.13 (d, J=0.8 Hz, 3H), 2.04-1.91 (m, 4H), 1.33 (s, 9H). $^{19}$F NMR (479 MHz, DMSO-$d_6$) δ: −109.07. HPLC-MS (ESI+): m/z 614.2 [100%, (M+H)$^+$], 307 [5% (M+2H)$^{2+}$]. HRMS (ESI+): m/z calcd for $C_{29}H_{34}ClFN_7O_2S$ (M+H)$^+$ 614.2111, found 614.2099.

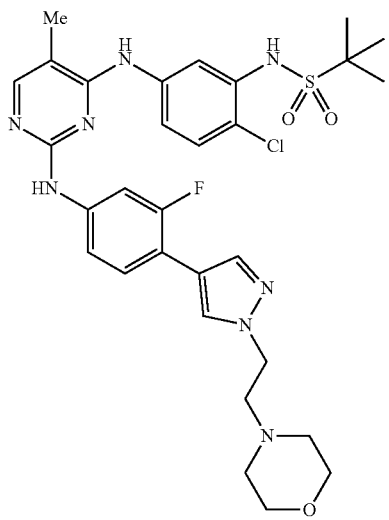

PN1-038

N-(2-Chloro-5-((2-((3-fluoro-4-(1-(2-morpholinoethyl)-1H-pyrazol-4-yl)phenyl)amino)-5-methylpyrimidin-4-yl)amino)phenyl)-2-methylpropane-2-sulfonamide (PN1-038). This was prepared using procedure C from the reaction of SG3-012 (100.0 mg, 0.256 mmol, 1.0 equiv.), PN1-032 (74.0 mg, 0.256 mmol, 1.0 equiv.), EtOH (1.0 mL) and 4M HCl (1.0 mL) for 15 min at 160° C. The title compound PN1-038 was isolated after chromatography as a light brown powder (69 mg, 41%). HPLC: 97% [$t_R$=13.72 min, gradient MeOH-water (with 0.1% formic acid), 5-95% over 20 min.]. $^1$H NMR (500 MHz, DMSO-$d_6$) δ: 9.34 (s, 1H), 9.20 (s, 1H), 8.58 (s, 1H), 8.05-8.03 (m, 1H), 7.97 (d, J=0.9 Hz, 1H), 7.81 (d, J=2.5 Hz, 2H), 7.75 (dd, J=14.5, 2.2 Hz, 1H), 7.50 (t, J=8.8 Hz, 1H), 7.43-7.33 (m, 2H), 4.26 (t, J=6.6 Hz, 2H), 3.71-3.49 (m, 6H), 2.73 (t, J=6.6 Hz, 2H), 2.43 (s, 3H), 2.13 (d, J=0.9 Hz, 3H), 1.33 (s, 9H). $^{19}$F NMR (479 MHz, DMSO-$d_6$) δ: −114.67 (dd, J=14.4, 9.1 Hz). HPLC-MS (ESI+): m/z 643.3 [40%, (M+H)$^+$], 322.2 [100% (M+2H)$^{2+}$]. HRMS (ESI+): m/z calcd for $C_{30}H_{37}ClFN_8O_2S$ (M+H)$^+$ 643.2376, found 643.2364.

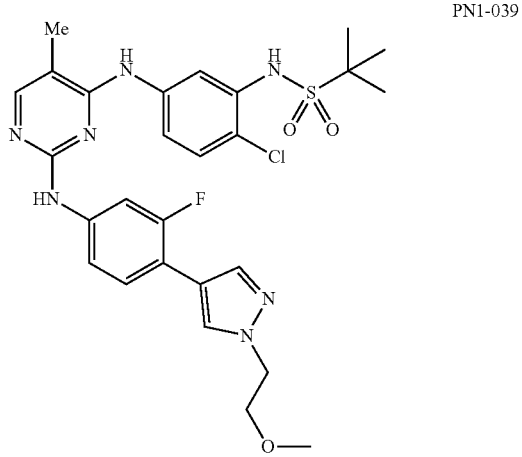 [SMILES: COCCn1cc(-c2ccc(Nc3ncc(C)c(Nc4ccc(Cl)c(NS(=O)(=O)C(C)(C)C)c4)n3)cc2F)cn1]

PN1-039

N-(2-chloro-5-((2-((3-fluoro-4-(1-(2-methoxyethyl)-1H-pyrazol-4-yl)phenyl)amino)-5-methylpyrimidin-4-yl)amino)phenyl)-2-methylpropane-2-sulfonamide (PN1-039). This was prepared using procedure C from the reaction of SG3-012 (100.0 mg, 0.256 mmol, 1.0 equiv.), PN1-034 (60.0 mg, 0.256 mmol, 1.0 equiv.), EtOH (1.0 mL) and 4M HCl (1.0 mL) for 15 min at 160° C. The title compound PN1-039 was isolated after chromatography as a light brown powder (46.6 mg, 31%). HPLC: 98% [$t_R$=16.1 min, gradient MeOH-water (with 0.1% formic acid), 5-95% over 20 min.]. $^1$H NMR (500 MHz, DMSO-$d_6$) δ: 9.34 (s, 1H), 9.20 (s, 1H), 8.58 (s, 1H), 7.82 (dd, J=4.6, 1.9 Hz, 2H), 7.79-7.72 (m, 2H), 7.50 (d, J=8.9 Hz, 1H), 7.45-7.35 (m, 1H), 4.30 (t, J=5.3 Hz, 2H), 3.71 (t, J=5.4 Hz, 2H), 3.25 (s, 3H), 2.13 (s, 3H), 1.33 (s, 9H). $^{19}$F NMR (479 MHz, DMSO-$d_6$) δ: −114.64 (t, J=12.0 Hz). HPLC-MS (ESI+): m/z 588.2 [100%, (M+H)$^+$], 294.7 [10% (M+2H)$^{2+}$]. HRMS (ESI+): m/z calcd for $C_{27}H_{32}ClFN_7O_3S$ (M+H)$^+$ 588.1954, found 588.1944.

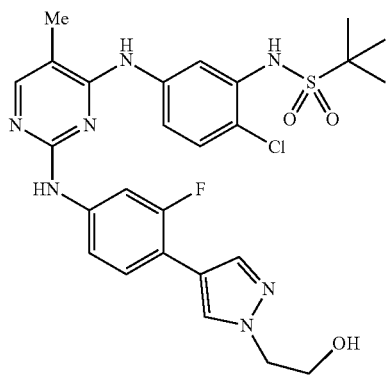

PN1-040

N-(2-chloro-5-((2-((3-fluoro-4-(1-(2-hydroxyethyl)-1H-pyrazol-4-yl)phenyl)amino)-5-methylpyrimidin-4-yl)amino)phenyl)-2-methylpropane-2-sulfonamide (PN1-040). This was prepared using procedure C from SG3-012 (70.0 mg, 0.18 mmol, 1.0 equiv.), PN1-035 (40.0 mg, 0.18 mmol, 1.0 equiv.), EtOH (1.0 mL) and 4M HCl (1.0 mL) for 15 min at 160° C. The title compound PN1-040 was isolated after chromatography as a light brown powder (50.6 mg, 49%). HPLC: 93.5% [$t_R$=15.43 min, gradient MeOH-water (with 0.1% formic acid), 5-95% over 20 min.]. $^1$H NMR (500 MHz, DMSO-$d_6$) δ: 9.34 (s, 1H), 9.19 (s, 1H), 8.58 (s, 1H), 8.01-7.93 (m, 2H), 7.82 (d, J=2.7 Hz, 2H), 7.80-7.73 (m, 2H), 7.51 (t, J=8.8 Hz, 1H), 7.44-7.34 (m, 2H), 4.92 (t, J=5.4 Hz, 1H), 4.18 (t, J=5.6 Hz, 2H), 3.76 (d, J=5.5 Hz, 2H), 2.13 (d, J=0.9 Hz, 3H), 1.33 (s, 9H). $^{19}$F NMR (479 MHz, DMSO-$d_6$) δ: −114.68 (t, J=12.0 Hz). HPLC-MS (ESI+): m/z 574.2 [100%, (M+H)$^+$], 287.6 [10% (M+2H)$^{2+}$]. HRMS (ESI+): m/z calcd for $C_{26}H_{30}ClFN_7O_3S$ (M+H)$^+$ 574.1798, found 574.1790.

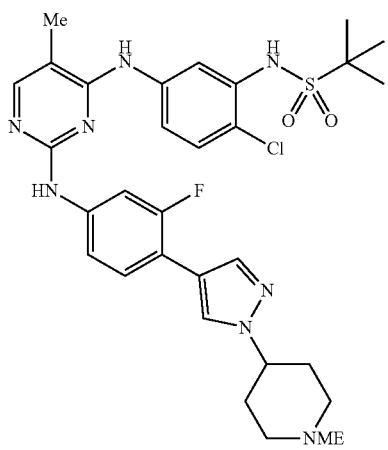

PN1-048

N-(2-chloro-5-((2-((3-fluoro-4-(1-(1-methylpiperidin-4-yl)-1H-pyrazol-4-yl)phenyl)amino)-5-methylpyrimidin-4-yl)amino)phenyl)-2-methylpropane-2-sulfonamide (PN1-048). This was prepared using procedure C from SG3-012 (70.0 mg, 0.18 mmol, 1.0 equiv.), PN1-046 (70.0 mg, 0.256 mmol, 1.0 equiv.), EtOH (1.0 mL) and 4M HCl (1.0 mL) for 15 min at 160° C. The title compound PN1-048 was isolated after chromatography as a light brown powder (27.0 mg, 17%). HPLC: 98% [$t_R$=12.0 min, gradient MeOH-water (with 0.1% formic acid), 5-95% over 20 min.]. $^1$H NMR (500 MHz, DMSO-$d_6$) δ: 9.35 (bs, 1H), 9.19 (s, 1H), 8.57 (s, 1h), 8.05 (m, 2H), 7.97 (m, 1H), 7.81 (m, 2H), 7.74 (m, 2H), 7.49 (t, J=8.8 Hz, 1H), 7.37 (m 2H), 4.16 (dq, J=13.0, 7.5 Hz, 1H), 2.88 (d, J=10.6 Hz, 2H), 2.22 (s, 3H), 2.13 (s, 3H), 2.12-1.96 (m, 4H), 1.33 (s, 9H). $^{19}$F NMR (471 MHz, DMSO-$d_6$) δ: −114.69 (dd, J=14.5, 9.2 Hz). HPLC-MS (ESI+): m/z 627.3 [20%, (M+H)$^+$], 314.2 [100% (M+2H)$^{2+}$]. HRMS (ESI+): m/z calcd for $C_{27}H_{37}ClFN_8O_2S$ (M+H)$^+$ 627.2427, found 627.2419.

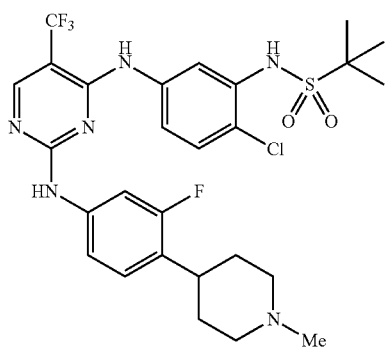

PN1-050

N-(2-Chloro-5-((2-((3-fluoro-4-(1-methylpiperidin-4-yl)phenyl)amino)-5-(trifluoromethyl)pyrimidin-4-yl)amino) phenyl)-2-methylpropane-2-sulfonamide (PN1-050). This was prepared using procedure C from PN1-026 (113.5 mg, 0.256 mmol, 1.0 equiv.), MA9-058 (53.3 mg, 0.256 mmol, 1.0 equiv.), EtOH (1.0 mL) and 4M HCl (1.0 mL) for 15 min at 160° C. The title compound PN1-050 was isolated after chromatography as a light brown powder (92.7 mg, 59%). HPLC: 96% [$t_R$=16.38 min, gradient MeOH-water (with 0.1% TFA), 5-95% over 20 min.]. $^1$H NMR (500 MHz, DMSO-$d_6$) δ: 9.79 (s, 1H), 8.98 (s, 1H), 8.40 (s, 1H), 7.69-7.55 (m, 1H), 7.45 (d, J=8.6 Hz, 1H), 7.33 (d, J=8.9 Hz, 2H), 7.27-7.14 (m, 1H), 7.05 (d, J=9.6 Hz, 1H), 3.11-2.72 (m, 2H), 2.22 (s, 3H), 2.05-1.97 (m, 2H), 1.76-1.54 (m, 4H), 1.29 (s, 9H). $^{19}$F NMR (471 MHz, DMSO-$d_6$) δ: −118.81, −59.39. HPLC-MS (ESI+): m/z 615.2 [100% (M+H)$^{2+}$]. HRMS (ESI+): m/z calcd for $C_{27}H_{32}ClF_4N_6O_2S$ (M+H)$^+$ 614.1927, found 615.1914.

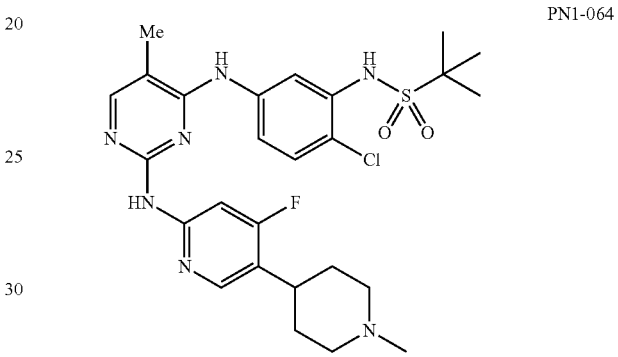

PN1-064

N-(2-Chloro-5-((2-((4-fluoro-5-(1-methylpiperidin-4-yl)pyridin-2-yl)amino)-5-methylpyrimidin-4-yl)amino)phenyl)-2-methylpropane-2-sulfonamide (PN1-064). The chloropyrimdine derivative SG3-012 (82.0 mg, 0.21 mmol, 1.4 equiv.), PN1-055 (32.0 mg, 0.15 mmol, 1.0 equiv.), Pd$_2$(dba)$_3$ (14.2 mg, 0.0155 mmol), Xantphos (18.0 mg, 0.031 mmol), and Cs$_2$CO$_3$ (98.0 mg, 0.3 mmol, 2.0 equiv.) were combined as a mixture, in a pressure tube, in degassed toluene (1 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$), and concentrated under reduced pressure to give a yellow oil. Purification by flash chromatography (SiO$_2$, 10% MeOH in DCM) provided PN1-064 (46.3 mg, 55%) as a white powder. HPLC: 99% [$t_R$=13.17 min, gradient MeOH-water (with 0.1% TFA), 5-95% over 20 min.]. $^1$H NMR (500 MHz, DMSO-$d_6$) δ: 9.25 (s, 1H), 9.11 (d, J=1.6 Hz, 1H), 8.57 (s, 1H), 8.07 (d, J=10.9 Hz, 1H), 7.95-7.86 (m, 3H), 7.72 (dd, J=8.8, 2.6 Hz, 1H), 7.28 (d, J=8.8 Hz, 1H), 2.81 (dt, J=11.8, 3.1 Hz, 2H), 2.64-2.47 (m, 1H), 2.14 (s, 3H), 2.09-2.03 (m, 3H), 1.98-1.86 (m, 2H), 1.79-1.58 (m, 2H), 1.26 (s, 9H). $^{19}$F NMR (479 MHz, DMSO-$d_6$) δ: −108.67 (d, J=12.5 Hz). HPLC-MS (ESI+): m/z 562.3 [20%, (M+H)$^+$], 281.8 [100% (M+2H)$^{2+}$]. HRMS (ESI+): m/z calcd for $C_{26}H_{34}ClFN_7O_2S$ (M+H)$^+$ 562.2162, found 561.2197.

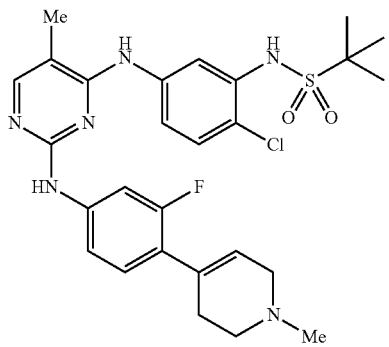

PN1-101

N-(2-Chloro-5-((2-((3-fluoro-4-(1-methyl-1,2,3,6-tetrahydropyridin-4-yl)phenyl)amino)-5-methylpyrimidin-4-yl)amino)phenyl)-2-methylpropane-2-sulfonamide (PN1-101). This was prepared using procedure C from SG3-012 (132.0 mg, 0.34 mmol, 1.0 equiv.), MA9-056 (71.0 mg, 0.34 mmol, 1.0 equiv.), EtOH (1.0 mL) and 4M HCl (140 μL) for 15 min at 160° C. The title compound PN1-101 was isolated after chromatography as a light brown powder (76.0 mg, 40%). HPLC: 99% [$t_R$=13.59 min, gradient MeOH-water (with 0.1% TFA), 5-95% over 20 min.]. $^1$H NMR (500 MHz, DMSO-$d_6$) δ: 9.34 (s, 1H), 9.19 (s, 1H), 8.57 (s, 1H), 7.96 (d, J=0.9 Hz, 1H), 7.78 (d, J=2.6 Hz, 1H), 7.74 (dd, J=8.7, 2.6 Hz, 1H), 7.67 (dd, J=15.0, 2.2 Hz, 1H), 7.38 (d, J=8.7 Hz, 1H), 7.32 (dd, J=8.6, 2.2 Hz, 1H), 7.15 (t, J=8.9 Hz, 1H), 3.00 (q, J=3.0 Hz, 2H), 2.55 (t, J=5.6 Hz, 2H), 2.43 (tt, J=5.5, 2.7 Hz, 2H), 2.28 (s, 3H), 2.13 (d, J=0.8 Hz, 3H), 1.32 (s, 9H). $^{19}$F NMR (479 MHz, DMSO-$d_6$) δ: −114.55 (dd, J=15.0, 9.3 Hz). HPLC-MS (ESI+): m/z 559.3 [40%, (M+H)$^+$], 280.3 [100% (M+2H)$^{2+}$]. HRMS (ESI+): m/z calcd for $C_{27}H_{33}ClFN_6O_2S$ (M+H)$^+$ 559.2053, found 559.2044.

PN1-102

N-(2-Chloro-5-((2-((2,5-difluoro-4-(1-methylpiperidin-4-yl)phenyl)amino)-5-methylpyrimidin-4-yl)amino)phenyl)-2-methylpropane-2-sulfonamide (PN1-102). This was prepared using procedure C from SG3-012 (100.0 mg, 0.254 mmol, 1.0 equiv.), PN1-098 (56.0 mg, 0.254 mmol, 1.0 equiv.), EtOH (1.0 mL) and 4M HCl (100 μL) for 15 min at 160° C. The title compound PN1-102 was isolated after chromatography as a light brown powder (14.7 mg, 10%). HPLC: 99% [$t_R$=13.47 min, gradient MeOH-water (with 0.1% TFA), 5-95% over 20 min.]. $^1$H NMR (500 MHz, DMSO-$d_6$) δ: 9.29 (s, 1H), 8.58 (s, 1H), 8.19 (d, J=1.8 Hz, 1H), 8.02 (d, J=2.6 Hz, 1H), 7.97-7.84 (m, 2H), 7.65 (dd, J=8.8, 2.6 Hz, 1H), 7.29 (d, J=8.8 Hz, 1H), 7.16 (dd, J=12.0, 6.9 Hz, 1H), 3.07-2.80 (m, 2H), 2.72-2.59 (m, 1H), 2.21 (s, 3H), 2.12 (d, J=0.9 Hz, 3H), 2.06-1.90 (m, 2H), 1.68 (ddt, J=9.5, 7.4, 3.6 Hz, 4H), 1.33 (s, 9H). $^{19}$F NMR (479 MHz, DMSO-$d_6$) δ: −120.42 (m), −131.86. HPLC-MS (ESI+): m/z 579.3 [40%, (M+H)$^+$], 290.2 [100% (M+2H)$^{2+}$]. HRMS (ESI+): m/z calcd for $C_{27}H_{34}ClF_2N_6O_2S$ (M+H)$^+$ 579.2115, found 579.2107.

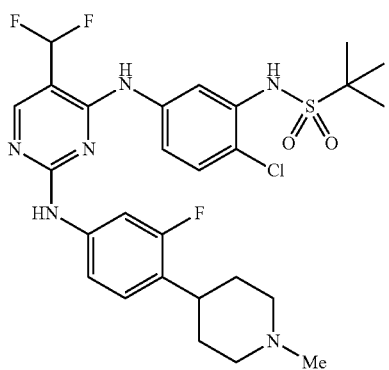

PN1-117

N-(2-Chloro-5-((5-(difluoromethyl)-2-((3-fluoro-4-(1-methylpiperidin-4-yl)phenyl)amino)pyrimidin-4-yl)amino)phenyl)-2-methylpropane-2-sulfonamide (PN1-117). This was prepared using procedure C from PN1-012 (51.0 mg, 0.12 mmol, 1.0 equiv.), MA9-058 (25.0 mg, 0.12 mmol, 1.0 equiv.), EtOH (1.0 mL) and 4M HCl (5 μL) for 20 h at 70° C. The title compound PN1-117 was isolated after chromatography as a light brown powder (36.5 mg, 51%). HPLC: 99% [$t_R$=14.4 min, gradient MeOH-water (with 0.1% TFA), 5-95% over 20 min.]. $^1$H NMR (500 MHz, DMSO-$d_6$) δ: 9.67 (s, 1H), 9.07 (s, 1H), 8.37 (s, 1H), 7.71 (d, J=2.5 Hz, 1H), 7.67-7.51 (m, 2H), 7.47 (d, J=8.7 Hz, 1H), 7.40-7.22 (m, 2H), 7.17 (d, J=3.2 Hz, 1H), 3.10-2.86 (m, 2H), 2.70 (d, J=4.2 Hz, 1H), 2.28 (s, 3H), 2.14-2.00 (m, 1H), 1.73 (qd, J=10.9, 9.7, 4.3 Hz, 4H), 1.36 (s, 9H). $^{19}$F NMR (479 MHz, DMSO-$d_6$) δ: −112.41 (d, J=54.6 Hz), −116.47 (m). HPLC-MS (ESI+): m/z 597.3 [90%, (M+H)$^+$], 299.2 [100% (M+2H)$^{2+}$]. HRMS (ESI+): m/z calcd for $C_{27}H_{33}ClF_3N_6O_2S$ (M+H)$^+$ 597.2021, found 597.2011.

PN1-118

N-(2-Chloro-5-((2-((3-fluoro-4-(1-methylpiperidin-4-yl)phenyl)amino)-5-iodopyrimidin-4-yl)amino)phenyl)-2-methylpropane-2-sulfonamide (PN1-118). This was prepared using procedure C from PN1-008 (100.0 mg, 0.2 mmol, 1.0 equiv.), MA9-058 (41.6 mg, 0.2 mmol, 1.0 equiv.), ⁱPrOH (0.5 mL) and 4M HCl (50 μL) for 20 h at 70° C. The title compound PN1-118 was isolated after chromatography as a light brown powder (54 mg, 40%). HPLC: 98% [t$_R$=15.35 min, gradient MeOH-water (with 0.1% TFA), 5-95% over 20 min.]. $^1$H NMR (500 MHz, DMSO-d$_6$) δ: 9.48 (s, 1H), 9.38 (s, 2H), 8.59 (s, 1H), 8.44 (s, 1H), 7.76 (d, J=2.5 Hz, 1H), 7.68-7.49 (m, 2H), 7.47 (d, J=8.7 Hz, 1H), 7.28 (dd, J=8.5, 2.1 Hz, 1H), 7.12 (t, J=8.6 Hz, 1H), 3.28 (s, 2H), 2.86 (s, 1H), 2.69-2.57 (m, 5H), 1.84 (t, J=5.5 Hz, 4H), 1.37 (s, 9H). $^{19}$F NMR (479 MHz, DMSO-d$_6$) δ: −118.58. HPLC-MS (ESI+): m/z 673.1 [100%, (M+H)$^+$], 337.1 [80% (M+2H)$^{2+}$]. HRMS (ESI+): m/z calcd for C$_{26}$H$_{32}$ClFlN$_6$O$_2$S (M+H)$^+$ 673.1019, found 673.1006.

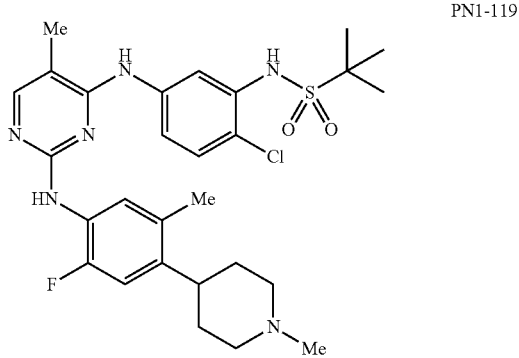 [SMILES: Cc1cc(Nc2ncc(C)c(Nc3ccc(Cl)c(NS(=O)(=O)C(C)(C)C)c3)n2)c(F)cc1C1CCN(C)CC1]

PN1-119

N-(2-Chloro-5-((2-((2-fluoro-5-methyl-4-(1-methylpiperidin-4-yl)phenyl)amino)-5-methylpyrimidin-4-yl)amino)phenyl)-2-methylpropane-2-sulfonamide (PN1-119). This was prepared using procedure C from SG3-012 (50.5 mg, 0.13 mmol, 1.0 equiv.), PN1-109 (29.0 mg, 0.13 mmol, 1.0 equiv.), ⁱPrOH (0.5 mL) and 4M HCl (50 μL) for 20 h at 70° C. The title compound PN1-119 was isolated after chromatography as a light brown powder (24.5 mg, 33%). HPLC: 98% [t$_R$=13.6 min, gradient MeOH-water (with 0.1% TFA), 5-95% over 20 min.]. $^1$H NMR (500 MHz, DMSO-d$_6$) δ: 8.48 (s, 1H), 8.07 (s, 1H), 7.89 (d, J=3.2 Hz, 2H), 7.70 (dd, J=8.8, 2.6 Hz, 1H), 7.60 (d, J=8.6 Hz, 1H), 7.22 (d, J=8.8 Hz, 1H), 7.01 (d, J=12.6 Hz, 1H), 2.91 (d, J=11.0 Hz, 2H), 2.59 (t, J=7.7 Hz, 1H), 2.24 (s, 3H), 2.17 (s, 3H), 2.10 (s, 3H), 2.05 (s, 2H), 1.66 (dd, J=8.1, 3.3 Hz, 4H), 1.32 (s, 9H). $^{19}$F NMR (479 MHz, DMSO-d$_6$) δ: −128.49. HPLC-MS (ESI+): m/z 288.3 [100%, (M+H)$^+$], 575.3 [10% (M+2H)$^{2+}$]. HRMS (ESI+): m/z calcd for C$_{28}$H$_{37}$ClFN$_6$O$_2$S (M+H)$^+$ 575.2366, found 575.2356.

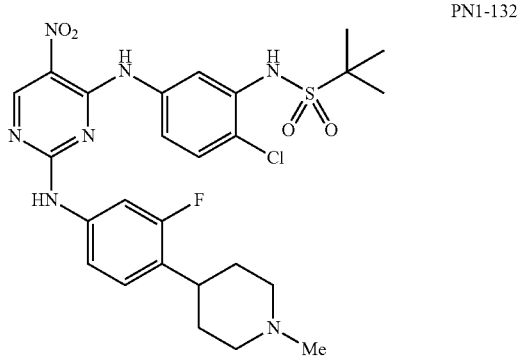 [SMILES: CN1CCC(c2ccc(Nc3ncc([N+](=O)[O-])c(Nc4ccc(Cl)c(NS(=O)(=O)C(C)(C)C)c4)n3)cc2F)CC1]

PN1-132

N-(2-Chloro-5-((2-((3-fluoro-4-(1-methylpiperidin-4-yl)phenyl)amino)-5-nitropyrimidin-4-yl)amino)phenyl)-2-methylpropane-2-sulfonamide (PN1-132). This was prepared using procedure C from PN1-127 (50.2 mg, 0.12 mmol, 1.0 equiv.), MA9-058 (25.0 mg, 0.12 mmol, 1.0 equiv.), EtOH (0.5 mL) and 4M HCl (50 μL) for 20 h at 70° C. The title compound PN1-132 was isolated after chromatography as a yellow powder (49.0 mg, 69%). HPLC: 98% [t$_R$=17.5 min, gradient MeOH-water, 5-95% over 20 min.]. $^1$H NMR (500 MHz, DMSO-d$_6$) δ: 10.57 (bs, 1H), 10.49-10.36 (m, 1H), 9.15 (s, 1H), 7.71 (d, J=2.4 Hz, 1H), 7.56 (d, J=8.5 Hz, 1H), 7.44 (bs, 4H), 7.28 (bs, 1H), 7.15 (s, 1H), 2.99 (d, J=11.1 Hz, 2H), 2.76-2.68 (m, 1H), 2.32 (s, 3H), 2.15 (bs, 2H), 1.84-1.65 (m, 4H), 1.33 (s, 9H). $^{19}$F NMR (479 MHz, DMSO-d$_6$) δ: −118.33. HPLC-MS (ESI+): m/z 592.3 [100%, (M+H)$^+$], 296.8 [10% (M+2H)$^{2+}$]. HRMS (ESI+): m/z calcd for C$_{26}$H$_{32}$ClFN$_7$O$_4$S (M+H)$^+$ 592.1904, found 592.1894.

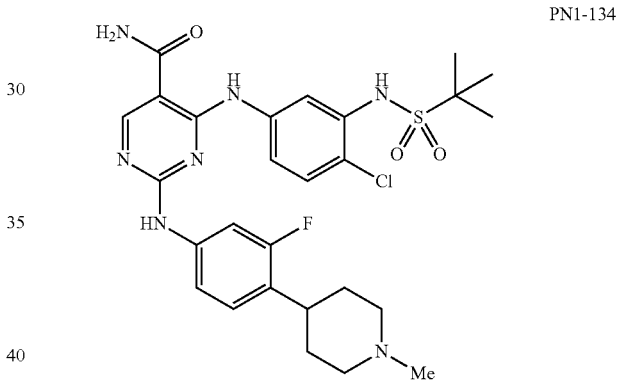

PN1-134

4-((4-Chloro-3-((1,1-dimethylethyl)sulfonamido)phenyl)amino)-2-((3-fluoro-4-(1-methylpiperidin-4-yl)phenyl)amino)pyrimidine-5-carboxamide (PN1-134). This was prepared using procedure C from PN1-126 (50.2 mg, 0.12 mmol, 1.0 equiv.), MA9-058 (25.0 mg, 0.12 mmol, 1.0 equiv.), EtOH (0.5 mL) and 4M HCl (50 μL) for 20 h at 70° C. The title compound PN1-134 was isolated after chromatography as a yellow powder (30.5 mg, 43%). HPLC: 98% [t$_R$=14.76 min, gradient MeOH-water (with 0.1% TFA), 5-95% over 20 min.]. $^1$H NMR (500 MHz, DMSO-d$_6$) δ:11.51 (s, 1H), 9.70 (s, 1H), 9.40 (s, 1H), 8.67 (s, 1H), 8.01 (s, 1H), 7.77 (s, 1H), 7.52 (d, J=13.5 Hz, 1H), 7.45 (d, J=2.6 Hz, 1H), 7.35-7.27 (m, 2H), 7.15 (t, J=8.6 Hz, 1H), 2.87-2.79 (m, 2H), 2.71-2.53 (m, 1H), 1.96 (td, J=11.5, 3.1 Hz, 2H), 1.72-1.54 (m, 4H), 1.23 (s, 9H). $^{19}$F NMR (479 MHz, DMSO-d$_6$) δ: −118.96 (d, J=11.9 Hz). HPLC-MS (ESI+): m/z 590.3 [80%, (M+H)$^+$], 295.7 [100% (M+2H)$^{2+}$]. HRMS (ESI+): m/z calcd for C$_{27}$H$_{34}$ClFN$_7$O$_3$S (M+H)$^+$ 590.2111, found 590.2101.

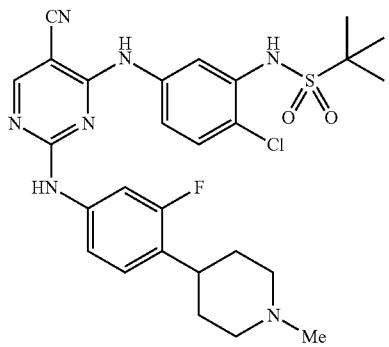

PN1-138

N-(2-Chloro-5-((5-cyano-2-((3-fluoro-4-(1-methylpiperidin-4-yl)phenyl)amino)pyrimidin-4-yl)amino)phenyl)-2-methylpropane-2-sulfonamide (PN1-138). This was prepared from the reaction of PN1-118 (47 mg, 0.07 mmol, 1.0 equiv.), Zn(CN)$_2$ (4.9 mg, 0.047 mmol, 0.6 equiv.) Pd$_2$(dba)$_3$ (0.2 mg), Xantphos (0.4 mg), and TMEDA (1.63 mg, 0.014 mmol, 0.2 equiv.) were combined as a mixture, in a pressure tube, in DMF (0.5 mL) in microwave vial. Then the resulting solution was placed in microwave reactor at 150° C. After 5 min, the reaction mixture was quenched with sat. NH$_4$Cl and extracted with EtOAc (20 mL). The combined organic layers were dried over (Na$_2$SO$_4$) and purified by the flash chromatography to afford PN1-138 (27.2 mg, 68%) as a brown powder HPLC: 93.5% [t$_R$=15.77 min, gradient MeOH-water (with 0.1% TFA), 5-95% over 20 min.]. $^1$H NMR (500 MHz, DMSO-d$_6$) δ: 10.07 (bs, 1H), 9.82 (bs, 1H), 8.56 (bs, 1H), 7.70 (s, 1H), 7.48 (m, 2H), 7.43 (d, J=8.7 Hz, 1H), 7.28 (s, 1H), 7.38 (t, J=5.4 Hz, 1H), 7.14 (s, 1H), 3.12 (m, 2H), 2.79 (m, 1H), 2.45 (m, 2H), 1.76 (s, 4H), 1.31 (s, 9H). $^{19}$F NMR (479 MHz, DMSO-d$_6$) δ: -118.44. HPLC-MS (ESI+): m/z 572.3 [100%, (M+H)$^+$], 286.7 [20% (M+2H)$^{2+}$]. HRMS (ESI+): m/z calcd for C$_{27}$H$_{35}$ClFN$_6$O$_2$S (M+H)$^+$ 572.2005, found 572.1999.

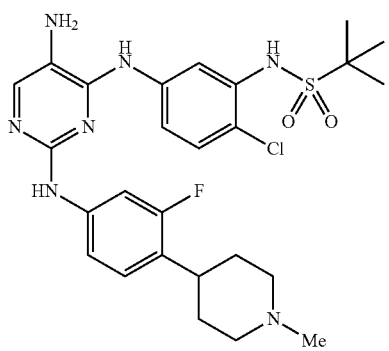

PN1-140

N-(5-((5-Amino-2-((3-fluoro-4-(1-methylpiperidin-4-yl)phenyl)amino)pyrimidin-4-yl)amino)-2-chlorophenyl)-2-methylpropane-2-sulfonamide (PN1-140). This was prepared by reduction of PN1-132 (40 mg, 0.067 mmol), 1.0 equiv.) in the presence of FeCl$_3$·H$_2$O (36 mg, 0.014 mmol, 0.2 equiv.), N$_2$H$_4$·H$_2$O (5.2 mg, 0.014 mmol, 0.2 equiv.), and charcoal (16 mg) were dissolved in dioxane (4 mL) and resulting solution was placed in pre-heated oil bath at 70° C. for 6 h. Then the reaction mixture was filtered through the celite and crude material was subjected to the flash chromatography to afford the PN1-140 (15.7 mg, 42%). HPLC: 99% [t$_R$=13.48 min, gradient MeOH-water (with 0.1% TFA), 5-95% over 20 min.]. $^1$H NMR (500 MHz, DMSO-d$_6$) δ: 8.83 (s, 1H), 8.53 (s, 1H), 8.01 (dd, J=8.8, 2.6 Hz, 1H), 7.80 (d, J=2.6 Hz, 1H), 7.74 (s, 1H), 7.69 (dd, J=14.2, 2.2 Hz, 1H), 7.41 (d, J=8.8 Hz, 1H), 7.32 (dd, J=8.5, 2.2 Hz, 1H), 7.16 (t, J=8.7 Hz, 1H), 4.58 (s, 2H), 2.97 (d, J=11.5 Hz, 2H), 2.78-2.62 (m, 1H), 2.30 (s, 3H), 2.17-2.04 (m, 2H), 1.75 (dq, J=13.0, 5.0, 4.1 Hz, 4H), 1.38 (s, 9H). $^{19}$F NMR (479 MHz, DMSO-d$_6$) δ: -119.35 (dd, J=14.1, 9.0 Hz). HPLC-MS (ESI+): m/z 562.3 [20%, (M+H)$^+$], 281.8 [100% (M+2H)$^{2+}$]. HRMS (ESI+): m/z calcd for C$_{26}$H$_{32}$ClFN$_7$O$_2$S (M+H)$^+$ 562.2162, found 562.2154.

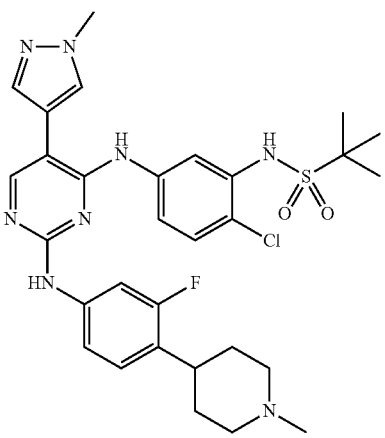

PN1-145

N-(2-Chloro-5-((2-((3-fluoro-4-(1-methylpiperidin-4-yl)phenyl)amino)-5-(1-methyl-1H-pyrazol-4-yl)pyrimidin-4-yl)amino)phenyl)-2-methylpropane-2-sulfonamide (PN1-145). This was prepared using procedure C from PN1-129 (68.0 mg, 0.15 mmol, 1.0 equiv.), MA9-058 (31.2 mg, 0.15 mmol, 1.0 equiv.), EtOH (0.5 mL) and 4M HCl (50 μL) for 48 h at 70° C. The title compound PN1-145 was isolated after chromatography as a light brown powder (47.9 mg, 51%). HPLC: 99% [t$_R$=13.1 min, gradient MeOH-water (with 0.1% TFA), 5-95% over 20 min.]. $^1$H NMR (500 MHz, DMSO-d$_6$) δ: 9.34 (s, 1H), 8.48 (s, 1H), 8.12 (s, 1H), 8.03 (s, 1H), 7.77 (d, J=2.6 Hz, 1H), 7.71 (s, 1H), 7.65 (dd, J=11.2, 2.4 Hz, 2H), 7.44 (d, J=8.7 Hz, 1H), 7.36 (dd, J=8.5, 2.1 Hz, 1H), 7.16 (t, J=8.7 Hz, 1H), 3.96 (s, 3H), 2.97 (d, J=10.2 Hz, 2H), 2.81-2.64 (m, 1H), 2.30 (s, 2H), 2.12 (d, J=10.3 Hz, 2H), 1.83-1.66 (m, 3H), 1.37 (s, 9H). $^{19}$F NMR (479 MHz, DMSO-d$_6$) δ: -119.10 (d, J=11.2 Hz). HPLC-MS (ESI+): m/z 627.3 [20%, (M+H)$^+$], 314.2 [100% (M+2H)$^{2+}$]. HRMS (ESI+): m/z calcd for C$_{30}$H$_{37}$ClFN$_6$O$_2$S (M+H)$^+$ 627.2427, found 627.2416.

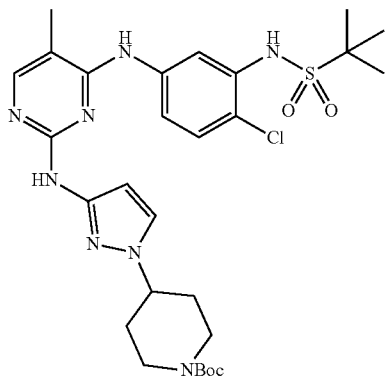

PN2-017

Butyl 4-(3-((4-((4-Chloro-3-((1,1-dimethylethyl)sulfonamido)phenyl)amino)-5-methylpyrimidin-2-yl)amino)-1H-pyrazol-1-yl)piperidine-1-carboxylate (PN2-017). This was prepared using general procedure C from SG3-012 (100.0 mg, 0.256 mmol, 1.0 equiv.), tert-butyl 4-(3-amino-1H-pyrazol-1-yl)piperidine-1-carboxylate (70.0 mg, 0.256 mmol, 1.0 equiv.), $^i$PrOH (2.0 mL) and TFA (30 mg, 0.256 mmol, 1.0 equiv.) for 20 h at 70° C., to afford the title compound PN2-017 (97.0 mg, 61%) after chromatography as a white powder. HPLC: 99% [$t_R$=13.1 min, gradient MeOH-water (with 0.1% TFA), 5-95% over 20 min.]. $^1$H NMR (500 MHz, DMSO-d$_6$) δ: 9.33 (s, 1H), 8.79 (s, 1H), 8.48 (s, 1H), 7.87 (d, J=0.9 Hz, 1H), 7.70 (s, 1H), 7.41 (d, J=8.6 Hz, 1H), 7.34 (s, 1H), 4.18-3.80 (m, 2H), 2.88 (s, 3H), 2.19-1.97 (m, 2H), 1.90 (d, J=12.1 Hz, 2H), 1.64 (d, J=12.4 Hz, 2H), 1.42 (s, 9H), 1.33 (s, 9H). HPLC-MS (ESI+): m/z 619.3 [100%, (M+H)$^+$].

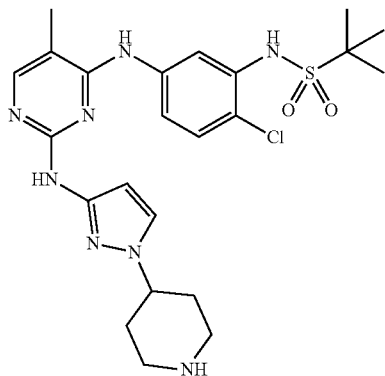

PN2-019

N-(2-Chloro-5-((5-methyl-2-((1-(piperidin-4-yl)-1H-pyrazol-3-yl)amino)pyrimidin-4-yl)amino)phenyl)-2-methylpropane-2-sulfonamide (PN2-019). To a solution of the PN2-017 (213 g, 0.35 mmol) in DCM (2 mL) was added TFA (2 mL) under an argon atmosphere and the reaction mixture was stirred at room temperature. After completion of the reaction (2 h) as determined by total loss of starting material SM, the solvents were removed in vacuo and the residue was diluted with DCM (5 mL). The mixture was cooled to 0° C. and neutralized with sat aq NaHCO$_3$ and extracted with DCM (10×2 ml). The combined organic layers were dried over (Na$_2$SO$_4$) and evaporated to provide pure PN1-019 (167 mg, 89%) as light brown powder. HPLC: 99% [$t_R$=12.1 min, gradient MeOH-water (with 0.1% TFA), 5-95% over 20 min.]. $^1$H NMR (500 MHz, DMSO-d$_6$) δ: 8.92 (s, 1H), 8.20 (s, 1H), 7.86 (d, J=2.5 Hz, 1H), 7.79 (d, J=36.3 Hz, 2H), 7.35 (d, J=8.4 Hz, 1H), 7.17 (s, 1H), 6.76-6.62 (m, 1H), 4.39 (dt, J=11.5, 6.1 Hz, 1H), 3.60-3.43 (m, 2H), 2.98 (dt, J=12.5, 6.1 Hz, 2H), 2.10 (s, 3H), 2.02-1.81 (m, 4H), 1.26 (s, 9H). HPLC-MS (ESI+): m/z 260.1 [100%, (M+H)$^+$], 519.3 [20% (M+2H)$^{2+}$]. HRMS (ESI+): m/z calcd for C$_{23}$H$_{31}$ClN$_8$O$_2$S (M+H)$^+$ 518.1979, found 518.1984.

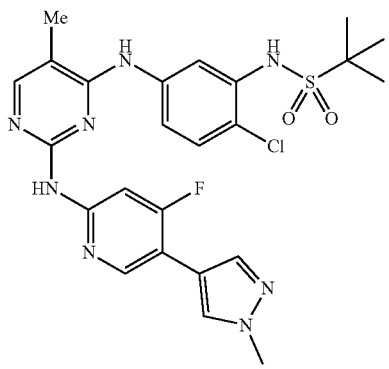

PN2-034

N-(2-Chloro-5-((2-((4-fluoro-5-(1-methyl-1H-pyrazol-4-yl)pyridin-2-yl)amino)-5-methylpyrimidin-4-yl)amino)phenyl)-2-methylpropane-2-sulfonamide (PN2-034). The chloropyrimidine SG3-012 (70.0 mg, 0.20 mmol, 1.0 equiv.), PN2-020 (31.4 mg, 0.22 mmol, 1.1 equiv.), Pd$_2$(dba)$_3$ (13, 0.014 mmol), Xantphos (16.2 mg, 0.048 mmol), and Cs$_2$CO$_3$ (130 mg, 0.4 mmol, 2.0 equiv.) were combined as a mixture, in a pressure tube, in degassed toluene (1 mL) and heated at 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried over (MgSO$_4$) and concentrated under reduced pressure to give a yellow oil. Purification by flash chromatography (SiO$_2$, 10% MeOH in DCM) provided PN2-034 (59 mg, 54%) as a white powder. HPLC: 99% [$t_R$=7.52 min, gradient MeOH-water (with 0.1% TFA), 5-95% over 20 min.]. $^1$H NMR (500 MHz, DMSO-d$_6$) δ: 9.37 (s, 1H), 8.73 (s, 1H), 8.63 (d, J=11.2 Hz, 1H), 8.23-8.13 (m, 2H), 8.12-8.02 (m, 2H), 7.96-7.87 (m, 3H), 7.44 (d, J=8.8 Hz, 1H), 3.95 (s, 3H), 2.38 (s, 3H), 1.39 (s, 9H). $^{19}$F NMR (479 MHz, DMSO-d$_6$) δ: −105.69 (t, J=12.9 Hz). HPLC-MS (ESI+): m/z 545.2 [100%, (M+H)$^+$]. HRMS (ESI+): m/z calcd for C$_{24}$H$_{27}$ClFN$_8$O$_2$S (M+H)$^+$ 545.1645, found 545.1667.

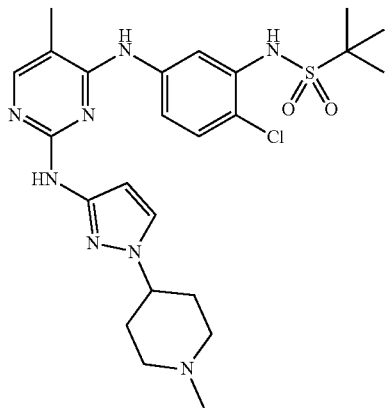

PN2-042

N-(2-Chloro-5-((5-methyl-2-((1-(1-methylpiperidin-4-yl)-1H-pyrazol-3-yl)amino)pyrimidin-4-yl)amino)phenyl)-2-methylpropane-2-sulfonamide (PN2-042). According to the general procedure C, the reaction of SG3-012 (100 mg, 0.256 mmol, 1.0 equiv.), PN2-040 (46 mg, 0.256 mmol, 1.0 equiv.), EtOH (1.0 mL) and 4M HCl (1.0 mL) for 15 min at 160° C., afforded the title compound PN1-042 (58.6 mg, 43%) after chromatography as a white powder. HPLC: 99% [$t_R$=12.2 min, gradient MeOH-water (with 0.1% TFA), 5-95% over 20 min.]. $^1$H NMR (500 MHz, DMSO-$d_6$) δ: 8.97 (s, 1H), 8.39 (s, 1H), 7.99-7.79 (m, 2H), 7.70 (s, 1H), 7.50 (d, J=8.6 Hz, 1H), 7.23 (s, 1H), 7.10 (s, 1H), 4.15 (dt, J=12.0, 6.7 Hz, 1H), 3.18 (m, 2H), 2.51-2.35 (m, 5H), 2.12 (s, 3H), 1.96-1.74 (m, 4H), 1.33 (s, 9H). HPLC-MS (ESI+): m/z 533.3 [20%, (M+H)$^+$], 267.2 [100% (M+2H)$^{2+}$]. HRMS (ESI+): m/z calcd for $C_{24}H_{34}ClN_8O_2S$ (M+H)$^+$ 533.2208, found 533.2207.

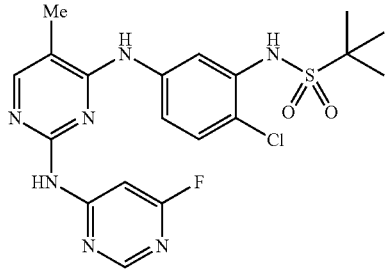

PN2-064

N-(2-Chloro-5-((2-((6-fluoropyrimidin-4-yl)amino)-5-methylpyrimidin-4-yl)amino)phenyl)-2-methylpropane-2-sulfonamide (PN2-064). The chloropyrimidine SG3-012 (82.3 mg, 0.21 mmol, 1.4 equiv.), PN2-062 (31.4 mg, 0.15 mmol, 1.0 equiv.), Pd$_2$(dba)$_3$ (14.2, 0.0155 mmol), Xantphos (18 mg, 0.031 mmol), and Cs$_2$CO$_3$ (98 mg, 0.3 mmol, 2.0 equiv.) were combined as a mixture, in a pressure tube, in degassed toluene (1 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried over (MgSO$_4$) and concentrated under reduced pressure to give a yellow oil. Purification by flash chromatography (SiO$_2$, 10% MeOH in DCM) provided PN2-064 (41 mg, 60%) as a light brown powder. HPLC: 98% [$t_R$=6.78 min, gradient MeOH-water (with 0.1% TFA), 5-95% over 20 min.]. $^1$H NMR (500 MHz, DMSO-$d_6$) δ: 10.27 (s, 1H), 9.36 (s, 1H), 8.82 (s, 1H), 8.51 (d, J=2.4 Hz, 1H), 8.08 (d, J=1.0 Hz, 1H), 7.86 (d, J=2.6 Hz, 1H), 7.83 (dd, J=8.7, 2.6 Hz, 1H), 7.76 (s, 1H), 2.18 (d, J=0.8 Hz, 3H), 1.33 (s, 9H). $^{19}$F NMR (479 MHz, DMSO-$d_6$) δ: −63.69. HPLC-MS (ESI+): m/z 466.2 [100%, (M+H)$^+$]. HRMS (ESI+): m/z calcd for $C_{19}H_{23}ClFN_7O_2S$ (M+H)$^+$ 466.1223, found 466.1225.

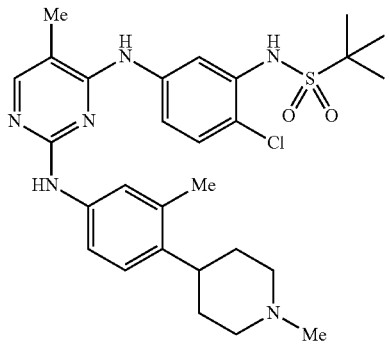

PN2-080

N-(2-Chloro-5-((5-methyl-2-((4-methyl-5-(1-methylpiperidin-4-yl)pyridin-2-yl)amino)pyrimidin-4-yl)amino)phenyl)-2-methylpropane-2-sulfonamide (PN2-080). The chloropyrimidine SG3-012 (82.0 mg, 0.21 mmol, 1.2 equiv.), PN2-068 (31 mg, 0.15 mmol, 1.0 equiv.), Pd$_2$(dba)$_3$ (14.2, 0.0155 mmol), Xantphos (18 mg, 0.031 mmol), and Cs$_2$CO$_3$ (98 mg, 0.3 mmol, 2.0 equiv.) were combined as a mixture, in a pressure tube, in degassed toluene (1 mL) and heated at 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$) and concentrated under reduced pressure to give a yellow oil which was purified by flash chromatography (SiO$_2$, 10% MeOH in DCM) to provide PN2-080 (27 mg, 33%) as a white powder. HPLC: 99% [$t_R$=5.44 min, gradient MeOH-water (with 0.1% TFA), 5-95% over 20 min.]. $^1$H NMR (500 MHz, DMSO-$d_6$) δ: 8.60 (s, 1H), 8.51 (s, 1H), 7.94 (s, 1H), 7.92-7.85 (m, 2H), 7.83 (s, 1H), 7.65 (dd, J=8.7, 2.5 Hz, 1H), 7.29 (d, J=8.7 Hz, 1H), 2.82 (d, J=11.1 Hz, 2H), 2.48 (m, 1H), 2.15 (s, 3H), 2.08 (s, 3H), 2.06 (s, 3H), 1.99-1.89 (m, 2H), 1.60 (m, 4H), 1.25 (s, 9H). HPLC-MS (ESI+): m/z 558.3 [70%, (M+H)$^+$], 279.8 [100% (M+2H)$^{2+}$]. HRMS (ESI+): m/z calcd for $C_{27}H_{37}ClN_7O_2S$ (M+H)$^+$ 559.2412, found 559.2408.

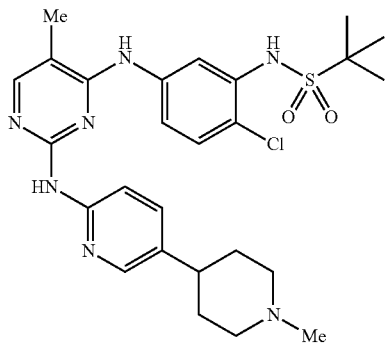

PN2-081

N-(2-Chloro-5-((5-methyl-2-((5-(1-methylpiperidin-4-yl)pyridin-2-yl)amino)pyrimidin-4-yl)amino)phenyl)-2-methylpropane-2-sulfonamide (PN2-081). The chloropyrimidine SG3-012 (82.0 mg, 0.21 mmol, 1.2 equiv.), PN2-066 (31 mg, 0.15 mmol, 1.0 equiv.), Pd$_2$(dba)$_3$ (14.2, 0.0155 mmol), Xantphos (18 mg, 0.031 mmol), and Cs$_2$CO$_3$ (98 mg, 0.3 mmol, 2.0 equiv.) were combined as a mixture, in a pressure tube, in degassed toluene (1 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$) and concentrated under reduced pressure to give a yellow oil. Purification by flash chromatography (SiO$_2$, 10% MeOH in DCM) provided PN2-081 (24 mg, 29%) as a light brown powder. HPLC: 99% [t$_R$=5.6 min, gradient MeOH-water (with 0.1% TFA), 5-95% over 20 min.]. $^1$H NMR (500 MHz, DMSO-d$_6$) δ: 8.72 (s, 1H), 8.49 (s, 1H), 8.15-7.97 (m, 3H), 7.90 (s, 1H), 7.69 (dd, J=8.8, 2.6 Hz, 1H), 7.49 (dd, J=8.7, 2.5 Hz, 1H), 7.31 (d, J=8.8 Hz, 1H), 2.85 (d, J=11.0 Hz, 2H), 2.40-2.35 (m, 1H), 2.18 (s, 3H), 2.07 (s, 3H), 1.99 (m, 2H), 1.72-1.57 (m, 4H), 1.26 (s, 9H). HPLC-MS (ESI+): m/z 544.3 [40%, (M+H)$^+$], 272.7 [100% (M+2H)$^{2+}$]. HRMS (ESI+): m/z calcd for C$_{26}$H$_{35}$ClFN$_7$O$_2$S (M+H)$^+$ 544.2256, found 544.2251.

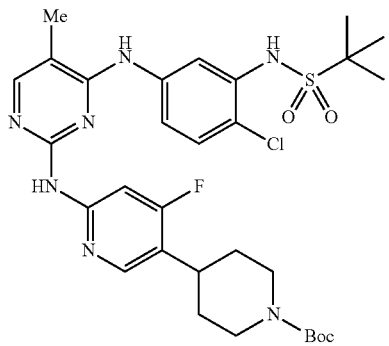

PN2-082

SG3-012 (164.0 mg, 0.42 mmol, 1.2 equiv.), PN2-077 (88 mg, 0.3 mmol, 1.0 equiv.), Pd$_2$(dba)$_3$ (29, 0.031 mmol), Xantphos (36 mg, 0.06 mmol), and Cs$_2$CO$_3$ (195 mg, 0.6 mmol, 2.0 equiv.) were combined as a mixture, in a pressure tube, in degassed toluene (2 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$) and concentrated under reduced pressure to give a yellow oil. Purification by flash chromatography (SiO$_2$, 10% MeOH in DCM) provided PN2-082 as a light brown powder (103 mg, 53%). $^1$H NMR (500 MHz, DMSO-d$_6$) δ: 9.32 (s, 1H), 9.24 (s, 1H), 8.66 (s, 1H), 8.16 (d, J=10.8 Hz, 1H), 8.04-7.92 (m, 3H), 7.82 (dd, J=8.7, 2.5 Hz, 1H), 7.36 (d, J=8.8 Hz, 1H), 4.09 (m, 2H), 2.96-2.71 (m, 3H), 2.14 (d, J=0.9 Hz, 3H), 1.81-1.68 (m, 2H), 1.60 (dd, J=12.6, 4.2 Hz, 2H), 1.42 (s, 9H), 1.33 (s, 9H). HPLC-MS (ESI+): m/z 648.3 [100%, (M+H)$^+$].

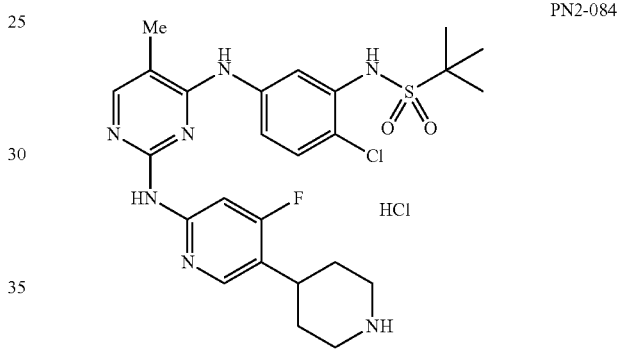

PN2-084

N-(2-Chloro-5-((2-((4-fluoro-5-(piperidin-4-yl)pyridin-2-yl)amino)-5-methylpyrimidin-4-yl)amino)phenyl)-2-methylpropane-2-sulfonamide hydrochloride (PN2-084). To a solution of the PN2-082 (141 mg, 0.22 mmol) in DCM (5 mL) at was added 4 mL of 4M HCl (in dioxane) under an argon atmosphere and the reaction mixture was stirred at room temperature. After 2 hours, the solvent was removed in vacuo and the residue diluted with DCM. The mixture was cooled to 0° C. and neutralized with sat aq NaHCO$_3$ and extracted with DCM (10×2 ml). The combined organic layers were dried (Na$_2$SO$_4$) and evaporated to provide pure the PN1-084.HCl salt (127 mg, 98%) as a brown oil. HPLC: 99% [t$_R$=6.11 min, gradient MeOH-water (with 0.1% TFA), 5-95% over 20 min.]. $^1$H NMR (500 MHz, DMSO-d$_6$) δ: 11.53 (s, 1H), 10.02 (s, 1H), 9.53 (s, 1H), 9.28-9.03 (m, 2H), 8.27 (d, J=10.0 Hz, 1H), 8.04 (d, J=1.2 Hz, 1H), 7.76 (d, J=2.5 Hz, 1H), 7.71 (dd, J=8.7, 2.5 Hz, 1H), 7.55 (d, J=8.7 Hz, 1H), 7.18 (d, J=11.6 Hz, 1H), 3.41-3.25 (m, 2H), 3.19-3.10 (m, 1H), 3.03 (d, J=12.1 Hz, 2H), 2.24-1.93 (m, 2H), 1.91 (m, 2H), 1.34 (s, 9H). $^{19}$F NMR (479 MHz, DMSO-d$_6$) δ: −104.89 (d, J=22.7, 11.4 Hz). HPLC-MS (ESI+): m/z 548.2 [30%, (M+H)$^+$], 274.7 [100% (M+2H)$^{2+}$]. HRMS (ESI+): m/z calcd for C$_{25}$H$_{32}$ClFN$_7$O$_2$S (M+H)$^+$ 548.2005, found 548.2000.

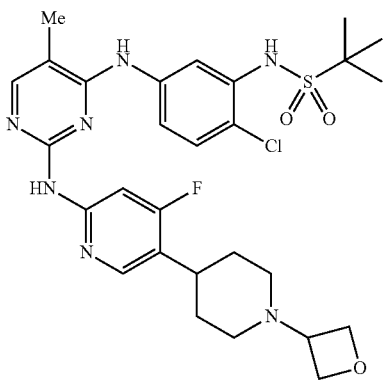

N-(2-Chloro-5-((2-((4-fluoro-5-(1-(oxetan-3-yl)piperidin-4-yl)pyridin-2-yl)amino)-5-methylpyrimidin-4-yl)amino)phenyl)-2-methylpropane-2-sulfonamide (PN2-085). The piperidine PN2-084 (87 mg, 0.15 mmol, 1.0 equiv.) was dissolved in dry DCM (5 mL) and oxetan-3-one (16.2 mg, 0.225 mmol, 1.5 equiv.) was added. The resulting solution was cooled in an ice-bath. Sodium triacetoxyborohydride (64 mg, 0.3 mmol, 2.0 equiv.) was added portion-wise over 5 mins. The ice bath was removed and stirred at room temperature overnight. The resulting white suspension was quenched by addition of 2M sodium carbonate solution (pH=8) and concentrated under reduced pressure to remove DCM. The mixture was then extracted with EtOAc (3×250 mL). The combined organic extracts were dried over (MgSO$_4$), filtered and concentrated under reduced pressure to give a yellow oil. Purification by flash chromatography (SiO$_2$, 10% MeOH in DCM) provided PN2-085 (19%, 17 mg) as a light yellow powder. HPLC: 99% [$t_R$=12.4 min, gradient MeOH-water (with 0.1% TFA), 5-95% over 20 min.]. $^1$H NMR (500 MHz, DMSO-d$_6$) δ: 9.32 (s, 1H), 9.27-9.19 (m, 1H), 8.67 (s, 1H), 8.17 (d, J=10.8 Hz, 1H), 8.07-7.93 (m, 3H), 7.81 (dd, J=8.8, 2.5 Hz, 1H), 7.37 (d, J=8.8 Hz, 1H), 4.56 (m, 2H), 4.47 (m, 2H), 4.11 (q, J=5.3 Hz, 1H), 2.82 (m, 2H), 2.69 (m, 1H), 2.15 (s, 3H), 1.76 (m, 6H), 1.33 (s, 9H). $^{19}$F NMR (479 MHz, DMSO-d$_6$) δ: −108.66 (dd, J=22.7, 11.4 Hz). HPLC-MS (ESI+): m/z 604.3 [100%, (M+H)$^+$], 302.7 [40% (M+2H)$^{2+}$]. HRMS (ESI+): m/z calcd for C$_{28}$H$_{36}$ClFN$_7$O$_2$S (M+H)$^+$ 604.2267, found 604.2265.

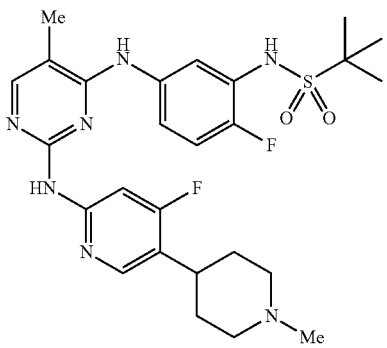

N-(2-Fluoro-5-((2-((4-fluoro-5-(1-methylpiperidin-4-yl)pyridin-2-yl)amino)-5-methylpyrimidin-4-yl)amino)phenyl)-2-methylpropane-2-sulfonamide (PN2-089). MA4-025 (60.0 mg, 0.16 mmol, 1.2 equiv.), PN1-055 (27 mg, 0.13 mmol, 1.0 equiv.), Pd$_2$(dba)$_3$ (12.0 mg, 0.013 mmol), Xantphos (15.0 mg, 0.026 mmol), and Cs$_2$CO$_3$ (84 mg, 0.3 mmol, 2.0 equiv.) were combined as a mixture, in a pressure tube, in degassed toluene (1 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried over (MgSO$_4$) and concentrated under reduced pressure to give a yellow oil. Purification by flash chromatography (SiO$_2$, 10% MeOH in DCM) provided PN2-089 (33 mg, 47%) as a light brown powder. HPLC: 99% [$t_R$=12.67 min, gradient MeOH-water (with 0.1% TFA), 5-95% over 20 min.]. $^1$H NMR (500 MHz, DMSO-d$_6$) δ: 9.54 (s, 1H), 9.18 (d, J=1.5 Hz, 1H), 8.57 (s, 1H), 8.13 (d, J=10.9 Hz, 1H), 7.97 (d, J=1.0 Hz, 1H), 7.91 (d, J=14.0 Hz, 1H), 7.77 (dd, J=7.3, 2.7 Hz, 1H), 7.67 (ddd, J=8.9, 4.3, 2.7 Hz, 1H), 7.17 (dd, J=10.2, 8.9 Hz, 1H), 2.90 (d, J=11.0 Hz, 2H), 2.67-2.58 (m, 1H), 2.23 (s, 2H), 2.13 (s, 2H), 1.99 (s, 3H), 1.83-1.68 (m, 2H), 1.30 (s, 9H). $^{19}$F NMR (479 MHz, DMSO-d$_6$) δ: −108.54 (d, J=12.6 Hz), −129.30. HPLC-MS (ESI+): m/z 546.3 [30%, (M+H)$^+$], 273.8 [100% (M+2H)$^{2+}$]. HRMS (ESI+): m/z calcd for C$_{26}$H$_{34}$FN$_7$O$_2$S (M+H)$^+$ 546.2387, found 546.2457.

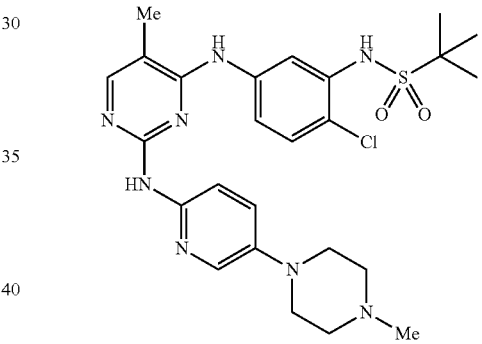

N-(2-Chloro-5-((5-methyl-2-((5-(4-methylpiperazin-1-yl)pyridin-2-yl)amino)pyrimidin-4-yl)amino)phenyl)-2-methylpropane-2-sulfonamide (PN2-091). The chloropyrimidine SG3-012 (60.0 mg, 0.16 mmol, 1.2 equiv.), 5-(4-methylpiperazin-1-yl)pyridin-2-amine (27 mg, 0.13 mmol, 1.0 equiv.), Pd$_2$(dba)$_3$ (12.0 mg, 0.013 mmol), Xantphos (15.0 mg, 0.026 mmol), and Cs$_2$CO$_3$ (84 mg, 0.3 mmol, 2.0 equiv.) were combined as a mixture, in a pressure tube, in degassed toluene (1 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried over (MgSO$_4$) and concentrated under reduced pressure to give a yellow oil. Purification by flash chromatography (SiO$_2$, 10% MeOH in DCM) provided PN2-091 (50 mg, 51%) as a white powder. HPLC: 99% [$t_R$=12.40 min, gradient MeOH-water (with 0.1% TFA), 5-95% over 20 min.]. $^1$H NMR (500 MHz, DMSO-d$_6$) δ: 9.31 (s, 1H), 8.59 (s, 1H), 8.51 (s, 1H), 8.11 (d, J=2.6 Hz, 1H), 8.00 (d, J=9.1 Hz, 1H), 7.98-7.88 (m, 2H), 7.79 (dd, J=8.8, 2.6 Hz, 1H), 7.49-7.30 (m, 2H), 3.09 (t, J=5.0 Hz, 4H), 2.48 (t, J=5.0 Hz, 4H), 2.24 (s, 3H), 2.13 (d, J=0.9 Hz, 3H), 1.33 (s, 9H).

HPLC-MS (ESI+): m/z 545.3 [100%, (M+H)+], 273.2 [60% (M+2H)$^{2+}$]. HRMS (ESI+): m/z calcd for $C_{25}H_{34}ClN_8O_2S$ (M+H)+ 545.2208, found 545.2210.

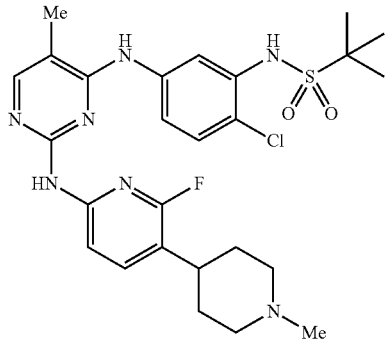

PN2-102

N-(2-Chloro-5-((2-((6-fluoro-5-(1-methylpiperidin-4-yl)pyridin-2-yl)amino)-5-methylpyrimidin-4-yl)amino)phenyl)-2-methylpropane-2-sulfonamide (PN2-102). The chloropyrimdine SG3-012 (70.0 mg, 0.18 mmol, 1.2 equiv.), PN2-100 (31.4 mg, 0.15 mmol, 1.0 equiv.), Pd$_2$(dba)$_3$ (14.2, 0.0155 mmol), Xantphos (18 mg, 0.031 mmol), and Cs$_2$CO$_3$ (98 mg, 0.3 mmol, 2.0 equiv.) were combined as a mixture, in a pressure tube, in degassed toluene (1 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$) and concentrated under reduced pressure to give a yellow oil. Purification by flash chromatography (SiO$_2$, 10% MeOH in DCM) provided PN2-102 (58 mg, 69%) as a white powder. HPLC: 99% [t$_R$=7.52 min, gradient MeOH-water (with 0.1% TFA), 5-95% over 20 min.]. $^1$H NMR (500 MHz, DMSO-d$_6$) δ: 9.36 (s, 1H), 9.23 (s, 1H), 8.60 (s, 1H), 8.06-7.94 (m, 3H), 7.87 (dd, J=8.8, 2.6 Hz, 1H), 7.71 (dd, J=10.4, 8.3 Hz, 1H), 7.38 (d, J=8.8 Hz, 1H), 2.96 (d, J=11.0 Hz, 2H), 2.74-2.60 (m, 1H), 2.29 (s, 3H), 2.15 (s, 5H), 1.82-1.66 (m, 4H), 1.33 (s, 9H). $^{19}$F NMR (479 MHz, DMSO-d$_6$) δ: −75.86. HPLC-MS (ESI+): m/z 562.2 [60%, (M+H)+], 281.7 [100% (M+2H)$^{2+}$]. HRMS (ESI+): m/z calcd for $C_{26}H_{34}ClFN_7O_2S$ (M+H)+ 562.2162, found 562.2157.

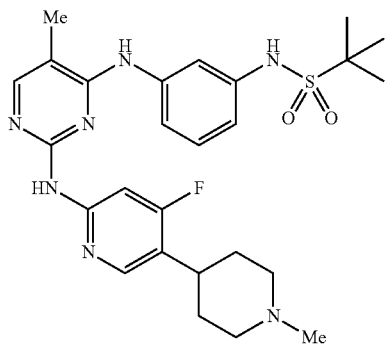

PN2-103

N-(3-((2-((4-Fluoro-5-(1-methylpiperidin-4-yl)pyridin-2-yl)amino)-5-methylpyrimidin-4-yl)amino)phenyl)-2-methylpropane-2-sulfonamide (PN2-103). The chloropyrimidine SG3-053 (67.3 mg, 0.19 mmol, 1.2 equiv.), PN1-055 (33.5 mg, 0.16 mmol, 1.0 equiv.), Pd$_2$(dba)$_3$ (14.7, 0.016 mmol), Xantphos (19 mg, 0.032 mmol), and Cs$_2$CO$_3$ (104 mg, 0.32 mmol, 2.0 equiv.) were combined as a mixture, in a pressure tube, in degassed toluene (1 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$) and concentrated under reduced pressure to give a yellow oil. Purification by flash chromatography (SiO$_2$, 10% MeOH in DCM) provided PN2-103 (51 mg, 61%) as a white powder. HPLC: 99% [t$_R$=3.85 min, gradient MeOH-water (with 0.1% TFA), 5-95% over 20 min.]. $^1$H_NMR (500 MHz, DMSO-d$_6$) δ: 9.54 (s, 1H), 9.07 (d, J=1.7 Hz, 1H), 8.50 (s, 1H), 8.15 (d, J=10.8 Hz, 1H), 8.02 (d, J=13.9 Hz, 1H), 7.97 (dd, J=14.0, 1.6 Hz, 2H), 7.42-7.35 (m, 1H), 7.22 (t, J=8.1 Hz, 1H), 7.08-7.02 (m, 1H), 2.89 (d, J=10.9 Hz, 2H), 2.63 (d, J=11.0 Hz, 1H), 2.22 (s, 3H), 2.14 (s, 3H), 1.74 (dd, J=16.0, 3.8 Hz, 3H), 1.99 (m, 2H), 1.29 (s, 9H). $^{19}$F NMR (479 MHz, DMSO-d$_6$) δ: −108.26 (t, J=12.3 Hz). HPLC-MS (ESI+): m/z 528.3 [20%, (M+H)+], 264.7 [100% (M+2H)$^{2+}$]. HRMS (ESI+): m/z calcd for $C_{26}H_{35}FN_7O_2S$ (M+H)+ 528.2551, found 528.2547.

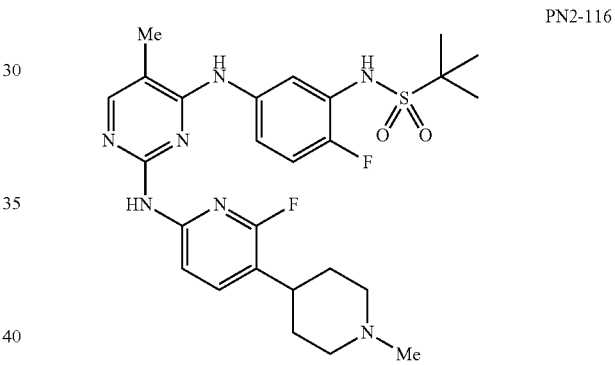

PN2-116

N-(2-Fluoro-5-((2-((6-fluoro-5-(1-methylpiperidin-4-yl)pyridin-2-yl)amino)-5-methylpyrimidin-4-yl)amino)phenyl)-2-methylpropane-2-sulfonamide (PN2-116). The chloropyrimidine MA4-025B2 (67.0 mg, 0.18 mmol, 1.2 equiv.), PN2-100 (31.3 mg, 0.16 mmol, 1.0 equiv.), Pd$_2$(dba)$_3$ (14.2, 0.0155 mmol), Xantphos (18 mg, 0.031 mmol), and Cs$_2$CO$_3$ (98 mg, 0.3 mmol, 2.0 equiv.) were combined as a mixture, in a pressure tube, in degassed toluene (1 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$) and concentrated under reduced pressure to give a yellow oil. Purification by flash chromatography (SiO$_2$, 10% MeOH in DCM) provided PN2-116 (51.6 mg, 63%) as a white powder. HPLC: 99% [t$_R$=5.21 min, gradient MeOH-water (with 0.1% TFA), 5-95% over 20 min.]. $^1$H NMR (500 MHz, DMSO-d$_6$) δ: 9.53 (s, 1H), 9.19 (s, 1H), 8.52 (s, 1H), 8.03-7.90 (m, 2H), 7.84 (dd, J=7.3, 2.7 Hz, 1H), 7.73 (ddd, J=9.0, 4.2, 2.7 Hz, 1H), 7.69-7.61 (m, 1H), 7.20 (dd, J=10.2, 8.9 Hz, 1H), 2.91 (d, J=11.0 Hz, 2H), 2.73-2.56 (m, 1H), 2.24 (s, 3H), 2.13 (d, J=0.9 Hz, 3H), 2.04 (s, 2H), 1.71 (d, J=11.4 Hz, 4H), 1.31 (s, 9H). $^{19}$F NMR (479 MHz, DMSO-d$_6$) δ: −76.00, −129.30

(t, J=11.7 Hz). HPLC-MS (ESI+): m/z 546.3 [20%, (M+H)+], 273.7 [100% (M+2H)$^{2+}$]. HRMS (ESI+): m/z calcd for $C_{26}H_{34}F_2N_7O_2S$ (M+H)+ 546.2457, found 546.2453.

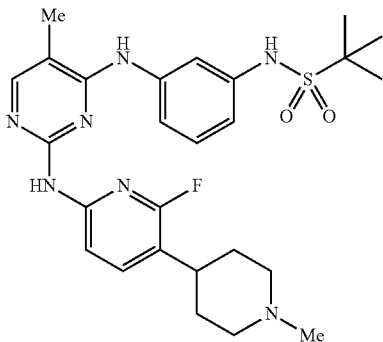

PN2-117

N-(3-((2-((6-Fluoro-5-(1-methylpiperidin-4-yl)pyridin-2-yl)amino)-5-methylpyrimidin-4-yl)amino)phenyl)-2-methylpropane-2-sulfonamide (PN2-117). The chloropyrimidine SG3-053 (64.0 mg, 0.18 mmol, 1.2 equiv.), PN2-100 (31.3 mg, 0.15 mmol, 1.0 equiv.), Pd$_2$(dba)$_3$ (14.2, 0.0155 mmol), Xantphos (18 mg, 0.031 mmol), and Cs$_2$CO$_3$ (98 mg, 0.3 mmol, 2.0 equiv.) were combined as a mixture, in a pressure tube, in degassed toluene (1 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$), and concentrated under reduced pressure to give a yellow oil. Purification by flash chromatography (SiO$_2$, 10% MeOH in DCM) provided PN2-117 (47 mg, 59%) as a white powder. HPLC: 99% [t$_R$=12.68 min, gradient MeOH-water (with 0.1% TFA), 5-95% over 20 min.]. $^1$H NMR (500 MHz, DMSO-d$_6$) δ: 9.54 (s, 1H), 9.07 (s, 1H), 8.48 (s, 1H), 8.05 (dd, J=8.3, 1.7 Hz, 1H), 7.97 (dd, J=5.2, 1.5 Hz, 2H), 7.71-7.59 (m, 1H), 7.43 (dd, J=8.1, 2.0 Hz, 1H), 7.23 (t, J=8.1 Hz, 1H), 7.10-7.00 (m, 1H), 2.91 (d, J=11.0 Hz, 2H), 2.60 (s, 1H), 2.24 (s, 3H), 2.14 (s, 3H), 2.04 (s, 2H), 1.71 (t, J=3.8 Hz, 4H), 1.29 (s, 9H). $^{19}$F NMR (479 MHz, DMSO-d$_6$) δ: −76.12 (d, J=10.0 Hz). HPLC-MS (ESI+): m/z 528.3 [20%, (M+H)+], 264.7 [100% (M+2H)$^{2+}$]. HRMS (ESI+): m/z calcd for $C_{26}H_{35}FN_7O_2S$ (M+H)+ 528.2551, found 528.2547.

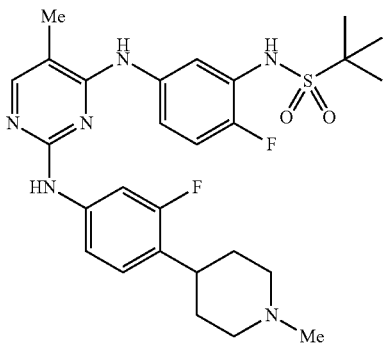

PN2-118

N-(2-Fluoro-5-((2-((3-fluoro-4-(1-methylpiperidin-4-yl)phenyl)amino)-5-methylpyrimidin-4-yl)amino)phenyl)-2-methylpropane-2-sulfonamide (PN2-118). The chloropyrimidine MA4-025B2 (67.0 mg, 0.18 mmol, 1.2 equiv.), MA9-058 (31.0 mg, 0.15 mmol, 1.0 equiv.), Pd$_2$(dba)$_3$ (14.2, 0.0155 mmol), Xantphos (18 mg, 0.031 mmol), and Cs$_2$CO$_3$ (98 mg, 0.3 mmol, 2.0 equiv.) were combined as a mixture, in a pressure tube, in degassed toluene (1 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$), and concentrated under reduced pressure to give a yellow oil. Purification by flash chromatography (SiO$_2$, 10% MeOH in DCM) provided PN2-118 (52 mg, 64%) as a white powder. HPLC: 99% [t$_R$=11.32 min, gradient MeOH-water (with 0.1% TFA), 5-95% over 20 min.]. $^1$H NMR (500 MHz, DMSO-d$_6$) δ: 9.51 (s, 1H), 9.06 (s, 1H), 8.46 (s, 1H), 7.91 (d, J=0.9 Hz, 1H), 7.67-7.52 (m, 3H), 7.28 (d, J=2.2 Hz, 1H), 7.19 (t, J=9.9 Hz, 1H), 7.08 (t, J=8.7 Hz, 1H), 3.00 (s, 2H), 2.69 (s, 1H), 2.34 (s, 3H), 2.23 (s, 2H), 2.11 (d, J=0.9 Hz, 3H), 1.80-1.62 (m, 4H), 1.30 (s, 9H). $^{19}$F NMR (479 MHz, DMSO-d$_6$) δ: −119.02, −129.19 (t, J=8.4 Hz). HPLC-MS (ESI+): m/z 543.3 [20%, (M+H)+], 273.2 [100% (M+2H)$^{2+}$]. HRMS (ESI+): m/z calcd for $C_{27}H_{35}F_2N_7O_2S$ (M+H)+ 545.2505, found 545.2498.

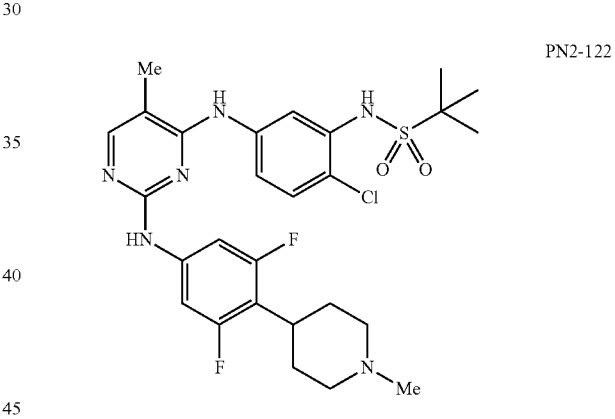

PN2-122

N-(2-Chloro-5-((2-((3,5-difluoro-4-(1-methylpiperidin-4-yl)phenyl)amino)-5-methylpyrimidin-4-yl)amino)phenyl)-2-methylpropane-2-sulfonamide (PN2-122). This was prepared according to the general procedure C, from SG3-012 (70.0 mg, 0.18 mmol, 1.0 equiv.), PN2-120 (34.0 mg, 0.15 mmol, 1.0 equiv.), EtOH (1.0 mL) and 4M HCl (80 µL) (15 min at 160° C.) to afford, after chromatography, the title compound PN1-122 (23 mg, 27%) as a light brown powder. HPLC: 99% [t$_R$=6.55 min, gradient MeOH-water (with 0.1% TFA), 5-95% over 20 min.]. $^1$H NMR (500 MHz, DMSO-d$_6$) δ: 9.28 (s, 1H), 8.60 (s, 1H), 7.96 (s, 1H), 7.71 (d, J=2.4 Hz, 2H), 7.43-7.30 (m, 3H), 2.86 (m, 2H), 2.75 (m, 1H), 2.20 (s, 3H), 2.12 (s, 3H), 2.02-1.85 (m, 4H), 1.58 (d, J=9.0 Hz, 2H), 1.32 (s, 9H). $^{19}$F NMR (479 MHz, DMSO-d$_6$) δ: −114.62 (d, J=12.0 Hz). HPLC-MS (ESI+): m/z 579.3 [40%, (M+H)+], 290.2 [100% (M+2H)$^{2+}$]. HRMS (ESI+): m/z calcd for $C_{27}H_{34}ClF_2N_6O_2S$ (M+H)+ 579.2115, found 579.2114.

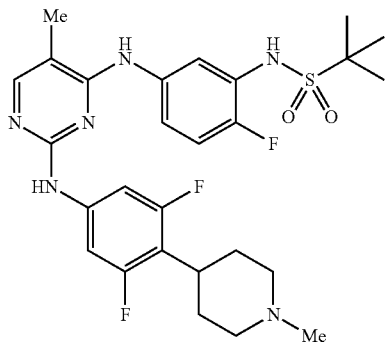

PN2-123

N-(5-((2-((3,5-Difluoro-4-(1-methylpiperidin-4-yl)phenyl)amino)-5-methylpyrimidin-4-yl)amino)-2-fluorophenyl)-2-methylpropane-2-sulfonamide (PN2-123). This was prepared according to the general procedure C, by reaction of MA4-025B2 (67.0 mg, 0.18 mmol, 1.0 equiv.), PN2-120 (34.0 mg, 0.15 mmol, 1.0 equiv.), EtOH (1.0 mL) and 4M HCl (80 μL) for 15 min at 160° C. to afford, after chromatography, the title compound PN1-123 (41 mg, 49%) as a light brown powder. HPLC: 99% [$t_R$=12.53 min, gradient MeOH-water (with 0.1% TFA), 5-95% over 20 min.]. $^1$H NMR (500 MHz, DMSO-$d_6$) δ: 9.53 (s, 1H), 9.26 (s, 1H), 8.52 (s, 1H), 7.92 (s, 1H), 7.56 (dd, J=7.2, 4.8 Hz, 2H), 7.32 (d, J=11.9 Hz, 2H), 7.19 (t, J=9.7 Hz, 1H), 2.92-2.79 (m, 2H), 2.72 (m, 1H), 2.18 (s, 3H), 2.11 (s, 3H), 2.05-1.78 (m, 4H), 1.63-1.52 (m, 2H), 1.29 (s, 9H). $^{19}$F NMR (479 MHz, DMSO-$d_6$) δ: −114.63 (d, J=12.1 Hz), −128.99. HPLC-MS (ESI+): m/z 563.3 [20%, (M+H)$^+$], 282.2 [100% (M+2H)$^{2+}$]. HRMS (ESI+): m/z calcd for $C_{27}H_{34}F_3N_6O_2S$ (M+H)$^+$ 563.2411, found 563.2405.

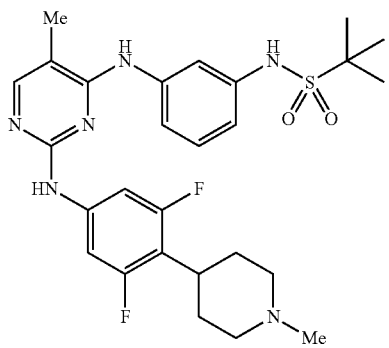

PN2-124

N-(3-((2-((3,5-Difluoro-4-(1-methylpiperidin-4-yl)phenyl)amino)-5-methylpyrimidin-4-yl)amino)phenyl)-2-methylpropane-2-sulfonamide (PN2-124). This was prepared according to the general procedure C, from the reaction of SG3-055 (64.0 mg, 0.18 mmol, 1.0 equiv.), PN2-120 (34.0 mg, 0.15 mmol, 1.0 equiv.), EtOH (1.0 mL) and 4M HCl (80 L) for 15 min at 160° C. to afford, after chromatography, the title compound PN1-124 (38 mg, 47%) as a light brown powder. HPLC: 99% [$t_R$=6.8 min, gradient MeOH-water (with 0.1% TFA), 5-95% over 20 min.]. $^1$H NMR (500 MHz, DMSO-$d_6$) δ: 9.59 (s, 1H), 9.23 (s, 1H), 8.48 (s, 1H), 7.93 (d, J=0.9 Hz, 1H), 7.44 (dd, J=8.1, 2.0 Hz, 1H), 7.41-7.30 (m, 3H), 7.24 (t, J=8.0 Hz, 1H), 7.13-6.95 (m, 1H), 2.85 (d, J=8.8 Hz, 2H), 2.75-2.66 (m, 1H), 2.19 (s, 3H), 2.11 (s, 3H), 1.99-1.85 (m, 4H), 1.56 (d, J=10.3 Hz, 2H), 1.28 (s, 9H). $^{19}$F NMR (479 MHz, DMSO-$d_6$) δ: −114.52 (d, J=12.0 Hz). HPLC-MS (ESI+): m/z 545.3 [40%, (M+H)$^+$], 273.2 [100% (M+2H)$^{2+}$]. HRMS (ESI+): m/z calcd for $C_{27}H_{35}F_2N_6O_2S$ (M+H)$^+$ 545.2505, found 545.2497.

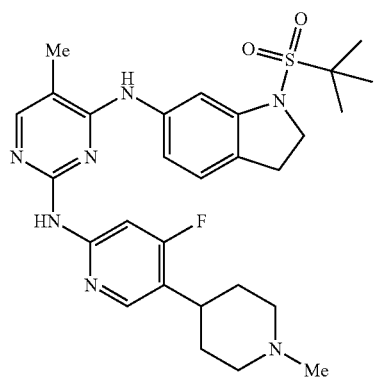

PN2-128

$N^4$-(1-(tert-Butylsulfonyl)indolin-6-yl)-$N^2$-(4-fluoro-5-(1-methylpiperidin-4-yl)pyridin-2-yl)-5-methylpyrimidine-2,4-diamine (PN2-128). The chloropyrimidine SG3-024B2 (64.4 mg, 0.18 mmol, 1.0 equiv.), PN1-055 (31.3 mg, 0.15 mmol, 1.0 equiv.), Pd$_2$(dba)$_3$ (14.2, 0.0155 mmol), Xantphos (18 mg, 0.031 mmol), and Cs$_2$CO$_3$ (98 mg, 0.3 mmol, 2.0 equiv.) were combined as a mixture, in a pressure tube, in degassed toluene (1 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried over (MgSO$_4$) and concentrated under reduced pressure to give a yellow oil. Purification by flash chromatography (SiO$_2$, 10% MeOH in DCM) provided PN2-128 (24 mg, 29%) as a white powder. HPLC: 98% [$t_R$=10.9 min, gradient MeOH-water (with 0.1% TFA), 5-95% over 20 min.]. $^1$H NMR (500 MHz, DMSO-$d_6$) δ: 9.03 (d, J=1.6 Hz, 1H), 8.52 (s, 1H), 8.11 (d, J=10.9 Hz, 1H), 7.94 (s, 1H), 7.90 (d, J=14.1 Hz, 1H), 7.45 (d, J=1.9 Hz, 1H), 7.34 (d, J=2.0 Hz, 1H), 7.19 (d, J=8.0 Hz, 1H), 4.09 (d, J=8.3 Hz, 2H), 3.11 (t, J=8.4 Hz, 2H), 2.91 (d, J=11.1 Hz, 2H), 2.62 (m, 1H), 2.24 (s, 3H), 2.13 (s, 3H), 2.05 (m, 2H), 1.84-1.63 (m, 2H), 1.35 (s, 9H). $^{19}$F NMR (479 MHz, DMSO-$d_6$) δ: −108.71 (t, J=12.8 Hz). HPLC-MS (ESI+): m/z 554.3 [60%, (M+H)$^+$], 277.7 [100% (M+2H)$^{2+}$]. HRMS (ESI+): m/z calcd for $C_{28}H_{37}FN_7O_2S$ (M+H)$^+$ 554.2708, found 554.2708.

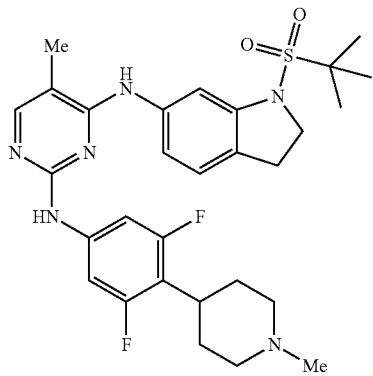

PN2-129

N4-(1-(tert-butylsulfonyl)indolin-6-yl)-N2-(3,5-difluoro-4-(1-methylpiperidin-4-yl)phenyl)-5-methylpyrimidine-2,4-diamine (PN2-129). This was prepared according to the general procedure C, by reaction of SG3-024B2 (68.5 mg, 0.18 mmol, 1.0 equiv.), PN2-120 (34.0 mg, 0.15 mmol, 1.0 equiv.), EtOH (1.0 mL) and 4M HCl (80 µL) for 15 min at 160° C. to afford, after chromatography, the title compound PN1-129 (29 mg, 34%) as a light brown powder. HPLC: 98% [$t_R$=10.9 min, gradient MeOH-water (with 0.1% TFA), 5-95% over 20 min.]. $^1$H NMR (500 MHz, DMSO-$d_6$) δ: 9.21 (s, 1H), 8.46 (s, 1H), 7.90 (d, J=1.0 Hz, 1H), 7.39-7.26 (m, 4H), 7.19 (d, J=7.9 Hz, 1H), 4.07 (t, J=8.4 Hz, 2H), 3.11 (t, J=8.3 Hz, 2H), 2.84 (d, J=8.7 Hz, 2H), 2.76-2.66 (m, 1H), 2.18 (s, 3H), 2.11 (s, 3H), 2.03-1.84 (m, 4H), 1.56 (d, J=10.1 Hz, 2H), 1.34 (s, 9H). $^{19}$F NMR (479 MHz, DMSO-$d_6$) δ: −114.81 (d, J=12.2 Hz). HPLC-MS (ESI+): m/z 571.3 [20%, (M+H)$^+$], 286.2 [100% (M+2H)$^{2+}$]. HRMS (ESI+): m/z calcd for $C_{29}H_{37}F_2N_6O_2S$ (M+H)$^+$ 571.2661, found 571.2654.

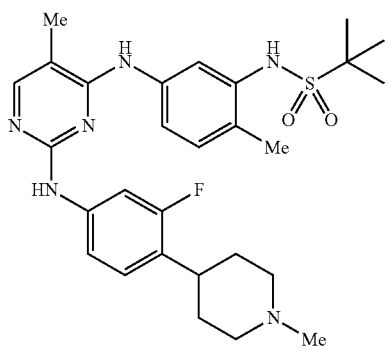

PN2-173

N-(5-((2-((3-Fluoro-4-(1-methylpiperidin-4-yl)phenyl)amino)-5-methylpyrimidin-4-yl)amino)-2-methylphenyl)-2-methylpropane-2-sulfonamide (PN2-173). This was prepared according to the general procedure C, by the reaction of PN2-172 (74 mg, 0.2 mmol, 1.0 equiv.), MA9-058 (42 mg, 0.2 mmol, 1.0 equiv.), EtOH (1.0 mL) and 4M HCl (100 µL) for 15 min at 160° C., to afford, after chromatography, the title compound PN1-173 (64 mg, 59%) as a light brown powder. HPLC: 99% [$t_R$=6.1 min, gradient MeOH-water (with 0.1% TFA), 5-95% over 20 min.]. $^1$H NMR (500 MHz, DMSO-$d_6$) δ: 8.98 (s, 1H), 8.84 (s, 1H), 8.36 (s, 1H), 7.89 (d, J=0.9 Hz, 1H), 7.60 (td, J=7.8, 7.0, 2.1 Hz, 2H), 7.54 (dd, J=8.2, 2.2 Hz, 1H), 7.31 (dd, J=8.5, 2.1 Hz, 1H), 7.15 (d, J=8.4 Hz, 1H), 7.08 (t, J=8.7 Hz, 1H), 2.85 (d, J=11.8 Hz, 2H), 2.61 (s, 1H), 2.35 (s, 3H), 2.19 (s, 3H), 2.10 (d, J=0.9 Hz, 3H), 2.00-1.89 (m, 2H), 1.77-1.55 (m, 4H), 1.31 (s, 9H). $^{19}$F NMR (479 MHz, DMSO-$d_6$) δ: −119.33 (dd, J=13.9, 8.8 Hz). HPLC-MS (ESI+): m/z 541.3 [20%, (M+H)$^+$], 271.2 [100% (M+2H)$^{2+}$]. HRMS (ESI+): m/z calcd for $C_{28}H_{38}FN_6O_2S$ (M+H)$^+$ 541.2755, found 541.2757.

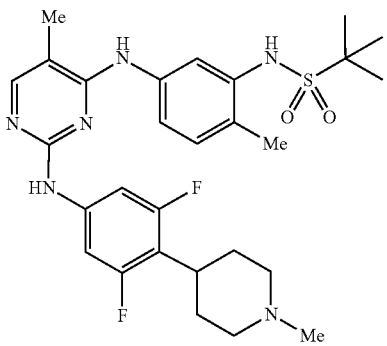

PN2-174

N-(5-((2-((3,5-Difluoro-4-(1-methylpiperidin-4-yl)phenyl)amino)-5-methylpyrimidin-4-yl)amino)-2-methylphenyl)-2-methylpropane-2-sulfonamide (PN2-174). This was prepared according to the general procedure C, by reaction of PN2-172 (74 mg, 0.2 mmol, 1.0 equiv.), PN2-120 (45 mg, 0.2 mmol, 1.0 equiv.), EtOH (1.0 mL) and 4M HCl (100 L) for 15 min at 160° C. to afford, after chromatography, the title compound PN1-174 (57 mg, 51%) as a light brown powder. HPLC: 99% [$t_R$=5.96 min, gradient MeOH-water (with 0.1% TFA), 5-95% over 20 min.]. $^1$H NMR (500 MHz, DMSO-$d_6$) δ: 9.20 (s, 1H), 8.84 (s, 1H), 8.44 (s, 1H), 7.90 (d, J=1.1 Hz, 1H), 7.57-7.43 (m, 2H), 7.34 (d, J=11.9 Hz, 2H), 7.15 (d, J=8.1 Hz, 1H), 2.84 (m, 2H), 2.71 (d, J=11.8 Hz, 1H), 2.35 (s, 3H), 2.18 (s, 3H), 2.11 (d, J=0.9 Hz, 3H), 2.00-1.83 (m, 4H), 1.62-1.46 (m, 2H), 1.31 (s, 9H). $^{19}$F NMR (479 MHz, DMSO-$d_6$) δ: −114.68 (d, J=11.8 Hz). HPLC-MS (ESI+): m/z 559.3 [20%, (M+H)$^+$], 280.2 [100% (M+2H)$^{2+}$]. HRMS (ESI+): m/z calcd for $C_{28}H_{37}F_2N_6O_2S$ (M+H)$^+$ 559.2661, found 559.2650.

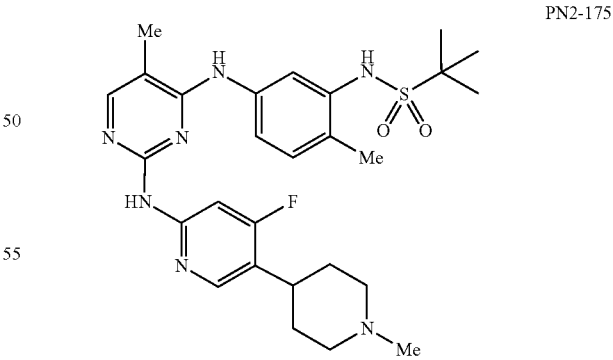

PN2-175

N-(5-((2-((4-Fluoro-5-(1-methylpiperidin-4-yl)pyridin-2-yl)amino)-5-methylpyrimidin-4-yl)amino)-2-methylphenyl)-2-methylpropane-2-sulfonamide (PN2-175). The chloropyrimidine SG3-024B2 (88 mg, 0.24 mmol, 1.2 equiv.), PN1-055 (42 mg, 0.2 mmol, 1.0 equiv.), Pd$_2$(dba)$_3$ (18.3, 0.0155 mmol), Xantphos (23 mg, 0.031 mmol), and Cs$_2$CO$_3$ (130 mg, 0.3 mmol, 2.0 equiv.) were combined as a mixture, in a pressure tube, in degassed toluene (1 mL) and heated to 120° C. for 16 h under N₂. The reaction mixture was cooled to room temperature and partitioned between saturated NH₄Cl (20 mL) and EtOAc (10 mL). The layers were separated, and the aqueous layer was extracted twice more with EtOAc (10 mL). The combined organic extracts were washed with brine, dried (MgSO₄) and concentrated under reduced pressure to give a yellow oil. Purification by flash chromatography (SiO₂, 15% MeOH in DCM) provided PN2-175 (31 mg, 29%) as a white powder. HPLC: 99% [$t_R$=12.45 min, gradient MeOH-water (with 0.1% TFA), 5-95% over 20 min.]. ¹H NMR (500 MHz, DMSO-$d_6$) δ: 9.02 (d, J=1.6 Hz, 1H), 8.86 (s, 1H), 8.48 (s, 1H), 8.13 (d, J=10.9 Hz, 1H), 8.04-7.88 (m, 2H), 7.79 (d, J=2.2 Hz, 1H), 7.52 (dd, J=8.2, 2.3 Hz, 1H), 7.14 (d, J=8.3 Hz, 1H), 2.87 (d, J=10.9 Hz, 2H), 2.65-2.54 (m, 1H), 2.34 (s, 3H), 2.20 (s, 3H), 2.13 (s, 3H), 1.98-1.89 (m, 2H), 1.82-1.60 (m, 4H), 1.32 (s, 9H). ¹⁹F NMR (479 MHz, DMSO-$d_6$) δ: −108.61 (t, J=12.5 Hz). HPLC-MS (ESI+): m/z 542.3 [40%, (M+H)⁺], 271.7 [100% (M+2H)²⁺]. HRMS (ESI+): m/z calcd for $C_{27}H_{37}FN_6O_2S$ (M+H)⁺ 542.2708, found 542.2709.

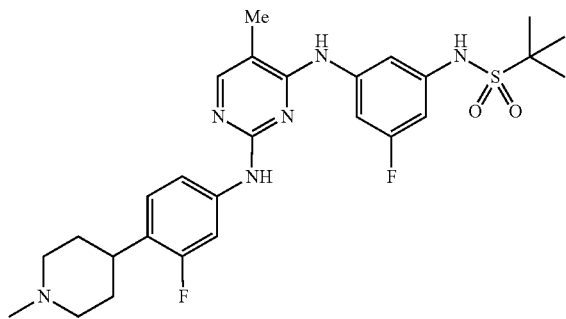

PN3-052

N-(3-Fluoro-5-((2-((3-fluoro-4-(1-methylpiperidin-4-yl)phenyl)amino)-5-methylpyrimidin-4-yl)amino)phenyl)-2-methylpropane-2-sulfonamide (PN3-052). The reaction, according to general procedure C, of PN3-048 (67.2 mg, 0.18 mmol, 1.2 equiv.), MA9-058 (31.2 mg, 0.15 mmol, 1.0 equiv.), EtOH (1.0 mL) and 4M HCl (100 µL) for 15 min at 160° C. afforded, after chromatography, the title compound PN3-052 (35 mg, 43%) as a light brown powder. HPLC: 99% [$t_R$=12.45 min, gradient MeOH-water (with 0.1% TFA), 5-95% over 20 min.]. ¹H NMR (500 MHz, DMSO-$d_6$) δ: 9.88 (s, 1H), 9.17 (s, 1H), 8.61 (s, 1H), 8.01 (d, J=0.9 Hz, 1H), 7.69 (dd, J=13.9, 2.2 Hz, 1H), 7.61-7.50 (m, 1H), 7.49-7.29 (m, 2H), 7.16 (t, J=8.7 Hz, 1H), 6.85 (dt, J=10.7, 2.2 Hz, 1H), 2.92 (d, J=11.0 Hz, 2H), 2.72-2.67 (m, 1H), 2.26 (bs, 3H), 2.17 (d, J=0.9 Hz, 3H), 2.03 (m, 2H), 1.84-1.66 (m, 4H), 1.36 (s, 9H). ¹⁹F NMR (479 MHz, DMSO-$d_6$) δ: −112.01 (d, J=11.3 Hz), −119.14 (t, J=11.7 Hz). HPLC-MS (ESI+): m/z 545.2 [40%, (M+H)⁺], 273.3 [100% (M+2H)²⁺]. HRMS (ESI+): m/z calcd for $C_{27}H_{35}F_2N_6O_2S$ (M+H)⁺ 544.2432, found 544.2436.

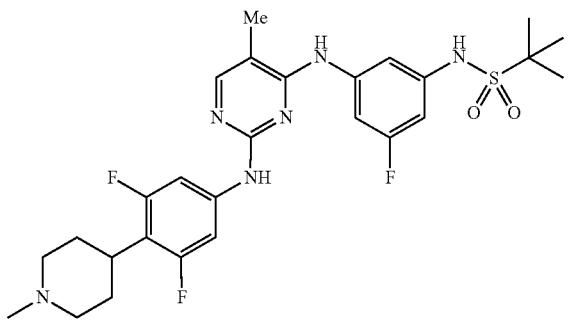

PN3-053

N-(3-((2-((3,5-Difluoro-4-(1-methylpiperidin-4-yl)phenyl)amino)-5-methylpyrimidin-4-yl)amino)-5-fluorophenyl)-2-methylpropane-2-sulfonamide (PN3-053). The reaction according to general procedure C, of PN3-048 (56 mg, 0.15 mmol, 1.2 equiv.), PN1-120 (28.3 mg, 0.15 mmol, 1.0 equiv.), EtOH (1.0 mL) and 4M HCl (100 µL) for 15 min at 160° C., afforded, after chromatography, the title compound PN3-053 (33 mg, 47%) as a light brown powder. HPLC: 99% [$t_R$=12.45 min, gradient MeOH-water (with 0.1% TFA), 5-95% over 20 min.]. ¹H NMR (500 MHz, DMSO-$d_6$) δ: 9.76 (s, 1H), 9.27 (s, 1H), 8.55 (s, 1H), 7.91 (d, J=1.0 Hz, 1H), 7.48-7.33 (m, 1H), 7.30 (d, J=11.8 Hz, 2H), 7.16 (d, J=1.9 Hz, 1H), 6.75 (dt, J=10.7, 2.2 Hz, 1H), 2.80 (m, 2H), 2.67 (m, 1H), 2.13 (bs, 3H), 2.05 (d, J=0.9 Hz, 3H), 1.89 (m, 4H), 1.50 (d, J=10.0 Hz, 2H), 1.23 (s, 9H). ¹⁹F NMR (479 MHz, DMSO-$d_6$) δ: −111.96 (t, J=11.2 Hz), −114.58 (d, J=12.1 Hz). HPLC-MS (ESI+): m/z 563.3 [40%, (M+H)⁺], 282.2 [100% (M+2H)²⁺]. HRMS (ESI+): m/z calcd for $C_{26}H_{34}F_3N_6O_2S$ (M+H)⁺ 563.2411, found 563.2417.

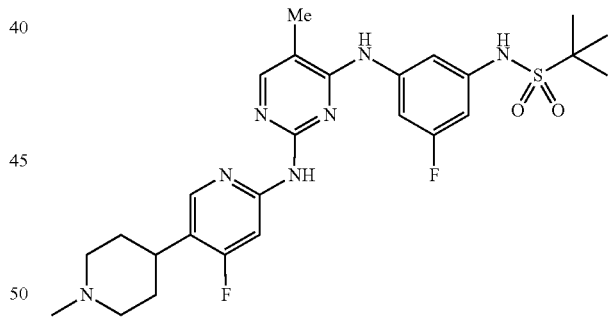

PN3-054

N-(3-Fluoro-5-((2-((4-fluoro-5-(1-methylpiperidin-4-yl)pyridin-2-yl)amino)-5-methylpyrimidin-4-yl)amino)phenyl)-2-methylpropane-2-sulfonamide (PN3-054). The chloropyrimidine PN3-048 (50.3 mg, 0.135 mmol, 1.2 equiv.), PN1-055 (23.5 mg, 0.1125 mmol, 1.0 equiv.), Pd₂(dba)₃ (10.3, 0.0135 mmol), Xantphos (14 mg, 0.027 mmol), and Cs₂CO₃ (73 mg, 0.225 mmol, 2.0 equiv.) were combined as a mixture, in a pressure tube, in degassed toluene (0.8 mL) and heated to 120° C. for 16 h under N₂. The reaction mixture was cooled to room temperature and partitioned between saturated NH₄Cl (20 mL) and EtOAc (10 mL). The layers were separated, and the aqueous layer was extracted twice more with EtOAc (10 mL). The combined organic extracts were washed with brine, dried (MgSO₄) and concentrated under reduced pressure to give a yellow oil.

Purification by flash chromatography (SiO$_2$, 15% MeOH in DCM) provided PN3-054 (18 mg, 29%) as a white powder. HPLC: 99% [t$_R$=12.45 min, gradient MeOH-water (with 0.1% TFA), 5-95% over 20 min.]. $^1$H NMR (500 MHz, DMSO-d$_6$) δ: 9.78 (s, 1H), 9.32 (d, J=1.5 Hz, 1H), 8.61 (s, 1H), 8.17 (d, J=10.9 Hz, 1H), 8.09 (m, 2H), 7.79 (s, 1H), 7.47 (dt, J=11.5, 2.2 Hz, 1H), 7.42 (m, 1H), 6.82 (dt, J=10.7, 2.2 Hz, 1H), 2.92 (m, 2H), 2.64 (m, 1H), 2.25 (bs, 3H), 2.15 (d, J=1.0 Hz, 3H), 1.84 (m, 4H), 1.31 (s, 9H). $^{19}$F NMR (479 MHz, DMSO-d$_6$) δ: −108.46, −112.01. HPLC-MS (ESI+): m/z 546.3 [40%, (M+H)$^+$], 273.7 [100% (M+2H)$^{2+}$]. HRMS (ESI+): m/z calcd for C$_{27}$H$_{34}$FN$_7$O$_2$S (M+H)$^+$ 546.2457, found 546.2456.

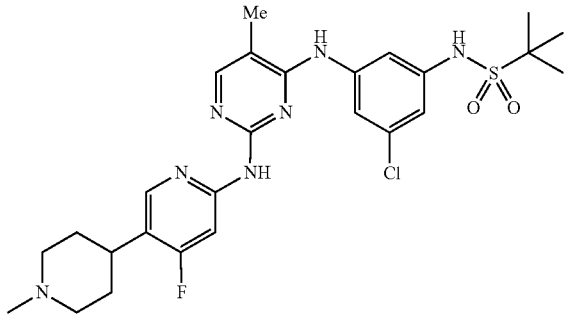

PN3-074

N-(3-Chloro-5-((2-((4-fluoro-5-(1-methylpiperidin-4-yl)pyridin-2-yl)amino)-5-methylpyrimidin-4-yl)amino)phenyl)-2-methylpropane-2-sulfonamide (PN3-074). The chloropyrimidine PN3-071 (70 mg, 0.18 mmol, 1.2 equiv.), PN1-055 (31.1 mg, 0.15 mmol, 1.0 equiv.), Pd$_2$(dba)$_3$ (14 mg, 0.015 mmol), Xantphos (18 mg, 0.03 mmol), and Cs$_2$CO$_3$ (98 mg, 0.3 mmol, 2.0 equiv.) were combined as a mixture, in a pressure tube, in degassed toluene (0.8 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$) and concentrated under reduced pressure to give a yellow oil. Purification by flash chromatography (SiO$_2$, 15% MeOH in DCM) provided PN3-074 (39 mg, 47%) as a white powder. HPLC: 99% [t$_R$=12.45 min, gradient MeOH-water (with 0.1% TFA), 5-95% over 20 min.]. $^1$H NMR (500 MHz, DMSO-d$_6$) δ: 9.79 (s, 1H), 9.19 (d, J=1.5 Hz, 1H), 8.62 (s, 1H), 8.17 (d, J=10.8 Hz, 1H), 8.06-7.86 (m, 3H), 7.49 (t, J=1.9 Hz, 1H), 7.05 (t, J=1.9 Hz, 1H), 2.93-2.79 (m, 2H), 2.65-2.56 (m, 1H), 2.20 (s, 3H), 2.16-2.08 (m, 3H), 2.02-1.91 (m, 2H), 1.83-1.62 (m, 4H), 1.31 (s, 9H). $^{19}$F NMR (479 MHz, DMSO-d$_6$) δ: −107.98 (t, J=12.4 Hz). HPLC-MS (ESI+): m/z 562.3 [40%, (M+H)$^+$], 281.8 [100% (M+2H)$^{2+}$]. HRMS (ESI+): m/z calcd for C$_{26}$H$_{34}$FClN$_7$O$_2$S (M+H)$^+$ 562.2162, found 562.2159.

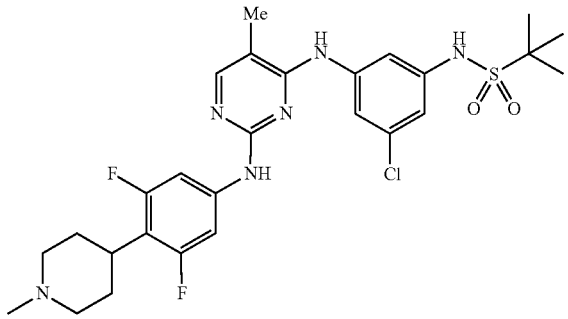

PN3-075

N-(3-Chloro-5-((2-((3,5-difluoro-4-(1-methylpiperidin-4-yl)phenyl)amino)-5-methylpyrimidin-4-yl)amino)phenyl)-2-methylpropane-2-sulfonamide (PN3-075). The chloropyrimidine PN3-071 (70 mg, 0.18 mmol, 1.2 equiv.), PN1-120 (34.1 mg, 0.15 mmol, 1.0 equiv.), Pd$_2$(dba)$_3$ (14 mg, 0.015 mmol), Xantphos (18 mg, 0.03 mmol), and Cs$_2$CO$_3$ (98 mg, 0.3 mmol, 2.0 equiv.) were combined as a mixture, in a pressure tube, in degassed toluene (0.8 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$), and concentrated under reduced pressure to give a yellow oil. Purification by flash chromatography (SiO$_2$, 15% MeOH in DCM) provided PN3-075 (34 mg, 39%) as a white powder. HPLC: 99% [t$_R$=12.45 min, gradient MeOH-water (with 0.1% TFA), 5-95% over 20 min.]. $^1$H NMR (500 MHz, DMSO-d$_6$) δ: 9.84 (s, 1H), 9.33 (s, 1H), 8.63 (s, 1H), 7.98 (d, J=1.0 Hz, 1H), 7.50 (t, J=1.9 Hz, 1H), 7.40 (t, J=1.9 Hz, 1H), 7.33 (d, J=11.9 Hz, 2H), 7.05 (t, J=1.9 Hz, 1H), 2.86 (m, 2H), 2.73 (m, 1H), 2.20 (bs, 3H), 2.12 (s, 3H), 1.93 (d, J=21.1 Hz, 4H), 1.56 (d, J=9.9 Hz, 2H), 1.30 (s, 9H). $^{19}$F NMR (479 MHz, DMSO-d$_6$) δ: −114.25 (d, J=12.1 Hz). HPLC-MS (ESI+): m/z 579.3 [40%, (M+H)$^+$], 290.3 [100% (M+2H)$^{2+}$]. HRMS (ESI+): m/z calcd for C$_{27}$H$_{34}$F$_2$ClN$_6$O$_2$S (M+H)$^+$ 579.2115, found 579.2111.

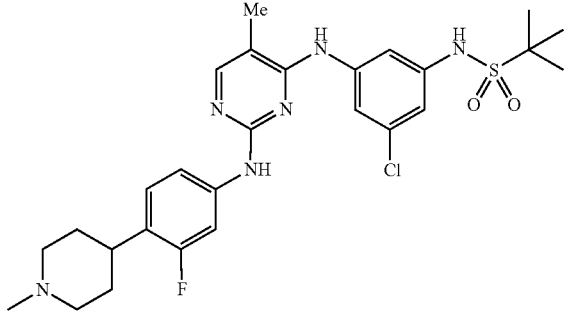

PN3-076

N-(3-Chloro-5-((2-((3-fluoro-4-(1-methylpiperidin-4-yl)phenyl)amino)-5-methylpyrimidin-4-yl)amino)phenyl)-2-methylpropane-2-sulfonamide (PN3-076). The chloropyrimidine PN3-071 (70 mg, 0.18 mmol, 1.2 equiv.), MA9-058 (31.3 mg, 0.15 mmol, 1.0 equiv.), Pd$_2$(dba)$_3$ (14 mg, 0.015 mmol), Xantphos (18 mg, 0.03 mmol), and Cs$_2$CO$_3$ (98 mg, 0.3 mmol, 2.0 equiv.) were combined as a mixture, in a pressure tube, in degassed toluene (0.8 mL) and heated to 120° C. for 16 h under $N_2$. The reaction mixture was cooled to room temperature and partitioned between saturated $NH_4Cl$ (20 mL) and EtOAc (10 mL). The layers were separated, and the aqueous layer was extracted twice more with EtOAc (10 mL). The combined organic extracts were washed with brine, dried ($MgSO_4$), and concentrated under reduced pressure to give a yellow oil. Purification by flash chromatography ($SiO_2$, 15% MeOH in DCM) provided PN3-076 (43 mg, 51%) as a white powder. HPLC: 99% [$t_R$=12.45 min, gradient MeOH-water (with 0.1% TFA), 5-95% over 20 min.]. $^1$H NMR (500 MHz, DMSO-$d_6$) δ: 9.84 (s, 1H), 9.10 (s, 1H), 8.56 (s, 1H), 7.96 (s, 1H), 7.69-7.49 (m, 2H), 7.47 (d, J=2.1 Hz, 1H), 7.34 (dd, J=8.5, 2.2 Hz, 1H), 7.11 (t, J=8.7 Hz, 1H), 7.03 (t, J=1.9 Hz, 1H), 2.85 (d, J=11.4 Hz, 2H), 2.71-2.57 (m, 1H), 2.19 (s, 3H), 2.11 (s, 3H), 2.00-1.89 (m, 2H), 1.74-1.53 (m, 4H), 1.30 (s, 9H). $^{19}$F NMR (479 MHz, DMSO-$d_6$) δ: −115.33-132.37 (m). HPLC-MS (ESI+): m/z 561.3 [40%, (M+H)$^+$], 281.2 [100% (M+2H)$^{2+}$]. HRMS (ESI+): m/z calcd for $C_{27}H_{35}FClN_6O_2S$ (M+H)$^+$ 561.2209, found 561.2207.

PN3-099

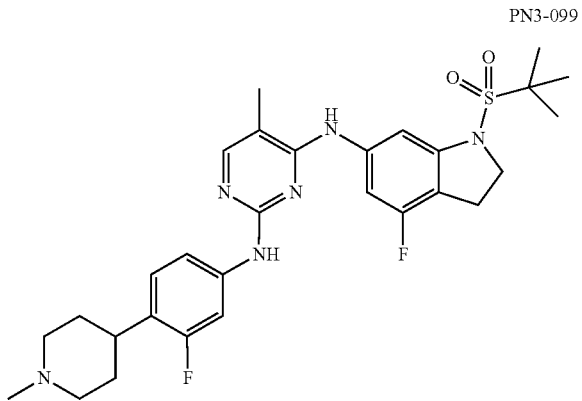 [SMILES: Cc1cnc(Nc2cc(F)c(C3CCN(C)CC3)cn2)nc1Nc1cc(F)c2c(c1)N(S(=O)(=O)C(C)(C)C)CC2]

$N^4$-(1-(tert-Butylsulfonyl)-4-fluoroindolin-6-yl)-$N^2$-(3-fluoro-4-(1-methylpiperidin-4-yl)phenyl)-5-methylpyrimidine-2,4-diamine (PN3-099). The chloropyrimidine PN3-059 (70 mg, 0.175 mmol, 1.2 equiv.), MA9-058 (30.0 mg, 0.146 mmol, 1.0 equiv.), Pd$_2$(dba)$_3$ (14 mg, 0.015 mmol), Xantphos (18 mg, 0.03 mmol), and Cs$_2$CO$_3$ (98 mg, 0.3 mmol, 2.0 equiv.) were combined as a mixture, in a pressure tube, in degassed toluene (0.8 mL) and heated to 120° C. for 16 h under $N_2$. The reaction mixture was cooled to room temperature and partitioned between saturated $NH_4Cl$ (20 mL) and EtOAc (10 mL). The layers were separated, and the aqueous layer was extracted twice more with EtOAc (10 mL). The combined organic extracts were washed with brine, dried (MgSO$_4$), and concentrated under reduced pressure to give a yellow oil. Purification by flash chromatography (SiO$_2$, 15% MeOH in DCM) provided PN3-099 (22 mg, 27%) as a white powder. HPLC: 99% [$t_R$=12.45 min, gradient MeOH-water (with 0.1% TFA), 5-95% over 20 min.]. $^1$H NMR (500 MHz, DMSO-$d_6$) δ: 9.13 (s, 1H), 8.50 (s, 1H), 7.93 (s, 1H), 7.63 (dd, J=14.0, 2.2 Hz, 1H), 7.56 (dd, J=11.4, 1.7 Hz, 1H), 7.31 (dd, J=8.5, 2.2 Hz, 1H), 7.24 (d, J=1.7 Hz, 1H), 7.10 (t, J=8.7 Hz, 1H), 4.12 (t, J=8.4 Hz, 2H), 3.13 (t, J=8.4 Hz, 2H), 2.87 (d, J=11.0 Hz, 2H), 2.67-2.58 (m, 1H), 2.20 (bs, 3H), 2.12 (s, 3H), 2.03-1.91 (m, 2H), 1.82-1.56 (m, 4H), 1.39 (s, 9H). $^{19}$F NMR (479 MHz, DMSO-$d_6$) δ: −117.67 (d, J=12.1 Hz), −119.29 (d, J=11.2 Hz). HPLC-MS (ESI+): m/z 571.5 [40%, (M+H)$^+$], 286.3 [100% (M+2H)$^{2+}$]. HRMS (ESI+): m/z calcd for $C_{27}H_{37}FN_6O_2S$ (M+H)$^+$ 571.2661, found 571.2661.

PN3-100

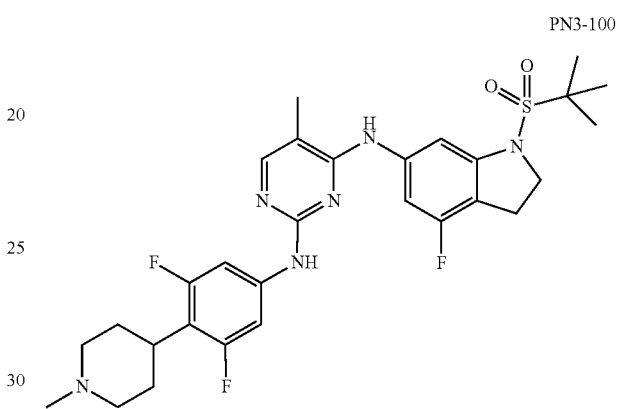

$N^4$-(1-(tert-Butylsulfonyl)-4-fluoroindolin-6-yl)-$N^2$-(3,5-difluoro-4-(1-methylpiperidin-4-yl)phenyl)-5-methylpyrimidine-2,4-diamine (PN3-100). The chloropyrimidine PN3-059 (60 mg, 0.15 mmol, 1.2 equiv.), PN1-055 (26.0 mg, 0.125 mmol, 1.0 equiv.), Pd$_2$(dba)$_3$ (12 mg, 0.0125 mmol), Xantphos (15 mg, 0.025 mmol), and Cs$_2$CO$_3$ (81.0 mg, 0.25 mmol, 2.0 equiv.) were combined as a mixture, in a pressure tube, in degassed toluene (0.8 mL) and heated to 120° C. for 16 h under $N_2$. The reaction mixture was cooled to room temperature and partitioned between saturated $NH_4Cl$ (20 mL) and EtOAc (10 mL). The layers were separated, and the aqueous layer was extracted twice more with EtOAc (10 mL). The combined organic extracts were washed with brine, dried (MgSO$_4$), and concentrated under reduced pressure to give a yellow oil. Purification by flash chromatography (SiO$_2$, 15% MeOH in DCM) provided PN3-100 (33 mg, 47%) as a white powder. HPLC: 99% [$t_R$=12.45 min, gradient MeOH-water (with 0.1% TFA), 5-95% over 20 min.]. $^1$H NMR (500 MHz, DMSO-$d_6$) δ: 9.34 (s, 1H), 8.58 (s, 1H), 7.95 (d, J=0.9 Hz, 1H), 7.42 (d, J=11.1 Hz, 1H), 7.36 (d, J=11.9 Hz, 2H), 7.20 (d, J=1.6 Hz, 1H), 4.12 (t, J=8.4 Hz, 2H), 3.13 (t, J=8.4 Hz, 2H), 2.86 (d, J=8.4 Hz, 2H), 2.74 (s, 1H), 2.19 (s, 3H), 2.12 (d, J=0.9 Hz, 3H), 2.04-1.85 (m, 4H), 1.57 (d, J=10.4 Hz, 2H), 1.38 (s, 9H). $^{19}$F NMR (479 MHz, DMSO-$d_6$) δ: −114.76 (d, J=12.1 Hz), −117.65 (d, J=11.5 Hz). HPLC-MS (ESI+): m/z 589.4 [20%, (M+H)$^+$], 295.3 [100% (M+2H)$^{2+}$]. HRMS (ESI+): m/z calcd for $C_{29}H_{36}F_3N_7O_2S$ (M+H)$^+$ 589.2567, found 589.2566.

PN3-108

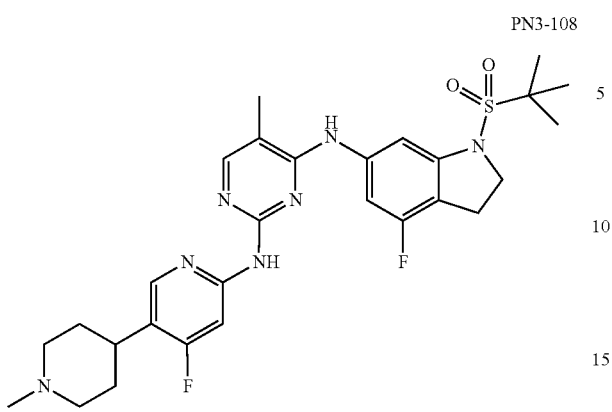

N⁴-(1-(tert-Butylsulfonyl)-4-fluoroindolin-6-yl)-N²-(4-fluoro-5-(1-methylpiperidin-4-yl)pyridin-2-yl)-5-methylpyrimidine-2,4-diamine (PN3-108). The chloropyrimidine PN3-059 (70 mg, 0.175 mmol, 1.2 equiv.), PN2-120 (33.0 mg, 0.146 mmol, 1.0 equiv.), Pd$_2$(dba)$_3$ (14 mg, 0.015 mmol), Xantphos (18 mg, 0.03 mmol), and Cs$_2$CO$_3$ (98 mg, 0.3 mmol, 2.0 equiv.) were combined as a mixture, in a pressure tube, in degassed toluene (0.8 mL) and heated to 120° C. for 16 h under N$_2$. The reaction mixture was cooled to room temperature and partitioned between saturated NH$_4$Cl (20 mL) and EtOAc (10 mL). The layers were separated, and the aqueous layer was extracted twice more with EtOAc (10 mL). The combined organic extracts were washed with brine, dried (MgSO$_4$), and concentrated under reduced pressure to give a yellow oil. Purification by flash chromatography (SiO$_2$, 15% MeOH in DCM) provided PN3-108 (20 mg, 24%) as a white powder. HPLC: 99% [t$_R$=12.45 min, gradient MeOH-water (with 0.1% TFA), 5-95% over 20 min.]. $^1$H NMR (500 MHz, DMSO-d$_6$) δ: 9.39 (d, J=1.6 Hz, 1H), 8.59 (s, 1H), 8.15 (d, J=10.9 Hz, 1H), 7.99 (d, J=1.1 Hz, 1H), 7.91 (d, J=14.0 Hz, 1H), 7.62 (dd, J=11.4, 1.7 Hz, 1H), 7.35 (d, J=1.7 Hz, 1H), 4.12 (t, J=8.5 Hz, 2H), 3.12 (t, J=8.4 Hz, 2H), 2.86 (d, J=11.3 Hz, 2H), 2.66-2.54 (m, 1H), 2.19 (s, 3H), 2.14 (d, J=0.9 Hz, 3H), 2.01-1.87 (m, 2H), 1.84-1.62 (m, 4H), 1.38 (s, 9H). $^{19}$F NMR (479 MHz, DMSO-d$_6$) δ: -108.95 (t, J=12.9 Hz), -117.57 (d, J=11.7 Hz). HPLC-MS (ESI+): m/z 572.4 [20%, (M+H)$^+$], 286.8 [100% (½M+H)$^{2+}$]. HRMS (ESI+): m/z calcd for C$_{28}$H$_{36}$F$_2$N$_7$O$_2$S (M+H)$^+$ 572.6614, found 572.2618.

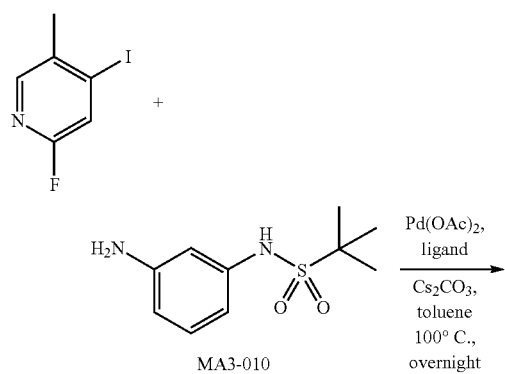

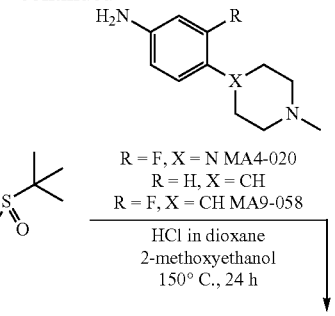

R = F, X = N MA4-020
R = H, X = CH
R = F, X = CH MA9-058

HCl in dioxane
2-methoxyethanol
150° C., 24 h

SY2-183

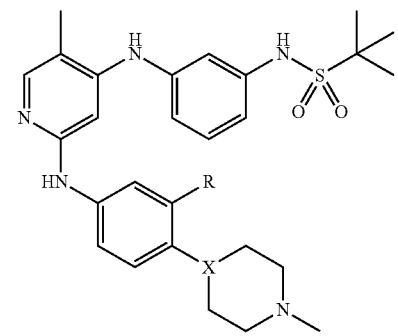 [SMILES: Cc1cnc(Nc2ccc(N3CCN(C)CC3)c(F)c2)cc1Nc1cccc(NS(=O)(=O)C(C)(C)C)c1]

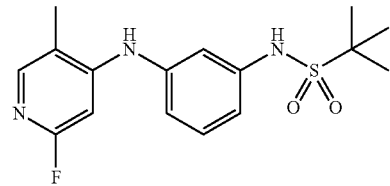

N-(3-((2-Fluoro-5-methylpyridin-4-yl)amino)phenyl)-2-methylpropane-2-sulfonamide (SY2-183). A 20 mL vial was charged with Pd(OAc)$_2$ (2 mg, 8.4 μmol) and BINAP (10 mg, 0.0168 mmol) and then degassed toluene (0.5 mL) was added. The mixture was stirred for 5 min under argon. 2-Fluoro-4-iodo-5-methylpyridine (0.1 g, 0.42 mmol), MA3-010 (0.12 g, 0.51 mmol), Cs$_2$CO$_3$ (0.25 g, 0.84 mmol) and toluene (5 mL) were added. The mixture was degassed for 5 min by bubbling argon and then the vial was sealed. The mixture was stirred at 100° C. overnight. The mixture was quenched with water and extracted with EtOAc. The organic layers were dried (MgSO$_4$), filtered and concentrated. The residue was triturated with CH$_2$Cl$_2$ and hexanes to give the title compound as a beige solid (60 mg, 50%). $^1$H NMR (500 MHz, DMSO-d$_6$) δ 9.69 (s, 1H), 8.16 (s, 1H), 7.75 (s, 1H), 7.28 (t, J=8.0 Hz, 1H), 7.24 (t, J=2.1 Hz, 1H), 7.03 (ddd, J=8.2, 2.2, 1.0 Hz, 1H), 6.93 (ddd, J=8.2, 2.1, 0.9 Hz, 1H) 6.38 (s, 1H), 2.17 (s, 3H), 1.29 (s, 9H). HPLC-MS (ESI+): m/z 697.3 (2M+Na)$^+$, 338.2 (M+1)$^+$.

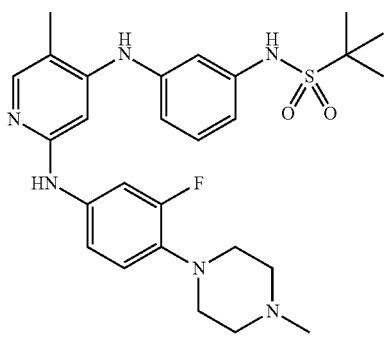

N-(3-((2-((3-Fluoro-4-(4-methylpiperazin-1-yl)phenyl)amino)-5-methylpyridin-4-yl)amino)phenyl)-2-methylpropane-2-sulfonamide (SY3-005). A 5 mL vial was charged with SY2-183 (50 mg, 0.148 mmol), MA4-020 (31 mg, 0.148 mmol) and 2-methoxyethanol (0.5 mL). Then 4 M HCl in dioxane (60 µL, 0.24 mmol) was added. The vial was sealed and heated at 150° C. for 24 h. The mixture was quenched with saturated NaHCO$_3$ (aq) and extracted with EtOAc three times. The organic layers were dried (MgSO$_4$), filtered and concentrated under reduced pressure. The residue was purified by chromatography on SiO$_2$ (0-20% gradient elution, MeOH/CH$_2$Cl$_2$). The solid material obtained from column chromatography was triturated using CH$_2$Cl$_2$ and hexanes to afford title compound as yellow solid (32 mg, 41%). HPLC: 99% [t$_R$=13.41 min, 5-95% gradient elution MeOH/water (with 0.1% TFA), 20 min, 254 nm] $^1$H NMR (500 MHz, DMSO-d$_6$) δ 9.63 (s, 1H), 8.57 (s, 1H), 7.76 (s, 1H), 7.68 (dd, J=15.7, 2.5 Hz, 1H), 7.66 (s, 1H), 7.23 (t, J=8.1 Hz, 1H), 7.17 (t, J=2.1 Hz, 1H), 7.09 (m, 1H), 6.96 (m, 1H), 6.90 (m, 2H), 6.41 (s, 1H), 2.96 (br s, 4H), 2.48 (br s, 4H), 2.24 (s, 3H), 2.10 (s, 3H), 1.29 (s, 9H). $^{13}$C NMR (125 MHz, DMSO-d$_6$) δ 155.9 (d, J=238.8 Hz), 155.2, 150.2, 147.6, 142.1, 140.9, 138.3 (d, J=11.3 Hz), 132.0 (d, J=9.6 Hz), 129.5, 119.4 (d, J=4.2 Hz), 116.3, 113.5, 113.1 (d, J=2.7 Hz), 112.5, 112.4, 105.6 (d, J=25.7 Hz), 93.2, 60.9, 64.6, 50.5, 45.7, 24.3, 14.2. $^{19}$F NMR (471 MHz, DMSO-d$_6$) δ −122.49 (dd, J=15.8, 10.0 Hz). HPLC-MS (ESI+): m/z 527.3 (M+1)$^+$. HRMS (ESI+): m/z calcd for C$_{27}$H$_{36}$FN$_6$O$_2$S (M+H)$^+$ 527.2604, found 527.2607.

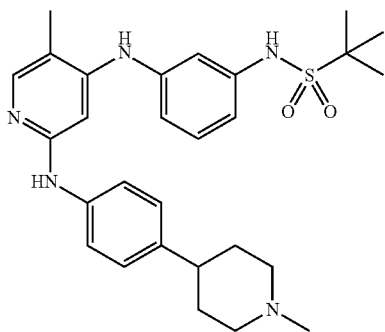 [SMILES: Cc1cnc(Nc2ccc(C3CCN(C)CC3)cc2)cc1Nc1cccc(NS(=O)(=O)C(C)(C)C)c1]

2-Methyl-N-(3-((5-methyl-2-((4-(1-methylpiperidin-4-yl)phenyl)amino)pyridin-4-yl)amino)phenyl)propane-2-sulfonamide (SY3-030). This compound was synthesized by the same procedure described for SY3-005 using SY2-183 and 4-(1-methylpiperidin-4-yl)aniline (0.028 g, 0.148 mmol) to afford an off-white solid (0.03 g, 40%). HPLC: 99% [t$_R$=11.27 min, 5-95% gradient elution MeOH/water (with 0.1% TFA), 20 min, 254 nm]. $^1$H NMR (500 MHz, DMSO-d$_6$) δ 9.61 (br s, 1H), 8.42 (s, 1H), 7.74 (s, 1H), 7.63 (s, 1H), 7.45 (d, J=9 Hz, 2H), 7.22 (t, J=8 Hz, 1H), 7.18 (t, J=2 Hz, 1H), 7.05 (d, J=9 Hz, 2H), 6.95 (dd, J=8, 2 Hz, 1H), 6.90 (dd, J=8, 2 Hz, 1H), 6.44 (s, 1H), 5.75 (s. 1H), 2.84-2.82 (m, 2H), 2.34-2.91 (m, 1H), 2.17 (s, 3H), 2.09 (s, 3H), 1.95 (td, J=11.5, 2.5 Hz, 2H), 1.68-1.58 (m, 4H), 1.28 (s, 9H). $^{13}$C NMR (125 MHz, DMSO-d$_6$) δ 155.5, 150.0, 147.8, 142.2, 140.9, 140.4, 137.3, 129.4, 129.5, 117.7, 116.1, 113.3, 112.2, 112.1, 93.2, 60.9, 55.9, 46.2, 40.5, 32.3, 24.3, 14.2. HPLC-MS (ESI+): m/z 508.3 (M+1)$^+$. HRMS (ESI+): m/z calcd for C$_{28}$H$_{38}$N$_5$O$_2$S (M+H)$^+$ 508.2741, found 508.2736.

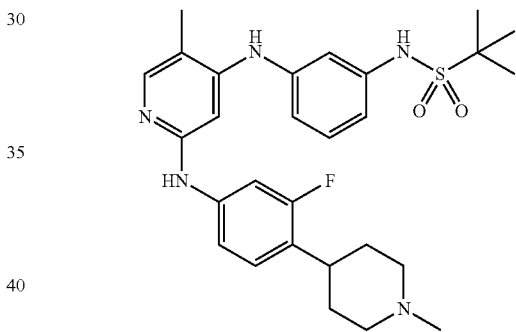

N-(3-((2-((3-Fluoro-4-(1-methylpiperidin-4-yl)phenyl)amino)-5-methylpyridin-4-yl)amino)phenyl)-2-methylpropane-2-sulfonamide (SY3-039). This compound was synthesized by the same procedure described for SY3-005 using SY2-183 (0.05 g, 0.148 mmol) and MA9-058 (0.0308 g, 0.148 mmol) to afford a yellow solid (0.006 g, 8%). HPLC: 95% [t$_R$=11.53 min, 5-95% gradient elution MeOH/water (with 0.1% TFA), 20 min, 254 nm]. $^1$H NMR (500 MHz, DMSO-d$_6$) δ 9.63 (br s, 1H), 8.69 (s, 1H), 7.78 (s, 1H), 7.67 (dd, J=14.5, 2 Hz, 1H), 7.23 (t, J=8 Hz, 1H), 7.17 (t, J=2 Hz, 1H), 7.13-7.06 (m, 2H), 6.96 (dd, J=8, 1 Hz, 1H), 6.91 (dd, J=8, 2 Hz, 1H), 6.43 (s, 1H), 5.75 (s, 1H), 2.85 (d, J=11 Hz, 2H), 2.61 (m, 1H), 2.18 (s, 3H), 2.10 (s, 3H), 1.94 (m, 2H), 1.67-1.62 (m, 4H), 1.28 (s, 9H). $^{19}$F NMR (471 MHz, DMSO-d$_6$) δ −119.2 (dd, J=14.1, 8.8 Hz). HPLC-MS (ESI+): m/z 526.3 (M+1)$^+$. HRMS (ESI+): m/z calcd for C$_{28}$H$_{37}$FN$_5$O$_2$S (M+H)$^+$ 526.2647, found 526.2643.

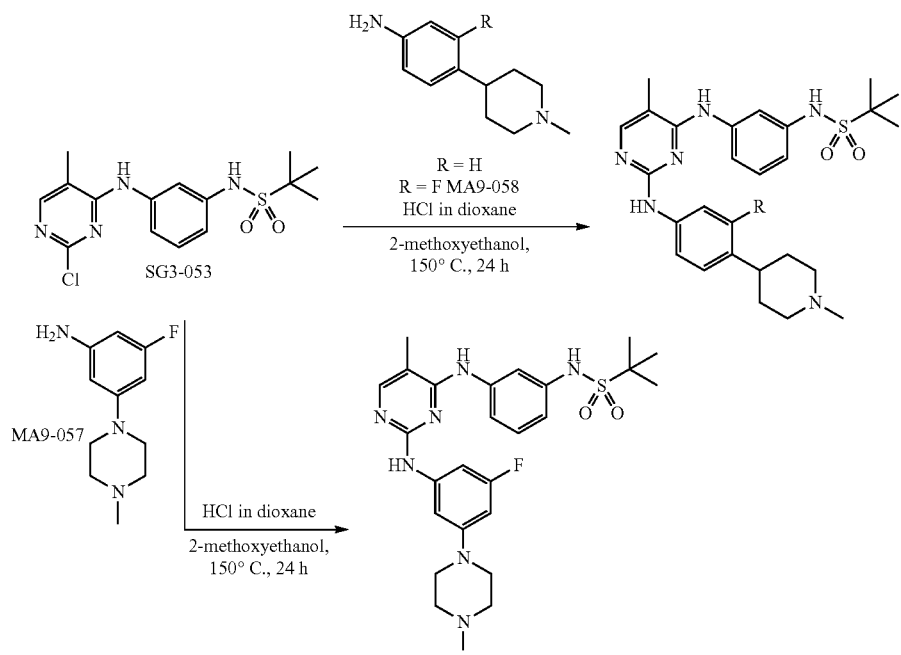

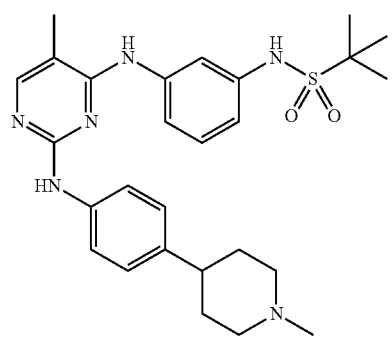

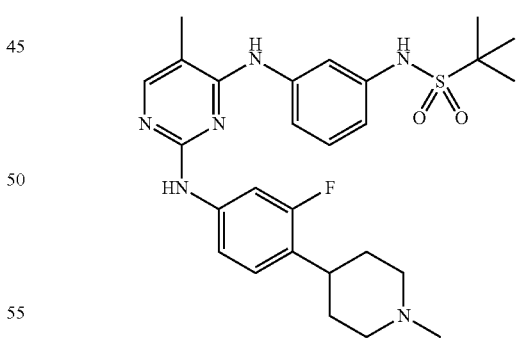

2-Methyl-N-(3-((5-methyl-2-((4-(1-methylpiperidin-4-yl)phenyl)amino)pyrimidin-4-yl)amino)phenyl)propane-2-sulfonamide (SY3-034). This compound was synthesized by the same procedure described for SY3-005 using SG3-053 (0.05 g, 0.141 mmol) and 4-(1-methylpiperidin-4-yl)aniline (0.0268 g, 0.141 mmol) to afford an off-white solid (0.043 g, 60%). HPLC: 96% [$t_R$=11.19 min, 5-95% gradient elution MeOH/water (with 0.1% TFA), 20 min, 254 nm]. $^1$H NMR (500 MHz, DMSO-$d_6$) δ 9.57 (br s, 1H), 8.71 (s, 1H), 8.33 (s, 1H), 7.86 (s, 1H), 7.57-7.54 (m, 3H), 7.49 (d, J=8 Hz, 1H), 7.22 (t, J=8 Hz, 1H), 7.03-7.69 (m, 3H), 2.86 (d, J=11.5 Hz, 2H), 2.33 (tt, J=12, 4 Hz, 1H), 2.19 (s, 3H), 2.09 (s, 3H), 1.94 (t, J=9 Hz, 2H), 1.69-1.59 (m, 4H), 1.28 (s, 9H). $^{13}$C NMR (125 MHz, DMSO-$d_6$) δ 159.2, 158.1, 155.7, 140.5, 139.9, 139.0, 128.5, 126.4, 118.5, 117.9, 114.3, 113.8, 105.6, 60.9, 55.9, 46.2, 40.5, 33.1, 24.4, 13.6. HPLC-MS (ESI+): m/z 509.3 (M+H)$^+$. HRMS (ESI+): m/z calcd for $C_{27}H_{37}N_6O_2S$ (M+H)$^+$ 509.2693, found 509.2685.

N-(3-((2-((3-Fluoro-4-(1-methylpiperidin-4-yl)phenyl)amino)-5-methylpyrimidin-4-yl)amino)phenyl)-2-methylpropane-2-sulfonamide (SY3-038). This compound was synthesized by the same procedure described for SY3-005 using SG3-053 (0.05 g, 0.141 mmol) and MA9-058 (0.029 g, 0.141 mmol) to afford a yellow solid (0.052 g, 67%). HPLC: 99% [$t_R$=11.41 min, 5-95% gradient elution MeOH/water (with 0.1% TFA), 20 min, 254 nm]. $^1$H NMR (500 MHz, DMSO-$d_6$) δ 9.58 (s, 1H), 8.99 (s, 1H), 8.40 (s, 1H), 7.90 (d, J=1 Hz, 1H), 7.64 (dd, J=14, 2.5 Hz, 1H), 7.48-7.46

(m, 2H), 7.30 (dd, J=8.5, 2 Hz, 1H), 7.22 (t, J=8 Hz, 1H), 7.06 (t, J=9 Hz, 1H), 7.03 (m, 1H), 2.85 (d, J=11.5 Hz, 2H), 2.60 (m, 1H), 2.18 (s, 3H), 2.11 (s, 3H), 1.93 (m, 2H), 1.69-1.60 (m, 4H), 1.28 (s, 9H). $^{13}$C NMR (125 MHz, DMSO-$d_6$) δ 160.8 (d, J=238 Hz), 159.3, 157.8, 155.7, 140.7 (d, J=11.3 Hz), 140.3, 140.1, 128.7, 127.2 (d, J=6.3 Hz), 123.7 (d, J=15 Hz), 118.1, 114.5, 114.0 (d, J=5 Hz), 60.8, 55.9, 46.2, 34.1, 31.8, 24.3, 13.6. $^{19}$F NMR (471 MHz, DMSO-$d_6$) δ −119.1 (dd, J=14.1, 8.8 Hz). HPLC-MS (ESI+): m/z 527.3 (M+1)$^+$. HRMS (ESI+): m/z calcd for $C_{27}H_{36}FN_6O_2S$ (M+H)$^+$ 527.2599, found 527.2291.

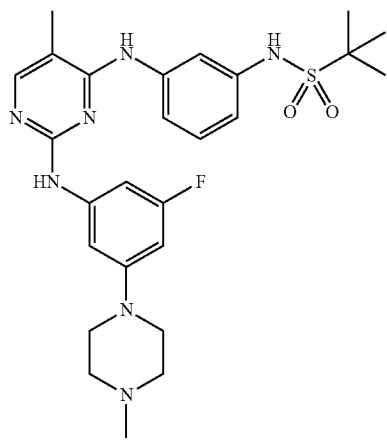 [SMILES: Cc1cnc(Nc2cc(F)cc(N3CCN(C)CC3)c2)nc1Nc1cccc(NS(=O)(=O)C(C)(C)C)c1]

N-(3-((2-((3-Fluoro-5-(4-methylpiperazin-1-yl)phenyl)amino)-5-methylpyrimidin-4-yl)amino)phenyl)-2-methylpropane-2-sulfonamide (SY3-040). This compound was synthesized by the same procedure described for SY3-005 using SG3-053 (0.05 g, 0.141 mmol) and MA9-057 (0.029 g, 0.141 mmol) to afford a yellow solid (0.04 g, 54%). HPLC: 99% [$t_R$=11.73 min, 5-95% gradient elution MeOH/water (with 0.1% TFA), 20 min, 254 nm]. $^1$H NMR (500 MHz, DMSO-$d_6$) δ 9.55 (br s, 1H), 8.84 (s, 1H), 8.39 (s, 1H), 7.92 (s, 1H), 7.55 (d, J=8.5 Hz, 1H), 7.47 (t, J=2 Hz, 1H), 7.20-7.15 (m, 2H), 6.99 (dd, J=8, 2.5 Hz, 1H), 6.93 (t, J=2.5 Hz, 1H), 6.24 (dt, J=12, 2 Hz, 1H), 3.01 (t, J=5 Hz, 4H), 2.38 (t, J=5 Hz, 4H), 2.20 (s, 3H), 2.11 (s, 3H), 1.28 (s, 9H). $^{13}$C NMR (125 MHz, DMSO-$d_6$) δ 164.3 (d, J=234 Hz), 159.1, 157.8, 155.7, 152.3 (d, J=12.5 Hz), 143.0 (d, J=13.8 Hz), 140.4, 140.0, 128.6, 117.5, 114.2, 113.3, 106.5, 100.1, 95.7 (d, J=27.5 Hz), 94.5 (d, J=25 Hz), 60.8, 54.4, 47.7, 45.7, 24.3, 13.6. $^{19}$F NMR (471 MHz, DMSO-$d_6$) δ −112.6 (t, J=12.3 Hz). HPLC-MS (ESI+): m/z 528.3 (M+1)$^+$. HRMS (ESI+): m/z calcd for $C_{26}H_{35}FN_7O_2S$ (M+H)$^+$ 528.2551, found 528.2543.

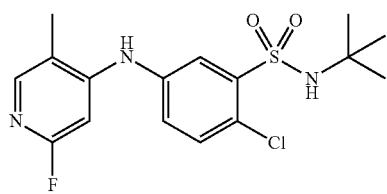 [SMILES: Cc1cnc(F)cc1Nc1ccc(Cl)c(S(=O)(=O)NC(C)(C)C)c1]

N-(tert-Butyl)-3-((2-fluoro-5-methylpyridin-4-yl)amino)benzenesulfonamide (SY3-014). A 20 mL vial was charged with Pd(OAc)$_2$ (7.1 mg, 0.032 mmol) and Xantphos (37 mg, 0.063 mmol) and then degassed toluene (0.5 mL) was added. The mixture was stirred for 5 min under argon. 2-Fluoro-4-iodo-5-methylpyridine (0.3 g, 1.27 mmol), SG3-142 (0.33 g, 1.27 mmol), Cs$_2$CO$_3$ (0.82 g, 2.54 mmol) and toluene 5 mL were added. The mixture was degassed for 5 min by bubbling argon and then the vial was sealed. The mixture was stirred at 100° C. overnight. The mixture was quenched with water and extracted with EtOAc. The organic layers were dried over MgSO$_4$ and filtered. The filtrate was concentrated and the residue was triturated with CH$_2$Cl$_2$ and hexanes to give the title compound as beige solid (0.4 g, 85%). $^1$H NMR (500 MHz, DMSO-$d_6$) δ 8.46 (s, 1H), 7.91 (d, J=2.5 Hz, 1H), 7.69 (s, 1H), 7.59 (d, J=11.5 Hz, 1H), 7.50 (dd, J=11.5, 2.5 Hz, 1H), 6.49 (s, 1H), 2.19 (s, 3H), 1.15 (s, 9H). HPLC-MS (ESI+): m/z 697.3 (2M+Na)$^+$, 371.1 (M+1)$^+$.

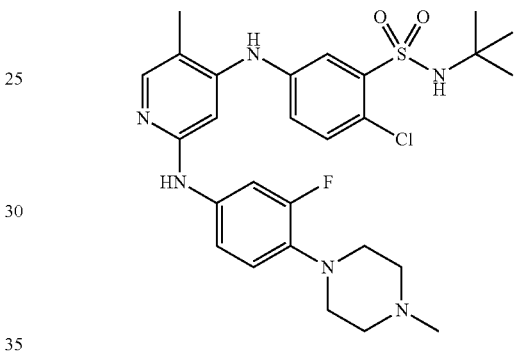

N-(tert-Butyl)-2-chloro-5-((2-((3-fluoro-4-(4-methylpiperazin-1-yl)phenyl)amino)-5-methylpyridin-4-1)amino)benzenesulfonamide (SY3-016). This compound was synthesized by the same procedure described for SY3-005 using SY3-014 (0.05 g, 0.134 mmol) and MA4-020 (0.028 mg, 0.134 mmol) to afford an off-white solid (0.02 g, 27%). $^1$H NMR (500 MHz, DMSO-$d_6$) δ 8.64 (s, 1H), 8.06 (s, 1H), 7.85 (d, J=2.7 Hz, 1H), 7.83 (s, 1H), 7.67 (dd, J=16, 2.5 Hz, 1H), 7.61 (s, 1H), 7.54 (d, J=8.5 Hz, 1H), 7.43 (dd, J=9, 3 Hz, 1H), 7.10 (dd, J=9, 2 Hz, 1H), 6.90 (t, J=9 Hz, 1H), 6.47 (s, 1H), 2.92 (br s, 4H), 2.47 (br s, 4H), 2.29 (s, 3H), 2.10 (s, 3H), 1.14 (s, 9H). $^{19}$F NMR (471 MHz, DMSO-$d_6$) δ −122.37 (dd, J=15.6, 10.0 Hz). HPLC-MS (ESI+): m/z 561.2 (M+1)$^+$. HRMS (ESI+): m/z calcd for $C_{28}H_{37}FN_5O_2S$ (M+H)$^+$ 561.2209, found 561.2203.

General Scheme for final compounds MA9-024-MA11-038

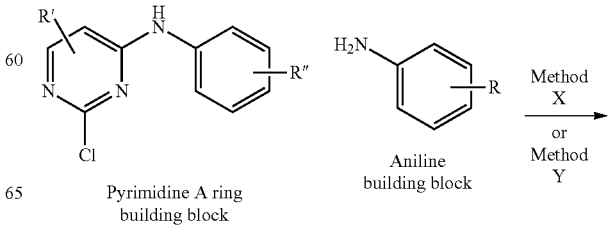

Pyrimidine A ring building block

Aniline building block

Method X or Method Y

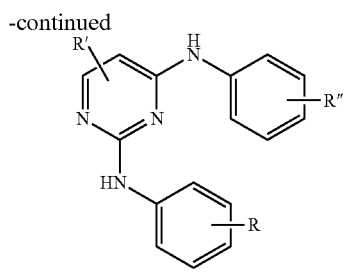

General Method X: A mixture of Pyrimidine A-ring building block (50 mg, 1.0 equiv.), the corresponding aniline (1.0 equiv.), 2 drops of 4M HCl, and EtOH (1 mL) was heated in a microwave reactor at 160° C. for 15 minutes. The reaction mixture was diluted with EtOAc (20 mL) and washed with saturated NaHCO$_3$ (20 mL). The aqueous layer was then re-extracted with EtOAc (20 mL). The combined organic layers were dried over Na$_2$SO$_4$ and concentrated under reduced pressure. Unless otherwise mentioned, all products were purified via column SiO$_2$ chromatography using DCM/MeOH gradient elution (0-10% MeOH or 0-15% MeOH in DCM).

General Method Y: A mixture of Pyrimidine A-ring building block (50 mg, 1.0 equiv.), the corresponding aniline (1.0 equiv.), 4M HCl in dioxane (1.1 equiv.), and 2-methoxyethanol (1 mL) was heated in an oil bath at 120° C. (oil bath temperature) for 16 h. The reaction mixture was diluted with EtOAc (20 mL) and washed with saturated NaHCO$_3$ (20 mL). The aqueous layer was then re-extracted with EtOAc (20 mL). The combined organic layers were dried over Na$_2$SO$_4$ and concentrated under reduced pressure. Unless otherwise mentioned, all products were purified via SiO$_2$ column chromatography using DCM/MeOH (0-10% or 0-15% MeOH in DCM).

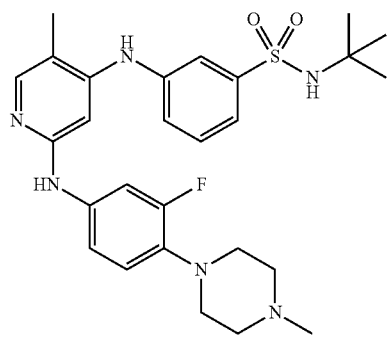 [SMILES: Cc1cnc(Nc2ccc(N3CCN(C)CC3)c(F)c2)cc1Nc1ccc(Cl)c(S(=O)(=O)NC(C)(C)C)c1]

MA9-024

N-(Tert-butyl)-3-((2-((3-fluoro-4-(4-methylpiperazin-1-yl)phenyl)amino)-5-methylpyridin-4-yl)amino)benzenesulfonamide (MA9-024): This was prepared using the general method Y by the reaction of MA9-016 (50.0 mg, 0.15 mmol), MA4-020 (31.0 mg, 0.15 mmol) in the presence of 4M HCl in dioxane (0.54 uL, 0.215 mmol) in 2-methoxy ethanol (0.5 mL). The purification was also carried out using the same method as described for MA9-060, to obtain the title compound as an off white solid (31 mg, 40%). HPLC: 99% [t$_R$=11.2 min, gradient MeOH-water (with 0.1% formic acid), 5-95% over 20 min.]. $^1$H NMR (500 MHz, Methanol-d$_4$): δ 7.74 (s, 1H), 7.73 (t, J=1.9 Hz, 1H), 7.54 (ddd, J=7.8, 1.7, 1.2 Hz, 1H), 7.49 (t, J=7.8 Hz, 1H), 7.42 (ddd, J=7.9, 2.2, 1.2 Hz, 1H), 7.20-7.11 (m, 1H), 7.02-6.93 (m, 2H), 6.50 (s, 1H), 3.08-2.99 (m, 4H), 2.68-2.58 (m, 4H), 2.36 (s, 3H), 2.17 (d, J=0.9 Hz, 3H), 1.18 (s, 9H). $^{19}$F NMR (471 MHz, DMSO-d$_6$): δ -122.43 (dd, J=15.6, 10.2 Hz). HPLC-MS (ESI+): m/z 527.3 [20%, (M+H)$^+$], 264.3 [100% (M+2H)$^{2+}$]. HRMS (ESI+): m/z calcd for C$_{27}$H$_{36}$FN$_6$O$_2$S (M+H)$^+$ 527.2599, found 527.2592.

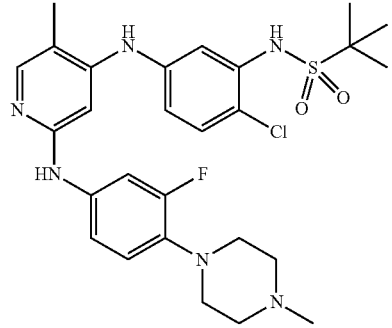

MA9-036

N-(2-Chloro-5-((2-((3-fluoro-4-(4-methylpiperazin-1-yl)phenyl)amino)-5-methylpyridin-4-yl)amino)phenyl)-2-methylpropane-2-sulfonamide (MA9-036): This was prepared using the general method Y by the reaction of MA9-014 (50.0 mg, 0.13 mmol), MA4-020 (28.0 mg, 0.13 mmol) in the presence of 4M HCl in dioxane (0.54 uL, 0.215 mmol) in 2-methoxy ethanol (0.5 mL). The purification was also carried out using the exact same method as described for MA9-060, to obtain the title compound as a beige solid (32 mg, 42%). HPLC: 99% [t$_R$=6.4 min, gradient MeOH-water (with 0.1% formic acid), 5-95% over 20 min.]; $^1$H NMR (500 MHz, DMSO-d$_6$): δ 9.36 (s, 1H), 8.61 (s, 1H), 7.82 (s, 1H), 7.79 (s, 1H), 7.66 (dd, J=15.7, 2.5 Hz, 1H), 7.48 (d, J=2.5 Hz, 1H), 7.40 (d, J=8.6 Hz, 1H), 7.08 (ddd, J=16.9, 8.7, 2.5 Hz, 2H), 6.91 (dd, J=10.1, 8.7 Hz, 1H), 6.43 (s, 1H), 2.93 (t, J=4.9 Hz, 4H), 2.54 (brs, 4H), 2.29 (s, 3H), 2.10 (s, 3H), 1.32 (s, 9H); $^{19}$F NMR (471 MHz, DMSO-d$_6$): δ -122.45 (dd, J=15.6, 10.0 Hz); HPLC-MS (ESI+): m/z 561.3 [20%, (M+H)$^+$], 281.3 [100% (M+2H)$^{2+}$]. HRMS (ESI+): m/z calcd for C$_{27}$H$_{35}$FClN$_6$O$_2$S (M+H)$^+$ 561.2209, found 561.2206.

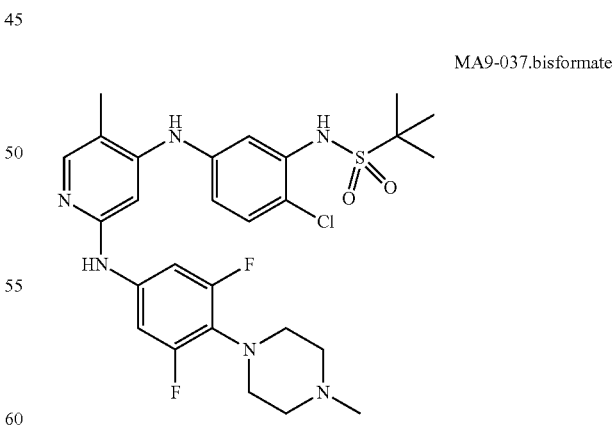

MA9-037.bisformate

N-(2-Chloro-5-((2-((3,5-difluoro-4-(4-methylpiperazin-1-yl)phenyl)amino)-5-methylpyridin-4-yl)amino)phenyl)-2-methylpropane-2-sulfonamide·bisformate (MA9-037.bisformate): This was prepared using the general method Y by the reaction of MA9-014 (45 mg, 0.12 mmol), 3,5-difluoro-4-(4-methylpiperazin-1-yl)aniline (27.5 mg, 0.12 mmol) in the presence of 4M HCl in dioxane (0.49 uL, 0.193 mmol) in 2-methoxy ethanol (0.45 mL). The purification using normal phase SiO₂ column failed to give the pure product therefore the title compound was purified using preparative HPLC purification (using a gradient of MeOH, Water with 0.1% formic acid, 10 mL/min, 20 minutes) to obtain the title compound as a white solid (2.81 mg, 4%). HPLC: 99% [$t_R$=11.4 min, gradient MeOH-water (with 0.1% formic acid), 5-95% over 20 min.]. ¹H NMR (500 MHz, Methanol-d₄): δ 8.50 (s, 2H), 7.77 (s, 1H), 7.64 (d, J=2.6 Hz, 1H), 7.39 (d, J=8.6 Hz, 1H), 7.07 (dd, J=8.7, 2.6 Hz, 1H), 7.01 (d, J=11.6 Hz, 2H), 6.48 (s, 1H), 3.25-3.19 (m, 4H), 3.10-2.88 (m, 4H), 2.61 (s, 3H), 2.18 (s, 3H), 1.38 (s, 9H). ¹⁹F NMR (471 MHz, Methanol-d₄): δ -121.42 (d, J=12.1 Hz). HPLC-MS (ESI+): m/z 579.3 [20%, (M+H)⁺], 290.2 [100% (M+2H)²⁺]. HRMS (ESI+): m/z calcd for $C_{27}H_{34}F_2ClN_6O_2S$ (M+H)⁺ 579.2115, found 579.2110.

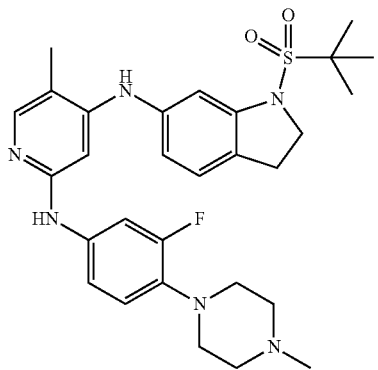

MA9-042

N⁴-(1-(tert-Butylsulfonyl)indolin-6-yl)-N²-(3-fluoro-4-(4-methylpiperazin-1-yl)phenyl)-5-methylpyridine-2,4-diamine (MA9-042): This was prepared using the general method Y by the reaction of MA9-040 (50 mg, 0.14 mmol), 3-fluoro-4-(4-methylpiperazin-1-yl)aniline (28.8 mg, 0.14 mmol) in the presence of 4M HCl in dioxane (0.55 uL, 0.22 mmol) in 2-methoxy ethanol (0.5 mL) using a similar procedure as described for the synthesis. The purification was also carried out using the exact same method as described for MA9-060 to get the product albeit with 90% HPLCMS purity. The title compound was further purified by triturating with EtOAc and hexane to obtain the title compound as a white solid (15 mg, 20%). HPLC: 99% [$t_R$=11.9 min, gradient MeOH-water (with 0.1% formic acid), 5-95% over 20 min.]; ¹H NMR (500 MHz, DMSO-d₆): δ 8.51 (s, 1H), 7.73 (s, 1H), 7.65 (dd, J=15.8, 2.2 Hz, 1H), 7.60 (s, 1H), 7.19 (d, J=7.9 Hz, 1H), 7.14 (d, J=1.9 Hz, 1H), 7.09 (dd, J=8.6, 2.4 Hz, 1H), 6.89 (dd, J=10.1, 8.8 Hz, 1H), 6.82 (dd, J=8.0, 2.0 Hz, 1H), 6.29 (s, 1H), 4.06 (t, J=8.4 Hz, 2H), 3.09 (t, J=8.4 Hz, 2H), 2.94 (brs, 4H), 2.70-2.56 (m, 4H), 2.33 (brs, 3H), 2.09 (s, 3H), 1.37 (s, 9H); ¹⁹F NMR (471 MHz, DMSO-d₆): δ -122.55 (dd, J=15.8, 10.0 Hz); HPLC-MS (ESI+): m/z 553.3 [20%, (M+H)⁺], 277.2 [100% (M+2H)²⁺]; HRMS (ESI+): m/z calcd for $C_{29}H_{38}FN_6O_2S$ (M+H)⁺ 553.2755, found 553.2750.

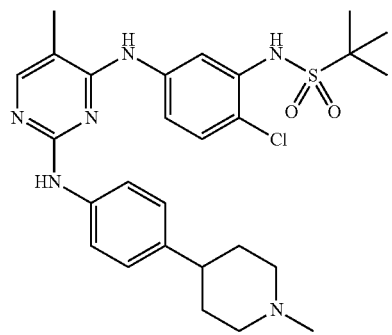

MA9-050

N-(2-Chloro-5-((5-methyl-2-((4-(1-methylpiperidin-4-yl)phenyl)amino)pyrimidin-4-yl)amino)phenyl)-2-methylpropane-2-sulfonamide (MA9-050): This was prepared using the general method Y by the reaction of N-(2-chloro-5-((2-chloro-5-methylpyrimidin-4-yl)amino)phenyl)-2-methyl-propane-2-sulfonamide (2.20 g, 5.65 mmol), MA9-065 (1.08 g, 5.65 g) in the presence of 4M HCl in dioxane (1.5 mL, 5.93 mmol) in 2-methoxy ethanol (20 mL). The purification was carried out using the exact same method as described for MA9-060, to obtain the title compound as an off white solid (1.72 g, 56%). HPLC: 98% [$t_R$=11.4 min, gradient MeOH-water (with 0.1% formic acid), 5-95% over 20 min.]; ¹H NMR (500 MHz, DMSO-d₆): δ 9.31, (brs, 1H), 8.79 (s, 1H), 8.46 (s, 1H), 7.90 (d, J=1.0 Hz, 1H), 7.87 (d, J=2.6 Hz, 1H), 7.74 (dd, J=8.8, 2.6 Hz, 1H), 7.54 (d, J=8.6 Hz, 2H), 7.35 (d, J=8.8 Hz, 1H), 7.06 (d, J=8.6 Hz, 2H), 2.88 (d, J=11.7 Hz, 2H), 2.41-2.33 (m, 1H), 2.22 (s, 3H), 2.13-2.08 (m, 3H), 2.06-1.95 (m, 2H), 1.76-1.59 (m, 4H), 1.32 (s, 9H); ¹³C NMR (126 MHz, DMSO-d₆): δ 159.39, 158.57, 156.48, 139.76, 139.45, 138.75, 136.00, 129.32, 126.96, 121.24, 120.97, 120.76, 119.03, 106.29, 60.95, 56.25, 46.45, 33.43, 24.39, 14.00; HPLC-MS (ESI+): m/z 543.3 [30%, (M+H)⁺], 272.2 [100% (M+2H)²⁺]; HRMS (ESI+): m/z calcd for $C_{27}H_{36}ClN_6O_2S$ (M+H)⁺ 543.2303, found 543.2295.

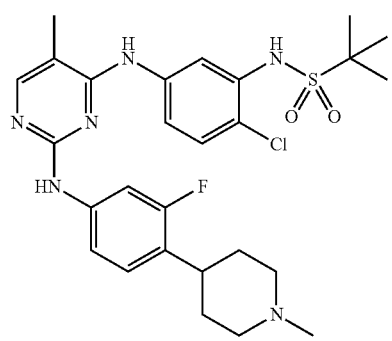

MA9-060

N-(2-Chloro-5-((2-((3-fluoro-4-(1-methylpiperidin-4-yl)phenyl)amino)-5-methylpyrimidin-4-yl)amino)phenyl)-2-methylpropane-2-sulfonamide (MA9-060): In a pressure tube, N-(2-chloro-5-((2-chloro-5-methylpyrimidin-4-yl)amino)phenyl)-2-methylpropane-2-sulfonamide (2.00 g, 5.14 mmol) and MA9-058 (1.07 g, 5.14 mmol) were dissolved in 2-methoxyethanol (20 mL) followed by the addition of 4M HCl in dioxane (1.93 mL, 7.71 mmol). The reaction was heated in an oil bath at 120° C. (oil bath temperature) for 16 h. After confirming the complete consumption of starting material (HPLC-MS), the crude reaction mixture was partitioned between EtOAc (~500 mL) and NaHCO$_3$ (~300 mL). Organic layer was washed with brine (~100 mL), dried (Na$_2$SO$_4$) and evaporated under reduced pressure. Crude was purified using 50 g SiO$_2$, eluting with a gradient of DCM-MeOH (up to 15% MeOH) to obtain the title compound as a white solid (1.72 g, 60%). HPLC: 98% [t$_R$=12.0 min, gradient MeOH-water (with 0.1% formic acid), 5-95% over 20 min.]; $^1$H NMR (400 MHz, DMSO-d$_6$): δ 9.33 (s, 1H), 9.06 (s, 1H), 8.53 (s, 1H), 7.93 (d, J=1.0 Hz, 1H), 7.78 (d, J=2.5 Hz, 1H), 7.73 (dd, J=8.7, 2.6 Hz, 1H), 7.61 (dd, J=14.0, 2.2 Hz, 1H), 7.36 (d, J=8.8 Hz, 1H), 7.29 (dd, J=8.5, 2.1 Hz, 1H), 7.10 (t, J=8.7 Hz, 1H), 2.87 (d, J=12.0, 3.2 Hz, 2H), 2.67-2.58 (m, 1H), 2.20 (s, 3H), 2.11 (d, J=0.9 Hz, 3H), 1.98 (td, J=11.5, 3.2 Hz, 2H), 1.74-1.60 (m, 4H), 1.32 (s, 9H); $^{19}$F NMR (471 MHz, DMSO-d$_6$): δ -119.27 (dd, J=13.9, 8.8 Hz); HPLC-MS (ESI+): m/z 561.3 [30%, (M+H)$^+$], 281.2 [100% (M+2H)$^{2+}$]; HRMS (ESI+): m/z calcd for C$_{27}$H$_{35}$ClFN$_6$O$_2$S (M+H)$^+$ 561.2209, found 561.2197.

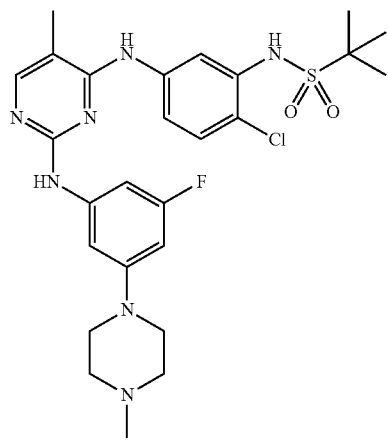

MA9-062

N-(2-Chloro-5-((2-((3-fluoro-5-(4-methylpiperazin-1-yl)phenyl)amino)-5-methylpyrimidin-4-yl)amino)phenyl)-2-methylpropane-2-sulfonamide (MA9-062): This compound was prepared using the general method X by the reaction of N-(2-chloro-5-((2-chloro-5-methylpyrimidin-4-yl)amino)phenyl)-2-methylpropane-2-sulfonamide (50 mg, 0.13 mmol), MA9-057 (28 mg, 0.13 mmol) in the presence of 4M HCl in H$_2$O (2 drops) in ethanol (0.5 mL). The purification was also carried out using the exact same method as described for MA9-060, to obtain the title compound as a white solid (37 mg, 51%). HPLC: 99% [t$_R$=12.6 min, gradient MeOH-water (with 0.1% formic acid), 5-95% over 20 min.]; $^1$H NMR (500 MHz, DMSO-d$_6$): δ 8.91 (s, 1H), 8.54 (s, 1H), 7.95 (d, J=1.0 Hz, 1H), 7.84 (dd, J=8.7, 2.6 Hz, 1H), 7.78 (d, J=2.6 Hz, 1H), 7.33 (d, J=8.8 Hz, 1H), 7.14 (dt, J=11.9, 2.0 Hz, 1H), 6.93 (d, J=2.0 Hz, 1H), 6.25 (dt, J=12.4, 2.3 Hz, 1H), 3.04 (t, J=5.1 Hz, 4H), 2.39 (t, J=5.0 Hz, 4H), 2.20 (s, 3H), 2.11 (d, J=0.9 Hz, 3H), 1.33 (s, 9H); $^{19}$F NMR (471 MHz, DMSO-d$_6$): δ -112.70 (t, J=12.1 Hz); HPLC-MS (ESI+): m/z 562.2 [100%, (M+H)$^+$], 281.8 [100% (M+2H)$^{2+}$]; HRMS (ESI+): m/z calcd for C$_{26}$H$_{34}$ClFN$_7$O$_2$S (M+H)$^+$ 562.2162, found 562.2156.

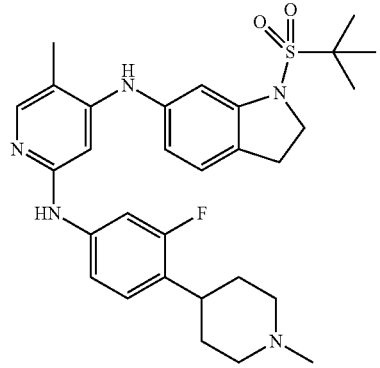

MA9-064

N4-(1-(Tert-butylsulfonyl)indolin-6-yl)-N2-(3-fluoro-4-(1-methylpiperidin-4-yl)phenyl)-5-methylpyridine-2,4-diamine (MA9-064): This was prepared using the general method Y by the reaction of MA9-040 (50 mg, 0.14 mmol), MA9-058 (29 mg, 0.14 mmol) in the presence of 4M HCl in dioxane (0.55 □L, 0.220 mmol) in 2-methoxy ethanol (0.5 mL). The purification was also carried out using the exact same method as described for MA9-060 to get the product albeit with 90% HPLCMS purity. The title compound was further purified by triturating with EtOAc and hexane to obtain the desired compound as a white solid (9.30 mg, 12%). HPLC: 96% [t$_R$=11.9 min, gradient MeOH-water (with 0.1% formic acid), 5-95% over 20 min.]; $^1$H NMR (500 MHz, DMSO-d$_6$): δ 8.62 (s, 1H), 7.75 (d, J=0.9 Hz, 1H), 7.65 (dd, J=14.1, 2.1 Hz, 1H), 7.61 (s, 1H), 7.19 (d, J=8.0 Hz, 1H), 7.16-7.05 (m, 3H), 6.82 (dd, J=8.0, 2.0 Hz, 1H), 6.32 (s, 1H), 4.06 (t, J=8.5 Hz, 2H), 3.09 (t, J=8.4 Hz, 2H), 2.89-2.77 (m, 2H), 2.64-2.55 (m, 2H), 2.17 (s, 3H), 2.10 (brs, 3H), 1.97-1.90 (m, 2H), 1.70-1.61 (m, 4H), 1.37 (s, 9H); $^{19}$F NMR (471 MHz, DMSO-d$_6$): δ -119.27 (dd, J=14.0, 8.5 Hz); HPLC-MS (ESI+): m/z 552.3 [100%, (M+H)$^+$], 276.7 [100% (M+2H)$^{2+}$]; HRMS (ESI+): m/z calcd for C$_{30}$H$_{39}$FN$_5$O$_2$S (M+H)$^+$ 552.2803, found 552.2798.

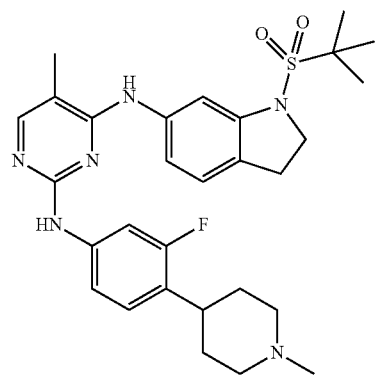

MA9-086

N4-(1-(Tert-butylsulfonyl)indolin-6-yl)-N2-(3-fluoro-4-(1-methylpiperidin-4-yl)phenyl)-5-methylpyrimidine-2,4-diamine (MA9-086): This was prepared using the general method X by the reaction of 1-(tert-butylsulfonyl)-N-(2-chloro-5-methylpyrimidin-4-yl)indolin-6-amine (50.0 mg, 0.13 mmol), MA9-058 (27.0 mg, 0.13 mmol) in the presence of 4M HCl in H$_2$O (2 drops) in ethanol (0.5 mL). The purification was also carried out using the exact same method as described for MA9-060, to obtain the title compound as a white solid (50 mg, 69%). HPLC: 99% [$t_R$=11.9 min, gradient MeOH-water (with 0.1% formic acid), 5-95% over 20 min.]; $^1$H NMR (500 MHz, DMSO-$d_6$): δ 8.98 (s, 1H), 8.38 (s, 1H), 7.88 (d, J=1.0 Hz, 1H), 7.63 (dd, J=14.2, 2.2 Hz, 1H), 7.39 (dd, J=8.1, 1.9 Hz, 1H), 7.32 (d, J=1.9 Hz, 1H), 7.25 (dd, J=8.5, 2.2 Hz, 1H), 7.18 (d, J=8.0 Hz, 1H), 7.04 (t, J=8.7 Hz, 1H), 4.07 (t, J=8.4 Hz, 2H), 3.10 (t, J=8.4 Hz, 2H), 3.11-2.91 (m, 2H), 2.73-2.58 (m, 1H), 2.28 (s, 3H), 2.21-2.08 (m, 5H), 1.68 (q, J=3.6 Hz, 4H), 1.35 (s, 9H); $^{19}$F NMR (471 MHz, DMSO-$d_6$): δ −119.19 (brs); HPLC-MS (ESI+): m/z 553.3 [30%, (M+H)$^+$], 277.2 [100% (M+2H)$^{2+}$]; HRMS (ESI+): m/z calcd for $C_{29}H_{38}FN_6O_2S$ (M+H)$^+$ 553.2755 found 553.2683.

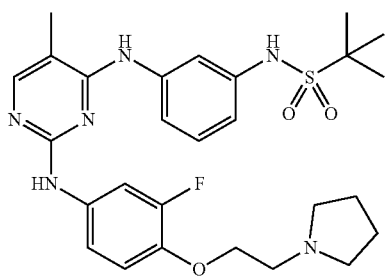

MA9-168

N-(3-((2-((3-Fluoro-4-(2-(pyrrolidin-1-yl)ethoxy)phenyl)amino)-5-methylpyrimidin-4-yl)amino)phenyl)-2-methylpropane-2-sulfonamide (MA9-168): This was prepared using the general method X by the reaction of N-(3-((2-chloro-5-methylpyrimidin-4-yl)amino)phenyl)-2-methylpropane-2-sulfonamide (100 mg, 0.28 mmol), MA9-137 (63 mg, 0.28 mmol) in the presence of 4M HCl in H$_2$O (78 uL, 0.31 mmol) in ethanol (1 mL). The purification was also carried out using the exact same method as described for MA9-060 to obtain the title compound as an off white solid (117 mg, 76%). HPLC: 98% [$t_R$=11.3 min, gradient MeOH-water (with 0.1% formic acid), 5-95% over 20 min.]; $^1$H NMR (500 MHz, Methanol-$d_4$): δ 7.80 (d, J=1.1 Hz, 1H), 7.69 (t, J=2.1 Hz, 1H), 7.49 (dd, J=13.9, 2.6 Hz, 1H), 7.35 (ddd, J=8.1, 2.1, 1.0 Hz, 1H), 7.24 (t, J=8.1 Hz, 1H), 7.14 (ddd, J=8.9, 2.6, 1.4 Hz, 1H), 7.06 (ddd, J=8.0, 2.2, 1.0 Hz, 1H), 6.96 (t, J=9.2 Hz, 1H), 4.15 (t, J=5.6 Hz, 2H), 2.95 (t, J=5.6 Hz, 2H), 2.81-2.65 (m, 4H), 2.13 (d, J=0.9 Hz, 3H), 1.88-1.83 (m, 4H), 1.36 (s, 9H); $^{19}$F NMR (471 MHz, Methanol-$d_4$): δ −134.60 (dd, J=15.2, 9.9 Hz); HPLC-MS (ESI+): m/z 543.3 [30%, (M+H)$^+$], 272.2 [100% (M+2H)$^{2+}$]; HRMS (ESI+): m/z calcd for $C_{27}H_{36}FN_6O_3S$ (M+H)$^+$ 543.2548, found 543.2536.

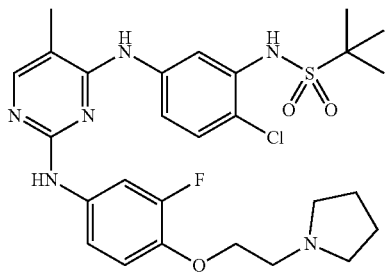

MA9-169

N-(2-Chloro-5-((2-((3-fluoro-4-(2-(pyrrolidin-1-yl)ethoxy)phenyl)amino)-5-methylpyrimidin-4-yl)amino)phenyl)-2-methylpropane-2-sulfonamide (MA9-169): This was prepared using the general method X by the reaction of N-(2-chloro-5-((2-chloro-5-methylpyrimidin-4-yl)amino)phenyl)-2-methylpropane-2-sulfonamide (100.0 mg, 0.26 mmol), MA9-137 (58.0 mg, 0.26 mmol) in the presence of 4M HCl in H$_2$O (71 uL, 0.28 mmol) in ethanol (1 mL). The purification was also carried out using the exact same method as described for MA9-060 to obtain the title compound as an off white solid (121 mg, 82%). HPLC: 98% [$t_R$=14.2 min, gradient MeOH-water (with 0.1% formic acid), 5-95% over 20 min.]; $^1$H NMR (500 MHz, Methanol-$d_4$): δ 8.13 (d, J=2.5 Hz, 1H), 7.82 (d, J=1.0 Hz, 1H), 7.52 (dd, J=5.8, 2.6 Hz, 1H), 7.49 (d, J=2.4 Hz, 1H), 7.32 (d, J=8.8 Hz, 1H), 7.11 (ddd, J=8.8, 2.6, 1.3 Hz, 1H), 6.99 (t, J=9.1 Hz, 1H), 4.16 (t, J=5.6 Hz, 2H), 2.94 (t, J=5.6 Hz, 2H), 2.75-2.68 (m, 4H), 2.13 (d, J=0.9 Hz, 3H), 1.88-1.81 (m, 4H), 1.39 (s, 9H); $^{19}$F NMR (471 MHz, Methanol-$d_4$) δ −134.71 (dd, J=15.2, 9.7 Hz); HPLC-MS (ESI+): m/z 577.3 [30%, (M+H)$^+$], 289.2 [100% (M+2H)$^{2+}$]; HRMS (ESI+): m/z calcd for $C_{27}H_{35}ClFN_6O_3S$ (M+H)$^+$ 577.2158, found 577.2135.

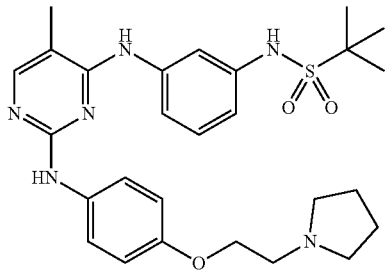

MA9-176

2-Methyl-N-(3-((5-methyl-2-((4-(2-(pyrrolidin-1-yl)ethoxy)phenyl)amino)pyrimidin-4-yl)amino)phenyl)propane-2-sulfonamide (MA9-176): This was prepared using the general method X by the reaction of N-(3-((2-chloro-5-methylpyrimidin-4-yl)amino)phenyl)-2-methylpropane-2-sulfonamide (100 mg, 0.28 mmol), 4-(2-(pyrrolidin-1-yl)ethoxy)aniline (58 mg, 0.28 mmol) in the presence of 4M HCl in H$_2$O (78 uL, 0.31 mmol) in ethanol (1 mL). The purification was also carried out using the exact same method as described for MA9-060 to obtain the title compound as an off white solid (93 mg, 63%). HPLC: 100% [$t_R$=12.5 min, gradient MeOH-water (with 0.1% formic acid), 5-95% over 20 min.]; $^1$H NMR (500 MHz, Methanol-$d_4$): δ 7.75 (d, J=1.0 Hz, 1H), 7.74 (t, J=2.1 Hz, 1H), 7.40 (d, J=9.0 Hz, 2H), 7.34 (ddd, J=8.1, 2.1, 1.0 Hz, 1H), 7.21 (t, J=8.1 Hz, 1H), 7.04 (ddd, J=8.0, 2.1, 1.0 Hz, 1H), 6.83 (d, J=9.0 Hz, 2H), 4.11 (t, J=5.6 Hz, 2H), 2.95 (t, J=5.6 Hz, 2H), 2.77-2.64 (m, 4H), 2.12 (d, J=0.9 Hz, 3H), 1.91-1.76 (m, 4H), 1.36 (s, 9H); HPLC-MS (ESI+): m/z 525.3 [30%, (M+H)$^+$], 263.2 [100% (M+2H)$^{2+}$]; HRMS (ESI+): m/z calcd for $C_{27}H_{37}N_6O_3S$ (M+H)$^+$ 525.2642, found 525.2631.

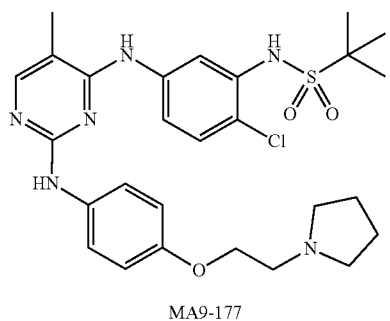 [SMILES: Cc1cnc(Nc2ccc(OCCN3CCCC3)cc2)nc1Nc1ccc(Cl)c(NS(=O)(=O)C(C)(C)C)c1]

MA9-177

N-(2-Chloro-5-((5-methyl-2-((4-(2-(pyrrolidin-1-yl)ethoxy)phenyl)amino)pyrimidin-4-yl)amino)phenyl)-2-methylpropane-2-sulfonamide (MA9-177): This compound was prepared using the general method X by the reaction of N-(2-chloro-5-((2-chloro-5-methylpyrimidin-4-yl)amino)phenyl)-2-methylpropane-2-sulfonamide SG3-012 (100 mg, 0.26 mmol), 4-(2-(pyrrolidin-1-yl)ethoxy)aniline (53 mg, 0.26 mmol) in the presence of 4M HCl in H$_2$O (71 uL, 0.28 mmol) in ethanol (1 mL). The purification was also carried out using the exact same method as described for MA9-060 to obtain the title compound as a white solid (113 mg, 70%). HPLC: 96% [t$_R$=12.5 min, gradient MeOH-water (with 0.1% formic acid), 5-95% over 20 min.]; $^1$H NMR (500 MHz, Methanol-d$_4$): δ 8.06 (d, J=2.6 Hz, 1H), 7.68 (d, J=1.0 Hz, 1H), 7.40 (dd, J=8.8, 2.6 Hz, 1H), 7.18 (d, J=8.8 Hz, 1H), 6.77 (d, J=9.0 Hz, 2H), 4.02 (t, J=5.6 Hz, 2H), 2.83 (t, J=5.7 Hz, 2H), 2.66-2.53 (m, 4H), 2.02 (d, J=0.9 Hz, 4H), 1.78-1.72 (m, 4H), 1.29 (s, 9H); HPLC-MS (ESI+): m/z 559.3 [30%, (M+H)$^+$], 280.2 [100% (M+2H)$^{2+}$]; HRMS (ESI+): m/z calcd for C$_{27}$H$_{36}$ClN$_6$O$_3$S (M+H)$^+$ 559.2253, found 559.2232.

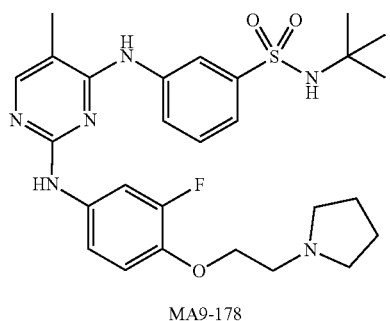 [SMILES: Cc1cnc(Nc2ccc(OCCN3CCCC3)c(F)c2)nc1Nc1cccc(S(=O)(=O)NC(C)(C)C)c1]

MA9-178

N-(Tert-butyl)-3-((2-((3-fluoro-4-(2-(pyrrolidin-1-yl)ethoxy)phenyl)amino)-5-methylpyrimidin-4-yl)amino)benzenesulfonamide (MA9-178): This was prepared using the general method X by the reaction of N-(tert-butyl)-3-((2-chloro-5-methylpyrimidin-4-yl)amino)benzenesulfonamide (100 mg, 0.28 mmol), MA9-137 (63 mg, 0.28 mmol) in the presence of 4M HCl in H$_2$O (78 uL, 0.31 mmol) in ethanol (1 mL). The purification was also carried out using the same method as described for MA9-060 to obtain the title compound as an off white solid (92 mg, 60%). HPLC: 100% [t$_R$=12.8 min, gradient MeOH-water (with 0.1% formic acid), 5-95% over 20 min.]; $^1$H NMR (500 MHz, DMSO-d$_6$): δ 9.00 (s, 1H), 8.61 (s, 1H), 8.18-8.10 (m, 1H), 8.05 (d, J=2.5 Hz, 1H), 7.94 (d, J=0.9 Hz, 1H), 7.67 (dd, J=14.4, 2.6 Hz, 1H), 7.55 (s, 1H), 7.53-7.46 (m, 2H), 7.27 (ddd, J=9.0, 2.6, 1.3 Hz, 1H), 7.01 (t, J=9.4 Hz, 1H), 4.06 (t, J=5.9 Hz, 2H), 2.79 (t, J=6.0 Hz, 2H), 2.60-2.52 (m, 4H), 2.13 (d, J=0.9 Hz, 3H), 1.74-1.63 (m, 4H), 1.12 (s, 9H); $^{19}$F NMR (471 MHz, DMSO-d$_6$): δ −131.57-135.12 (m); HPLC-MS (ESI+): m/z 543.3 [30%, (M+H)$^+$], 272.3 [100% (M+2H)$^{2+}$]; HRMS (ESI+): m/z calcd for C$_{27}$H$_{36}$FN$_6$O$_3$S (M+H)$^+$ 543.2548, found 543.2548.

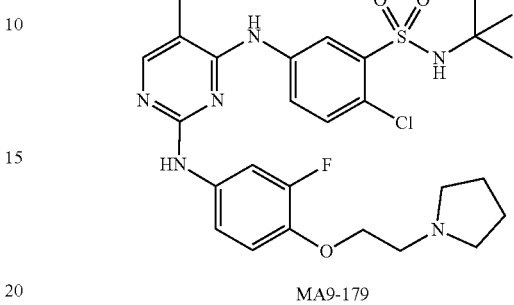

MA9-179

N-(Tert-butyl)-2-chloro-5-((2-((3-fluoro-4-(2-(pyrrolidin-1-yl)ethoxy)phenyl)amino)-5-methylpyrimidin-4-yl)amino)benzenesulfonamide (MA9-179): This compound was prepared using the general method X by the reaction of N-(tert-butyl)-2-chloro-5-((2-chloro-5-methylpyrimidin-4-yl)amino)benzenesulfonamide (100 mg, 0.26 mmol), MA9-137 (58 mg, 0.28 mmol) in the presence of 4M HCl in H$_2$O (71 uL, 0.28 mmol) in ethanol (1 mL). The purification was also carried out using the same method described for MA9-060 to obtain the title compound as an off white solid (105 mg, 71%). HPLC: 96% [t$_R$=12.5 min, gradient MeOH-water (with 0.1% formic acid), 5-95% over 20 min.]; $^1$H NMR (500 MHz, DMSO-d$_6$): δ 9.05 (s, 1H), 8.72 (s, 1H), 8.24 (s, 1H), 8.22 (d, J=2.4 Hz, 1H), 7.96 (d, J=1.0 Hz, 1H), 7.66 (dd, J=14.4, 2.6 Hz, 1H), 7.50 (d, J=8.4 Hz, 1H), 7.26 (ddd, J=8.9, 2.5, 1.3 Hz, 1H), 7.04 (t, J=9.4 Hz, 1H), 4.07 (t, J=6.0 Hz, 2H), 3.18 (s, 3H), 2.77 (t, J=5.9 Hz, 2H), 2.56-2.52 (m, 4H), 2.13 (d, J=0.9 Hz, 3H), 1.74-1.63 (m, 4H), 1.14 (s, 9H); $^{19}$F NMR (471 MHz, DMSO-d$_6$): δ −133.65 (dd, J=15.3, 10.0 Hz); HPLC-MS (ESI+): m/z 577.2 [30%, (M+H)$^+$], 289.2 [100% (M+2H)$^{2+}$]; HRMS (ESI+): m/z calcd for C$_{27}$H$_{35}$ClFN$_6$O$_3$S (M+H)$^+$ 577.2158, found 577.2156.

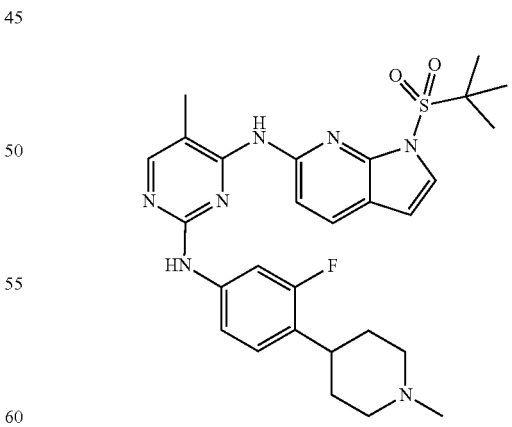

MA10-148

N4-(1-(Tert-butylsulfonyl)-1H-pyrrolo[2,3b]pyridin-6-yl)-N2-(3-fluoro-4-(1-methylpiperidin-4-yl)phenyl)-5-methylpyrimidine-2,4-diamine (MA10-148): This was prepared using the general method Y by the reaction of MA9-

058 (27.4 mg, 0.132 mmol), MA10-146 (50.00 mg, 0.132 mmol) in the presence of 4M HCl in dioxane (0.54 uL, 0.215 mmol) in 2-methoxyethanol (0.5 mL). The purification was also carried out using the exact same method as described for MA9-060, to obtain the title compound as a white solid (45 mg, 67%). HPLC: 95.57% [$t_R$=6.027 min, gradient MeOH-water (with 0.1% TFA), 5-95% 20 min.]; HPLC-MS (ESI+): m/z 276.7 [100%, (M+2H)$^{2+}$], 552.3 [40%, (M+H)$^+$]; HPLC-MS (ESI-): m/z 550.2 [40% (M-H)$^+$]; HRMS (ESI+): m/z calcd for $C_{28}H_{35}FN_7O_2S$ (M+H)$^+$ 552.2551 found 552.2545.

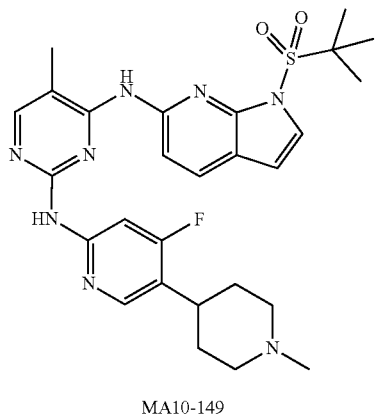 [SMILES: Cc1cnc(Nc2cc(F)c(C3CCN(C)CC3)cn2)nc1Nc1ccc2ccn(S(=O)(=O)C(C)(C)C)c2n1]

MA10-149

N4-(1-(tert-butylsulfonyl)-1H-pyrrolo[2,3-b]pyridin-6-yl)-N2-(4-fluoro-5-(1-methylpiperidin-4-yl)pyridin-2-yl)-5-methylpyrimidine-2,4-diamine (MA10-149): In a microwave vial MA10-146 (76.2 mg, 0.200 mmol), PN1-055 (35.00 mg, 0.167 mmol), Pd$_2$(dba)$_3$ (23.0 mg, 0.025 mmol), xantphos (29.0 mg, 0.05 mmol) were mixed in anhydrous toluene (0.6 ml), and argon was bubbled through for 5 min. Then Cs$_2$CO$_3$ (109.00 mg, 0.334 mmol) was added and argon was bubbled through the mixture again for about 10 min. The vial was capped and heated in an oil bath for 16 h, at 100° C. The TLC showed completion of the reaction (i.e no starting materials left in the mixture). The crude mixture was filtered and concentrated and purified using SiO$_2$ chromatography (DCM/MeOH gradient elution) to obtain the desired compound (52 mg, 56%) as a light brown solid. HPLC: 99.84% [$t_R$=6.48 min, gradient MeOH-water (with 0.1% TFA), 5-95% 20 min.]; HPLC-MS (ESI+): m/z 277.2 [100%, (M+2H)$^{2+}$], 553.3 [50%, (M+H)$^+$]; HPLC-MS (ESI-): m/z 551.3 [50% (M-H)$^+$]; HRMS (ESI+): m/z calcd for $C_{27}H_{34}FN_8O_2S$ (M+H)$^+$ 553.2504 found 553.2495.

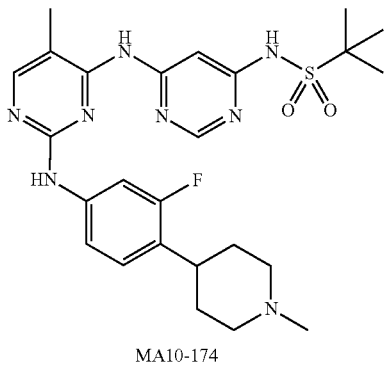 [SMILES: Cc1cnc(Nc2ccc(C3CCN(C)CC3)c(F)c2)nc1Nc1cc(NS(=O)(=O)C(C)(C)C)ncn1]

MA10-174

N-(6-((2-((3-fluoro-4-(1-methylpiperidin-4-yl)phenyl)amino)-5-methylpyrimidin-4yl)amino) pyrimidin-4-yl)-2-methylpropane-2-sulfonamide (MA10-174): In a 2 mL microwave vial, MA10-171 (50 mg, 0.140 mmol), MA9-058 (29.2 mg, 0.140 mmol) were dissolved in EtOH (0.5 ml), and added 4M HCl. The reaction mixture was heated in a Biotage microwave reactor at 180° C. for 15 min. The crude mixture was partitioned with EtOAc and saturated NaHCO$_3$, and the organic layer was separated and concentrated. The crude product was purified using SiO$_2$ chromatography (DCM/MeOH gradient elution) to obtain the desired compound (37 mg, 50%) as an off white solid. HPLC: 99.30% [$t_R$=12.68 min, gradient MeOH-water (with 0.1% TFA), 5-95% 20 min.]; HPLC-MS (ESI+): m/z 265.2 [100%, (M+2H)$^{2+}$], 529.3 [40%, (M+H)$^+$]; HPLC-MS (ESI-): m/z 527.3 [100% (M-H)$^+$]; HRMS (ESI+): m/z calcd for $C_{25}H_{34}FN_8O_2S$ (M+H)$^+$ 529.2504 found 529.2494.

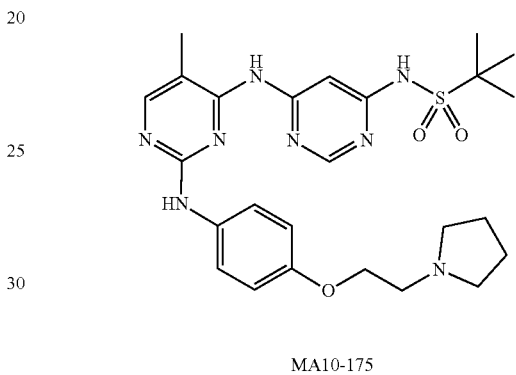

MA10-175

N-(6-((2-((3-fluoro-4-(2-(pyrrolidin-1-yl)ethoxy)phenyl)amino)-5-methylpyrimidin-4-yl)amino)pyrimidin-4-yl)-2-methylpropane-2-sulfonamide (MA10-175): This compound was prepared using the synthesis and purification procedures described for MA10-174 using MA10-171 (50.00 mg, 0.140 mmol) and 4-(2-(pyrrolidin-1-yl)ethoxy)aniline (28.9 mg, 0.140 mmol) to obtain the desired compound (42 mg, 57%) as an off white solid. HPLC: 100% [$t_R$=16.31 min, gradient MeOH-water (with 0.1% TFA), 5-95% 20 min.]; HPLC-MS (ESI+): m/z 264.2 [100%, (M+2H)$^{2+}$], 527.3 [40%, (M+H)$^+$]; HPLC-MS (ESI-): m/z 525.3 [100% (M-H)$^+$]; HRMS (ESI+): m/z calcd for $C_{25}H_{35}N_8O_3S$ (M+H)$^+$ 527.2547 found 527.2540.

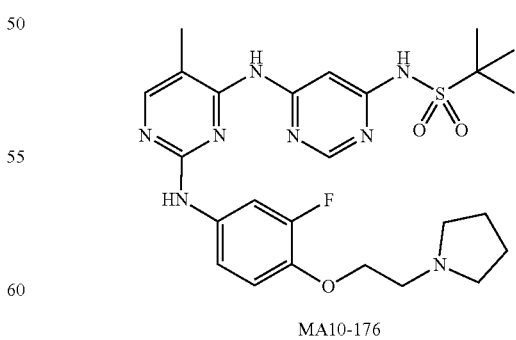

MA10-176

N-(6-((2-((3-fluoro-4-(2-(pyrrolidin-1-yl)ethoxy)phenyl)amino)-5-methylpyrimidin-4-yl)amino)pyrimidin-4-yl)-2-methylpropane-2-sulfonamide (MA10-176): This compound was prepared using the synthesis and purification procedures described MA10-174 using MA10-171 (50.00 mg, 0.140 mmol) and MA9-137 (31.40 mg, 0.140 mmol) to obtain the desired compound (44 mg, 58%) as a white solid. HPLC: 100% [$t_R$=3.95 min, gradient MeOH-water (with 0.1% TFA), 5-95% 20 min.]; HPLC-MS (ESI+): m/z 273.2 [100%, (M+2H)$^{2+}$], 545.3 [40%, (M+H)$^+$]; HPLC-MS (ESI−): m/z 543.3 [100% (M−H)$^+$]; HRMS (ESI+): m/z calcd for $C_{25}H_{34}FN_8O_3S$ (M+H)$^+$ 545.2453 found 545.2442.

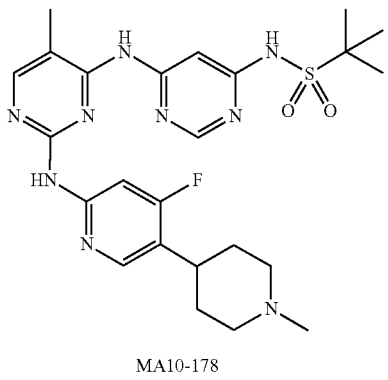 [SMILES: Cc1cnc(Nc2cc(F)c(C3CCN(C)CC3)cn2)nc1Nc1cc(NS(=O)(=O)C(C)(C)C)ncn1]

MA10-178

N-(6-((2-((4-fluoro-5-(1-methylpiperidin-4-yl)pyridin-2-yl)amino)-5-methylpyrimidin-4-yl)amino)pyrimidin-4-yl)-2-methylpropane-2-sulfonamide (MA10-178): This compound was prepared using the procedure described for MA10-149 using PN1-055 (35 mg, 0.167 mmol)) and MA10-171 (71.6 mg, 0.200 mmol), Pd$_2$(dba)$_3$ (23.00 mg, 0.025 mmol), xantphos (29.00 mg, 0.050 mmol) and Cs$_2$CO$_3$ (109.0 mg, 0.334 mmol) in toluene (0.6 ml) to obtain the crude product, which was dissolved in DCM and partitioned with saturated NaHCO$_3$. The organic layer was concentrated and purified using SiO$_2$ chromatography (DCM/MeOH gradient elution) and the product obtained was triturated EtOAc/hexanes to provide the desired product (27 mg, 31%) as a light yellow solid (27 mg, 31%). HPLC: 96.4% [$t_R$=12.89 min, gradient MeOH-water (with 0.1% TFA), 5-95% 20 min.]; HPLC-MS (ESI+): m/z 265.7 [100%, (M+2H)$^{2+}$], 530.3 [10%, (M+H)$^+$], HPLC-MS (ESI−): m/z 528.3 [100% (M−H)$^+$]; HRMS (ESI+): m/z calcd for $C_{24}H_{33}FN_9O_2S$ (M+H)$^+$ 530.2456 found 530.2445.

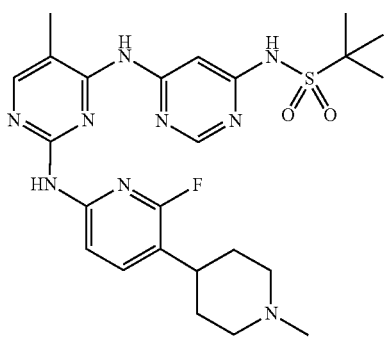

MA10-179

N-(6-((2-((6-fluoro-5-(1-methylpiperidin-4-yl)pyridin-2-yl)amino)-5-methylpyrimidin-4-yl)amino)pyrimidin-4-yl)-2-methylpropane-2-sulfonamide (MA10-179): This compound was prepared using the procedure described for MA10-149 using PN2-100 (35.0 mg, 0.167 mmol)) and MA10-171 (71.6 mg, 0.200 mmol), Pd$_2$(dba)$_3$ (23.00 mg, 0.025 mmol), xantphos (29.00 mg, 0.050 mmol) and Cs$_2$CO$_3$ (109.0 mg, 0.334 mmol) in toluene (0.6 ml) to obtain the crude product, which was dissolved in DCM and partitioned with saturated NaHCO$_3$. The organic layer was concentrated and purified using SiO$_2$ chromatography (DCM/MeOH gradient elution) and the product obtained was triturated EtOAc/hexanes to provide the desired product (23 mg, 26%) as a beige solid. HPLC: 96.76% [$t_R$=12.99 min, gradient MeOH-water (with 0.1% TFA), 5-95% 20 min.]; HPLC-MS (ESI+): m/z 265.7 [100%, (M+2H)$^{2+}$], 530.3 [10%, (M+H)$^+$], HPLC-MS (ESI−): m/z 528.3 [100% (M−H)$^+$]; HRMS (ESI+): m/z calcd for $C_{24}H_{33}FN_9O_2S$ (M+H)$^+$ 530.2456 found 530.2447.

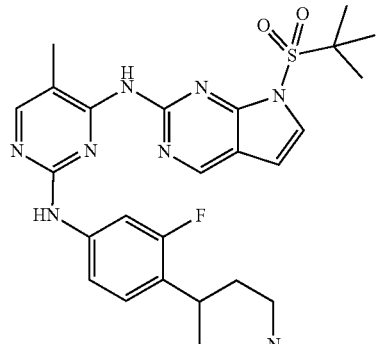

MA11-003

N4-(7-(tert-butylsulfonyl)-7H-pyrrolo[2,3-d]pyrimidin-2-yl)-N2-(3-fluoro-4-(1-methylpiperidin-4-yl)phenyl)-5-methylpyrimidine-2,4-diamine (MA11-003): This compound was prepared using the procedure described for MA10-149 using MA9-058 (25.00 mg, 0.120 mmol), MA10-180 (50.00 mg, 0.132 mmol), Pd$_2$(dba)$_3$ (16.5 mg, 0.018 mmol), xantphos (20.8 mg, 0.036 mmol) and Cs$_2$CO$_3$ (58.7 mg, 0.180 mmol) in dioxane:DMF (6:1, 0.6 ml) to obtain the crude product, which was dissolved in DCM and partitioned with saturated NaHCO$_3$. The organic layer was concentrated and purified using SiO$_2$ chromatography (DCM/MeOH gradient elution) to provide the desired product (41 mg, 62%) as a light yellow solid. HPLC: 100% [$t_R$=14.0 min, gradient MeOH-water (with 0.1% TFA), 5-95% 20 min.]; HPLC-MS (ESI+): m/z 553.3 [100%, (M+H)$^+$], HPLC-MS (ESI−): m/z 551.2 [100% (M−H)$^+$]; HRMS (ESI+): m/z calcd for $C_{27}H_{34}FN_8O_2S$ (M+H)$^+$ 553.2504, found 553.2496.

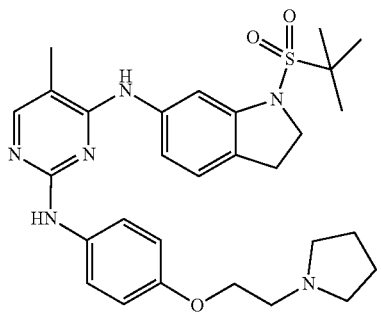

MA11-006

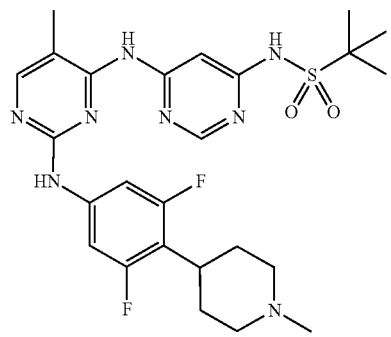

MA11-009

N4-(1-(tert-butylsulfonyl)indolin-6-yl)-5-methyl-N2-(4-(2-(pyrrolidin-1-yl)ethoxy)phenyl)pyrimidine-2,4-diamine (MA11-006): This compound was prepared using the general method X by the reaction of 1-(tert-butylsulfonyl)-N-(2-chloro-5-methylpyrimidin-4-yl)indolin-6-amine (50.00 mg, 0.131 mmol), 4-(2-(pyrrolidin-1-yl)ethoxy)aniline 4-(2-(pyrrolidin-1-yl)ethoxy)aniline (27.00 mg, 0.131 mmol) in the presence of 4M HCl in H$_2$O (32 uL, 0.14 mmol) in ethanol (0.5 mL). The purification was also carried out using the exact same method as described for MA9-060 and triturated using EtOAc/hexanes to obtain the title compound as a white solid (49 mg, 68%). HPLC: 100% [t$_R$=18.4 min, gradient MeOH-water (with 0.1% TFA), 5-95% 20 min.]; HPLC-MS (ESI+): m/z 276.2 [100%, (M+2H)$^{2+}$], 551.3 [40%, (M+H)$^+$]; HRMS (ESI+): m/z calcd for C$_{29}$H$_{39}$N$_6$O$_3$S (M+H)$^+$ 551.2799 found 551.2790.

N-(6-((2-((3,5-difluoro-4-(1-methylpiperidin-4-yl)phenyl)amino)-5-methylpyrimidin-4-yl)amino)pyrimidin-4-yl)-2-methylpropane-2-sulfonamide (MA11-009): This compound was prepared using the general method X by the reaction of MA10-171 (50.00 mg, 0.140 mmol), PN2-120 (31.70 mg, 0.140 mmol) in the presence of 4M HCl in H$_2$O (38.5 uL, 0.144 mmol) in ethanol (0.5 mL). The purification was also carried out using the exact same method as described for MA9-060 (DCM/MeOH gradient elution, and the compound was eluted with 20% MeOH in DCM) to obtain the title compound as a white solid (20 mg, 26%). HPLC-MS (ESI+): m/z 274.2 [100%, (M+2H)$^{2+}$], 547.3 [40%, (M+H)$^+$]; HPLC-MS (ESI−): m/z 545.2 [100% (M−H)$^+$]; HRMS (ESI+): m/z calcd for C$_{25}$H$_{33}$F$_2$N$_8$O$_2$S (M+H)$^+$ 547.2410 found 547.2400.

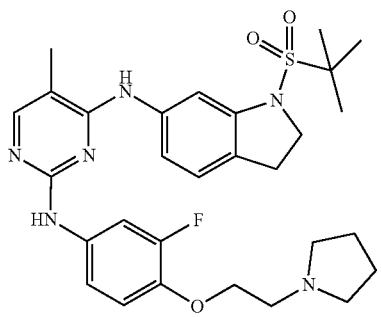

MA11-007

N4-(1-(tert-butylsulfonyl)indolin-6-yl)-N2-(3-fluoro-4-(2-(pyrrolidin-1-yl)ethoxy)phenyl)-5-methylpyrimidine-2,4-diamine (MA11-007): This compound was prepared using the general method X by the reaction of 1-(tert-butylsulfonyl)-N-(2-chloro-5-methylpyrimidin-4-yl)indolin-6-amine (50.00 mg, 0.131 mmol), MA9-137 (29.40 mg, 0.131 mmol) in the presence of 4M HCl in H$_2$O (32 uL, 0.144 mmol) in ethanol (0.5 mL). The purification was also carried out using the exact same method as described for MA9-060 and the product obtained was further triturated with EtOAc/Hexanes to obtain the title compound as a white solid (47 mg, 63%). HPLC: 97.37% [t$_R$=12.81 min, gradient MeOH-water (with 0.1% TFA), 5-95% 20 min.]; HPLC-MS (ESI+): m/z 285.2 [100%, (M+2H)$^{2+}$], 569.3 [40%, (M+H)$^+$]; HPLC-MS (ESI−): m/z 567.4 [60% (M−H)$^+$]; HRMS (ESI+): m/z calcd for C$_{29}$H$_{38}$FN$_6$O$_3$S (M+H)$^+$ 569.2705 found 569.2697.

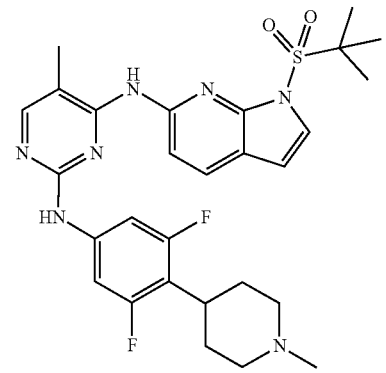

MA11-012

N4-(1-(tert-butylsulfonyl)-1H-pyrrolo[2,3-b]pyridin-6-yl)-N2-(3,5-difluoro-4-(1-methylpiperidin-4-yl)phenyl)-5-methylpyrimidine-2,4-diamine (MA11-012): This compound was prepared using the procedure and purification described for MA11-003 using MA10-146 (60.40 mg, 0.159 mmol), PN2-120 (30.00 mg, 0.132 mmol), Pd$_2$(dba)$_3$ (18.20 mg, 0.019 mmol) xantphos (23.00 mg, 0.039 mmol) and Cs$_2$CO$_3$ (64.80 mg, 0.199 mmol) in dioxane:DMF (6:1, 0.6 ml) to obtain the desired product (17 mg, 23%) as a light yellow solid. HPLC: 100% [t$_R$=4.66 min, gradient MeOH-water (with 0.1% TFA), 5-95% 20 min.]; HPLC-MS (ESI+): m/z 285.8 [100%, (M+2H)$^{2+}$], 570.5 [50%, (M+H)$^+$].

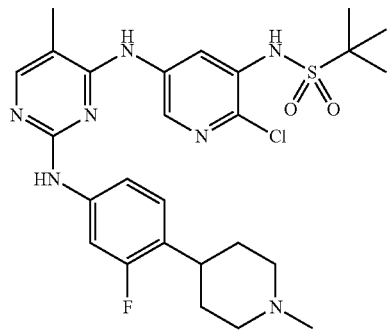

MA11-016

N-(2-chloro-5-((2-((3-fluoro-4-(1-methylpiperidin-4-yl)phenyl)amino)-5-methylpyrimidin-4-yl)amino)pyridin-3-yl)-2-methylpropane-2-sulfonamide (MA11-016): This compound was prepared using the general method X by reaction of MA11-011 (50.00 mg, 0.128 mmol), MA9-058 (26.70 mg, 0.128 mmol) in the presence of 4M HCl in H$_2$O (35.2 uL, 0.140 mmol) in ethanol (0.5 mL). The purification was a carried out by triturating the crude compound with MeOH followed by rinsing with hexanes to obtain the desired pure compound as an off white solid (56 mg, 78%). HPLC: 97.05% [t$_R$=12.28 min, gradient MeOH-water (with 0.1% TFA), 5-95% 20 min.]; HPLC-MS (ESI+): m/z 281.8 [100%, (M+2H)$^{2+}$], 562.1 [40%, (M+H)$^+$]; HPLC-MS (ESI−): m/z 560.2 [100% (M−H)$^+$].

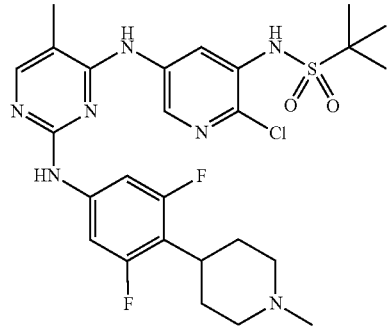

MA11-017

N-(2-chloro-5-((2-((3,5-difluoro-4-(1-methylpiperidin-4-yl)phenyl)amino)-5-methylpyrimidin-4-yl)amino)pyridin-3-yl)-2-methylpropane-2-sulfonamide (MA11-017): This compound was prepared using the general method X by the reaction of MA11-011 (50.00 mg, 0.128 mmol), PN2-120 (29.00 mg, 0.128 mmol) in the presence of 4M HCl in H$_2$O (35.2 uL, 0.140 mmol) in ethanol (0.5 mL). The purification was a carried out by triturating the crude compound with MeOH followed by rinsing with hexanes to obtain the desired pure compound as a white solid (45 mg, 61%). HPLC: 99.37% [t$_R$=11.77 min, gradient MeOH-water (with 0.1% TFA), 5-95% 20 min.]; HPLC-MS (ESI+): m/z 290.7 [100%, (M+2H)$^{2+}$], 580.3 [50%, (M+H)$^+$].

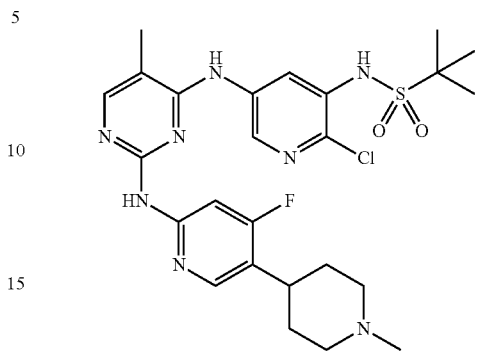

MA11-022

N-(2-chloro-5-((2-((4-fluoro-5-(1-methylpiperidin-4-yl)pyridin-2-yl)amino)-5-methylpyrimidin-4-yl)amino)pyridin-3-yl)-2-methylpropane-2-sulfonamide (MA11-022): This compound was prepared using the procedure described for MA10-149 using MA11-011 (56.00 mg, 0.144 mmol), PN1-055 (25.00 mg, 0.119 mmol), Pd$_2$(dba)$_3$ (16.40 mg, 0.018 mmol) xantphos (20.70 mg, 0.036 mmol) and Cs$_2$CO$_3$ (59.00 mg, 0.180 mmol) in dioxane:DMF (6:1, 0.6 ml) to obtain the desired product (34 mg, 46%) as a light yellow solid. The crude compound was purified by SiO$_2$ chromatography with DCM/MeOH (gradient elution) followed by trituration with EtOAc-hexanes to obtain the pure compound (34 mg, 46%). HPLC: 99.53% [t$_R$=12.29 min, gradient MeOH-water (with 0.1% TFA), 5-95% 20 min.]; HPLC-MS (ESI+): m/z 282.2, 283.0 [100%, (M+2H)$^{2+}$−$^{35}$Cl isotope and 40% (M+2H)$^{2+}$−$^{36}$Cl isotope respectively); 563.3 [20%, (M+H)$^+$]; HPLC-MS (ESI−): m/z 561.3 and 562.2 [100% (M−H)$^+$−$^{35}$Cl isotope and 40% (M−H)$^+$−$^{36}$Cl isotope respectively].

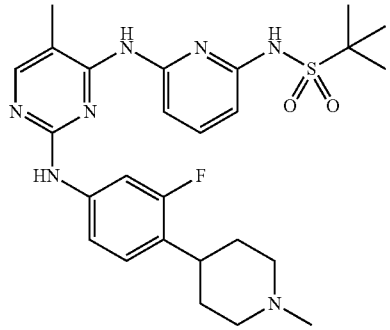

MA11-032

N-(6-((2-((3-fluoro-4-(1-methylpiperidin-4-yl)phenyl)amino)-5-methylpyrimidin-4-yl)amino)pyridin-2-yl)-2-methylpropane-2-sulfonamide (MA11-032): This compound was prepared using the general method X by the reaction of MA11-024 (50.00 mg, 0.140 mmol), MA9-058 (29.30 mg, 0.140 mmol) in the presence of 4M HCl in H$_2$O (39 uL, 0.154 mmol) in ethanol (0.5 mL). The purification was carried out using SiO$_2$ chromatography (DCM:MeOH gradient elution) followed by triturating the compound with EtOAc-hexanes to obtain the desired pure compound as an off white solid (34 mg, 46%). HPLC: 93.84% [t$_R$=11.867 min, gradient MeOH-water (with 0.1% TFA), 5-95% 20 min.]; HPLC-MS (ESI+): m/z 264.7 [100%, (M+2H)$^{2+}$], 528.3 [40%, (M+H)$^+$]; HPLC-MS (ESI-): m/z 526.3 [100% (M-H)$^+$]; HRMS (ESI+): m/z calcd for C$_{26}$H$_{35}$FN$_7$O$_2$S (M+H)$^+$ 528.2551 found 528.2540.

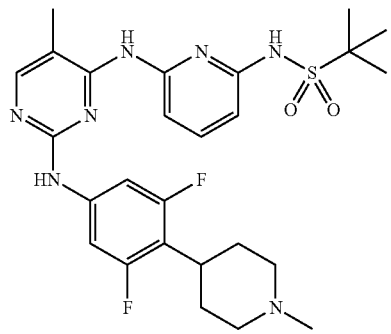

MA11-035

N-(6-((2-((3,5-difluoro-4-(1-methylpiperidin-4-yl)phenyl)amino)-5-methylpyrimidin-4-yl)amino)pyridin-2-yl)-2-methylpropane-2-sulfonamide (MA11-035): This compound was prepared using the general method X by the reaction of MA11-024 (50.00 mg, 0.140 mmol), PN2-120 (31.80 mg, 0.140 mmol) in the presence of 4M HCl in H$_2$O (38.6 uL, 0.154 mmol) in ethanol (0.5 mL). The purification was a carried out using SiO$_2$ chromatography (DCM:MeOH gradient elution, up to 15% MeOH) followed by triturating the compound with MeOH/DCM to obtain the desired pure compound as a yellow solid (18 mg, 24%). HPLC: 98.67% [t$_R$=11.867 min, gradient MeOH-water (with 0.1% TFA), 5-95% 20 min.]; HPLC-MS (ESI+): m/z 273.7 [60%, (M+2H)$^{2+}$], 546.3 [100%, (M+H)$^+$]; HRMS (ESI+): m/z: calcd for C$_{26}$H$_{34}$F$_2$N$_7$O$_2$S (M+H)$^+$ 546.2457 found 546.2460.

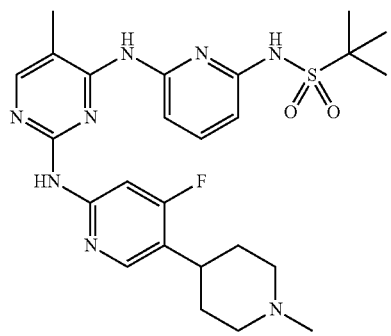

MA11-038

N-(6-((2-((4-fluoro-5-(1-methylpiperidin-4-yl)pyridin-2-yl)amino)-5-methylpyrimidin-4-yl)amino)pyridin-2-yl)-2-methylpropane-2-sulfonamide (MA11-038): This compound was prepared using the procedure described for MA10-149 using MA11-024 (48.90 mg, 0.137 mmol), PN1-055 (24.00 mg, 0.137 mmol), Pd$_2$(dba)$_3$ (15.75 mg, 0.017 mmol), xantphos (19.91 mg, 0.034 mmol) and Cs$_2$CO$_3$ (56.00 mg, 0.172 mmol) in dioxane:DMF (6:1, 0.6 ml) to obtain the crude product, which was dissolved in DCM and partitioned with saturated NaHCO$_3$. The organic layer was concentrated and purified using SiO$_2$ chromatography (DCM/MeOH gradient elution) to provide the desired product (16 mg, 35%) as a light yellow solid. HPLC: 99.04% [t$_R$=6.97 min, gradient MeOH-water (with 0.1% TFA), 5-95% 20 min.]; HPLC-MS (ESI+): m/z 265.2 [100%, (M+2H)$^{2+}$], 529.3 [10%, (M+H)$^+$].

Building Block Synthesis for MA9-024-MA11-038

Procedure A: A mixture of substituted 2,4-dichloropyrimidine (1.0 equiv.) and substituted aniline (1.15 equiv.) in MeOH/water (1:1.5, 0.2 M) was stirred at 45° C. The reaction time is indicated below in each experiment below. Upon cooling to ambient temperature, the desired product precipitated and was filtered, washed with MeOH/water (1:1.5, 20 mL), and dried.

Procedure B: A mixture of substituted 2,4-dichloropyrimidine (1.0 equiv.), and substituted aniline (1.0-1.05 equiv.), and DIPEA (1.2 equiv.) in isopropanol (0.1 M) was stirred and heated at reflux. The reaction time, work-up, and product isolation procedure are described below.

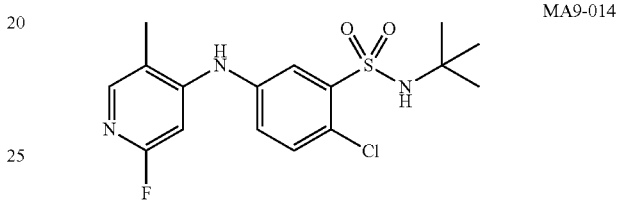

MA9-014

N-(Tert-butyl)-2-chloro-5-((2-fluoro-5-methylpyridin-4-yl)amino)benzenesulfonamide (MA9-014): 2-Fluoro-4-iodo-5-methylpyridine (100 mg, 0.421 mmol), 5-amino-N-(tert-butyl)-2-chlorobenzenesulfonamide SG3-105 (133 mg, 0.506), BINAP (11.6 mg, 0.018 mmol), Pd(OAc)$_2$ (2.0 mg 0.009 mmol) and Cs$_2$CO$_3$ (283 mg, 1.48 mmol) were combined in a pressure tube (with a septum) and the vessel was evacuated and backfilled with argon (3 times). Subsequently, toluene (2.5 mL) was added and argon was purged through the reaction (~15 minutes). Reaction was heated in oil bath (100° C.) for 2.5 days at which point TLC indicated complete consumption of 2-Fluoro-4-iodo-5-methylpyridine input. Crude product was partitioned between EtOAc (~100 mL) and water (50 mL×2). Organic layer was dried Na$_2$SO$_4$ and evaporated. The crude product was triturated using EtOAc and DCM to obtain the pure product as yellow solid (107 mg, 68%). $^1$H NMR (500 MHz, MeOD): δ 7.72 (d, J=1.0 Hz, 1H), 7.70 (d, J=2.6 Hz, 1H), 7.43 (d, J=8.6 Hz, 1H), 7.06 (dd, J=8.6, 2.6 Hz, 1H), 6.51 (s, 1H), 2.22 (s, 3H), 1.41 (s, 9H); $^{19}$F NMR (471 MHz, MeOD): δ -75.40. HPLC-MS (ESI+): m/z 374.1 [40%, (M$^{37}$Cl+H)$^+$], 372.1 [100%, (M$^{35}$Cl+H)$^+$].

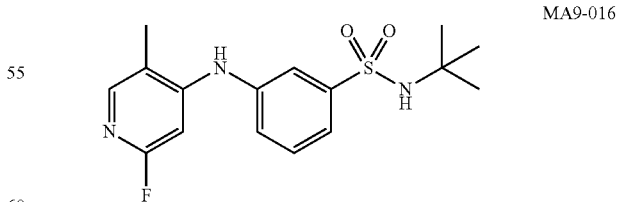

MA9-016

N-(tert-butyl)-3-((2-fluoro-5-methylpyridin-4-yl)amino) benzenesulfonamide (MA9-016): This compound was prepared by the reaction of 2-Fluoro-4-iodo-5-methylpyridine (100 mg, 0.421 mmol) and 3-amino-N-(tert-butyl)benzenesulfonamide (115.6 mg, 0.51 mmol) using the same procedure as described for the synthesis of MA9-014. After aqueous work up, the crude was triturated to get the pure product as a beige solid (116 mg, 82%). ¹H NMR (500 MHz, MeOD): δ 7.78 (t, J=1.9 Hz, 1H), 7.75 (d, J=1.0 Hz, 1H), 7.67 (ddd, J=7.8, 1.8, 1.0 Hz, 1H), 7.57 (t, J=7.9 Hz, 1H), 7.47 (ddd, J=8.0, 2.2, 1.0 Hz, 1H), 6.44 (s, 1H), 2.24 (s, 3H), 1.22 (s, 9H); HPLC-MS (ESI+): m/z 338.2 [100%, (M+H)⁺].

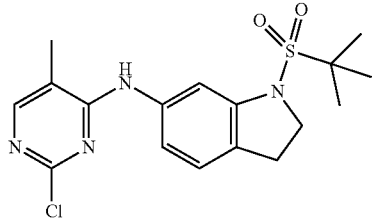

MA9-040

1-(tert-butylsulfonyl)-N-(2-fluoro-5-methylpyridin-4-yl) indolin-6-amine (MA9-040): This compound was prepared by the reaction of 2-Fluoro-4-iodo-5-methylpyridine (350 mg, 1.48 mmol) and SG4-020 (376 mg, 1.48 mmol) using the same procedure as described for the synthesis of MA9-014. After aqueous work up, the crude was triturated to get the pure product as a yellow solid (488 mg, 91%). ¹H NMR (500 MHz, MeOD): δ 7.67 (d, J=1.1 Hz, 1H), 7.27 (d, J=2.0 Hz, 1H), 7.23 (dt, J=7.9, 1.2 Hz, 1H), 6.85 (dd, J=7.9, 1.9 Hz, 1H), 6.31 (s, 1H), 4.15 (t, J=8.5 Hz, 2H), 3.15 (t, J=8.4 Hz, 2H), 2.20 (s, 3H), 1.46 (s, 9H); ¹⁹F NMR (471 MHz, MeOD): δ −76.03 (brs); HPLC-MS (ESI+): m/z 364.2 [100%, (M+H)⁺].

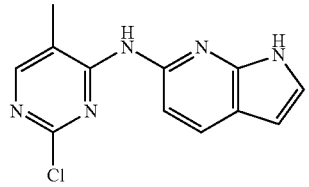

MA10-134

N-(2-chloro-5-methylpyrimidin-4-yl)-1H-pyrrolo[2,3-b] pyridin-6-amine (MA10-134): This compound was prepared by the reaction of 2,4-dichloro-5-methylpyrimidine (200 mg, 1.23 mmol) and 1H-pyrrolo[2,3-b]pyridin-6-amine (165 mg, 1.23 mmol) in the presence of DIPEA (476 mg, 3.68 mmol) using the general procedure B. The crude product mixture was purified by trituration with DCM/hexane to obtain the title compound as a yellow solid (258 mg, 81%). ¹H NMR (500 MHz, DMSO-d₆): δ 11.46 (s, 1H), 9.14 (s, 1H), 8.08 (s, 1H), 7.98 (d, J=8.4 Hz, 1H), 7.58 (d, J=8.4 Hz, 1H), 7.38 (d, J=3.5 Hz, 1H), 6.43 (d, J=3.4 Hz, 1H), 2.20 (s, 3H); HPLC-MS (ESI+): m/z 262.2 [40%, (M³⁷Cl+H)⁺], 260.1 [100%, (M³⁵Cl+H)⁺].

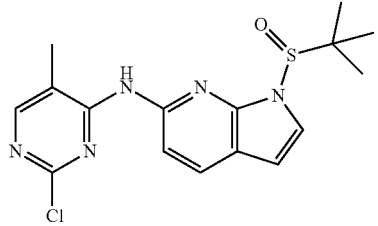

MA10-143

1-(tert-butylsulfinyl)-N-(2-chloro-5-methylpyrimidin-4-yl)-1H-pyrrolo[2,3-b]pyridin-6-amine (MA10-143B2): The MA10-134 (150 mg, 0.577 mmol) was dissolved in dry DMF (1.8 mL) and the mixture was cooled to 0° C. followed by the addition of NaH (24.3 mg, 0.61 mmol, 60% dispersion on oil). The mixtures was stirred at 0° C. for 1 h followed by the dropwise addition of 2-methylpropane-2-sulfinic chloride (84 mg, 0.578 mmol). The reaction was stirred at 0° C. for 1 h and at r.t. for overnight. The reaction mixture was cooled to 0° C. and quenched with sat.NH₄Cl (~5 mL). The yellow precipates formed were stirred at rt for ~15 minutes, sonicated, filtered and rinsed with water (~10 mL) and hexane (~10 mL) to obtain the title compound as a yellow solid (178 mg, 85%). ¹H NMR (500 MHz, DMSO-d₆): δ 9.29 (s, 1H), 8.16 (s, 1H), 8.10 (d, J=8.5 Hz, 1H), 7.67 (d, J=8.4 Hz, 1H), 7.59 (d, J=3.9 Hz, 1H), 6.79 (d, J=3.9 Hz, 1H), 2.24 (s, 3H), 1.25 (s, 9H; HPLC-MS (ESI+): m/z 364.2 [100%, (M+H)⁺].

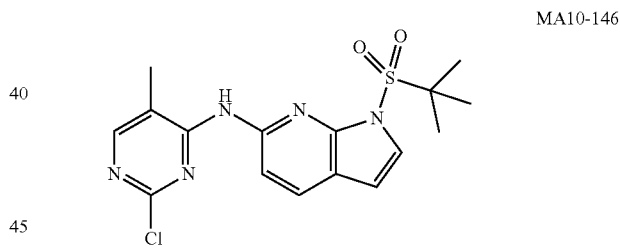

MA10-146

1-(tert-butylsulfonyl)-N-(2-chloro-5-methylpyrimidin-4-yl)-1H-pyrrolo[2,3-b]pyridin-6-amine (MA10-146): This was obtained by the oxidation of MA10-143 (230 mg, 0.632 mmol) in the presence of mCPBA (156 mg, 0.695 mmol) in DCM (3 mL) at r.t. initially for 3 h, and the reaction was monitored by TLC. The reaction was at r.t. for total of 16 h (TLC showed no starting material left). The crude mixture was diluted with DCM (30 mL), and washed with 1M NaOH (2×30 mL). The organic layer washed with water (50 mL), and brine (50 mL), dried (Na₂SO₄) and concentrated. The crude product was triturated with EtOAc/hexane to obtain the pure product as a yellow solid (201 mg, 82%). ¹H NMR (500 MHz, DMSO-d₆): δ 9.23 (s, 1H), 8.17 (d, J=1.0 Hz, 1H), 8.13 (d, J=8.5 Hz, 1H), 7.64 (d, J=8.5 Hz, 1H), 7.59 (d, J=4.0 Hz, 1H), 6.79 (d, J=4.0 Hz, 1H), 2.23 (d, J=0.9 Hz, 3H), 1.40 (s, 9H); HPLC-MS (ESI+): m/z 380.2 [100%, (M+H)⁺].

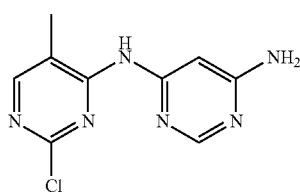

MA10-155

N4-(2-chloro-5-methylpyrimidin-4-yl)pyrimidine-4,6-diamine (MA10-155): This compound was prepared by the reaction of pyrimidine-4,6-diamine (2.0 g, 18.16 mmol) and 2,4-dichloro-5-methylpyrimidine (2.96 g, 18.16 mmol) in the presence of DIPEA (7.0 g, 54.49 mmol) using the general procedure B. After 3 days heating at 140° C. in oil bath, the crude was evaporated and stirred with MeOH (50 mL) for ~30 minutes and filtered. The precipitates were rinsed with hexane (~50 mL) to get semi-pure product (~HPLCMS purity ~90%) which was used for the next step without further purification. Yield (1.81 g, 42%). $^1$H NMR (500 MHz, DMSO-d$_6$): δ 9.98 (s, 1H), 8.49 (d, J=0.8 Hz, 1H), 8.10 (d, J=1.0 Hz, 1H), 7.21 (d, J=1.1 Hz, 1H), 6.80-6.61 (m, 2H), 2.22 (s, 3H); HPLC-MS (ESI+): m/z 237.2 [100%, (M+H)$^+$].

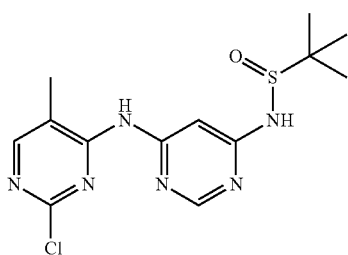

MA10-166

N-(6-((2-chloro-5-methylpyrimidin-4-yl)amino)pyrimidin-4-yl)-2-methylpropane-2-sulfinamide (MA10-166): The MA10-155 (100 mg, 0.422 mmol) was suspended in dry THF (2 mL) and cooled to 0 C followed by the dropwise addition of LiHDMS (1.27 mL, 0.422 mmol, 1M in THF) over a period of 30 minutes. The mixture was stirred at 0° C. for 1 h and then 2-methylpropane-2-sulfinic chloride (61 mg, 0.422 mmol, 97%) was added dropwise (~20 minutes) as a solution in THF (2 mL). Reaction was stirred at 0 C for 30 minutes and at r.t. for overnight. The reaction was quenched with NH$_4$Cl (~3 mL) and the crude mixture was partitioned between EtOAc (~3×20 mL) and NaHCO$_3$ (~30 mL). The organic layer was dried (Na$_2$SO$_4$) and evaporated. The crude compound was subjected to SiO$_2$ column while eluting with a gradient of MeOH in DCM (up to 10% MeOH). The title compound was obtained as a yellow solid (78 mg, 54%). $^1$H NMR (500 MHz, DMSO-d$_6$): δ 10.46 (s, 1H), 9.43 (s, 1H), 8.54 (d, J=0.9 Hz, 1H), 8.36 (d, J=1.1 Hz, 1H), 7.74 (d, J=1.0 Hz, 1H), 2.25 (s, 3H), 1.24 (s, 9H); HPLC-MS (ESI+): m/z 343.1 [40%, (M$^{37}$Cl+H)$^+$], 341.1 [100%, (M$^{35}$Cl+H)$^+$].

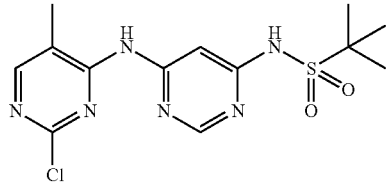

MA10-171

N-(6-((2-chloro-5-methylpyridin-4-yl)amino)pyrimidin-4-yl)-2-methylpropane-2-sulfonamide (MA10-171): This compound was obtained by the oxidation of MA10-166 (520 mg, 1.53 mmol) in the presence of mCPBA (290 mg, 1.68 mmol, 77%) in DCM (15 mL) using the general procedure as described for the synthesis of MA10-146. The title compound purified by a combination of SiO$_2$ chromatography (eluents MeOH-DCM) and trituration EtOAc/hexanes to yield the product as a white solid (335 mg, 62%). $^1$H NMR (500 MHz, DMSO-d$_6$): δ 10.62 (s, 1H), 8.57 (d, J=0.9 Hz, 1H), 8.33 (s, 1H), 8.16 (s, 1H), 2.25 (s, 3H), 1.35 (s, 9H).

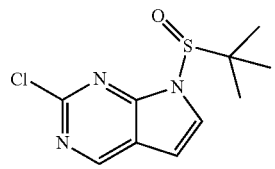

MA10-169

7-(tert-butylsulfinyl)-2-chloro-7H-pyrrolo[2,3-d]pyrimidine (MA10-169): 2-Chloro-7H-pyrrolo[2,3-d]pyrimidine (1.0 g, 6.51 mmol) was dissolved in dry DMF (12 mL) and the mixture was cooled to 0° C. followed by the addition of NaH (265 mg, 6.63 mmol, 60% dispersion on oil). The mixtures was stirred at 0° C. for 40 min followed by the dropwise addition of 2-methylpropane-2-sulfinic chloride (84 mg, 0.578 mmol) as a solution in dry DMF (6 mL). The reaction allowed to warm to r.t. and stirred overnight. The reaction mixture was quenched at 0° C. and with sat.NH$_4$Cl (~5 mL). The crude mixture was purified using SiO$_2$ chromatography while eluting with a gradient of EtOAc/hexane to yield the title compound as an off white solid (1.02 g, 61%). $^1$H NMR (500 MHz, DMSO-d$_6$): δ 9.05 (s, 1H), 7.79 (d, J=3.9 Hz, 1H), 6.97 (d, J=3.9 Hz, 1H), 1.24 (s, 9H); HPLC-MS (ESI+): m/z 260.1 [40%, (M$^{37}$Cl+H)$^+$], 258.0 [100%, (M$^{35}$Cl+H)$^+$].

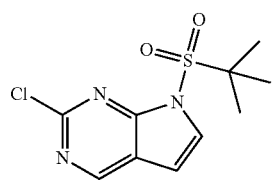

MA10-170

7-(tert-butylsulfonyl)-2-chloro-7H-pyrrolo[2,3-d]pyrimidine (MA10-170): This was obtained by the oxidation of MA10-169 (500 mg, 1.53 mmol) in the presence of mCPBA (290 mg, 1.68 mmol, 77%) using the general procedure as described for the synthesis of MA10-146. The title compound was purified by a combination of SiO$_2$ chromatography (eluents MeOH-DCM) and trituration with MeOH to yield the product as a white solid (335 mg, 62%). $^1$H NMR (500 MHz, DMSO-$d_6$): δ 9.11 (s, 1H), 7.80 (d, J=4.0 Hz, 1H), 6.98 (d, J=4.0 Hz, 1H), 1.42 (s, 9H); HPLC-MS (ESI+): m/z 276.1 [40%, (M$^{37}$Cl+H)$^+$], 274.1 [100%, (M$^{35}$Cl+H)$^+$].

MA10-180

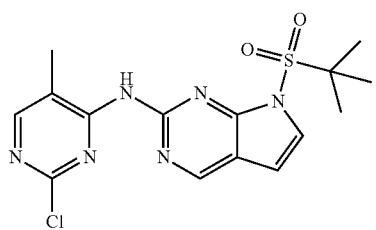

7-(tert-butylsulfonyl)-N-(2-chloro-5-methylpyrimidin-4-yl)-7H-pyrrolo[2,3-d]pyrimidin-2-amine (MA10-180): Xantphos and Pd$_2$(dba)$_3$ were dissolved in a mixture of dioxane-DMF (6:1, 0.5 mL) and argon was bubble through the mixture for 15 minutes. 2-Chloro-5-methylpyrimidin-4-amine (22 mg, 0.153 mmol), MA10-170 (54.5 mg (0.199 mmol) and Cs$_2$CO$_3$ (75 mg, 230 mmol) were added to the reaction mixture under argon and argon bubbling was continued for another 10 minutes. The reaction vessel was closed and heated in microwave at 120° C. for 30 minutes (at which point TLC showed complete consumption of limiting reagent). The crude mixture was partitioned between EtOAc (~30 mL) and sat.NaHCO$_3$ (~20 mL). Organic layer was dried (Na$_2$SO$_4$) and evaporated. Crude compound was subjected to SiO$_2$ chromatography eluting with a gradient of EtOAc-hexane. The title compound was obtained as an off white solid (29 mg, 50%). $^1$H NMR (500 MHz, DMSO-$d_6$): δ 10.08 (s, 1H), 9.01 (s, 1H), 8.33 (d, J=0.9 Hz, 1H), 7.59 (d, J=4.0 Hz, 1H), 6.85 (d, J=4.0 Hz, 1H), 2.20 (d, J=0.9 Hz, 3H), 1.42 (s, 9H); HPLC-MS (ESI+): m/z 383.1 [40%, (M$^{37}$Cl+H)$^+$], 381.1 [100%, (M$^{35}$Cl+H)$^+$].

MA9-115

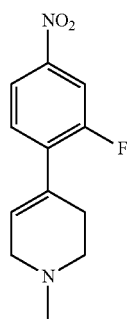

4-(2-Fluoro-4-nitrophenyl)-1-methyl-1,2,3,6-tetrahydropyridine (MA9-115): 4-Bromo-3-fluoronitrobenzene (5 g, 22.73 mmol) and 1-methyl-4-(4,4,5,5-tetramethyl-1,3,2-dioxaborolan-2-yl)-1,2,3,6-tetrahydropyridine (5.58 g, 25.00 mmol) were dissolved in dioxane (100 mL, already degassed for 35 minutes). To this mixture was added a 3M solution of Na$_2$CO$_3$ (22.7 mL, 68.18 mmol) and the combined mixture was further degassed under argon for 20 minutes. Finally, Pd(PPh$_3$)$_4$ (867 mg, 0.75 mmol) was added under argon and the reaction was heated at reflux for 16 h. After confirming the reaction completion (TLC, HPLC-MS), the crude was partitioned between EtOAc (~200 mL×2) and water (~100 mL×3). Organic layer was washed with brine (~50 mL), dried (Na$_2$SO$_4$) and evaporated under reduced pressure. The crude was purified using SiO$_2$ column on a Biotage Isolera purification system, eluting with a gradient of DCM and solvent mixture (DCM:MeOH:NH$_4$OH, 9:1:0.1). The title compound was obtained as a yellow oil (3.92 g, 73%). $^1$H NMR (500 MHz, CDCl$_3$): δ 7.99 (ddd, J=8.5, 2.3, 0.8 Hz, 1H), 7.91 (dd, J=10.6, 2.3 Hz, 1H), 7.43 (dd, J=8.5, 7.5 Hz, 1H), 6.13 (tt, J=3.4, 1.6 Hz, 1H), 3.24 (dt, J=3.5, 2.7 Hz, 2H), 2.77 (d, J=5.7 Hz, 1H), 2.64-2.59 (m, 2H), 2.47 (s, 3H). $^{19}$F NMR (471 MHz, CDCl$_3$): δ −110.66 (dd, J=11.8, 8.0 Hz); HPLC-MS (ESI+): m/z 237.2 [100%, (M+H)$^+$].

MA9-058

3-Fluoro-4-(1-methylpiperidin-4-yl)aniline (MA9-058): An oven dried 2-neck round bottom flask was evacuated and backfilled with argon (twice) followed by the addition of Pd/C (400 mg, ~10%). THF was added to the flask and the suspension was degassed for ~15 minutes (via argon bubbling). Flask was re-evacuated and backfilled with argon (twice). Finally, the argon line was replaced with a hydrogen balloon and after ~5 minutes, MA9-115 (3.91 g, 16.55 mmol) dissolved in dry THF (20 mL) was added via a syringe. The reaction was stirred at rt under hydrogen atmosphere for overnight at which point, HPLC-MS and TLC showed complete consumption of the starting material. The crude was filtered through a short plug of celite and the celite was rinsed with MeOH (~20 mL×2) and EtOAc (~30 mL). The filtrate was concentrated under reduced pressure to furnish the title compound as a light brown solid (3.12 g, 91%). Mp: 91.2-92.4° C. $^1$HNMR (500 MHz, CDCl$_3$): δ 6.99 (t, J=8.3 Hz, 1H), 6.41 (dd, J=8.2, 2.4 Hz, 1H), 6.35 (dd, J=12.1, 2.4 Hz, 1H), 3.64 (s, 2H), 3.00-2.89 (m, 2H), 2.77-2.64 (m, 1H), 2.31 (s, 3H), 2.11-1.99 (m, 2H), 1.76 (ddd, J=10.4, 6.8, 3.5 Hz, 4H); $^{19}$F NMR (471 MHz, CDCl$_3$): δ −119.23 (dd, J=12.1, 8.2 Hz); HPLC-MS (ESI+): m/z 209.3 [100%, (M+H)$^+$].

MA9-063

1-Methyl-4-(4-nitrophenyl)-1,2,3,6-tetrahydropyridine (MA9-063): This was prepared from 4-Iodonitrobenze (1.85 g, 7.43 mmol) and 1-methyl-4-(4,4,5,5-tetramethyl-1,3,2-dioxaborolan-2-yl)-1,2,3,6-tetrahydropyridine (1.99 g, 8.92 mmol) in the presence of Pd(PPh$_3$)$_4$ (284 mg, 0.25 mmol) and K$_2$CO$_3$ (4.11 g, 29.13 mmol) using a similar procedure as descried for the synthesis of MA9-115 (except for Na$_2$CO$_3$ which was replaced with K$_2$CO$_3$). The crude was purified using SiO$_2$ chromatography, eluting with a gradient of DCM-MeOH (up to 10% MeOH) to obtain the title compound as a dark brown oil (1.50 g, 93%). $^1$H NMR (500 MHz, CDCl$_3$): δ 8.19 (dd, J=8.9, 2.1 Hz, 2H), 7.54 (dd, J=8.9, 2.1 Hz, 2H), 6.29 (tt, J=3.6, 1.6 Hz, 1H), 3.19 (dt, J=3.7, 2.7 Hz, 2H), 2.72 (td, J=5.6, 0.7 Hz, 2H), 2.67-2.58 (m, 2H), 2.45 (s, 3H); HPLC-MS (ESI+): m/z 219.2 [100%, (M+H)$^+$].

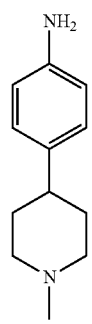

MA9-065

4-(1-Methylpiperidin-4-yl)aniline (MA9-065): This was prepared by the reduction of MA9-063 (1.48 g, 6.78 mmol) in THF (30 mL) using the same general hydrogenation procedure described for MA9-058. After the reaction completion (monitored by HPLC-MS), the solvent was evaporated and the crude was triturated with EtOAc/hexane to obtain the title compound MA9-065 as a beige solid (1.08 g, 83%). $^1$H NMR (400 MHz, DMSO-d$_6$): δ 6.86 (dd, J=8.5, 2.1 Hz, 2H), 6.48 (dd, J=8.5, 2.1 Hz, 2H), 4.80 (s, 2H), 2.82 (d, J=11.3 Hz, 2H), 2.23 (tt, J=11.9, 3.9 Hz, 1H), 2.16 (s, 3H), 1.90 (td, J=11.7, 2.6 Hz, 2H), 1.67-1.60 (m, 2H), 1.60-1.49 (m, 2H); HPLC-MS (ESI+): m/z 191.2 [100%, (M+H)$^+$].

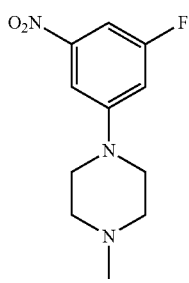

MA9-056

1-(3-Fluoro-5-nitrophenyl)-4-methylpiperazine (MA9-056): 3,5-Difluorobenzene (1.0 g, 6.29 mmol) and N-methylpiperazine (629.6 mg (6.29 mmol) were dissolved in anhydrous DMSO (25 mL) and the reaction mixture was heated in a sealed tube at 100° C. (oil bath) for overnight. Crude was cooled to r.t. and vigorously stirred with NaHCO$_3$ (~30 mL) for ~20 minutes. The precipitate was filtered and rinsed with hexane (~15 mL). This semipure product was further purified by SiO$_2$ column chromatography eluting with a gradient of EtoAc/hexane to get the title compound as yellow solid (1.20 g, 80%). $^1$H NMR (500 MHz, CDCl$_3$): δ 7.52 (t, J=2.2 Hz, 1H), 7.31 (dt, J=8.2, 2.1 Hz, 1H), 6.83 (dt, J=11.4, 2.3 Hz, 1H), 3.39-3.26 (m, 4H), 2.64-2.51 (m, 4H), 2.36 (s, 3H); $^{19}$F NMR (471 MHz, CDCl$_3$): δ −108.90 (dd, J=11.5, 8.0 Hz). HPLC-MS (ESI+): m/z 240.2 [100%, (M+H)$^+$].

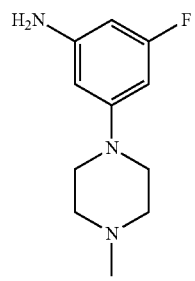

MA9-057

3-Fluoro-5-(4-methylpiperazin-1-yl)aniline (MA9-057): This was obtained using a standard hydrogenation conditions as described for the synthesis of MA9-058. Hydrogenating MA9-056 (1.15 g, 4.81 mmol) in the presence of 10% Pd/C (110 mg) in THF (50 mL) for overnight, yielded the title compound MA9-057 as light brown gummy solid (872 mg, 87%). $^1$H NMR (500 MHz, CDCl$_3$): δ 6.04 (dt, J=12.3, 2.2 Hz, 1H), 5.97 (d, J=2.1 Hz, 1H), 5.90 (dt, J=10.2, 2.1 Hz, 1H), 3.68 (s, 2H), 3.17 (t, J=5.1 Hz, 4H), 2.53 (t, J=5.0 Hz, 4H), 2.33 (s, 3H); 19F NMR (471 MHz, CDCl$_3$): δ −112.73 (t, J=11.2 Hz); HPLC-MS (ESI+): m/z 210.2 [100%, (M+H)$^+$].

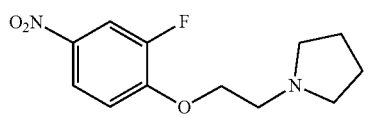

MA9-136

1-(2-(2-Fluoro-4-nitrophenoxy)ethyl)pyrrolidine (MA9-136): In an oven dried rb flask, NaH (1.17 g, 48.71 mmol) was suspended in anhydrous THF (25 mL) and the mixture was cooled to 0° C. 2-(Pyrrolidin-1-yl)ethan-1-ol (3.98 g, 34.57 mmol) was added dropwise (~15 minutes) via a syringe and the mixture was stirred for an hour at 0° C. Subsequently, 1,2-difluoro-4-nitrobenzene (5.0 g, 31.43 mmol) was added dropwise (~20 minutes) via a syringe and the mixture was stirred at 0° C. for 1 h and at rt for 2 h. HPLC-MS showed complete consumption of the limiting reagent so reaction was quenched at 0° C. with cold water (~5 mL) and the crude was partitioned between sat.NaHCO$_3$ (~200 mL) and EtOAc (500 mL). The organic layer was washed with brine (~100 mL) and evaporated. The crude compound was purified using SiO$_2$ column chromatography while eluting with a gradient of EtOAc-hexane. The title compound was obtained as a dark brown solid (5.03 g, 63%). $^1$H NMR (500 MHz, DMSO-d$_6$): δ 8.15 (dd, J=11.1, 2.7 Hz, 1H), 8.11 (ddd, J=9.1, 2.8, 1.3 Hz, 1H), 7.43 (t, J=8.8 Hz, 1H), 4.31 (t, J=5.7 Hz, 2H), 2.85 (t, J=5.7 Hz, 2H), 2.57-2.48 (m, 5H), 1.73-1.62 (m, 4H); $^{19}$F NMR (471 MHz, DMSO-d$_6$): δ −131.48 (dd, J=11.1, 8.5 Hz); HPLC-MS (ESI+): m/z 355.2 [100%, (M+H)$^+$].

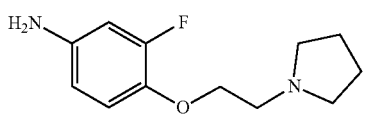

3-Fluoro-4-(2-(pyrrolidin-1-yl)ethoxy)aniline (MA9-137): This was prepared by the hydrogenation of MA9-136 (5.0 g, 19.66 mmol) in the presence of 10% Pd/C (100 mg) and $NH_2NH_2 \cdot H_2O$ (4.92 g, 98.32 mmol) in dry THF (100 mL) using the same procedure described for MA9-058 and purified using $SiO_2$ chromatography (EtOAc/hexane). The title compound was obtained as a yellow solid (4.1 g, 95%). 1H NMR (500 MHz, DMSO-$d_6$) δ 6.84 (dd, J=9.8, 8.7 Hz, 1H), 6.40 (dd, J=13.7, 2.6 Hz, 1H), 6.29 (ddd, J=8.7, 2.7, 1.2 Hz, 1H), 4.92 (s, 2H), 3.96 (t, J=6.0 Hz, 2H), 2.72 (t, J=6.0 Hz, 2H), 2.54-2.45 (m, 4H), 1.72-1.63 (m, 4H). $^{19}F$ NMR (471 MHz, DMSO-$d_6$): δ −133.72 (dd, J=14.0, 9.9 Hz). HPLC-MS (ESI+): m/z 225.2 [100%, (M+H)$^+$].

N-(2-chloro-5-((2-chloropyrimidin-4-yl)amino)pyridin-3-yl)-2-methylpropane-2-sulfonamide (MA11-011): This compound was synthesized using the route shown above. The starting material 2-chloro-3,5-dinitropyridine was reduced using standard synthetic protocols to obtain MA10-139, and this compound was used in the next step to obtain MA10-140 using general method Y (isopropanol was used). The MA10-140 was alkylated using the procedure described for MA10-166 (above) to obtain sulfinamide MA10-168. Subsequently MA10-168 was oxidized using mCPBA to MA11-011 using the procedure described for MA10-146 to get the desired product. This building block was used for synthesis of final compounds described in this application.

Synthetic Route for MA11-024

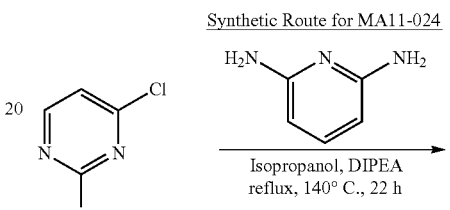

Synthetic Route for MA11-011

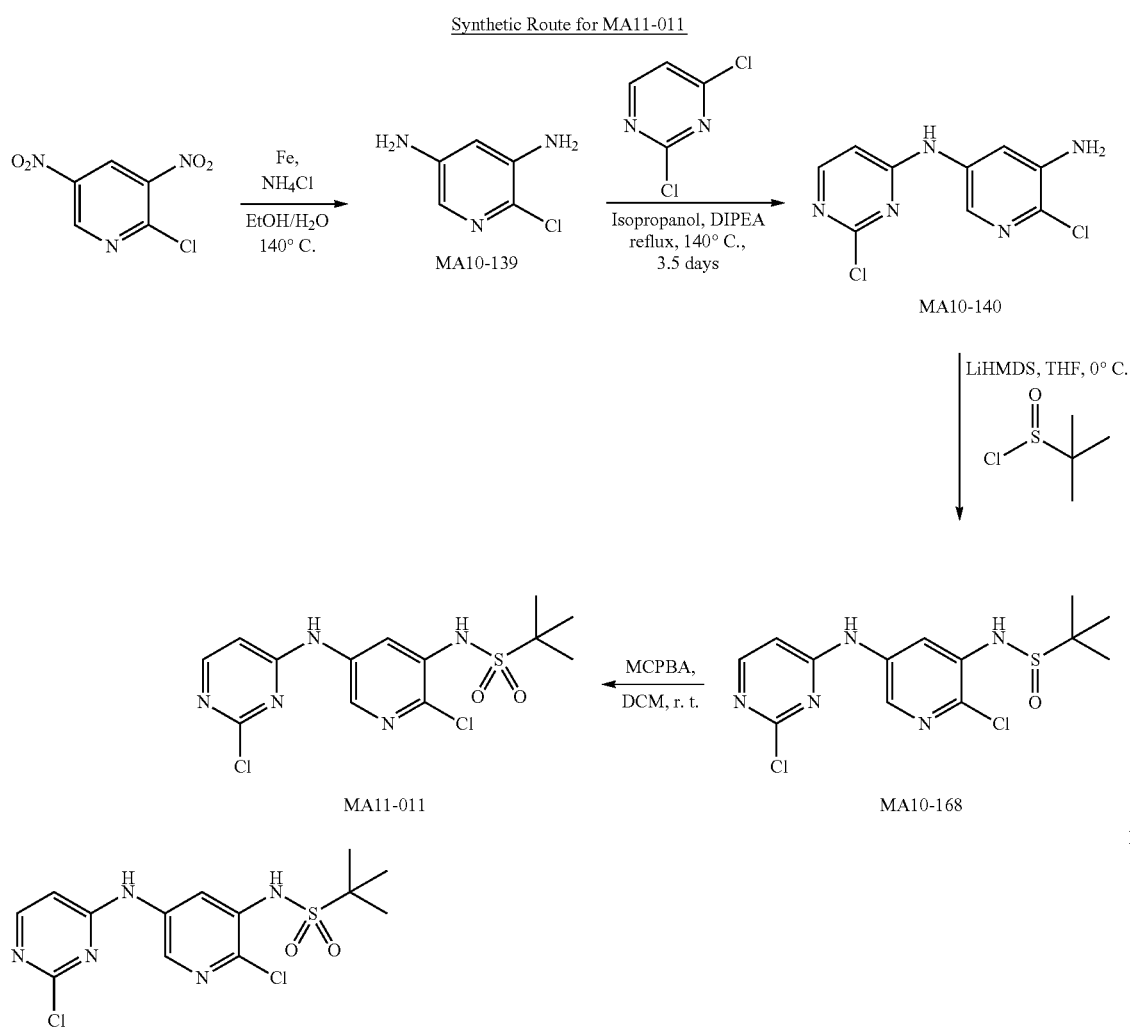

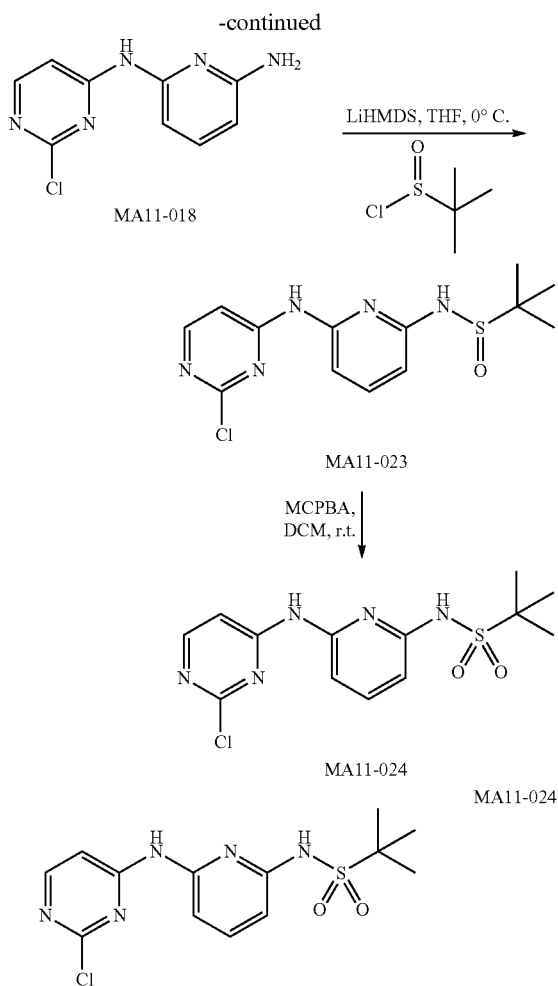

N-(6-((2-chloropyrimidin-4-yl)amino)pyridin-2-yl)-2-methylpropane-2-sulfonamide (MA11-024) This compound was synthesized using the route shown above. The 2,4-dichloropyrimidine was first reacted with pyridine-2,6-diamine using general method Y (isopropanol was used). The sulfnamide MA11-023 was obtained using the procedure described for MA10-166. The MA11-023 was oxidized using mCPBA to MA11-024 using the procedure described for MA10-146 to get the desired product. This building block was used for synthesis of final compounds described in this application.

Methods:

The ability to inhibit erythropoietin-independent erythroid colony (EEC) growth of primary cells from MPN patients is widely used to assess novel anti-MPN therapeutics. MA9-060 was superior to fedratinib and ruxolitinib, two FDA-approved JAK2 inhibitors for MPN, at inhibiting EEC formation in this assay. Little effect on CFU-G/M colonies was observed suggesting MA9-060 is not non-specifically toxic to primary human hematopoietic progenitor cells (FIG. 1). The enhanced efficacy of the dual inhibitor is consistent with ruxolitinib and JQ1 having enhanced inhibition over either drug alone in this assay.

Figure 2:
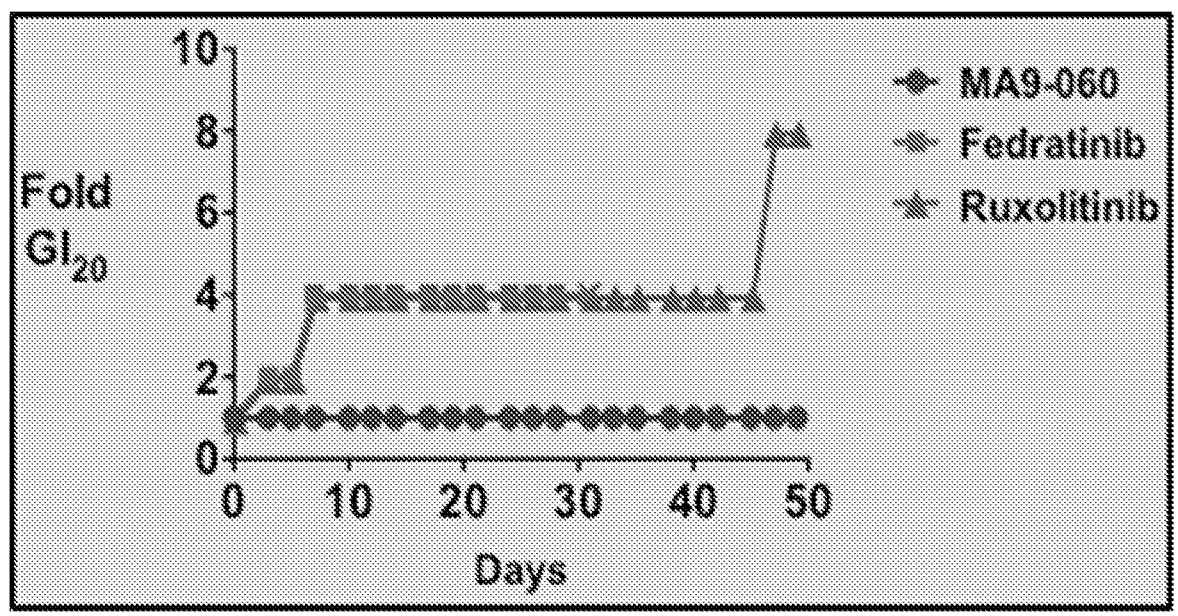
FIG. 2: JAK2-driven cells do not develop drug persistence to MA9-060, but do to Fedratinib and Ruxolitinib. UKE1 cells were incubated with DMSO, MA9-060, fedratinib, or ruxolitinib at their respective $GI_{20}$ concentrations. Cell growth was compared to DMSO. Cells were passed back to the same density after counting. Drug concentration was doubled if growth was >90% of DMSO. Fold $GI_{20}$ is plotted vs time, with drug persistence represented by upward steps of the lines. The final MA9-060, ruxolitinib, and fedratinib concentrations at the end of the experiment were 0.15, 0.6 and 2.4 uM, respectively. Fedratinib-treated cells lost complete viability after about 30 days (after 3 weeks in 2.4 uM).

While UKE1 MPN model cells persistently grew in increasing concentrations of fedratinib and ruxolitinib, these cells could not escape a low concentration of MA9-060 suggesting cells are less prone to developing drug persistence to this novel dual inhibitor (FIG. 2).

Figure 3A:
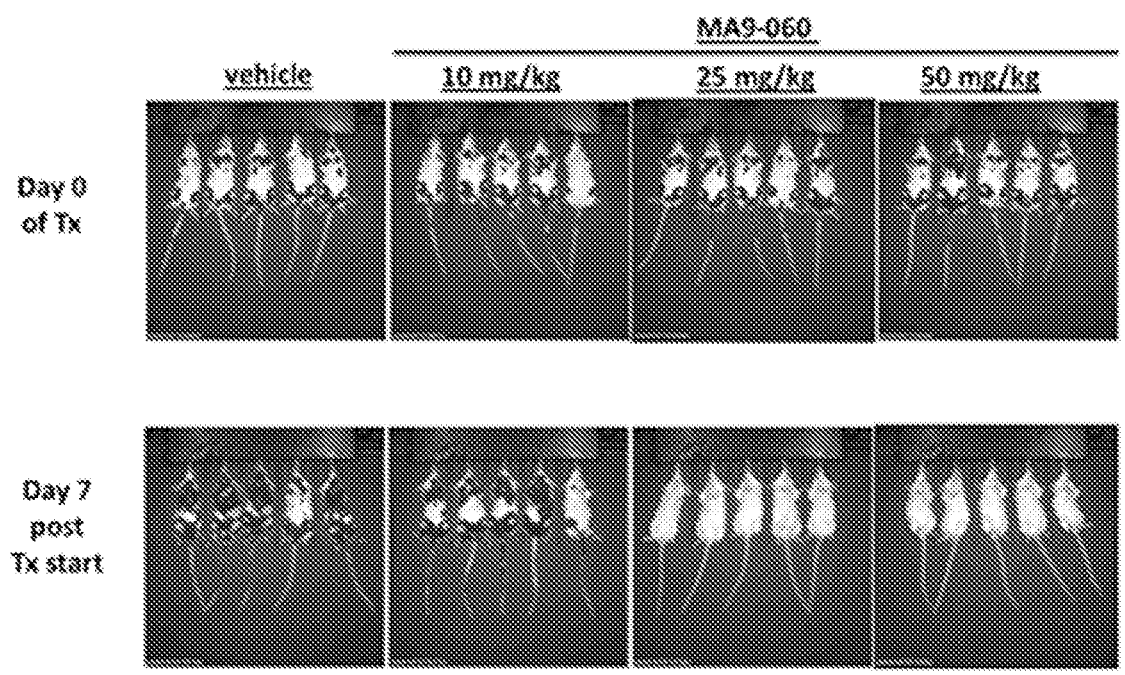
FIG. 3 shows in vivo efficacy MA9-060. Vehicle control and MA9-060 were administered orally twice daily at the indicated doses to Balb/c mice injected with BaF3-JAK2-V617F-luciferase cells. Mice were imaged for luciferase activity before (Day 0) and after 7 days of treatment (Tx) (FIG. 3A) with the mean total flux from target cells shown in (FIG. 3B). Mice were treated for 14 days and had a median survival of 15, 19, 26, and 31 days (post-treatment start) for vehicle, 10 mg/kg, 25 mg/kg, and 50 mg/kg respectively ($P<0.0031$) (FIG. 3C).
Figure 3B:
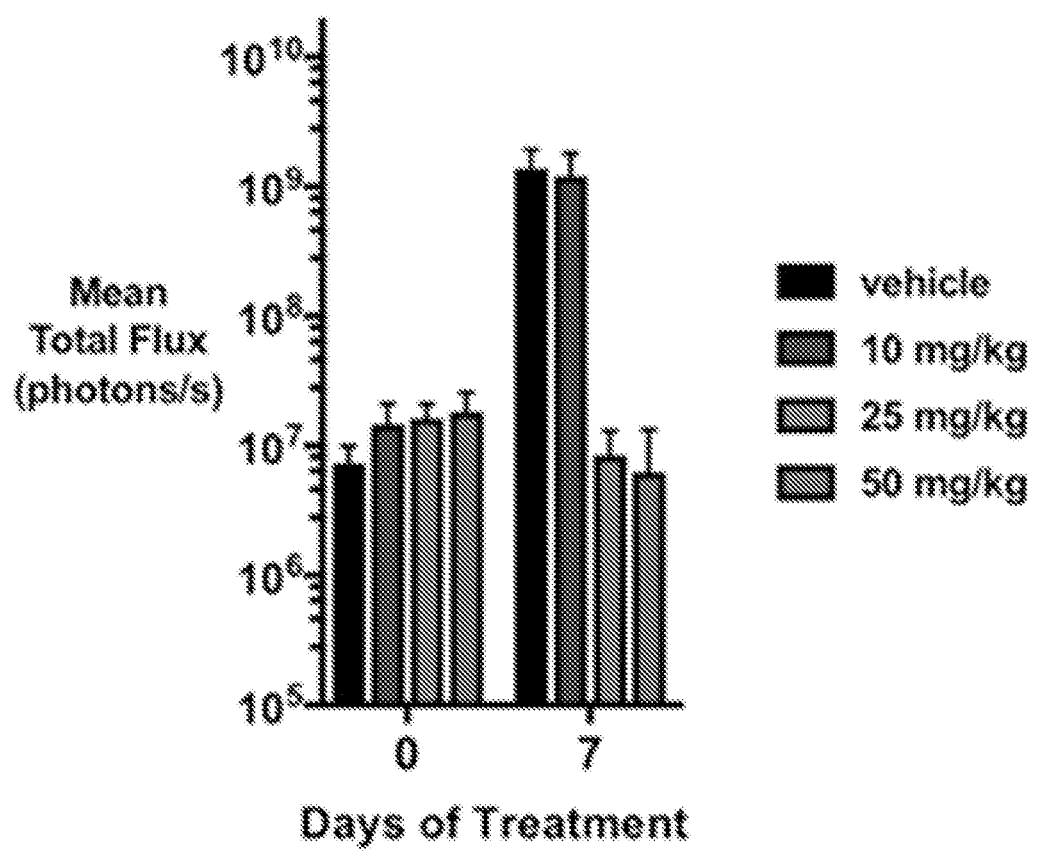
Figure 3C:
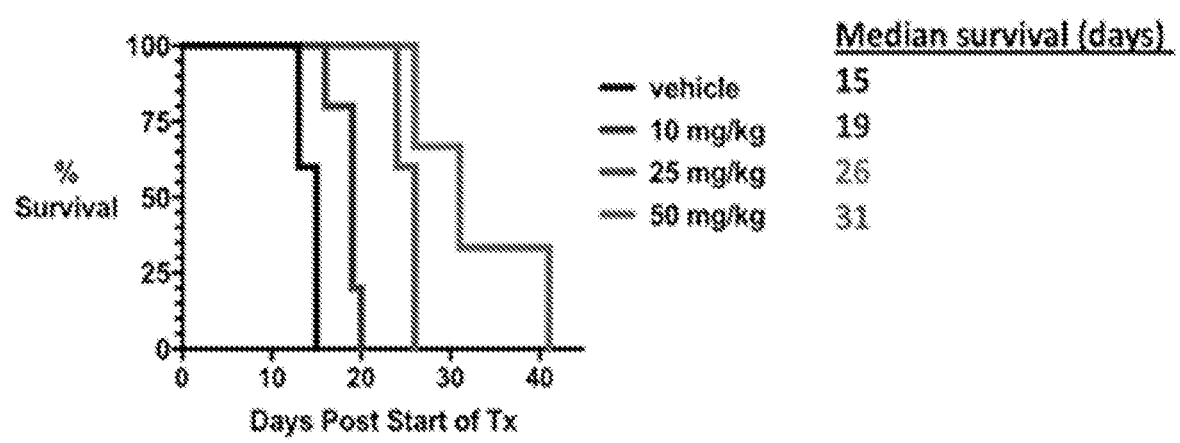

Early lead dual inhibitors displayed good stability in plasma but poor stability in liver microsomes. The basis of the metabolic liability was identified and overcome, and plasma and microsome stable compounds, which are orally bioavailable, were developed. Initial in vivo assessment of MA9-060 demonstrated dose-dependent inhibition of BaF3-JAK2-V617F-luciferase cells in Balb/c mice (FIG. 3). No toxicity was detected at 25 mg/kg (twice daily orally) and similar growth suppression was maintained for the duration of treatment (14 days) (not shown).

Table 2 below shows inhibitory activity of compounds disclosed herein.

TABLE 2

| ID | BRD4 DSF (ΔTm) ° C. | BRD4 (IC50) μM | JAK2 (IC50) μM | GI50 (UKE1) μM | GI50 (MM1S) μM |
|---|---|---|---|---|---|
| PN1-005 | | | | | |
| PN1-006 | | | | | |
| PN1-007 | | | | | |
| PN1-037 | | | | | |
| PN1-038 | | | | | |
| PN1-039 | | | | | |
| PN1-040 | | | | | |
| PN1-048 | | | | | |
| PN1-050 | | | | | |
| PN1-064 | 13.6 | | | 0.054 | 0.043 |
| PN1-101 | 13.5 | | | | 0.10 |
| PN1-102 | 11.4 | | | | 0.32 |
| PN1-117 | 12.7 | | | | 0.24 |
| PN1-118 | 11.6 | | | | 0.21 |
| PN1-119 | | | | | 0.39 |
| PN1-132 | 12.8 | | | | 0.36 |
| PN1-134 | 13.7 | | | | 0.58 |
| PN1-138 | 7.6 | | | | 0.89 |
| PN1-140 | 9.5 | | | | 1.8 |
| PN1-145 | 7.1 | | | | 0.22 |
| PN2-019 | | | | | |
| PN2-034 | | | | | |
| PN2-042 | | | | | |
| PN2-064 | 1.1 | | | | |
| PN2-080 | 12.7 | | | | |
| PN2-081 | 12.3 | | | | |
| PN2-084 | 14.5 | | | | |

TABLE 2-continued

| ID | BRD4 DSF (ΔTm) ° C. | BRD4 (IC50) μM | JAK2 (IC50) μM | GI50 (UKE1) μM | GI50 (MM1S) μM |
|---|---|---|---|---|---|
| PN2-085 | | | | | |
| PN2-089 | 13.4 | | | 0.134 | 0.072 |
| PN2-091 | 11.5 | | | | |
| PN2-102 | 13.0 | | | | 0.109 |
| PN2-103 | 12.4 | | | | |
| PN2-116 | 12.1 | | | | 0.104 |
| PN2-117 | 11.0 | | | | 0.153 |
| PN2-118 | 13.0 | | | | 0.083 |
| PN2-122 | 15.2 | | | | 0.093 |
| PN2-123 | 14.7 | | | | 0.081 |
| PN2-124 | 13.4 | | | | 0.080 |
| PN2-128 | 12.8 | | | 0.207 | 0.186 |
| PN2-129 | 13.8 | | | 0.222 | 0.152 |
| PN2-173 | 12.3 | | | 0.463 | |
| PN2-174 | 13.3 | | | 0.194 | |
| PN2-175 | 12.6 | | | 0.22 | |
| PN3-052 | | | | 0.27 | |
| PN3-053 | | | | 0.185 | |
| PN3-054 | | | | 0.449 | |
| PN3-074 | | | | 0.937 | |
| PN3-075 | | | | 0.556 | |
| PN3-076 | | | | 1.10 | |
| PN3-099 | | | | | |
| PN3-100 | | | | | |
| PN3-108 | | | | | |
| SY3-005 | 6.0 | 3.96 | >1 | 5.3 | 3.31 |
| SY3-030 | 6.3 | | | | |
| SY3-039 | 6.7 | | | | 1.6 |
| SY3-034 | 10.6 | | 0.0016 | 0.22 | 0.091 |
| SY3-038 | 12.3 | 0.087 | 0.0007 | 0.064 | |
| SY3-040 | 11.1 | 0.127 | 0.0031 | | 0.22 |
| SY3-016 | | | | | |
| MA9-024 | 4.1 | | | >24 | 4.79 |
| MA9-036 | 6.9 | | | 4.5 | 3.12 |
| MA9-037 | 6.6 | | | 5.7 | 2.83 |
| MA9-042 | 6.1 | | | | |
| MA9-050 | 12.3 | 0.143 | 0.0082 | 0.31 | 0.11 |
| MA9-060 | 14.5 | 0.026 | 0.0033 | 0.150 | 0.043 |
| MA9-062 | 11.3 | 0.049 | 0.017 | | 0.16 |
| MA9-064 | 8.2 | | | | 1.6 |
| MA9-086 | 13.4 | 0.0064 | 0.0011 | | 0.194 |
| MA9-168 | | | | | |
| MA9-169 | | | | | |
| MA9-176 | | | | | |
| MA9-177 | | | | | |
| MA9-178 | | | | | |
| MA9-179 | | | | | |
| MA10-148 | 7.6 | | | | |
| MA10-149 | 6.2 | | | | |
| MA10-174 | 0.9 | | | | |
| MA10-175 | 1.1 | | | | |
| MA10-176 | 1.4 | | | | |
| MA10-178 | 2.8 | | | | |
| MA10-179 | 1.4 | | | | |
| MA11-003 | 8.0 | | | | |
| MA11-006 | 11.0 | | | 0.502 | 0.499 |
| MA11-007 | 13.7 | | | 0.260 | 0.135 |
| MA11-009 | 1.1 | | | | |
| MA11-012 | 3.9 | | | 0.580 | |
| MA11-016 | 14.8 | | | 0.110 | |
| MA11-017 | 14.3 | | | 0.102 | |
| MA11-022 | | | | | |
| MA11-032 | | | | 0.385 | |
| MA11-035 | 5.1 | | | 0.761 | |
| MA11-038 | | | | 5.6 | |

What is claimed is:
1. A compound selected from
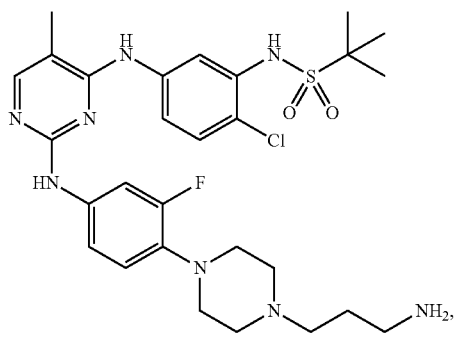
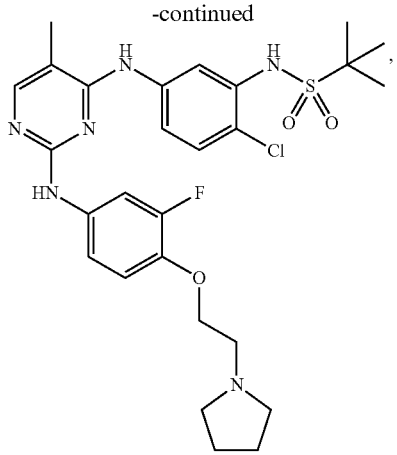
or a salt thereof.

2. A compound selected from
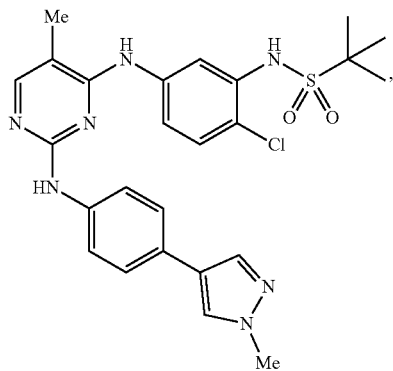
PN1-004
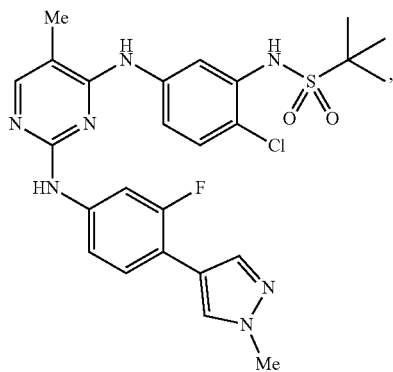
PN1-005
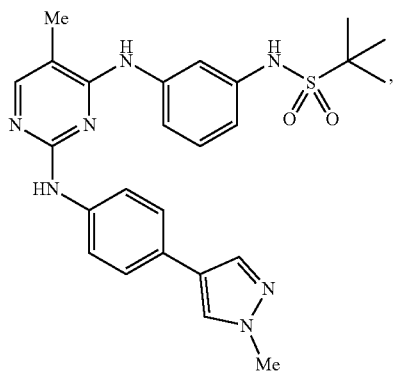
PN1-006
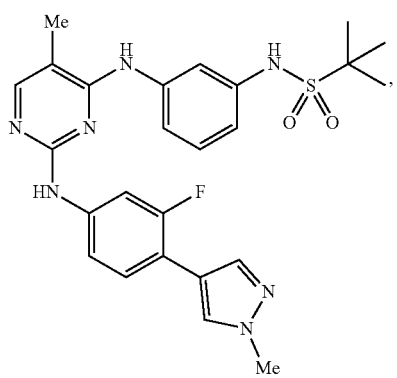
PN1-007
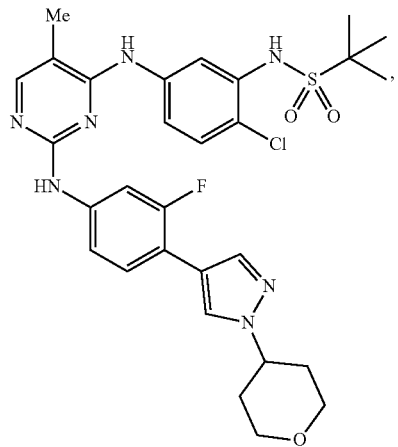
PN1-037
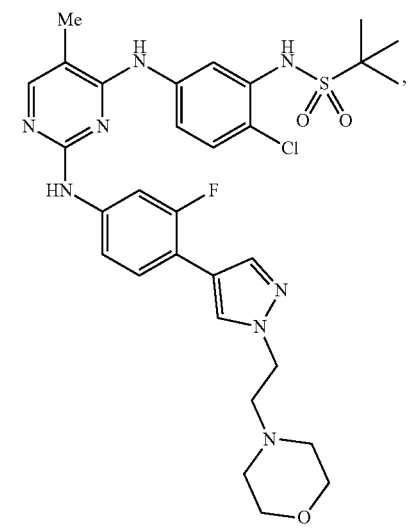
PN1-038
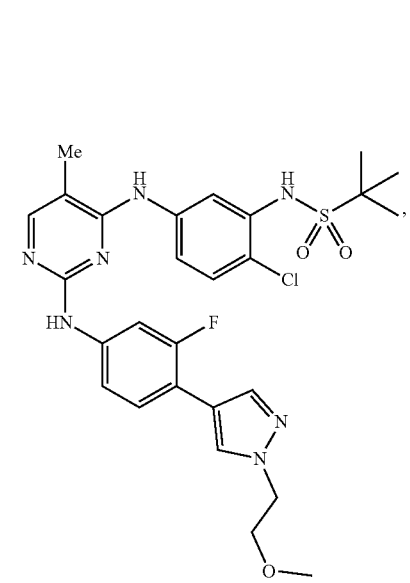
PN1-039

-continued
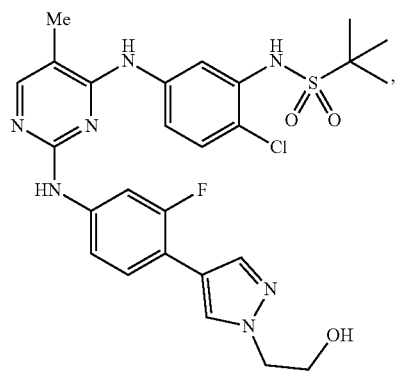
PN1-040
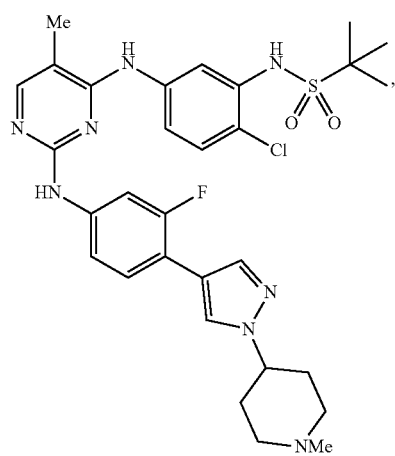
PN1-048
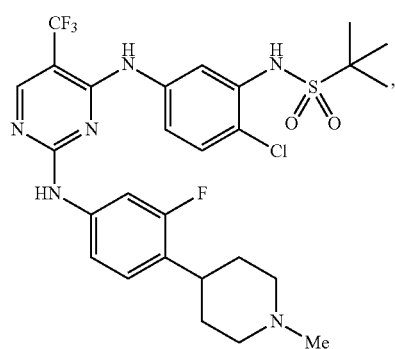
PN1-050
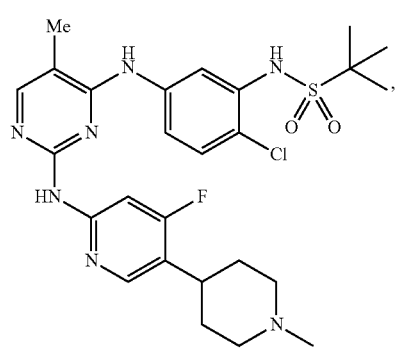
PN1-064
-continued
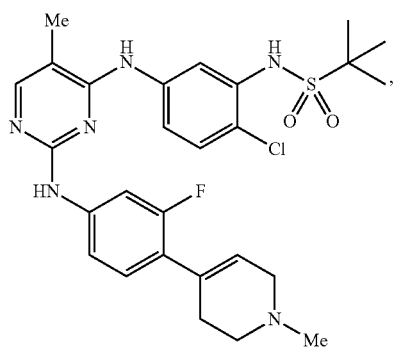
PN1-101
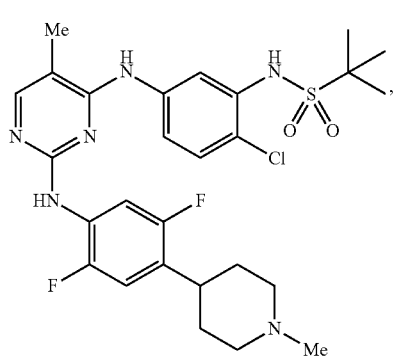
PN1-102
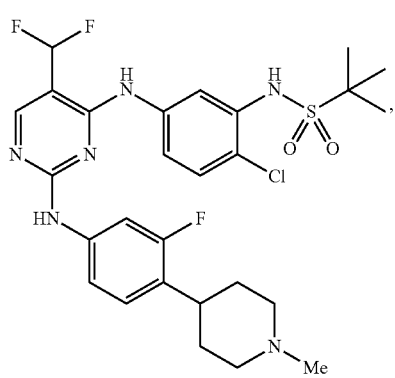
PN1-117
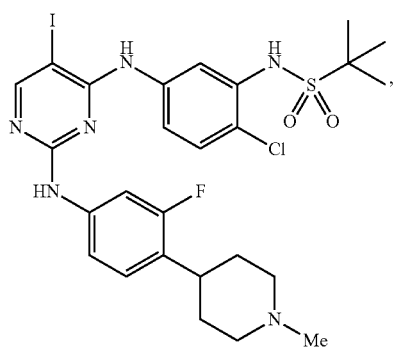
PN1-118

173
PN1-119
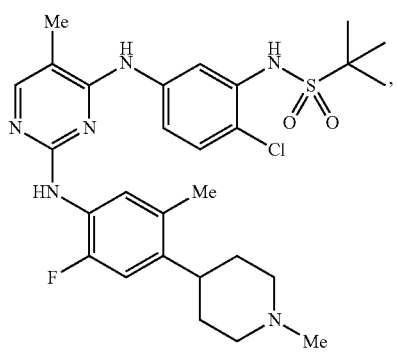
PN1-132
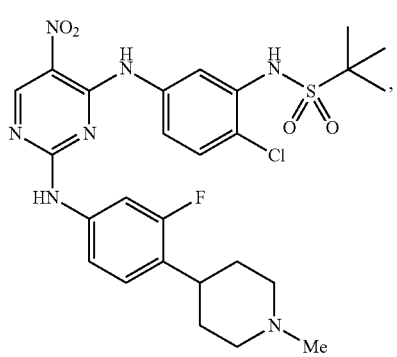
PN1-134
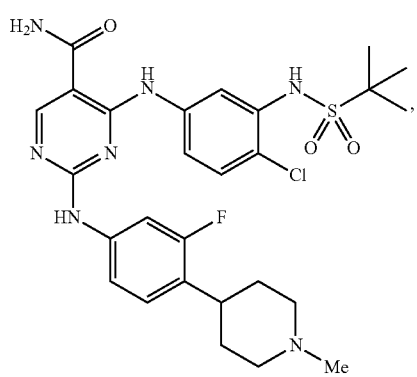
PN1-138
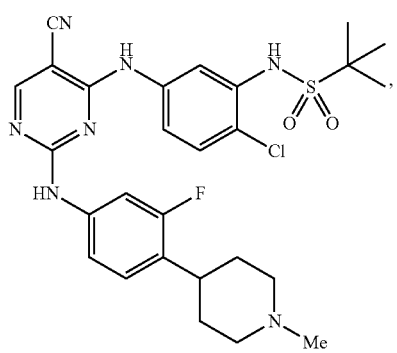
174
PN1-140
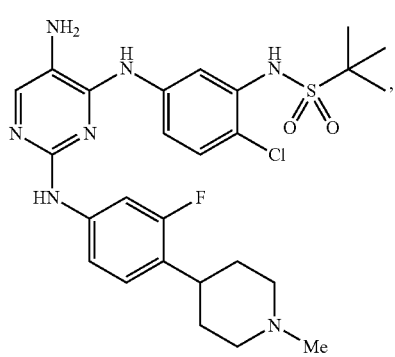
PN1-145
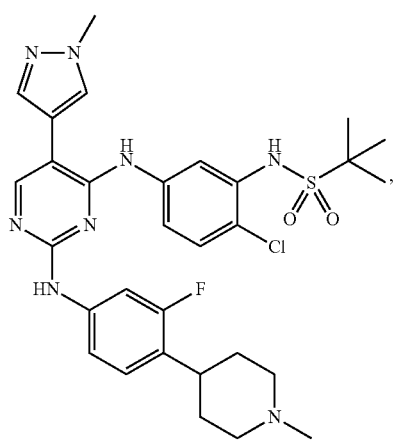
PN2-017
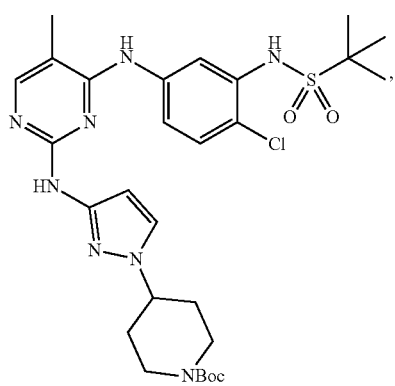
PN2-019
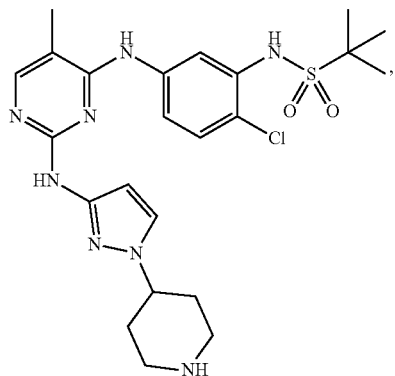

-continued
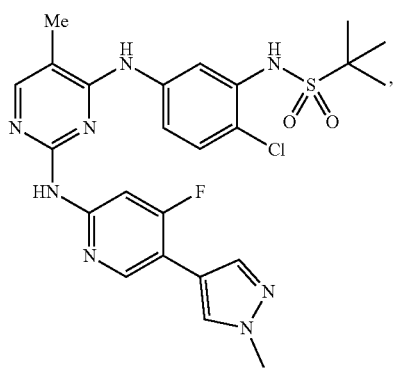
PN2-034
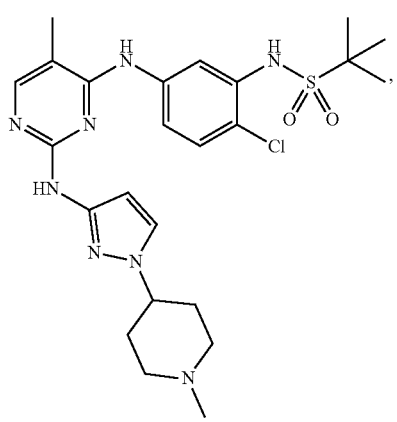
PN2-042
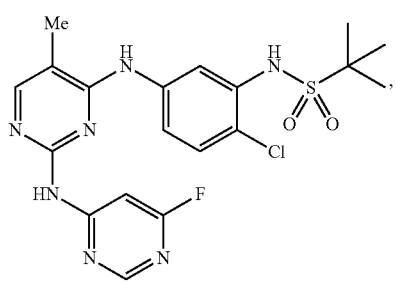
PN2-064
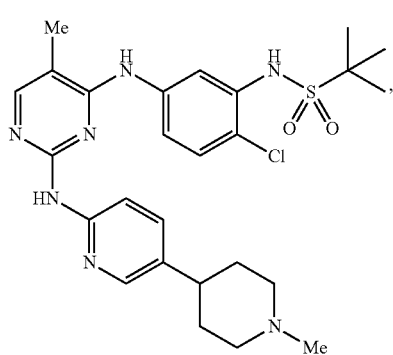
PN2-081
-continued
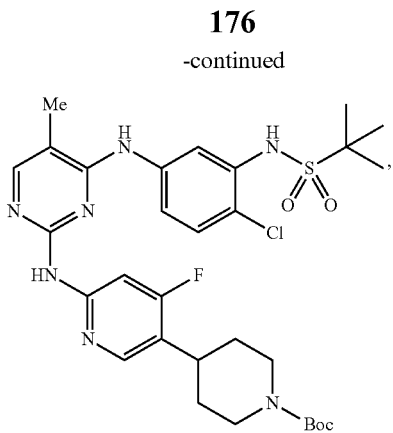
PN2-082
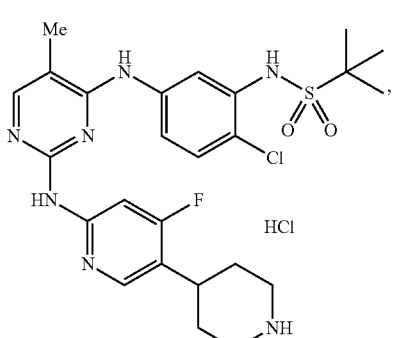
PN2-084
HCl
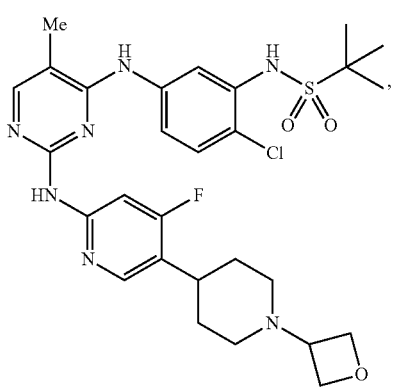
PN2-085
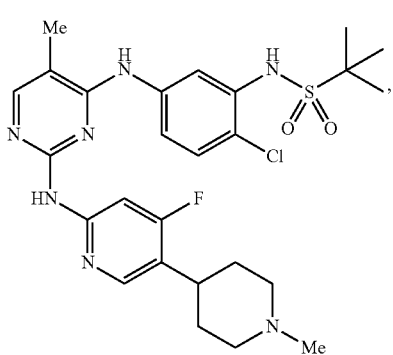
PN2-089

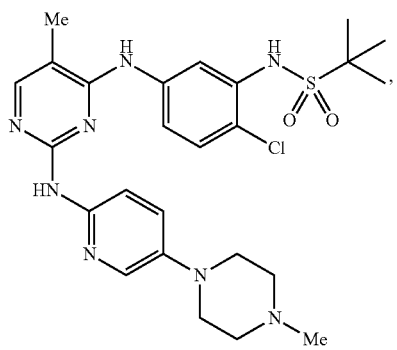
PN2-091
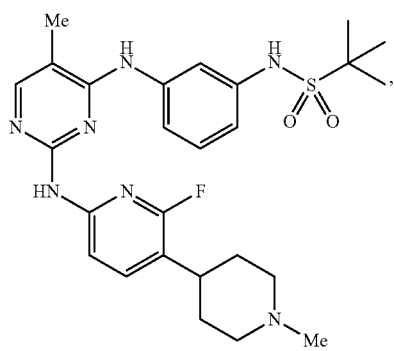
PN2-117
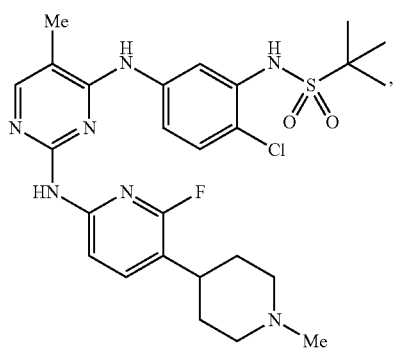
PN2-102
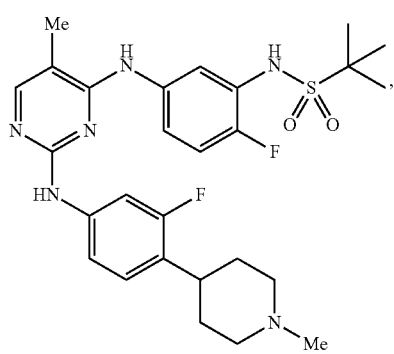
PN2-118
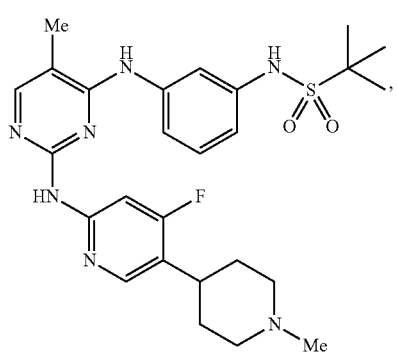
PN2-103
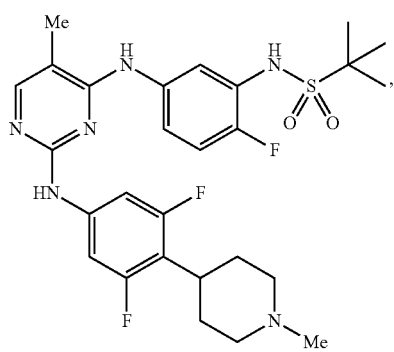
PN2-123
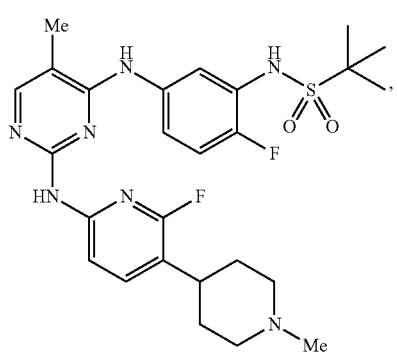
PN2-116
PN2-128

-continued
PN2-129
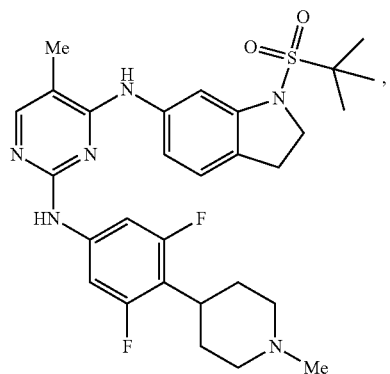
PN3-052
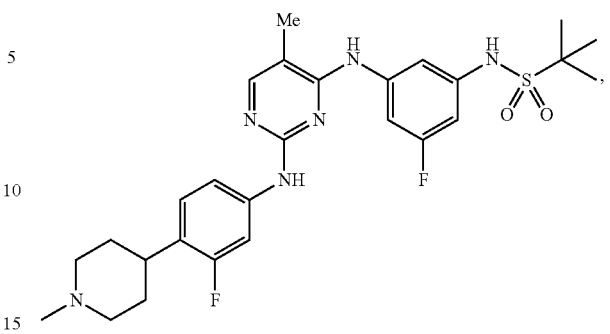
PN2-173
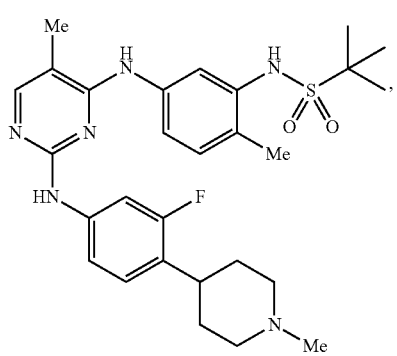
PN3-053
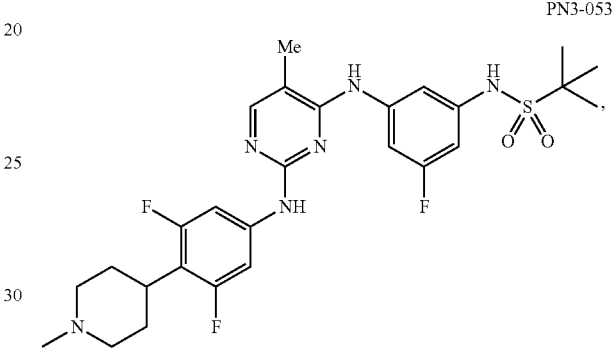
PN2-174
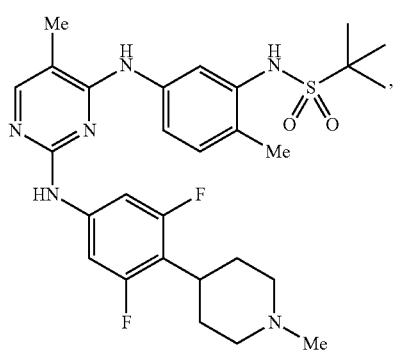
PN3-054
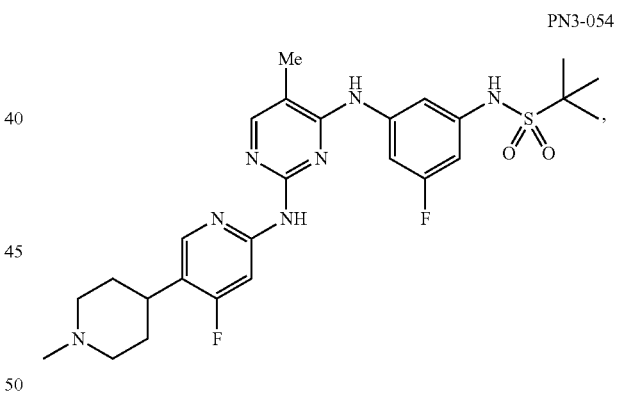
PN2-175
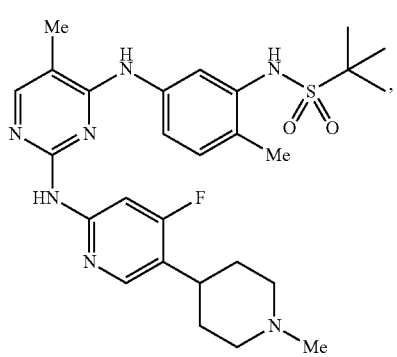
PN3-074
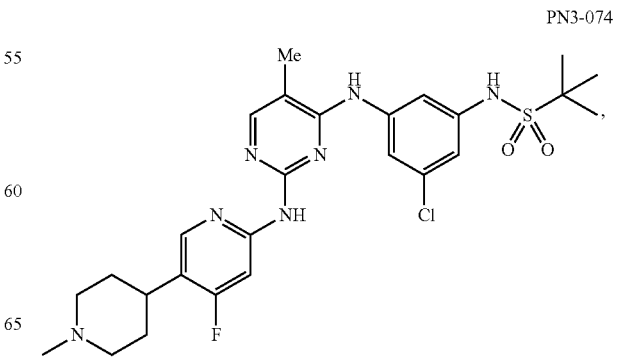

-continued
PN3-075
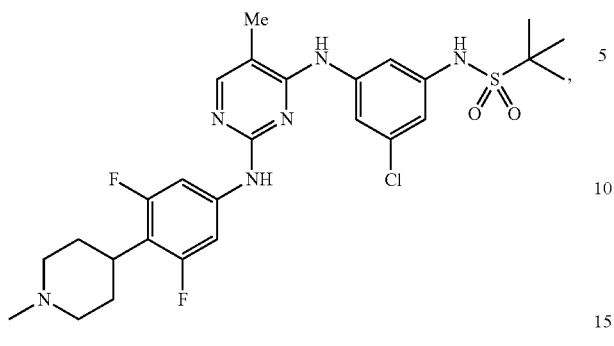
PN3-076
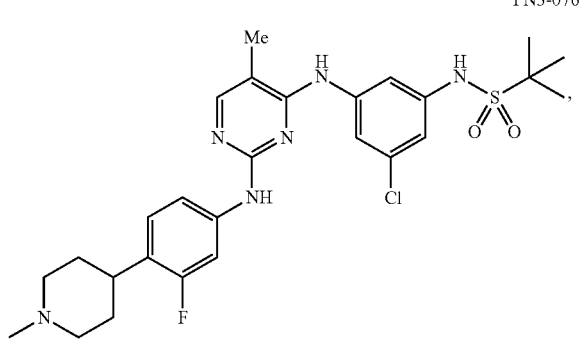
PN3-099
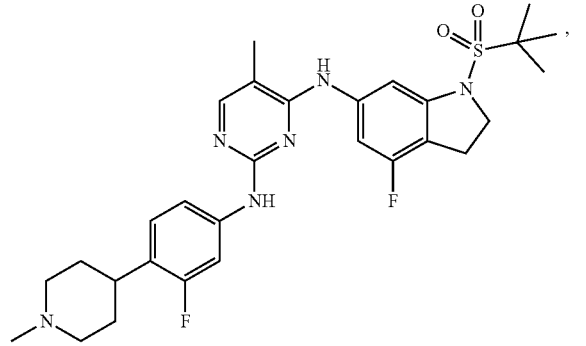
PN3-100
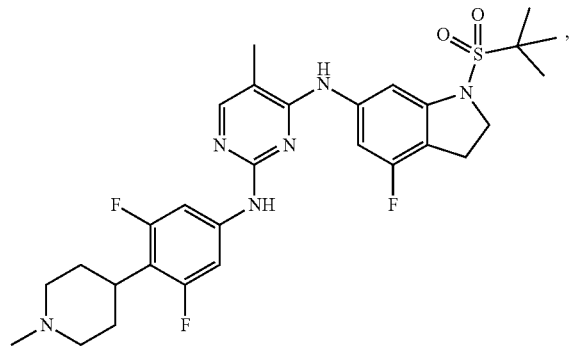
-continued
PN3-108
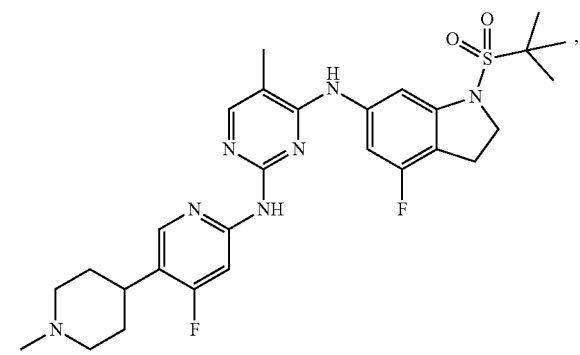
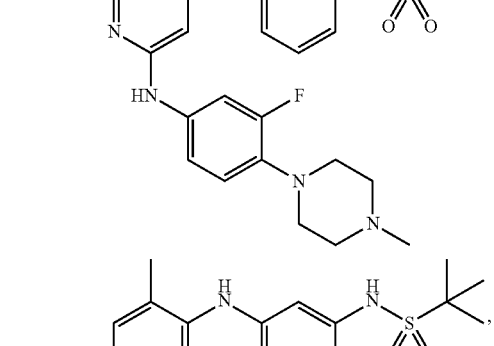
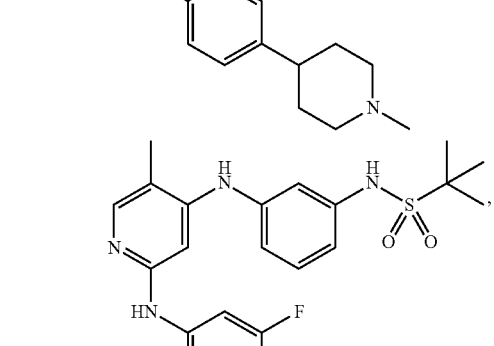
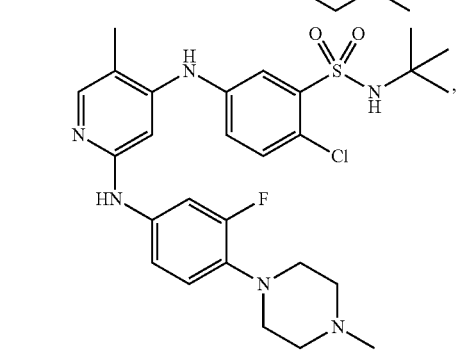

-continued
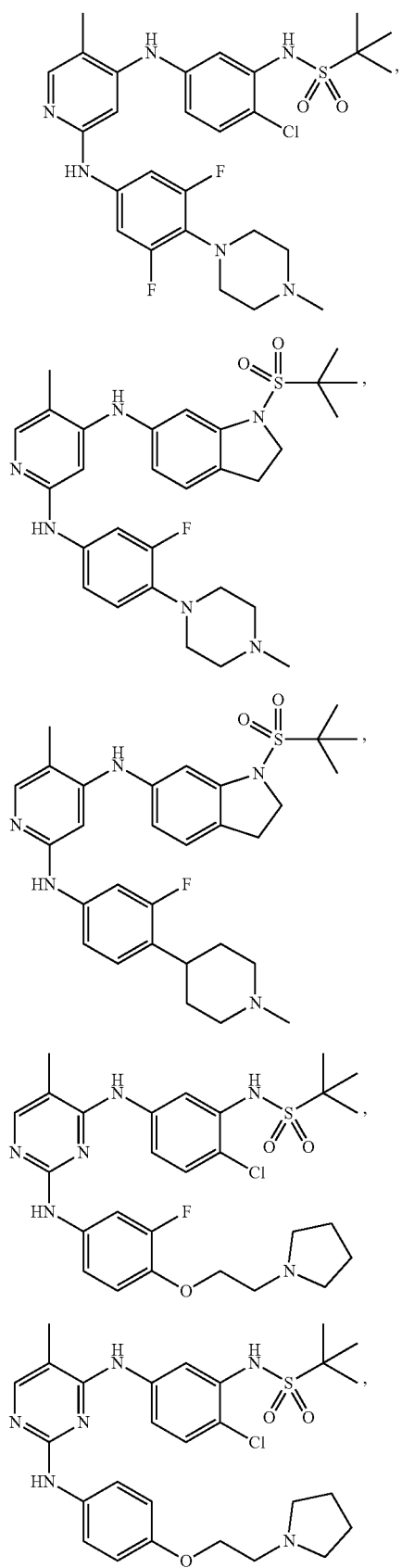
MA9-037.bisformate
MA9-042
MA9-064
MA9-169
MA9-177
-continued
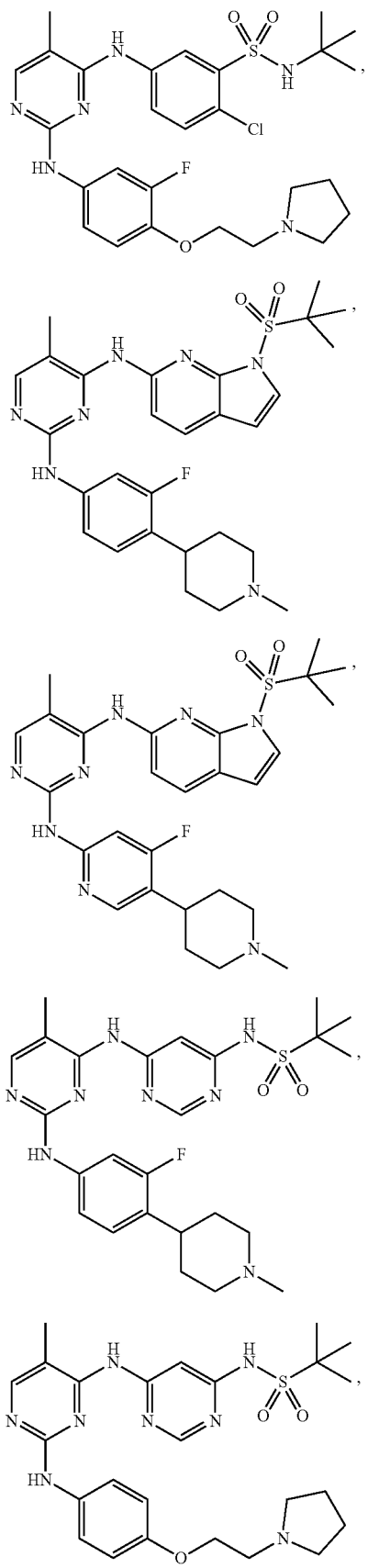
MA9-179
MA10-148
MA10-149
MA10-174
MA10-175

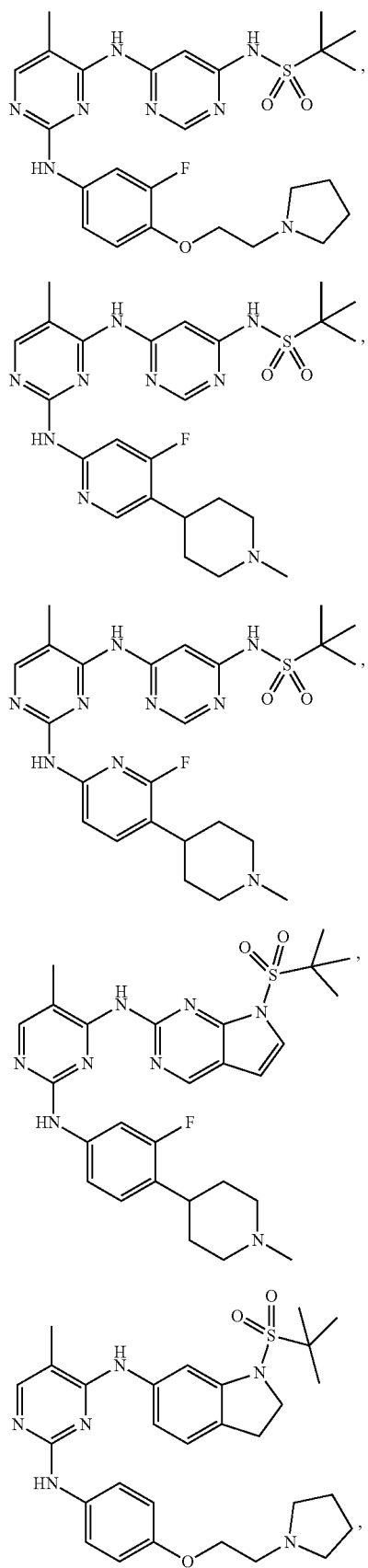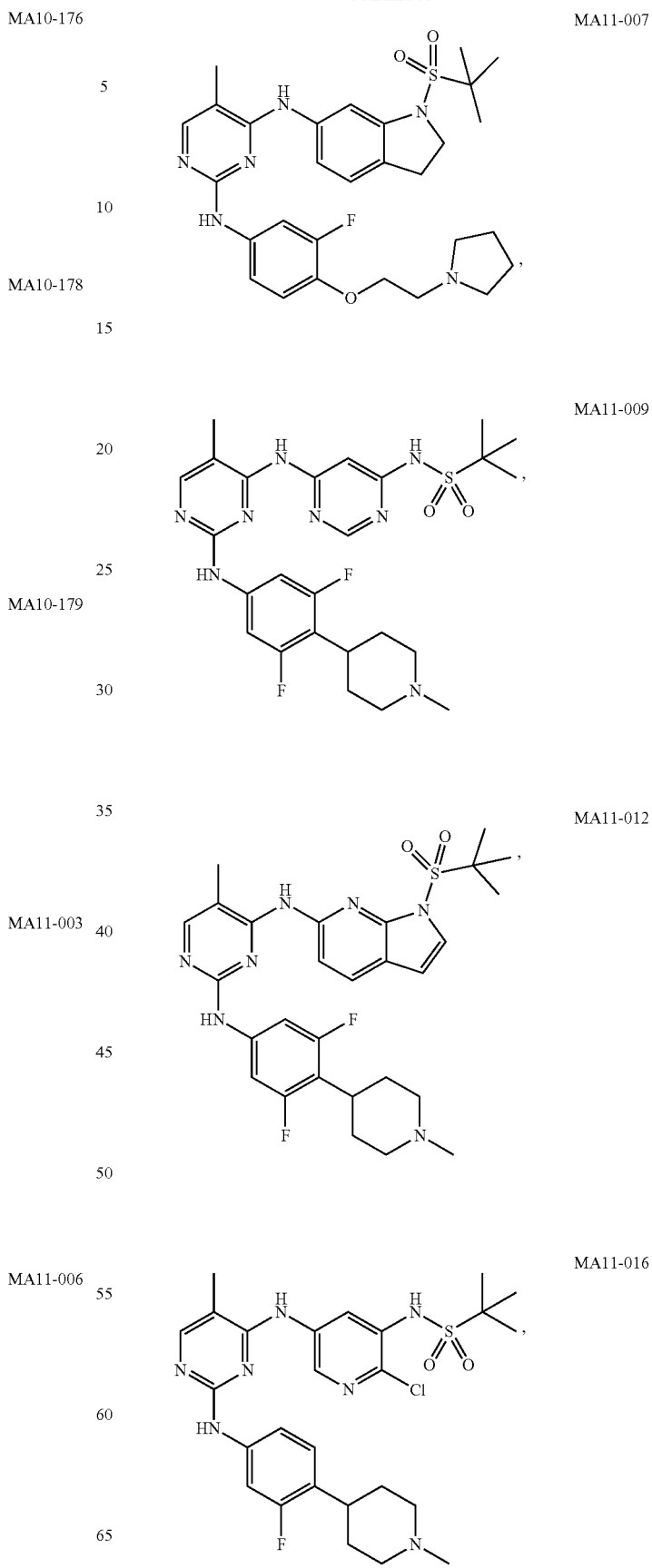

-continued

MA11-017

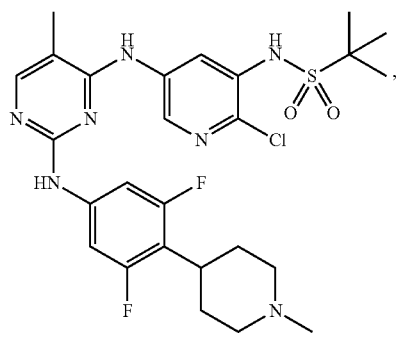

MA11-022

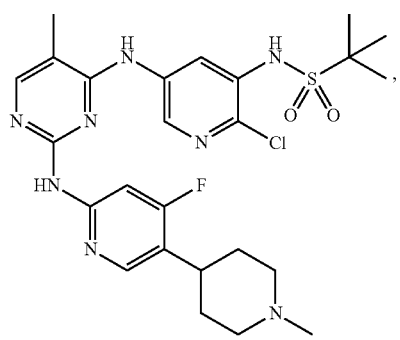

MA11-032

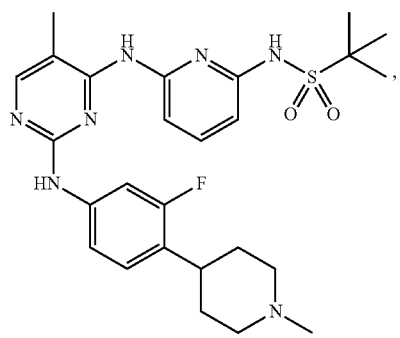

MA11-035

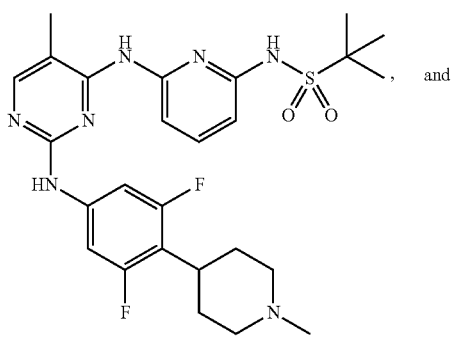, and

-continued

MA11-038

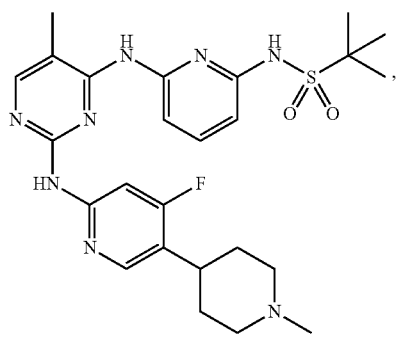

or a salt thereof.

3. A pharmaceutical composition comprising the compound of claim 1 and a pharmaceutically acceptable carrier.

4. A pharmaceutical composition comprising the compound of claim 2 and a pharmaceutically acceptable carrier.

5. A method of ameliorating or alleviating cancer in a subject comprising, administering to the subject an effective amount of a compound of claim 1.

6. The method of claim 5, wherein the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

7. A method of killing a tumor cell in a subject, comprising: contacting the tumor cell with an effective amount of a compound of claim 1.

8. A method of ameliorating or alleviating cancer in a subject comprising, administering to the subject an effective amount of a compound of claim 2.

9. The method of claim 8, wherein the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

10. A method of killing a tumor cell in a subject, comprising: contacting the tumor cell with an effective amount of a compound of claim 2.

* * * * *